US009233953B2

(12) United States Patent
Hoenke et al.

(10) Patent No.: US 9,233,953 B2
(45) Date of Patent: Jan. 12, 2016

(54) DERIVATIVES OF 4-(PIPERAZINYLCARBONYL)THIANE-1, 1-DIONE WHICH INHIBIT GLYT1

(71) Applicants: Christoph Hoenke, Biberach an der Riss (DE); Riccardo Giovannini, Verona (IT); Uta Lessel, Maselheim (DE); Holger Rosenbrock, Mittelbiberach (DE); Bernhard Schmid, Ingoldingen (DE)

(72) Inventors: Christoph Hoenke, Biberach an der Riss (DE); Riccardo Giovannini, Verona (IT); Uta Lessel, Maselheim (DE); Holger Rosenbrock, Mittelbiberach (DE); Bernhard Schmid, Ingoldingen (DE)

(73) Assignee: Boehringer Ingelheim International GmbH, Ingelhein am Rhein (DE)

( * ) Notice: Subject to any disclaimer, the term of this patent is extended or adjusted under 35 U.S.C. 154(b) by 0 days.

(21) Appl. No.: 14/513,918

(22) Filed: Oct. 14, 2014

(65) Prior Publication Data

US 2015/0105397 A1 Apr. 16, 2015

(30) Foreign Application Priority Data

Oct. 16, 2013 (EP) .................................... 13188904

(51) Int. Cl.

| | |
|---|---|
| ***A61K 31/496*** | (2006.01) |
| ***C07D 409/06*** | (2006.01) |
| ***C07D 409/14*** | (2006.01) |
| ***C07D 413/14*** | (2006.01) |
| ***C07D 417/14*** | (2006.01) |

(52) U.S. Cl.

CPC ............ *C07D 409/06* (2013.01); *C07D 409/14* (2013.01); *C07D 413/14* (2013.01); *C07D 417/14* (2013.01)

(58) Field of Classification Search

None

See application file for complete search history.

(56) References Cited

FOREIGN PATENT DOCUMENTS

| | | | |
|---|---|---|---|
| WO | 2004035556 | A1 | 4/2004 |
| WO | 2006094840 | A1 | 9/2006 |
| WO | 2006113704 | A2 | 10/2006 |
| WO | 2011003418 | A1 | 1/2011 |

OTHER PUBLICATIONS

Harada et al.European Journal of Phatmacology, vol. 685, pp. 59-69 (2012).*

Harvey et al. Nature Reviews/Drug Discovery vol. 12 pp. 866-885 (2013).*

Bitopertin, from Wikipedia, 1 page, retrieved from "http://en.wikipedia.org/w/index.php?title=Bitopertin&oldid=643636360", Feb. 8, 2015.*

Pinard et al., "Selective GlyT1 Inhibitors: Discovery of [4-(3-Fluoro-5-trifluoromethylpyridin-2-yl)piperazin-1-yl]-[5-methanesulfonyl-2-((S)-2,2,2-trifluoro-1-methylethoxy)phenyl]methanone (RG1678), a Promising Novel Medicine to Treat Schizophrenia", Journal of Medicinal Chemistry, vol. 53, May 21, 2010, pp. 4603-4614.

International Search Report, form PCT/ISA/210, and Written Opinion, form PCT/ISA/237, for correspomding application PCT/EP2014/072085, date of mailing Dec. 15, 2014.

* cited by examiner

*Primary Examiner* — Emily Bernhardt

(74) *Attorney, Agent, or Firm* — Michael P. Morris; Alan R. Stempel

(57) ABSTRACT

The present inventions relate to substituted piperazine derivatives of general formula (I)

(I)

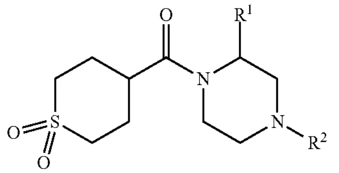

and to the manufacture of said compounds, pharmaceutical compositions comprising a compound according to general formula (I), and the use of said compounds for the treatment of various medical conditions related to glycine transporter-1 (GlyT1).

18 Claims, No Drawings

DERIVATIVES OF 4-(PIPERAZINYLCARBONYL)THIANE-1, 1-DIONE WHICH INHIBIT GLYT1

The present inventions relate to substituted piperazine derivatives of general formula (I)

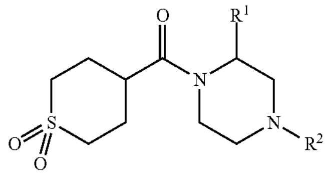

(I)

and to the manufacture of said compounds, pharmaceutical compositions comprising a compound according to general formula (I), and the use of said compounds for the treatment of various medical conditions related to glycine transporter-1.

BACKGROUND OF THE INVENTION

A general overview of the role of glycine transporter-1 (GlyT1) inhibitors for the treatment of diseases can be taken for example from WO2010/086251. This role of glycine transporter-1 (GlyT1) inhibitors is applicable for the present invention as well. In the following sectionexcerpts from pages 1 to 4 of WO2010/086251 will be cited in parts and/or modified and wherever considered appropriate further details, which are known in the art, are added, in order to provide state of the art background information for the present invention:

Schizophrenia is a progressive and devastating psychiatric disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, 2000, Neuron, 28: 325-33).

A hypothesis of schizophrenia was proposed in the mid-1960' based upon the psychotomimetic action caused by the blockade of the glutamate system by compounds like phencyclidine (PCP) and related agents (e.g. ketamine) which are non-competitive antagonists of the glutamate N-methyl-D-aspartate (NMDA) receptor. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45:668-679); see also Jentsch and Roth, 1999, Neuropsychopharmacology 20:201-225). Therefore, increasing NMDA-receptor neurotransmission in the central nervous system offers an opportunity for the development of novel treatment approaches for schizophrenia and also other neurological and psychiatric diseases related to NMDA-receptor and/or glutamatergic dysfunction. The NMDA-receptor is a ligand-gated ion channel composed of a combination of two NR1 and two NR2 subunits and requires the concomitant binding of glutamate at the NR2 subunit and glycine as a co-agonist at the NR1 subunit to be activated (Johnson and Ascher, 1987, Nature 325:529-531). One strategy to enhance NMDA receptor activity is to elevate the glycine concentration in the local microenvironment of synaptic NMDA receptors by inhibition of GlyT1 (Bergeron R. et al., 1998, Proc. Natl. Acad. Sci. USA 95:15730-15734). In fact, clinical studies with direct glycine site agonists D-serine and a prototype GlyT1-inhibitor, sarcosine, which increases glycine in the synaptic cleft, have demonstrated some efficacy for the treatment of negative symptoms and to a lesser extent, positive and cognitive symptoms of schizophrenia (Tsai et al., 2004, Biol. Psychiatry 44:1081-1089; Lane et al., 2005, Biol. Psychiatry 63:9-12). Recently, clinical efficacy regarding negative symptoms in schizophrenia patients was reported for the GlyT1-inhibitor RG1678 tested in a clinical phase II trial as adjunctive treatment to marketed antipsychotics (Umbricht et al., 2011, Schizophr. Bull. 37(Suppl. 1):324).

Efficacy in various animal models/tests for positive and negative symptoms of schizophrenia as well as in several memory tasks has been reported in the literature for different GlyT1-inhibitors. In detail, the selective GlyT1-inhibitors SSR504734 and SSR103800 were shown to be efficacious in two models for antipsychotic activity, i.e. reversal of NMDA-receptor antagonist induced hyperlocomotion and pre-pulse-inhibition, well known models for positive symptoms of schizophrenia (Depoortere et al., 2005 Neuropsychopharmacology 30:1963-1985; Boulay et al., 2008, Pharmacol. Biochem. Behav. 91:47-58). Regarding negative symptoms, SSR504734 was demonstrated to increase dopamine in the prefrontal cortex, a mechanistic in-vivo model for negative symptoms in schizophrenia (Depoortere et al., 2005, Neuropsychopharmacology 30:1963-1985). Regarding memory enhancement, the selective GlyT1-inhibitors SSR504734 and SSR103800 were efficacious in the social recognition test (Depoortere et al., 2005, Neuropsychopharmacology 30:1963-1985; Boulay et al., 2008, Pharmacol. Biochem. Behav. 91:47-58). Another GlyT1-inhibitor, NFPS, was shown to be active in the object recognition and social recognition test regarding reversal of MK-801-induced cognitive deficits (Karasawa et al., 2008, Behav. Brain Res. 186:78-83; Shimazaki et al., 2010, Psychopharmacology 209:263-270). In addition, an enhancing effect on long-term potentiation in hippocampal slices could be shown with NFPS demonstrating that inhibition of GlyT1 leads to strengthening of synaptic plasticity which is crucial for memory formation on a cellular level (Kinney et al., 2003, J. Neurosci. 23:7586-7591). In fact, glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Bliss T V and Collingridge G L, 1993, Nature, 361:31-39).

In addition, GlyT1-inhibitors were shown to be efficacious in animal models of depression, anxiety and sleep, such as chronic mild stress, ultrasonic distress calls in rat pups and increased latency of paradoxical sleep (Depoortere et al., 2005, Neuropsychopharmacology 30:1963-1985).

Two distinct glycine transporter genes have been cloned (GlyT1 and GlyT2) from mammalian brain, which give rise to two transporters having 50% amino acid sequence homology. GlyT1 presents four isoforms arising from alternative splicing and alternative promoter usage (1a, 1b, 1c and 1d). Only two of these isoforms have been found in rodent brain (GlyT1a and GlyT1b). GlyT2 also presents some degree of heterogeneity. Two GlyT2 isoforms (2a and 2b) have been identified in rodent brains. GlyT1 is known to be located in CNS and in some peripheral tissues, whereas GlyT2 is specific to the CNS, primarily in the hindbrain and spinal cord (Zafra et al., 1995, J. Neurosci. 15:3952-3969). GlyT1 is expressed in glia and neurons, and it is found to be located at glutamatergic synapses (Cubelos et al., 2005, Cereb. Cortex 15:448-459).

Glycine transporter inhibitors are suitable for the treatment of neurological and psychiatric disorders. The majority of diseases states implicated are psychoses, schizophrenia (Armer R E and Miller D J, 2001, Exp. Opin. Ther. Patents 11: 563-572), psychotic mood disorders such as severe major depressive disorder, mood disorders associated with psychotic disorders such as acute mania or depression, associated with bipolar disorders and mood disorders, associated with schizophrenia, (Pralong E T et al., 2002, Prog. Neurobiol., 67:173-202), autistic disorders (Carlsson M L, 1998, J. Neural Trans. 105:525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11:563-572).

Thus, increasing activation of NMDA receptors via GlyT1 inhibition may lead to agents that treat psychosis, schizophrenia (positive, negative and cognitive symptoms), dementia and other diseases in which cognitive processes are impaired, such as attention deficit disorders, Alzheimer's disease, or other neurological and psychiatric disorders.

The before mentioned concepts related to the inhibition of GlyT1 are of high interest, in particular with respect to cognitive impairment associated with Alzheimer's disease or Schizophrenia.

BRIEF SUMMARY OF THE INVENTION

The present inventions relates to substituted piperazine derivatives of general formula (I)

(I)

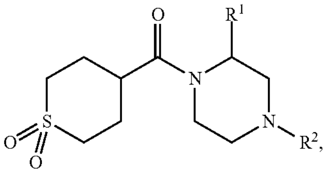

wherein $R^1$ and $R^2$ are as herein described or salts thereof, preferably a pharmaceutically acceptable salt thereof.

The invention further relates to the manufacture of said active compounds, pharmaceutical compositions comprising a compound according to general formula (I), and the use of said active compounds for the treatment of various medical conditions.

AIM OF THE INVENTION

The compounds of the invention according to general formula (I) show glycine transporter-1 (GlyT1) inhibiting properties. Consequently, one aspect of the present invention relates to compounds according to formula I and salts thereof as modulators of GlyT1.

A further aspect of the invention relates to the physiologically acceptable salts of the compounds of general formula (I) according to this invention with inorganic or organic acids.

In a further aspect the present invention relates to pharmaceutical compositions, containing at least one compound according to formula (I) or a physiologically acceptable salt thereof, optionally together with one or more inert carriers and/or diluents.

A further aspect of the present invention relates to compounds according to formula (I) or a physiologically acceptable salt thereof or pharmaceutical compositions comprising compounds according to formula (I) or physiologically acceptable salts thereof for the use in the prevention and/or treatment of GlyT1-related pathologies.

A further aspect of the present invention relates to compounds according to formula I or a physiologically acceptable salt thereof or pharmaceutical compositions comprising compounds according to formula I or physiologically acceptable salts thereof for the use in the prevention and/or treatment of diseases or conditions which can be influenced by inhibition of GlyT1, such as conditions concerning positive and negative symptoms of schizophrenia as well as cognitive impairments associated with schizophrenia, Alzheimer's Disease and other neurological and psychiatric disorders. The use comprises the manufacture of medicaments for the treatment of the corresponding diseases.

DETAILED DESCRIPTION OF THE INVENTION

In a first aspect the present invention relates to compounds of general formula (I)

(I)

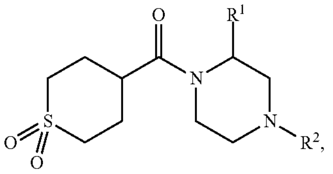

wherein $R^1$ is selected from the group $R^{1a}$ consisting of phenyl and a 5 or 6 membered monocyclic heteroaryl having 1, 2 or 3 heteroatoms independently selected from O, N or S, wherein the phenyl or the heteroaryl is optionally substituted with one or more $R^3$, preferably with one or two $R^3$;

$R^2$ is selected from the group $R^{2a}$ consisting of aryl, a 5 or 6 membered monocyclic heteroaryl and a 8 to 10 membered bicyclic heteroaryl, the mono- or bicyclic heteroaryl having 1, 2 or 3 heteroatoms independently selected from O, N or S, wherein the aryl or the heteroaryl is optionally substituted with one or more $R^4$, preferably with one or two $R^4$;

$R^3$ is selected from the group $R^{3a}$ consisting of halogen, a $—C_{1-4}$-alkyl and a $—C_{3-6}$-cycloalkyl, wherein the $—C_{1-4}$-alkyl or the $—C_{3-6}$-cycloalkyl is optionally substituted with one or more halogens;

$R^4$ is selected from the group $R^{4a}$ consisting of halogen, —CN, $—C_{1-4}$-alkyl, $—C_{3-6}$-cycloalkyl, $—C_{1-3}$-alkyl $—C_{3-6}$-cycloalkyl and $—O—C_{1-6}$-alkyl, wherein the $C_{1-4}$-alkyl, $—C_{3-6}$-cycloalkyl, $—C_{1-3}$-alkyl $—C_{3-6}$-cycloalkyl or the $—O—C_{1-6}$-alkyl is optionally substituted with one or more halogens;

or the tautomers thereof, the stereoisomers thereof, the mixtures thereof and the salts thereof.

Unless otherwise stated, the groups, residues, and substituents, particularly $R^1$, $R^2$, $R^3$ and $R^4$ are defined as above and hereinafter. If residues, substituents, or groups occur several times in a compound they may have the same or different meanings. Some preferred meanings of groups and substituents of the compounds according to the invention will be given hereinafter.

In a further embodiment of the present invention $R^1$ is selected from the group $R^{1b'}$ consisting of

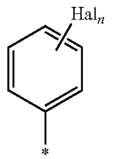

and

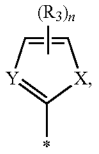

wherein Hal is a halogen, n is 0, 1 or 2,

X is S or O,

Y is N or CH.

In a further embodiment of the present invention $R^1$ is selected from the group $R^{1b}$ consisting of

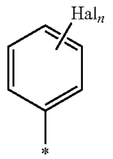

and

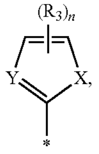

wherein Hal is a halogen, n is 1 or 2,

X is S or O,

Y is N or CH.

In a further embodiment of the present invention $R^1$ is selected from the group $R^{1c}$ consisting of

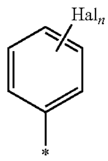

,

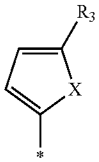

and

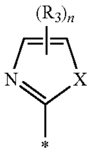

wherein Hal is —F or —Cl, n is 1 or 2,

X is S or O.

In a further embodiment of the present invention $R^1$ is selected from the group $R^{1d}$ consisting of

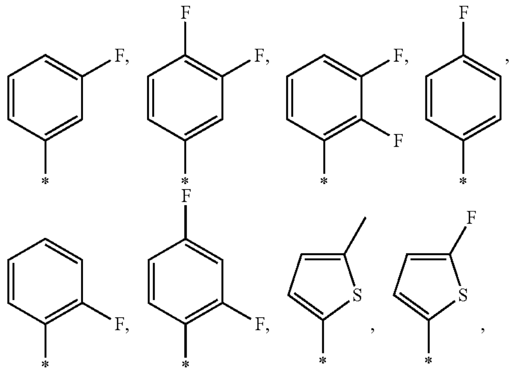

-continued

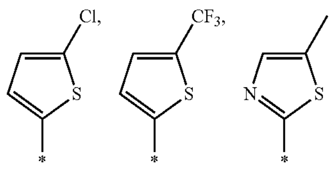

and

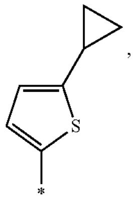

,

In a further embodiment of the present invention $R^1$ is selected from the group $R^{1e}$ consisting of

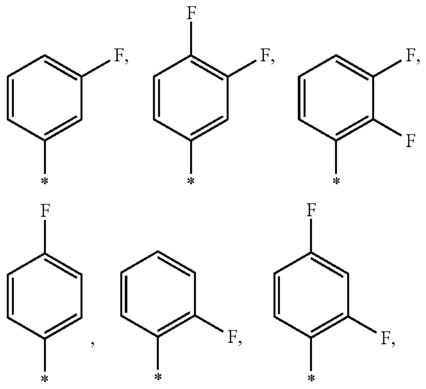

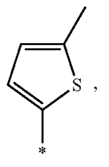

,

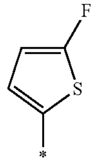

and

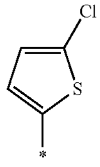

.

In a further embodiment of the present invention $R^1$ is selected from the group $R^{1e'}$ consisting of

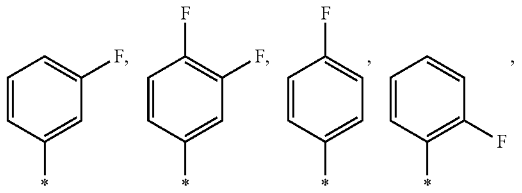

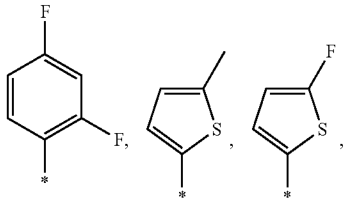

and

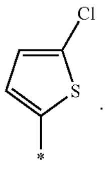

.

In a further embodiment of the present invention $R^1$ is selected from the group $R^{1f}$ consisting of

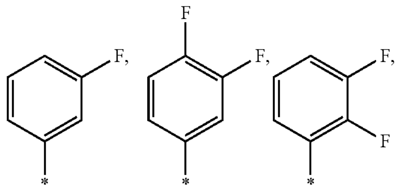

-continued

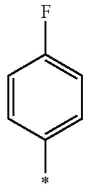 and 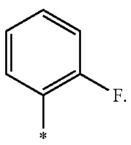

In a further embodiment of the present invention $R^1$ is selected from the group $R^{1g}$ consisting of

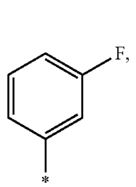, 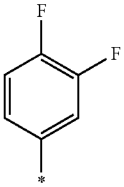, 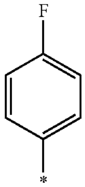 and 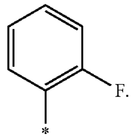

In a further embodiment of the present invention $R^3$ is selected from the group $R^{3b}$ consisting of F, Cl, $—CH_3$, $—CH_2CH_3$ or cyclopropyl, wherein the $—CH_3$, $—CH_2CH_3$ and the cyclopropyl is optionally substituted with one or more halogens selected from F or Cl.

In a further embodiment of the present invention $R^3$ is selected from the group $R^{1c}$ consisting of F, Cl, $—CH_3$, $—CF_3$ and cyclopropyl.

In a further embodiment of the present invention $R^2$ is selected from the group $R^{2b}$ consisting of naphthyl,

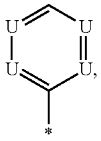, 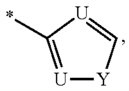, 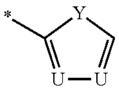 and 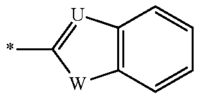

wherein U is independently from each other N or CH with the proviso that the ring system bears a maximum of three N-atoms, Y is O or S, W is O, S or NH and wherein the above mentioned ring systems are optionally substituted with one or more $R^4$, preferably with one or two $R^4$.

In a further embodiment of the present invention $R^2$ is selected from the group $R^{2c}$ consisting of

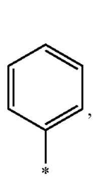, 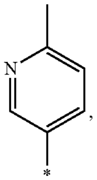, 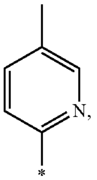, 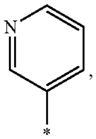,

-continued

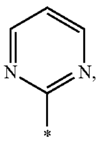, 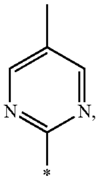, 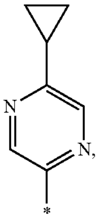, 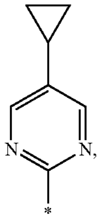,

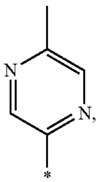, 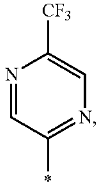, 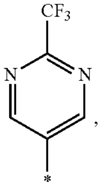, 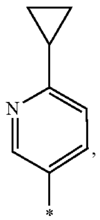,

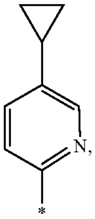, 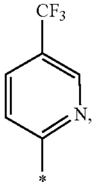, 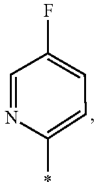, 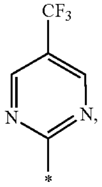,

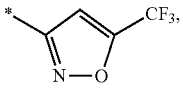, 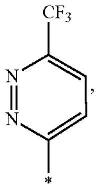, 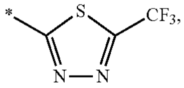,

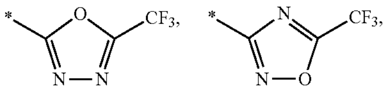,

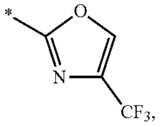, 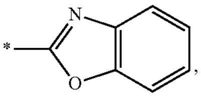,

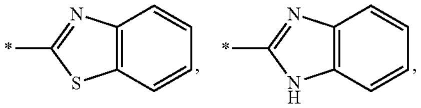,

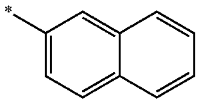 and 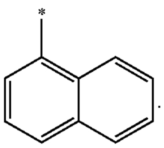.

In a further embodiment of the present invention $R^2$ is selected from the group $R^{2d}$ consisting of

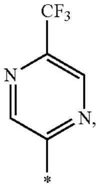, 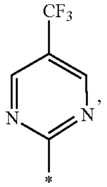, 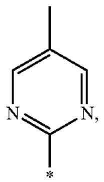, 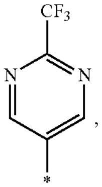,

-continued

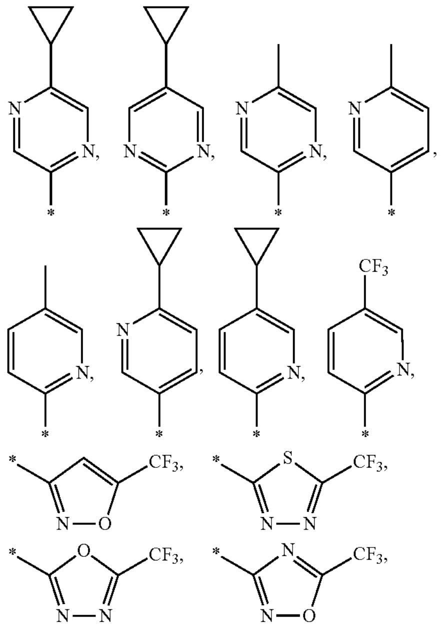

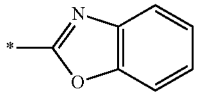

and

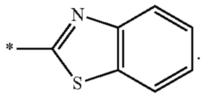

In a further embodiment of the present invention $R^2$ is selected from the group $R^{2e}$ consisting of

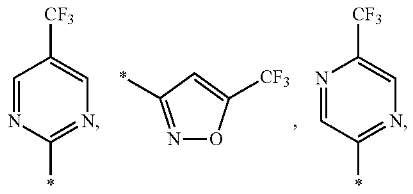

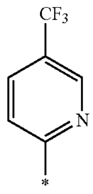

and

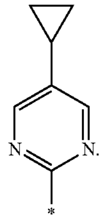

In a further embodiment of the present invention $R^2$ is selected from the group $R^{2f}$ consisting of

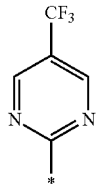

and

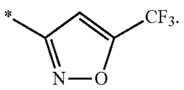

In a further embodiment of the present invention $R^4$ is selected from the group $R^{4b}$ consisting of F, Cl, Br, —CN, —$CH_3$, —$CH_2CH_3$ or cyclopropyl, wherein the —$CH_3$, —$CH_2CH_3$ and the cyclopropyl is optionally substituted with one or more halogens selected from F or Cl.

In a further embodiment of the present invention $R^4$ is selected from the group $R^{4c}$ consisting of F, Cl, —CN, —$CH_3$, —$CF_3$ and cyclopropyl.

In a further aspect the present invention relates to compounds or salts thereof according to the structure of formula (II):

(II)

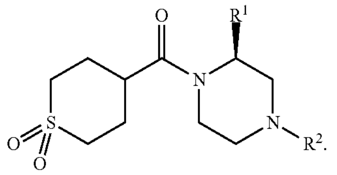

In a further aspect the present invention relates to compounds or salts thereof according to the structure of formula (III):

(III)

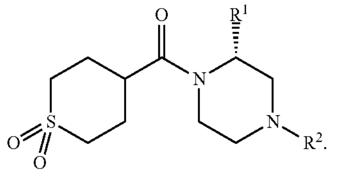

Each $R^{1x}$, $R^{2x}$, $R^{3x}$ and $R^{4x}$ represents a characterized, individual embodiment for the corresponding substituent as described above. Thus given the above definitions, preferred individual embodiments of the first aspect of the invention are fully characterized by the term ($R^{1x}$, $R^{2x}$, $R^{3x}$ and $R^{4x}$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows, exemplarily and in the order of increasing preference from the first line to the last line, such embodiments E-1 to E-18 of the invention that are considered preferred. This means that embodiment E-18, represented by the entries in the last row of Table 1, is the most preferred embodiment.

TABLE 1

Preferred embodiments E-1 to E-18 of the invention

| | $R^1$ | $R^2$ | $R^3$ | $R^4$ |
|---|---|---|---|---|
| E-1 | $R^{1a}$ | $R^{2a}$ | $R^{3a}$ | $R^{4a}$ |
| E-2' | $R^{1b'}$ | $R^{2a}$ | $R^{3a}$ | $R^{4a}$ |
| E-2 | $R^{1b}$ | $R^{2a}$ | $R^{3a}$ | $R^{4a}$ |
| E-3 | $R^{1a}$ | $R^{2b}$ | $R^{3a}$ | $R^{4a}$ |
| E-4 | $R^{1c}$ | $R^{2a}$ | $R^{3a}$ | $R^{4a}$ |
| E-5 | $R^{1b}$ | $R^{2b}$ | $R^{3a}$ | $R^{4a}$ |
| E-6 | $R^{1c}$ | $R^{2b}$ | $R^{3a}$ | $R^{4a}$ |
| E-7 | $R^{1c}$ | $R^{2b}$ | $R^{3b}$ | $R^{4b}$ |
| E-8 | $R^{1c}$ | $R^{2b}$ | $R^{3c}$ | $R^{4c}$ |
| E-9 | $R^{1c}$ | $R^{2c}$ | $R^{3c}$ | — |
| E-10 | $R^{1d}$ | $R^{2b}$ | — | $R^{4c}$ |
| E-11 | $R^{1d}$ | $R^{2c}$ | — | — |

TABLE 1-continued

| Preferred embodiments E-1 to E-18 of the invention | | | | |
|---|---|---|---|---|
| | $R^1$ | $R^2$ | $R^3$ | $R^4$ |
| E-12 | $R^{1d}$ | $R^{2d}$ | — | — |
| E-13 | $R^{1d}$ | $R^{2e}$ | — | — |
| E-14 | $R^{1e}$ | $R^{2e}$ | — | — |
| E-14' | $R^{1e'}$ | $R^{2e}$ | — | — |
| E-15 | $R^{1f}$ | $R^{2c}$ | — | — |
| E-15' | $R^{1g}$ | $R^{2c}$ | — | — |
| E-16 | $R^{1f}$ | $R^{2d}$ | — | — |
| E-16' | $R^{1g}$ | $R^{2d}$ | — | — |
| E-17 | $R^{1f}$ | $R^{2e}$ | — | — |
| E-17' | $R^{1g}$ | $R^{2e}$ | — | — |
| E-18 | $R^{1f}$ | $R^{2f}$ | — | — |
| E-18' | $R^{1g}$ | $R^{2f}$ | — | — |

and the tautomers thereof, the stereoisomers thereof, the mixtures thereof, and the salts thereof.

Accordingly, for example E-10 covers compounds of formula I, wherein $R^1$ is selected from the group consisting of

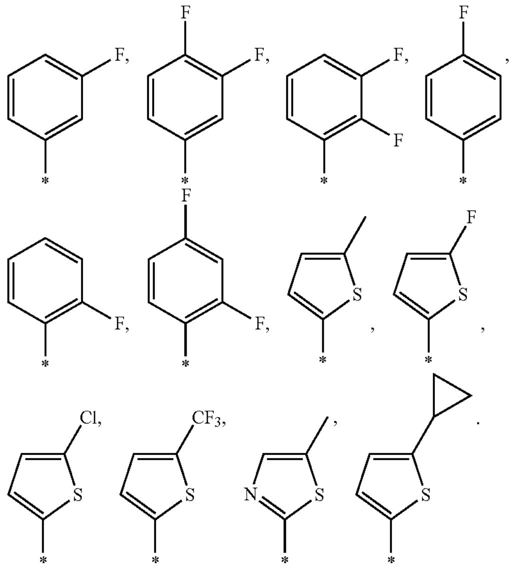

$R^2$ is selected from the group consisting of naphthyl,

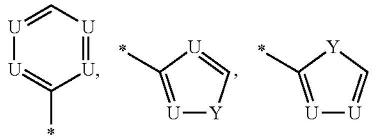

and

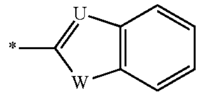

wherein U is independently from each other N or CH with the proviso that the ring system bears a maximum of three N-atoms, Y is O or S, W is O, S or NH and wherein the above mentioned ring systems are optionally substituted with one or more $R^4$ and wherein $R^4$ is selected from the group consisting of F, Cl, —CN, —$CH_3$, —$CF_3$ and cyclopropyl.

Terms And Definitions Used

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, the latter of which is bound to the core or to the group to which the substituent is attached.

An asterisk may be used in sub-formulas to indicate the bond which is connected to the core molecule as defined.

Stereochemistry/Solvates/Hydrates:

Unless specifically indicated (e.g. by stereochemical designators, perspective drawings, etc.), throughout the specification and the appended claims, a given chemical structure, formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and sovates thereof such as for instance hydrates including solvates of the free compounds or solvates of a salt of the compound.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Cycloalkyl:

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Halogen:

The term halogen generally denotes fluorine, chlorine, bromine and iodine.

Heteroaryl:

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

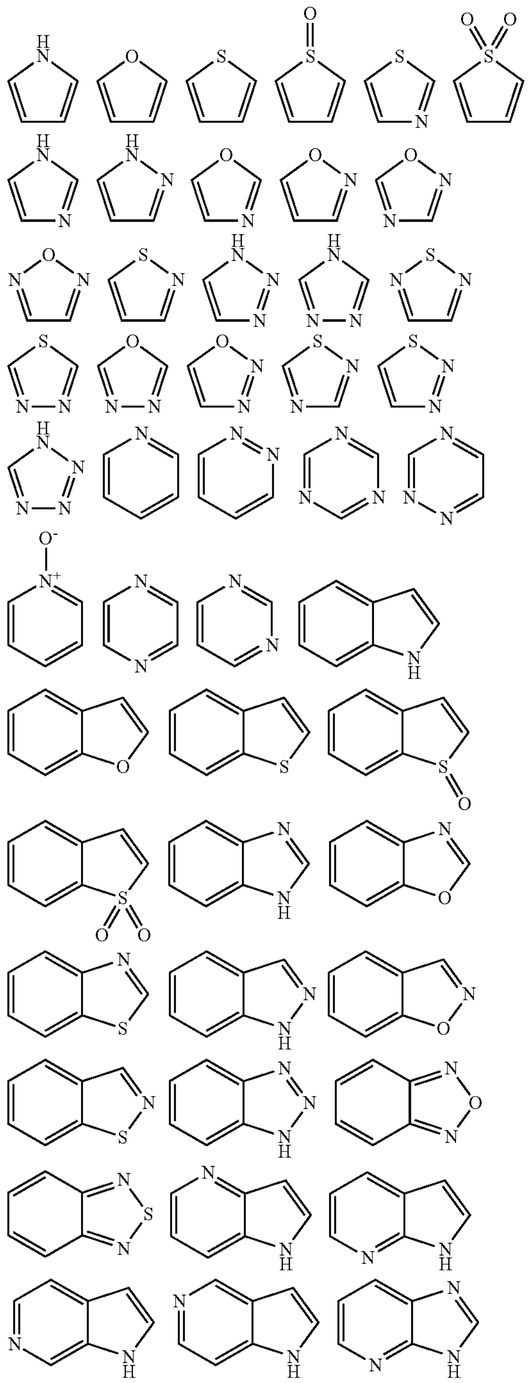

-continued

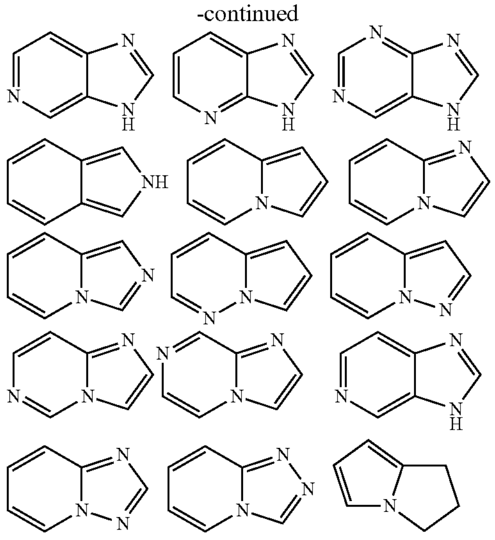

Many of the terms given above may be used repeatedly in the definition of a formula or group and in each case have one of the meanings given above, independently of one another.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The compounds according to the invention may be obtained using methods of synthesis known in principle. Preferably, the compounds are obtained by the following methods according to the invention which are described in more detail hereinafter.

Preparation

The following schemes shall illustrate generally how to manufacture the compounds according to general formula (I) and the corresponding intermediate compounds by way of example. The abbreviated substituents may be as defined above if not defined otherwise within the context of the schemes.

Scheme 1

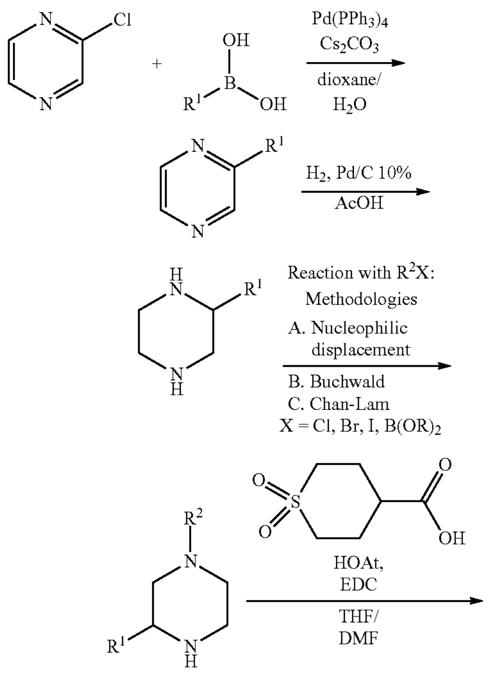

-continued

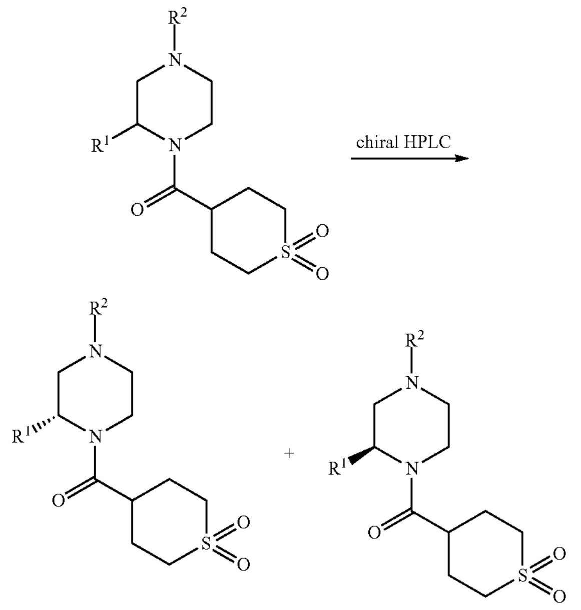

Scheme 1: In a first step a Suzuki cross coupling reaction, starting from commercially available 2-Chloro-pyrazine and the desired Boron derivative, is performed (cfr. Saito R., Tokita M., Uda K., *Tetrahedron,* 2009, 3019-3026); the following hydrogenation step allows to obtain the piperazine derivative bearing a substituent at position 2 ($R^1$) (cfr. Blythin D., Chen X., Piwinski J. J., et al., *Bioorg. Med. Chem. Lett.,* 2002, 3161-3165). The substituent $R^2$ is then introduced via an arylation procedure (cfr. Huang X., Buchwald S. L. Et al., *J. Am. Chem. Soc.,* 2003, 6653-6655. Scanio M., Shi L. et al., *J. Med. Chem,* 2011, 7678-7692. Charles M., Schultz P., Buchwald S. L., Org. Lett., 2005, 3965-3968. Chan D. M. T., Monaco K. L. et al., *Tetr. Lett.*, 1998, 2933-2936. Chan D. M. T., Lam. P. Y. S. et al, *Tetr. Lett.,* 2003, 3863-3866.) and the final amide coupling allows to obtain the final compounds as racemic mixtures. The single enantiomers can be obtained after separation of the corresponding racemic mixtures by HPLC employing a chiral stationary phase.

Scheme 2

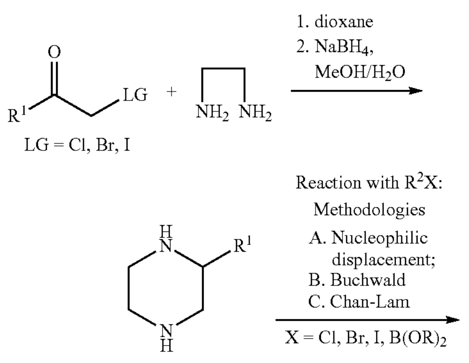

-continued

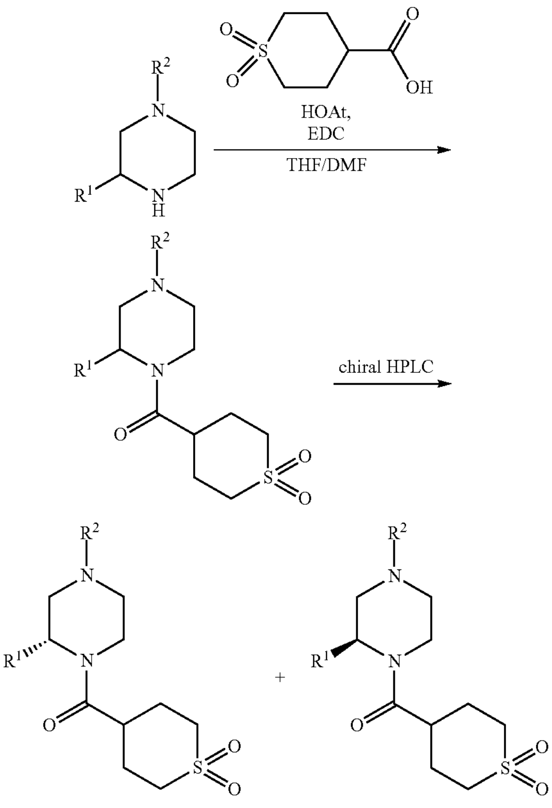

Scheme 2: in the first step the α-haloketone is reacted with Ethane-1,2-diamine to provide after treatment with a reducing agent such as sodiumboronhydride the piperazine derivative substituted at position 2 ($R^1$) (cfr. Jirkovsky I., Santroch G. et al, *J. Med. Chem.*, 1987, 388-394). The substituent $R^2$ is introduced via an arylation procedure and the final amide coupling allows to obtain the final compounds as racemic mixtures.

The single enantiomers can be obtained after separation of the corresponding racemic mixtures by HPLC employing a chiral stationary phase.

Scheme 3

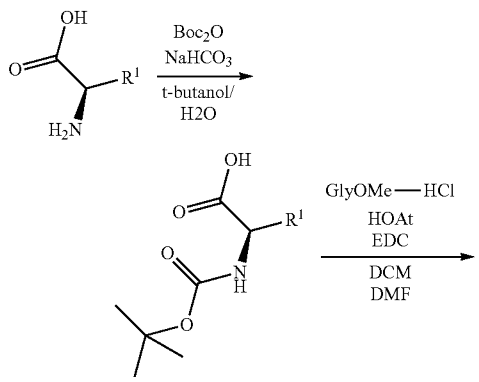

-continued

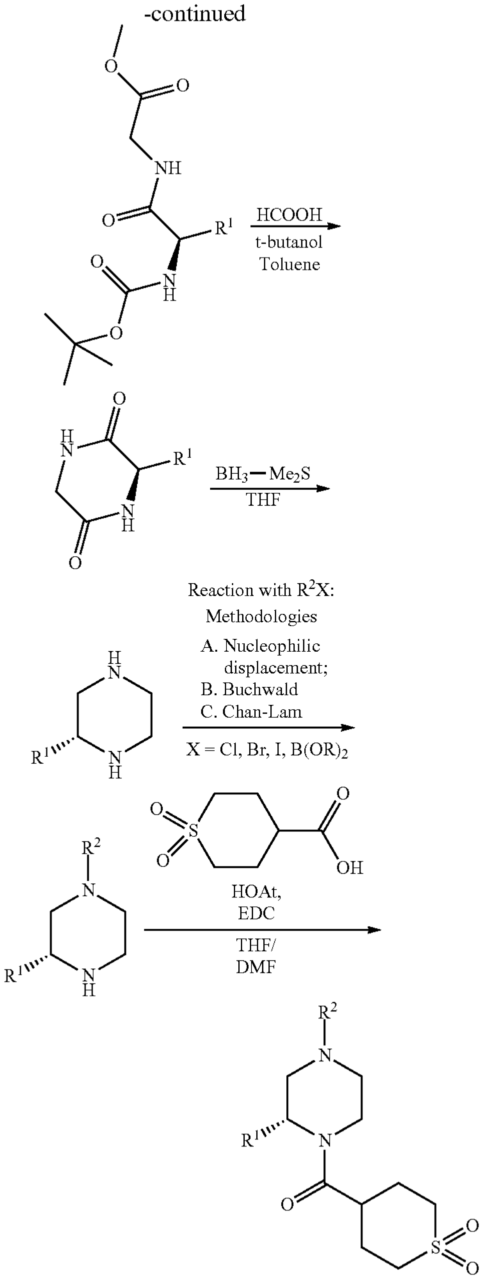

Scheme 3: in the first step the enantiomerically pure glycine derivative undergoes a protection step; then an amide formation takes place followed by the ring closure performed under acidic conditions. The di-ketopiperazine derivative is then reduced with borane to afford the enantiomerically pure piperazine derivative bearing the desired substituent at position 2 ($R^1$). The substituent $R^2$ is introduced via an arylation procedure and the amide coupling allows to obtain the final compounds. This route allows to obtain the final compounds with known absolute configuration (cfr. M. Barfield, F. A. Al-Obeidi, V. J. Hruby and S. R. Walter, *J. Am. Chem. Soc.*, 1982, 104, 3302-3306 and D. E. Nitecki, B. Halpern, J. W. Westley, *Journal of Organic Chemistry* 1967, 864).

Scheme 4

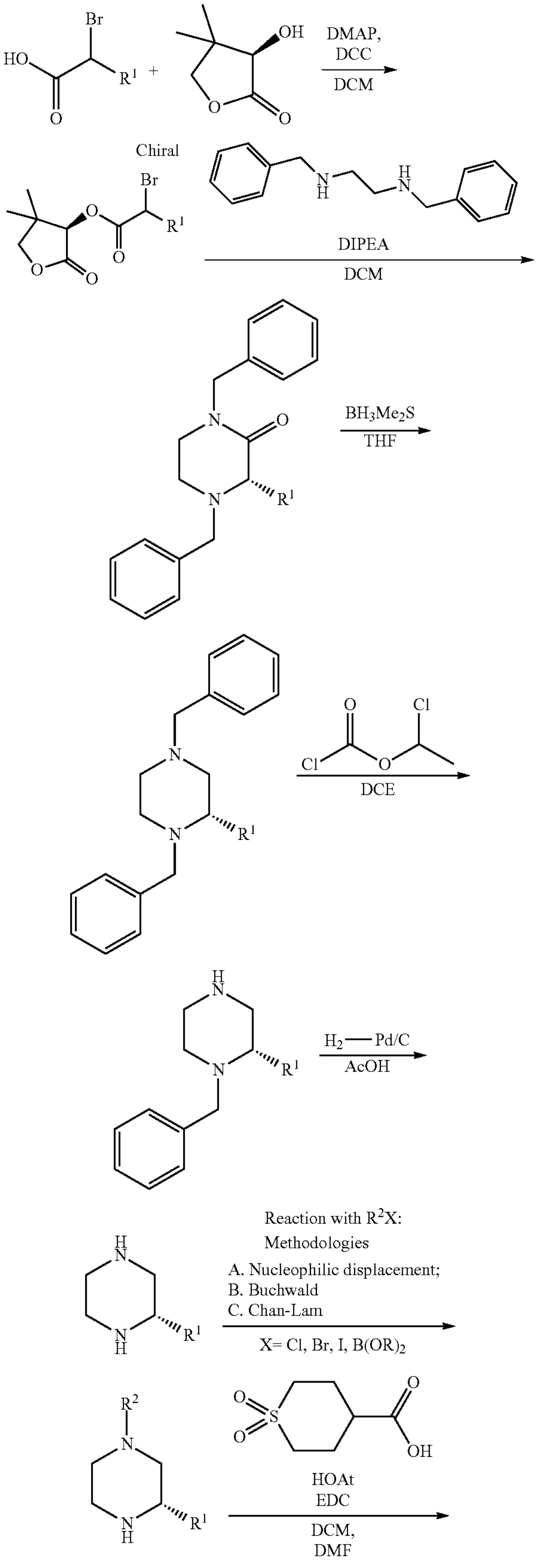

-continued

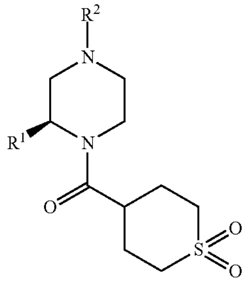

Scheme 4: in the first step the enantiomerically pure (R)-3-Hydroxy-4,4-dimethyl-dihydro-furan-2-one is acylated with a α-halogenated acid derivative; the following step allows to obtain the piperazinone derivative which is then reduced with Borane; the benzyl group is removed in two consecutive steps, the substituent $R^2$ is introduced via an arylation procedure and the amide coupling allows to obtain the final compounds. This route allows to obtain the final compounds with known absolute configuration (cfr. Jung in Jang, Seock Yong Kang, Kyoung Hee Kang, Yong Sun Park, *Tetrahedron,* 2011, 6221-6226).

Scheme 5

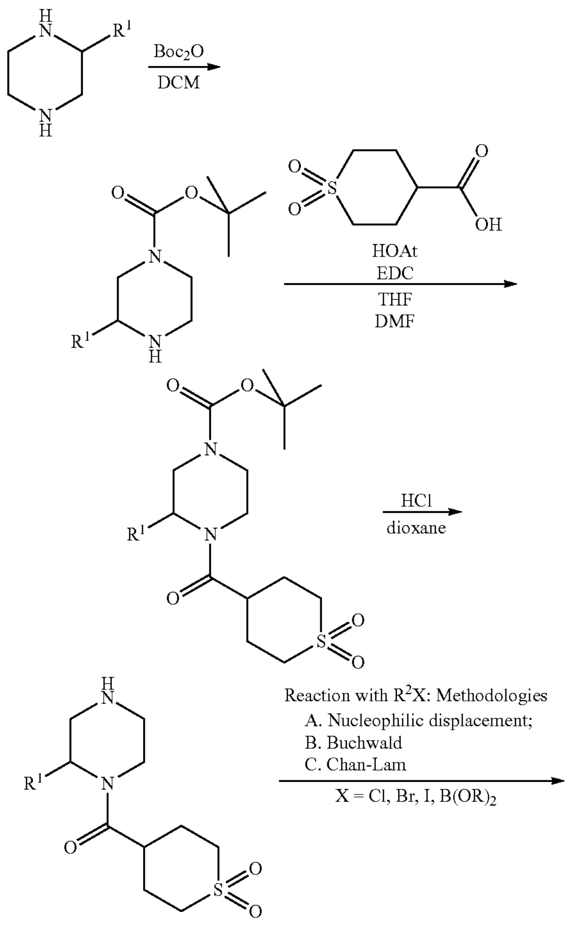

-continued

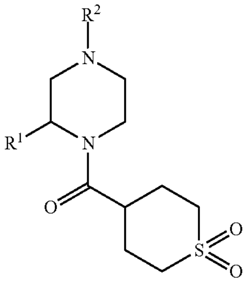

Scheme 5: the piperazine derivatives obtained as described in Scheme 1-3 can undergo a protection step before the formation of the amide derivative; the protecting group is then removed and the final step is characterized by the introduction of $R^2$ substituent applying known literature procedures.

The single enantiomers can be obtained after separation of the corresponding racemic mixtures by HPLC employing a chiral stationary phase.

Scheme 6

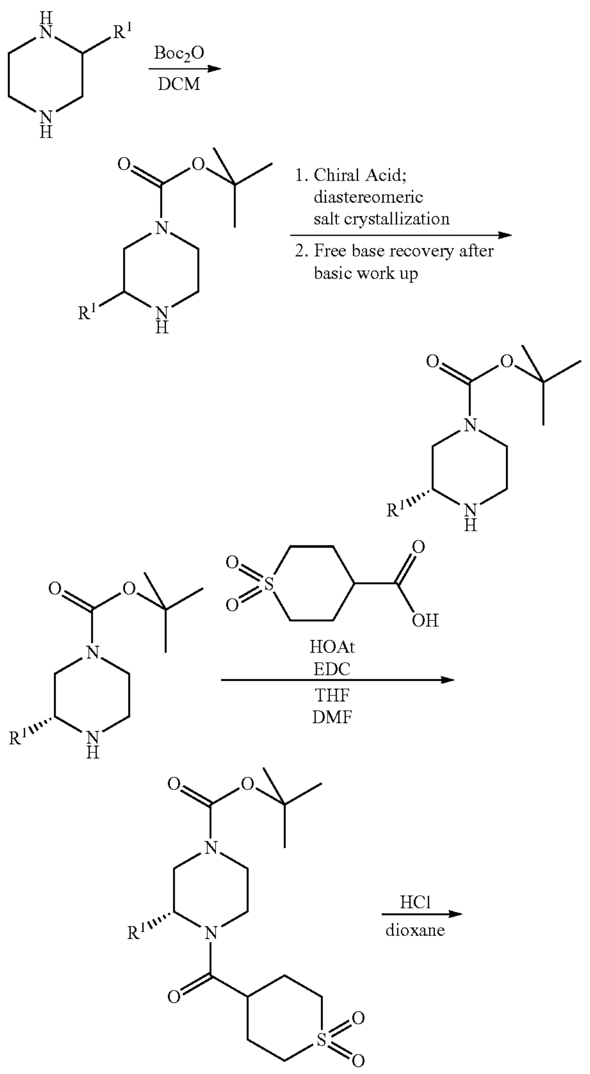

-continued

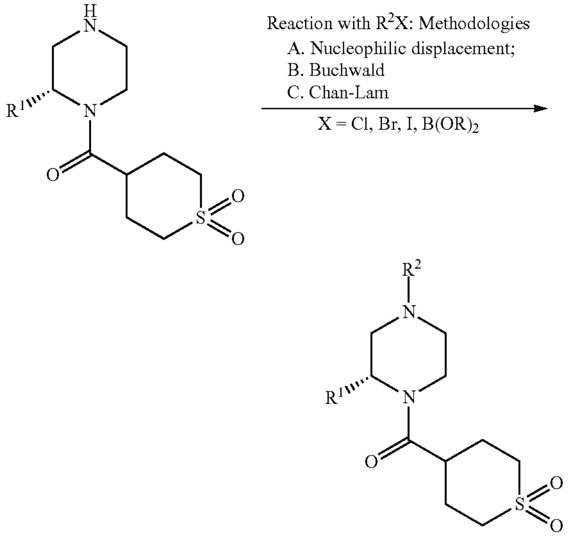

Scheme 6: the piperazine derivatives obtained as described in Schemes 1-3 can undergo, after a protection step, a diastereomeric salt formation reaction after treatment with an enantiomerically pure carboxylic acid; the diastereomeric salt can be crystallized and after a basic work up the enantiomerically pure piperazine derivative is then converted into an amide derivative. The protecting group is removed and the substituent $R^2$ is introduced via an arylation procedure performed according to described literature procedures.

Scheme 7

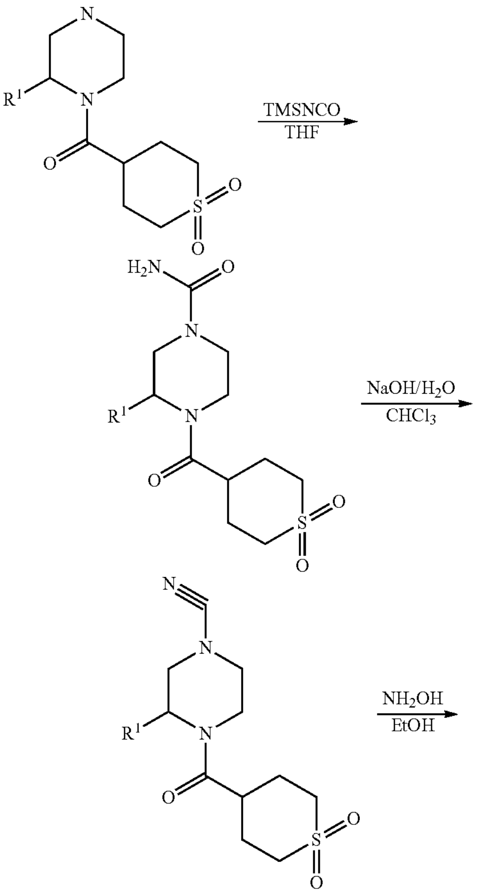

-continued

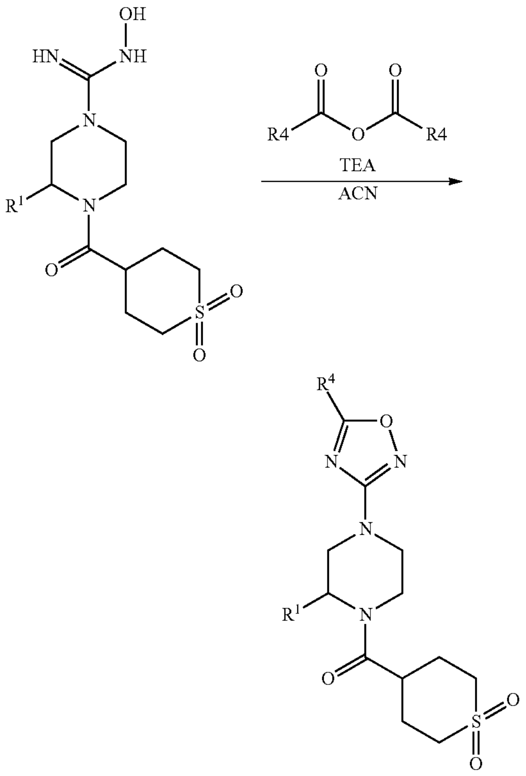

-continued

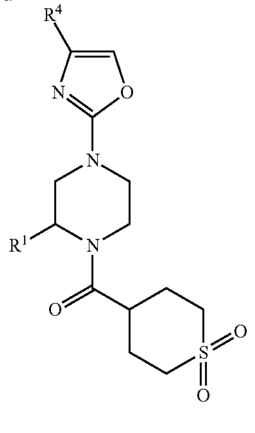

Scheme 8: the intermediate urea, obtained by reaction of the piperazine-amide derivative as described in Scheme 7, undergoes a cyclization reaction with a suitable bromomethyl-ketone to obtain the oxazole derivative.

The single enantiomers can be obtained after separation of the corresponding racemic mixtures by HPLC employing a chiral stationary phase.

Scheme 7: in the first step the piperazine-amide derivative, obtained as described in scheme 5, undergoes a reaction with trimethylsilyl isocyanate to form the intermediate urea; after dehydration by treatment with NaOH and $CHCl_3$, the cyano derivative can undergo a reaction with hydroxylamine and subsequent cyclization with a suitable anhydride to obtain the oxadiazole derivative.

The single enantiomers can be obtained after separation of the corresponding racemic mixtures by HPLC employing a chiral stationary phase.

Scheme 8

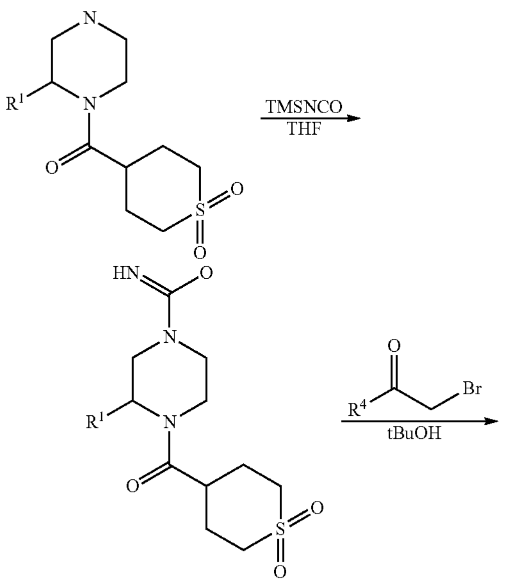

Scheme 9

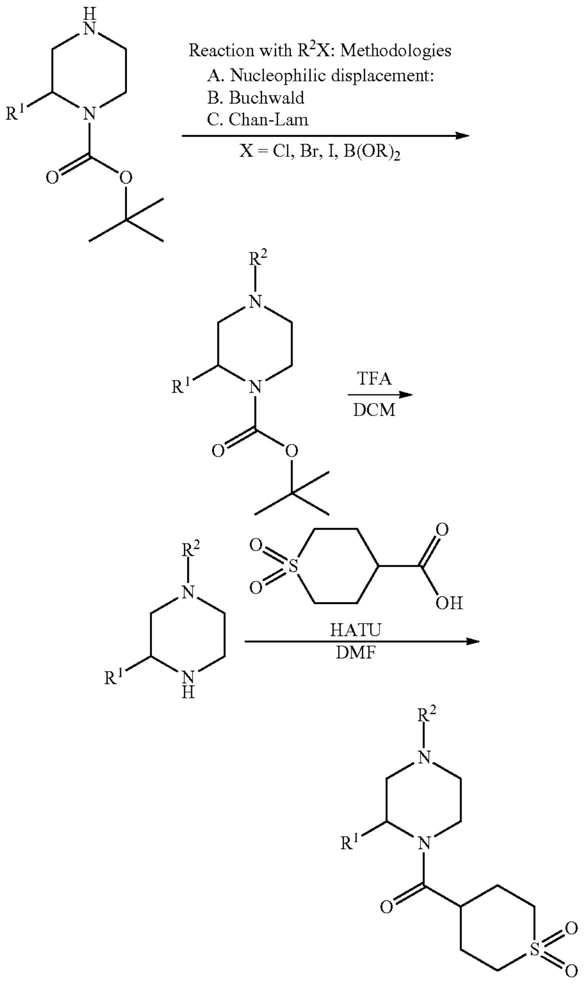

Scheme 9: in the first step the substituent $R^2$ is introduced on the Boc protected piperazine derivative via an arylation procedure then the protecting group is removed and the resulting amine can undergo a reaction with the carboxylic acid to obtain the final product.

The single enantiomers can be obtained after separation of the corresponding racemic mixtures by HPLC employing a chiral stationary phase.

Scheme 10

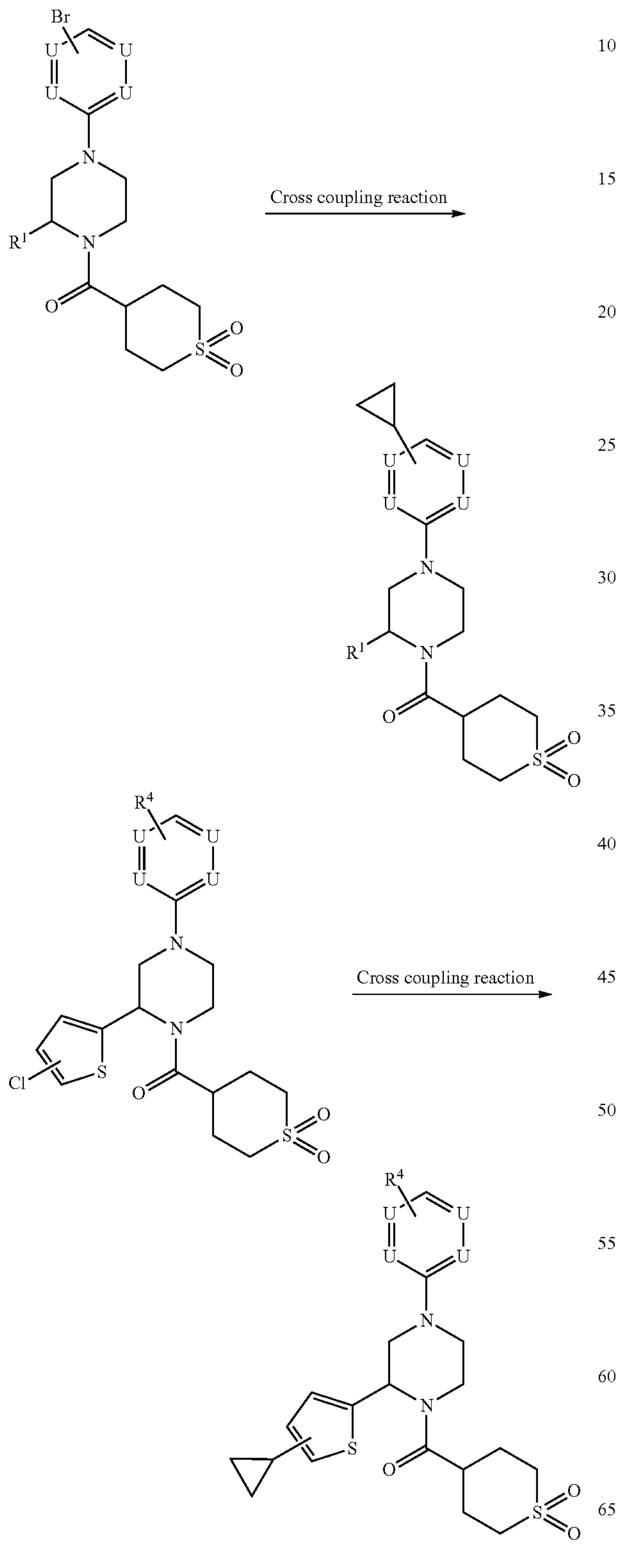

-continued

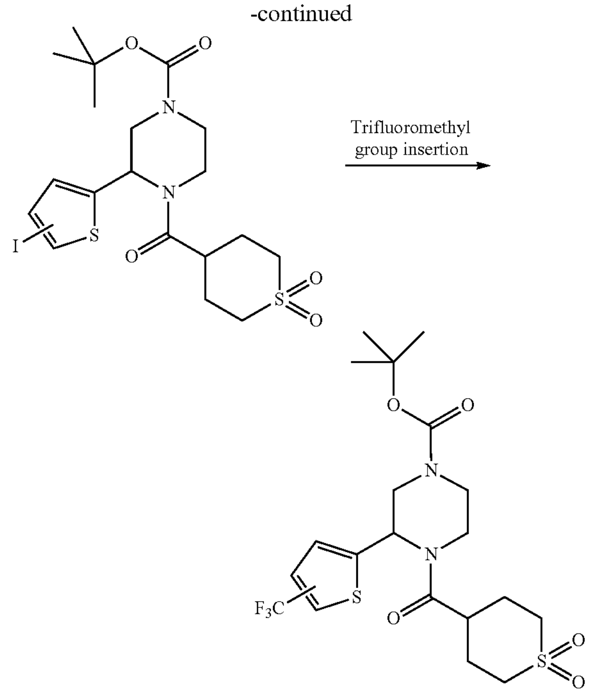

Scheme 10: In case $R^1$ and $R^2$ contain a halogen atom, substitution at $R^1$ and $R^2$ can be achieved using described synthetic methodologies; the insertion of the cyclopropyl ring can be obtained applying the methodology described in: Hasnik Z., Pohl R., Hocek M., *Synthesis,* 2009, 1309-1317; the insertion of the trifluoromethyl group can be achieved applying the methodology described in: Feng-Ling Qing, Junfa Fan, Hong-Bin Sun and Xiang-Jun Yue, *J. Chem. Soc., Perkin Trans.* 1, 1997, 3053-3057.

The compounds according to the invention are advantageously also obtainable using the methods described in the examples that follow, which may also be combined for this purpose with methods known to the skilled man from the literature.

Method of Treatment

The present invention refers to compounds, which are considered effective in the treatment of diseases ("active compounds" according to general formula (I) and specifically the compound family classes and the members thereof). These active compounds according to the invention are effective and selective inhibitors of glycine transporter-1 (GlyT1). Thus, the medicinal concepts discussed above, specifically in the section "Background of the Invention" at the introduction part of this description, are considered of high interest as field of application for the active compounds of the present invention. The active compounds of the present invention can be used for the development of medicaments. Such medicaments shall preferably be used for the treatment of diseases in which the inhibition of GlyT1 can evolve a therapeutic, prophylactic or disease modifying effect. Preferably the medicaments shall be used to treat illnesses such as psychoses, dysfunction in memory and learning, schizophrenia (positive and negative symptoms of schizophrenia and cognitive impairment associated with schizophrenia), dementia like Alzheimer's disease and other diseases in which cognitive processes are impaired, such as attention deficit disorders, Parkinson's disease, epilepsy and/or bipolar disorder.

The medicaments are for use in a method, preferably a therapeutic method, or a method for to improve perception, concentration, cognition, learning or memory, like those occurring in particular in conditions, diseases and/or syndromes such as:

mild cognitive impairment, amnestic mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, mild Alzheimer's disease, mild-to-moderate Alzheimer's disease, moderate-to-severe Alzheimer's disease, prodromal Alzheimer's disease, Lewy body dementia, dementia with degeneration of the frontal lobes, including Picks syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, Korsakoff s psychosis or cognitive impairment associated with schizophrenia, prodromal phase of schizophrenia, major depressive disorder, depression, Parkinson's disease, epilepsy, schizo-affective disorder or bipolar disorder.

Another aspect of the present invention concerns the treatment of a disease which is accessible by GlyT1-inhibition, in particular sleep disorders like insomnia or narcolepsy, bipolar disorder, depression, substance use disorders/abuse disorders, hearing disorders, attention deficit (hyperactive) disorder, inflammatory pain, neuropathic pain, autism spectrum disorders or disorders of impulse control.

Thus the medical aspect of the present invention can be summarized in that it is considered that a compound according to formula (I) as herein defined, in particular the specifically defined species active compounds for use in or as a medicament.

Such a medicament preferably is for a therapeutic or prophylactic, preferably therapeutic method in the treatment of a CNS disease.

In an alternative use, the medicament is for the treatment of a CNS disease, the treatment of which is accessible by the inhibition of GlyT1.

In an alternative use, the medicament is for the treatment of a disease that is accessible by the inhibition of GlyT1.

In an alternative use, the medicament is for the use in a method for the treatment of Alzheimer's disease, schizophrenia (positive and negative symptoms) or cognitive impairment associated with Alzheimer's disease or associated with schizophrenia.

In a further aspect of the invention, the present invention relates to the method of treatment or prevention of a condition or disease selected from the above listed groups of conditions and diseases, wherein the method comprises the administration of a therapeutically effective amount of an active compound according to the invention in a human being in need thereof.

The dose range of an active compound of the present invention applicable per day is usually from 0.1 to 5000 mg, preferably from 0.1 to 1000 mg, preferably from 2 to 500 mg, more preferably from 5 to 250 mg, most preferably from 10 to 100 mg. A dosage unit (e.g. a tablet) preferably may contain between 2 and 250 mg, particularly preferably between 10 and 100 mg of the active compounds according to the invention.

Another aspect of the invention concerns the active compounds of the inventions for use in a therapeutic method or for use as a medicament. If indicated the therapeutic method or the medicament is preferably for the treatment of a condition or a disease selected from the group of conditions or a diseases as outlined above in this section, which is entitled "Method of Treatment".

Pharmaceutical Composition

Suitable preparations for administering the active compounds according to the invention will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 0.05 to 90 wt.-%, preferably 0.1 to 50 wt.-% of the composition as a whole.

Suitable tablets may be obtained, for example, by mixing one or more active compounds according to formula (I) with known excipients, for example inert diluents, carriers, disintegrants, adjuvants, surfactants, binders and/or lubricants. The tablets may also consist of several layers.

EXAMPLES

Examples which might illustrate possible pharmaceutical formulations, without being meant to be limiting:

The term "active substance" denotes one or more active compounds according to the invention including the salts thereof. In the case of one of the aforementioned combinations with one or more other active substances the term "active substance" may also include the additional active substances. Standard procedures should be considered for the preparation of any the herein mentioned pharmaceutical formulations.

| HARD GELATINE CAPSULES | |
|---|---|
| active substance | 150.0 mg |
| lactose | 87.0 mg |
| corn starch (dried) | 80.0 mg |
| magnesium stearate | 3.0 mg |
| | 320.0 mg |

| SUPPOSITORY COMPOSITION | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2000.0 mg |

| TABLETS | | |
|---|---|---|
| active substance | 100.0 mg | 150.0 mg |
| lactose | 80.0 mg | 89.0 mg |
| corn starch | 34.0 mg | 40.0 mg |
| polyvinylpyrrolidone | 4.0 mg | 10.0 mg |
| magnesium stearate | 2.0 mg | 1.0 mg |
| | 220.0 mg | 290.0 mg |

Combination Therapy/Combination with Other Active Substances

In another aspect the present invention relates to a combination therapy in which an active compound according to the present invention is administered together with another active compound. Accordingly, the invention also refers to pharmaceutical formulations that provide such a combination of active ingredients, wherein one of which is an active compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, asenapine and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; anti-oxidants, such as e.g. vitamin E, *ginko biloba* or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists or positive allosteric modulators; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The active compounds according to the invention may also be used in combination with immunotherapies such as e.g. active immunisation with Abeta or parts thereof or passive immunisation with humanised anti-Abeta antibodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride (TOFRANIL), imipramine maleate (SURMONTIL), lofepramine, desipramine (NORPRAMIN), doxepin (SINEQUAN, ZONALON), trimipramine (SURMONTIL).

Or the active compounds according to the invention also may be combined with serotonin (5-HT) reuptake inhibitors such as alaproclate, citalopram (CELEXA, CIPRAMIL) escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited; in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.).

It is preferred that the active compounds of the invention be administered either three or fewer times, more preferably once or twice daily.

Biological Assay

In-Vitro Effect:

The in-vitro effect of the active compounds of the invention can be shown with the following biological assay.

GlyT1 Assay Protocol:

Cells expressing either endogenously the GlyT1 transporter like JAR cells (human placental choriocarcinoma cells; e.g. WO 2008/002583) or SK-N-MC cells (human neuroblastoma cells; Depoortere et al., 2005, Neuropsychopharmacology 30:1963-1985) or primary neurons or cells which have been transfected with a plasmid encoding the cDNA of a functional GlyT1 transporter and stably or transiently express GlyT1 (e.g. WO 2006/08200) can be used to monitor glycine uptake in cells. Different protocols for determination of the glycine uptake into the cells described above can be applied in order to identify and rank compounds which interfere with glycine uptake in the selected cell. Compounds outlined in the examples below were characterized using human SK-N-MC cells (ATCC number HTB-10) endogenously expressing the GlyT1 transporter which is responsible for the uptake of glycine into these cells and the uptake of glycine into these cells is monitored using the Cytostar-T assay format (GE Healthcare, RPNQ0162) which is based on the radioactive glycine taken up by the cells and brought into proximity with the scintillant contained within the base of the plate. The radioactive decay is converted to a light signal based on the integration of the scintillation matrix into the assay plate. The uptake is recorded as kinetic and the slope of the measured counts over time is used to calculate $IC_{50}$.

In detail, SK-N-MC cells are seeded into 96-well Cytostar-T assay plates at a density of 200,000 cells/well and grown for 16-18 hours to confluence in growth medium as recommended by ATCC. Before starting the assay, cells are washed once with HBSS (Hank's buffered salt solution; Sigma, H8264) cont. 5 mM alanine (referred in here as HBSS/Ala) and afterwards the following reagents are added:

1. 80 μl/well HBSS/A1a
2. 20 μl/well of HBSS/A1a containing 6× the concentration of compound in 6% DMSO
3. approx. 5-10 min incubation
4. 20 μl/well 3 μM glycine ($^3$H-glycine (Perkin Elmer, NET004001MC, specific activity: 52 Ci/mmol; diluted 1:1 with unlabelled glycine) in HBSS/A1a.

In the final assay, glycine concentration is 500 nM (250 nM derived from the $^3$H-glycine Perkin Elmer, 250 nM unlabelled glycine), DMSO concentration is 1%.

The assay plate is immediately after addition of the $^3$H-glycine placed into a Micro-Beta Counter (Perkin Elmer) and the signal is recorded over 60 min To calculate uptake, the slope in the linear range of the kinetics is determined using GraphPadPrism and for the different slopes at the selected concentrations $IC_{50}$ are calculated by curve fitting using the software GraphPadPrism.

Maximal glycine uptake in every experiment is determined by incubation of SK-N-MC cells with substrate but without inhibitor. Unspecific uptake of glycine by the cells is determined by incubating the cells with substrate and a reference GlyT1 inhibitor e.g. 10 μM RG-1678 (Pinard et al., 2010, J. Med. Chem. 53(12):4603-14).

Compounds are diluted from 10 mM stocks and in general, for $IC_{50}$ determination 8 compound concentrations are used.

TABLE

| IC50 data | |
|---|---|
| Example number | IC50 [nM] |
| 1 | 4 |
| 2 | 5 |
| 3 | 9620* |
| 4 | 9 |
| 5 | 5 |
| 6 | 175 |
| 7 | 9 |
| 8 | 4 |
| 9 | 680 |
| 10 | 11 |
| 11 | 6 |
| 12 | 180 |
| 13 | 5 |
| 14 | 5 |
| 15 | 2972* |
| 16 | 40 |
| 17 | 35 |
| 18 | 4 |
| 19 | 84 |
| 20 | 133 |
| 21 | 5 |
| 22 | 57 |
| 23 | 56 |
| 24 | 98 |
| 25 | 23 |
| 26 | 11 |
| 27 | 14 |
| 28 | 103 |
| 29 | 20 |
| 30 | 60 |
| 31 | 4 |
| 32 | 4 |
| 33 | 31 |
| 34 | 30 |
| 35 | 9 |
| 36 | 93 |
| 37 | 69 |
| 38 | 16 |
| 39 | 11 |
| 40 | 142 |
| 41 | 62 |
| 42 | 2 |
| 43 | 69 |
| 44 | 101 |
| 45 | 11 |
| 46 | 49 |
| 47 | 60 |
| 48 | 53 |
| 49 | 76 |
| 50 | 8 |
| 51 | 1 |
| 52 | 118 |
| 53 | 73 |
| 54 | 22 |
| 55 | 38 |
| 56 | 183 |
| 57 | 39 |
| 58 | 14 |
| 59 | 17 |
| 60 | 6 |
| 61 | 112 |
| 62 | 25 |
| 63 | 202 |
| 64 | 27 |
| 65 | 19 |
| 66 | 21 |
| 67 | 255 |
| 68 | 22 |
| 69 | 257 |
| 70 | 53 |
| 71 | 4 |
| 72 | 47 |
| 73 | 13 |
| 74 | 4 |
| 75 | 157 |
| 76 | 3 |

TABLE-continued

| IC50 data | |
|---|---|
| Example number | IC50 [nM] |
| 77 | 6 |
| 78 | 333 |
| 79 | 6 |
| 80 | 53 |
| 81 | 8 |
| 82 | 9 |
| 83 | 27 |
| 84 | 19 |
| 85 | 60 |
| 86 | 46 |
| 87 | 10 |
| 88 | 48 |
| 89 | 14 |
| 90 | 30 |
| 91 | 41 |
| 92 | 9 |
| 93 | 8 |
| 94 | 6 |
| 95 | 40 |
| 96 | 3 |
| 97 | 4 |
| 98 | 7 |
| 99 | 3 |
| 100 | 7 |
| 101 | 6 |
| 102 | 3 |
| 103 | 87 |
| 104 | 18 |
| 105 | 24 |
| 106 | 8 |
| 107 | 12 |
| 108 | 37 |
| 109 | 18 |
| 110 | 40 |
| 111 | 7 |
| 112 | 242 |
| 113 | 9 |
| 114 | 10 |
| 115 | 153 |
| 116 | 125 |
| 117 | 7 |
| 118 | 32 |
| 119 | 180 |
| 120 | 38 |
| 121 | 1 |
| 122 | 3 |
| 123 | 6 |
| 124 | 10 |
| 125 | 15 |
| 126 | 15 |
| 127 | 17 |
| 128 | 17 |
| 129 | 20 |
| 130 | 20 |
| 131 | 21 |
| 132 | 31 |
| 133 | 32 |
| 134 | 34 |
| 135 | 34 |
| 136 | 35 |
| 137 | 44 |
| 138 | 49 |
| 139 | 134 |
| 140 | 166 |
| 141 | 252 |
| 142 | 266 |
| 143 | 292 |
| 144 | 306 |
| 145 | 527 |
| 146 | 556 |
| 147 | 607 |
| 148 | 1 |
| 149 | 83 |
| 150 | 4 |
| 151 | 141 |
| 152 | 59 |

TABLE-continued

| IC50 data | |
|---|---|
| Example number | IC50 [nM] |
| 153 | 221 |
| 154 | 124 |
| 155 | 87 |
| 156 | 451 |
| 157 | 9 |
| 158 | 6 |
| 159 | 8 |
| 160 | 21 |
| 161 | 36 |

*The low solubility of the compound might have an impact on the determination of the IC50 values.

Compounds with an IC50 value of between 1 and 1000 nM are preferred, more preferred are active compounds with an IC50 value of between 1 and 100 nM, more preferred are compounds with an IC50 value of between 1 and 20 nM.

In-Vivo Effect:

It is believed that the positive in-vitro efficacy results of the active compounds of the present invention translate in positive in-vivo efficacy.

The in-vivo effect of the active compounds of this invention can be tested regarding glycine increase in CSF according to Perry et al. 2008 (Neuropharmacology 55:743-754), in the psychostimulant-induced hyperlocomotion test according to Boulay et al. 2008 (Pharmacol. Biochem. Behav. 91:47-58) or the social recognition test according to Shimazaki et al. 2010 (Psychopharmacology 209: 263-270). For further information concerning biological testing, it is also referred to these three citations.

Besides the inhibition property toward the target GlyT1 transporter, active compounds according to the present invention may provide further advantageous pharmacokinetic properties.

E.g. active compounds according to the invention may show one or more advantages in the area of safety, low risk of causing drug-drug interaction and low clearance.

Active compounds according to the invention also might show one or more additional or alternative advantages in the area of bioavailability, high fraction absorbed, blood brain transport properties, a favourable (e.g. high mean) mean residence time (mrt), favourable exposure in the effect compartment (Cerebrospinal fluid).

On the basis of the above mentioned features, active compounds according to the invention are believed to be suited for once daily administration for the treatment of diseases where an adequate exposure in the cerobrospinal fluid is considered to be essential.

Chemical Manufacture

Abbreviations

Ac Acetyl
ACN acetonitrile
APCI Atmospheric pressure chemical ionization (in MS)
amu atomic mass unit
Boc ter-butyloxycarbonyl
Burgess reagent: methoxycarbonylsulfamoyl-triethyl ammonium hydroxide inner salt
CDI 1,1'-carbonyldiimidazole
d day
dba dibenzylideneacetone
DCM dichloromethane
DIPEA diisopropylethylamine
DME 1,2-dimethoxyethane
DMF dimethylformamide
ESI electrospray ionization (in MS)

EtOAc ethylacetate
EtOH ethanol
$Et_2O$ diethylether
Exp. example
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
IPA isopropyl alcohol
M molar (mol/L)
MeOH methanol
min minute(s)
MS mass spectrometry
NMP 1-methyl-2-pyrrolidinone
RP reverse Phase
rt room temperature
$R_t$ retention time (in HPLC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography-mass spectrometry Methods:

UPLC-MS Methods:

Method 1

Instrument: LC/MS Waters Acquity UPLC System DAD, SQD single quadrupole; column: HSS C18 1.8 μm 2.1×50 mm, Temp 35° C.; mobile phase: A=$H_2O$ 90%+10% $CH_3CN$+$CF_3COOH$ 0.1%, B=$CH_3CN$ 90%+$H_2O$ 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ES+/ES−; scan range: 90-900 amu Method 2

Instrument: LC/MS Waters Acquity UPLC System DAD, SQD single quadrupole; column: BEH C18 1.7 μm 2.1×50 mm, Temp 35° C.; mobile phase: A=$H_2O$ 90%+10% $CH_3CN$+$NH_4COOH$ 5 mmol, B=$CH_3CN$ 90%+$H_2O$ 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ES+/ES−; scan range: 90-900 amu Method 23

Instrument: LC/MS Waters Acquity UPLC System DAD, SQD single quadrupole; column: BEH C18 1.7 μm 2.1×50 mm, Temp 35° C.; mobile phase: A=$H_2O$ 90%+10% $CH_3CN$+$NH_4COOH$ 5 mmol, B=$CH_3CN$ 90%+$H_2O$ 10%; gradient: 0.0 min 0% B→2.40 min 100% B→2.70 min 100% B→2.80 min 0% B→3.00 min 0% B; flow rate: 0.70 mL/min; detection: UV 254 nm; detection: SQD, single quadrupole; ion source: ES+/ES−; scan range: 90-900 amu GC-MS Methods:

Method 3

Instrument: GC/MS Thermo Scientific TRACE GC ULTRA, DSQ II MS single quadrupole; column: Agilent DB-5MS, 25 m×0.2 5 mmol×0.25 μm; carrier gas: Helium, 1 mL/min constant flow; oven program: 50° C., to 100° C. in 10° C./min, to 200° C. in 20° C./min, to 320° C. in 30° C./min (hold 10 min); detection: DSQ II MS single quadrupole; ion source: EI; scan range: 50-450 amu HPLC-MS Methods:

Method 4

Instrument: LC/MS ThermoFinnigan. Hplc Surveyor DAD, MSQ Quadrupole; column: Synergi Hydro RP100A, 2.5 μm, 3×50 mm; eluent A: 90% water+10% ACN+ammonium formate 10 mM; eluent B=ACN 90%+10% $H_2O$+$NH_4COOH$ 10 mM; gradient: 0.0 min 0% B→1.50 min 0% B→8.00 min 100% B→10.00 min 100% B→11.00 min 0% B→12.00 min 0% B; flow rate: 0.7 mL/min; UV Detection: 254 nm; Ion source: APCI+/APCI−

Method 5

Instrument: LC/MS ThermoFinnigan HPLC Surveyor DAD, MSQ single quadrupole; Column: Synergi Hydro RP100A, 2.5 μm, 3×50 mm; Eluent A: 90% water+10% ACN+NH4COOH 5 Mm; eluent B=ACN 90%+10% H2O; gradient: 0.0 min 0% B→4 min 100% B→5.30 min 100% B→5.50 min 0% B→6.00 min 0% B; flow rate: 1.2 mL/min; UV Detection: 254 nm; Ion source: APCI+/APCI−; scan range 100-900 amu Method 6

Instrument: LC/MS ThermoFinnigan HPLC Surveyor DAD, LCQFleet Ion Trap Column: Symmetry Shield RPB, 5 μm, 4.6×150 mm; Eluent A: 90% water+10% ACN+HCOOH 0.1%; eluent B: ACN 90%+$H_2O$ 10%+HCOOH 0.1%; gradient: 0.0 min 5% B→1.5 min 5% B→11.05 min 95% B→13 min 95% B→13.03 min 5% B→1.5 min 5% B; flow rate: 1.0 mL/min; UV Detection: 254 nm, Finnigan Fleet, Ion Trap; Ion source: ES+; scan range 100-900 amu Method 10

Instrument: LC/MS ThermoFinnigan HPLC Surveyor DAD, LCQFleet Ion Trap Column: Synergy Xselect CSH, 2.5 μm, 4.6×50 mm; Eluent A: 90% water+10% ACN+HCOOH 0.1%; eluent B: ACN 90%+$H_2O$ 10%+HCOOH 0.1%; gradient: 0.0 min 0% B→4 min 100% B→5.30 min 100% B→5.50 min 0% B→6.00 min 0% B; flow rate: 1.4 mL/min; UV Detection: 254 nm, Finnigan Fleet, Ion Trap; Ion source: ES+; scan range 100-900 amu Method 7

Instrument: LC/MS Waters Alliance 2695 HPLC System DAD, Quattro Micro Triple quadrupole; Column: Xbridge Phenyl 3.5 μm 3×30 mm, Temp 35° C.; Eluent A: 90% water+10% ACN+$NH_4HCO_3$ 5 min; eluent B: ACN 90%+$H_2O$ 10%; gradient: min 0% B→4.5 min 100% B→5.80 min 100% B→6.0 min 0% B; flow rate: 1.3 mL/min; UV Detection: 254 nm, Quattro Micro, triple quadrupole, Ion source: ES+/−; scan range 90-1000 amu.

Method 8

Instrument: LC/MS Waters Alliance 2695 HPLC System DAD, Quattro Micro Triple quadrupole; Column: Gemini 3 μm 4.6×50 mm, Temp 35° C.; Eluent A: 90% water+10% ACN+$CF_3COOH$ 0.1%; eluent B: ACN gradient: 0.0 min 0% B→3.5 min 90% B→4.5 min 90% B→4.6 min 0% B; flow rate: 1.3 mL/min; UV Detection: 254 nm, Quattro Micro, triple quadrupole, Ion source: ES+/−; scan range 120-900 amu Method 11

Instrument: LC/MS Waters Alliance 2695 HPLC System DAD, Quattro Micro Triple quadrupole; Column: SunFire C18 3.5 μm 4.6×50 mm, Temp 35° C.; Eluent A: 90% water+10% ACN+$CF_3COOH$ 0.05%; eluent B: 90% ACN+10% water gradient: 0.0 min 0% B→4.5 min 100% B→5.8 min 100% B→6.0 min 0% B; flow rate: 1.3 mL/min; UV Detection: 254 nm, Quattro Micro, triple quadrupole, Ion source: ES+/−; scan range 90-1000 amu.

Method 14

Instrument: LC/MS ThermoFinnigan HPLC Surveyor DAD, MSQ single quadrupole; Column: Synergi Hydro RP100A, 2.5 μm, 3×50 mm; Eluent A: 90% water+10% ACN+NH4COOH 5 Mm; eluent B=ACN 90%+10% H2O;

gradient: 0.0 min 0% B→1.50 min 0% B→9 min 100% B→10.50 min 100% B→11 min 0% B→12 min 0% B; flow rate: 1.2 mL/min; UV Detection: 254 nm; Ion source: APCI+/APCI−; scan range 100-900 amu.

Method 16

Instrument: LC/MS Waters Alliance 2695 HPLC System DAD, Quattro Micro Triple quadrupole; Column: Atlantis dC18 5 μm 4.6×50 mm, Temp 35° C.; Eluent A: 90% water+10% ACN+$CF_3COOH$ 0.05%; eluent B: 90% ACN+10% water gradient: 0.0 min 0% B→0.7 min 0% B→4.5 min 100% B→5.8 min 100% B→6.0 min 0% B; flow rate: 1.3 mL/min; UV Detection: 254 nm, Quattro Micro, triple quadrupole, Ion source: ES+/−; scan range 90-1000 amu.

Method 17

Instrument: LC/MS Waters Alliance 2695 HPLC System DAD, Quattro Micro Triple quadrupole; Column: zorbax Eclipse XDB-C18 3.5 μm 4.6×50 mm, Temp 35° C. Eluent A: 90% water+10% ACN+$NH_4COOH$ 5 nM; eluent B: 90% ACN+10% water gradient: 0.0 min 0% B→4.50 min 100% B→5.8 min 100% B→6.0 min 0% B; flow rate: 1.3 mL/min; UV Detection: 254 nm, Quattro Micro, triple quadrupole, Ion source: ES+/−; scan range 90-1000 amu.

Method 18

Instrument: LC/MS Waters 1525 with DA- and MS-Detector, Column: Sunfire C18_4.6×30 mm, 2.5 μm, Temp 60° C., Eluent A: Water+$CF_3COOH$ 0.1%; eluent B: MeOH; gradient: 0.0 min 5% B (4 mL/min)→0.05 min 5% B (3 mL/min)→2.05 min 100% B (3 mL/min)→2.1 min 100% B (4.5 mL/min)→2.4 min 100% B (4.5 mL/min).

Method 19

Instrument: LC/MS Waters 1525 with DA- and MS-Detector, Column: Sunfire C18_4.6×30 mm, 2.5 μm, Temp 60° C., Eluent A: Water+$CF_3COOH$ 0.1%; eluent B: Acetonitrile; gradient: 0.0 min 3% B (4 mL/min)→0.15 min 3% B (3 mL/min)→2.15 min 100% B (3 mL/min)→2.2 min 100% B (4.5 mL/min)→2.4 min 100% B (4.5 mL/min).

Method 20

Instrument: Agilent 1200 with DA- and MS-Detector, Column: XBridge C18_3.0×30 mm, 2.5 μm, Temp 60° C., Eluent A: Water+$NH_4OH$ 0.1%; eluent B: Acetonitrile; gradient: 0.0 min 3% B (2.2 mL/min)→0.2 min 3% B (2.2 mL/min)→1.2 min 100% B (2.2 mL/min)→1.25 min 100% B (3 mL/min)→1.4 min 100% B (3 mL/min).

Method 21

Instrument: Agilent 1100 with DAD, Waters Autosampler and MS-Detector, Column: SunFire C18_4.6×30 mm, 3.5 μm, Temp 50° C., Eluent A: Water+$CF_3COOH$ 0.1%; eluent B: Acetonitrile; gradient: 0.0 min 5% B (4 mL/min)→min 100% B→1.8 min 100% B; flow rate: 4 mL/min;

Method 22

Instrument: Agilent 1100 with DAD, CTC Autosampler and Waters MS-Detector; Column: XBridge C18_4.6×30 mm, 3.5 μm, Temp 60° C.; Eluent A: Water+$NH_4OH$ 0.1%; eluent B: Acetonitrile; gradient: 0.0 min 2% B (4 mL/min)→1.5 min 100% B→1.8 min 100% B; flow rate: 2.5 mL/min;

Method 27

Instrument: LC/MS ThermoFinnigan HPLC Surveyor DAD, MSQ single quadrupole; Column: Synergi Hydro RP100A, 2.5 μm, 3×50 mm Eluent A: 90% water+10% ACN+NH4COOH 10 Mm; eluent B=ACN 90%+10% H2O+NH4COOH 10 Mm; gradient: 0.0 min 0% B→6.50 min 100% B→7.50 min 100% B→8.0 min 0% B→9.00 min 0% B; flow rate: 1.2 mL/min; UV Detection: 254 nm; Ion source: APCI+/APCI−; scan range 100-900 amu Chiral HPLC Methods:

Method 9

HPLC apparatus type: Agilent 1100; column: Daicel chiralpack AD-H, 5.0 μm, 250 mm×10 mm; method: eluent hexane/IPA 70:30; flow rate: 1 mL/min, Temperature: 25° C.; UV Detection: 254 nm Method 12

HPLC apparatus type: Agilent 1100; column: Daicel chiralpack IA, 5.0 μm, 250 mm×10 mm; method: eluent hexane/IPA 60:40; flow rate: 1 mL/min, Temperature: 25° C.; UV Detection: 254 nm Method 13

HPLC apparatus type: Agilent 1100; column: Daicel chiralpack IA, 5.0 μm, 250 mm×10 mm; method: eluent hexane/IPA 60:40; flow rate: 1 mL/min, Temperature: 25° C.; UV Detection: 230 nm Method 15

HPLC apparatus type: Agilent 1100; column: Daicel chiralpack IA, 5.0 μm, 250 mm×10 mm; method: eluent hexane/IPA 70:30; flow rate: 1 mL/min, Temperature: 25° C.; UV Detection: 230 nm Method 24

HPLC apparatus type: Agilent 1100; column: Daicel chiralcel OD, 5.0 μm, 250 mm×10 mm; method: eluent hexane/IPA 90:10; flow rate: 0.5 mL/min, Temperature: 25° C.; UV Detection: 230 nm Method 25

HPLC apparatus type: Agilent 1100; column: Daicel chiralcel OJ, 4.6 μm, 250 mm×10 mm; method: eluent hexane/ethanol 97:3; flow rate: 1 mL/min, Temperature: 25° C.; UV Detection: 230 nm Method 26

HPLC apparatus type: Agilent 1100; column: Daicel chiralpack AD-H, 5.0 μm, 250 mm×10 mm; method: eluent hexane/IPA 80:20; flow rate: 1 mL/min, Temperature: 25° C.; UV Detection: 230 nm Microwave Heating:

Discover® CEM instruments, equipped with 10 and 35 mL vessels.

General Comment Concerning the Presentation of the Structures

Compounds with Stereogenic Centre(s):

If a chemical structure comprises one stereogenic centre and if no stereochemical indications (e.g. by stereochemical designators, perspective drawings etc.) are given, then that structure refers to the racemic mixture.

According to the synthetic Schemes 3 and 4, starting from enantiopure starting materials is possible to obtain the final compounds with known absolute configuration; the before mentioned synthetic approaches have been used in the synthesis of examples 74 and 75 in order to establish the absolute configuration of the more active enantiomer. The absolute configuration of Example 74 is R and the absolute configuration of Example 75 is S.

With the exception of examples 74 and 75 having known absolute configuration, a perspective drawing is intended to indicate a single enantiomer but not the absolute configuration.

Example 1a

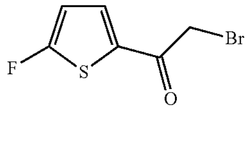

Pyridinium bromide perbromide (7.0 g, 21.9 mmol) is added to a solution of 1-(5-Fluoro-thiophen-2-yl)-ethanone (3.0 g, 20.8 mmol) dissolved in 75 ml of trichloromethane and the resulting mixture is stirred 3 hours.

$Et_2O$ and $H_2O$ are added, phases are separated then the organic layer is washed with brine, dried and concentrated under reduced pressure. The residue is purified by Silica gel flash chromatography using cyclohexane/EtOAc 95:5 as eluent to obtain the title compound (3.3 g, 69% yield).

GC-MS (Method 3): $R_t$=8.26 min

MS (EI): m/z=224 $[M]^+$

Example 1b

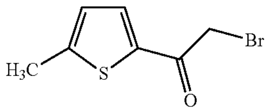

A solution of Bromoacetylbromide (1.6 ml, 18.8 mmol) dissolved in 10 ml of DCM is added dropwise to a stirred solution of triethylamine (5.2 ml, 37.6 mmol) dissolved in 50 ml of DCM. After 20 minutes stirring, a solution of 2-Methylthiophene (1.2 g, 12.5 mmol) is added and the reaction mixture is stirred overnight. 50 ml of icy water are added and after 30 minutes stirring the mixture is extracted with DCM. The organic layer is separated, washed with brine, dried and concentrated under reduced pressure. The residue is purified by silica gel flash chromatography, using cyclohexane/EtOAc 95:5 to 70:30 as eluent, to obtain 1.7 g of the title compound.

UPLC-MS (Method 1): $R_t$=1.07 min

MS (ES+): m/z=219-221 $[M+H]^+$

Example 2a

Racemic Mixture

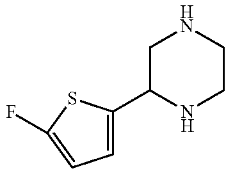 [SMILES: Fc1ccc(C2CNCCN2)s1]

A solution of ethane-1,2-diamine (4.8 ml, 71.8 mmol) dissolved in 10 ml of dioxane is added dropwise, under nitrogen atmosphere, to a 0° C. cooled solution of example 1a (3.3 g, 14.4 mmol) dissolved in 50 ml of dioxane. The resulting mixture is stirred overnight at room temperature. The solvent is removed under reduced pressure, the residue is dissolved in 60 ml of methanol and 3 ml of water; the solution is then cooled at 0° C., sodiumboronhydride (2.7 g, 71.8 mmol) is added portionwise and the reaction mixture is stirred overnight at room temperature. 50 ml of 1N HCl solution are added; the reaction mixture is stirred during 15 minutes and methanol is removed under reduced pressure.

DCM followed by NaOH aqueous solution (basic pH needs to be reached) is added; the phases are separated and the aqueous layer is extracted three times with DCM; the organic phase is dried and the solvents removed under reduced pressure.

The residue is purified by Silica gel flash chromatography using as eluent $DCM/MeOH/NH_4OH$ (from 95:5:1 to 80:20:1) to obtain the title compound (2.7 g, 53% yield).

GC-MS (Method 3): $R_t$=9.30 min

MS (EI): m/z=186 $[M]^+$

Example 2b

Racemic Mixture

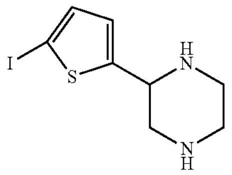 [SMILES: Ic1ccc(C2CNCCN2)s1]

Bromoacetylbromide (3.1 ml, 35.7 mmol) dissolved in 10 ml of anhydrous DCM is added to a stirred suspension of aluminum chloride (7.0 g, 52.5 mmol) in 80 ml of anhydrous DCM and the mixture is stirred 20 minutes. 2-Iodothiophene (2.6 ml, 23.8 mmol) dissolved in 10 ml of anhydrous DCM is added dropwise and the resulting mixture is stirred overnight. The reaction is cooled with an ice/water bath, water is added and the mixture is extracted with DCM; the organic layer is separated, washed with brine, dried and concentrated under reduced pressure. The residue is purified by Silica gel flash chromatography using cyclohexane/EtOAc 95:5 as eluent to give 1.9 g of intermediate 2-Bromo-1-(5-iodo-tiophen-2-yl)-ethanone. The title compound is synthesized as described for example 2a using ethane-1,2-diamine (2.1 ml, 31.7 mmol) dissolved in 10 ml of dioxane, 2-Bromo-1-(5-iodo-tiophen-2-yl)-ethanone (1.9 g, 5.8 mmol) dissolved in 40 ml of dioxane, sodiumborohydride (655 mg, 17.3 mmol), 50 ml of methanol and 2 ml of water, to give 720 mg (40% yield) of pure product.

HPLC-MS (Method 5): $R_t$=2.28 min

MS (APCI+): m/z=295 $[M+H]^+$

General Procedure for Examples 3b to 3h:

Tetrakis(Triphenylphosphine)Palladium(0) (1-3% mol) is added to a mixture of 2-Chloropyrazine (1 eq), Aryl/Heteroaryl boronic acid (1 eq) and base (2 eq) suspended into the solvent. The reaction mixture is heated until the reaction is completed, the solvent is removed under reduced pressure and the residue is partitioned between water and EtOAc (or 1N aqueous NaOH and EtOAc); organic layer is separated, dried, concentrated under reduced pressure and the residue is purified by Silica gel flash chromatography using a suitable eluent.

| Example | Product | Reactant, Base | Solvent, temperature | Product amount, yield | $R_t$ [min], method | MS (ESI + or APCI+, m/z) |
|---|---|---|---|---|---|---|
| 3b | 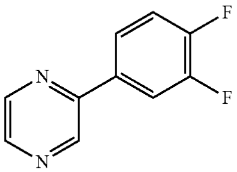 [SMILES: Fc1ccc(-c2cnccn2)cc1F] | 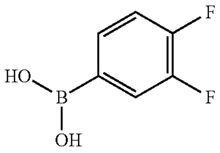 [SMILES: OB(O)c1ccc(F)c(F)c1] (3 g), $Cs_2CO_3$ (11.4 g) | Dioxane (40 ml), Water (10 ml), 80° C. | 3.1 g, 59% | 1.08 min, method 1 | 193 |
| 3c | 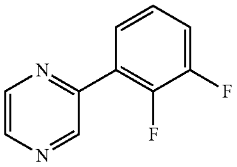 [SMILES: Fc1cccc(-c2cnccn2)c1F] | 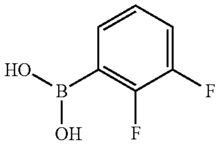 (3.5 g) $Na_2CO_3$ (2N aq. solution, 21.8 ml) | Anhydrous 1,2-Dimethoxyethane (60 ml), 85° C. | 3.2 g, 76% | 1.02 min, method 2 | 193 |
| 3d | 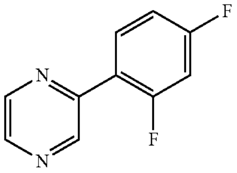 [SMILES: Fc1ccc(-c2cnccn2)c(F)c1] | 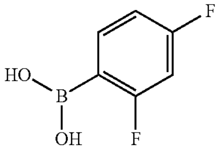 (3 g), $Cs_2CO_3$ (11.4 g) | Dioxane (40 ml), Water (10 ml), 70° C. | 2.5 g, 72% | 1.04 min, method 1 | 193 |
| 3e | 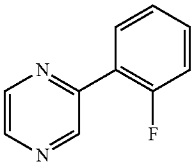 [SMILES: Fc1ccccc1-c1cnccn1] | 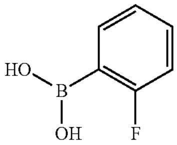 (3.5 g) $Na_2CO_3$ (2N aq. solution, 25 ml) | Anhydrous 1,2-Dimethoxyethane (120 ml), 80° C. | 4.0 g, 92% | 0.96 min, method 2 | 175 |
| 3f | 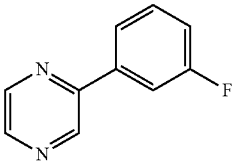 [SMILES: Fc1cccc(-c2cnccn2)c1] | 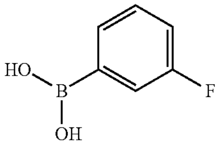 (2.6 g), $Cs_2CO_3$ (11.4 g) | Dioxane (60 ml), Water (15 ml), 80° C. | 3.7 g, 80% | 1.05 min, method 1 | 175 |
| 3g | 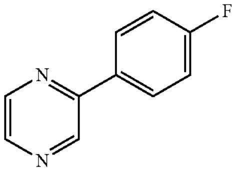 [SMILES: Fc1ccc(-c2cnccn2)cc1] | 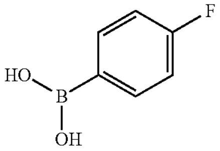 (3.9 g), $Cs_2CO_3$ (11.4 g) | Dioxane (60 ml), Water (15 ml), 70° C. | 3.0 g, 99% | 1.02 min, method 1 | 175 |

-continued

| Example | Product | Reactant, Base | Solvent, temperature | Product amount, yield | $R_t$ [min], method | MS (ESI + or APCI+, m/z) |
|---|---|---|---|---|---|---|
| 3h | 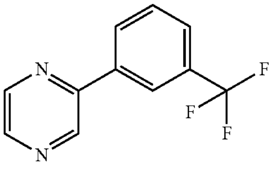 [SMILES: FC(F)(F)c1cccc(-c2cnccn2)c1] | 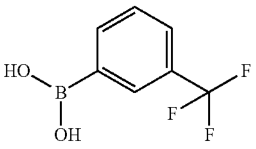 [SMILES: OB(O)c1cccc(C(F)(F)F)c1] (2.9 g), $Cs_2CO_3$ (9.6 g) | Dioxane (60 ml), Water (12 ml), 70° C. | 2.8 g, 84% | 1.18 min, method 2 | 225 |

General Procedure for Examples 3j to 3p (Racemic Mixture) Synthesis:

Example 3b to 3h are dissolved into the solvent, catalyst (10% w/w) is added and the resulting mixture is hydrogenated using a Parr equipment (starting $pH_2$ 4 bar) until reaction is complete. The mixture is filtered over a celite pad, the filtrate is concentrated under reduced pressure and the residue is used without further purification (for reactions performed in acetic acid the residue is then partitioned between DCM and aqueous NaOH and concentrated under reduced pressure).

| Example | Product | Reactant, Catalyst | Solvent, reaction time | Product amount, | $R_t$ [min], method | MS (ESI + or APCI+, m/z) |
|---|---|---|---|---|---|---|
| 3j | 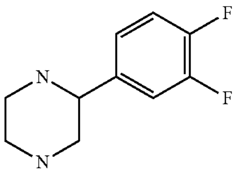 [SMILES: Fc1ccc(C2CNCCN2)cc1F] | 3b (3.0 g), 10% Pd/C (300 mg) | Acetic acid (70 ml), 6 hours | 2.6 g | 0.57 min, method 1 | 199 |
| 3k | 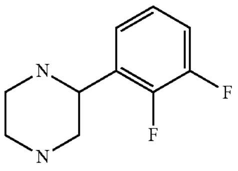 [SMILES: Fc1cccc(C2CNCCN2)c1F] | 3c (1.9 g), 10% Pd/C (200 mg) | Ethanol (50 ml), 3 hours | 1.8 g | 0.34 min, method 1 | 199 |
| 3l | 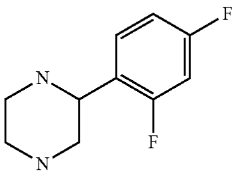 [SMILES: Fc1ccc(C2CNCCN2)c(F)c1] | 3d (2.5 g), 10% Pd/C (250 mg) | Acetic acid (60 ml), 3 hours | 2.1 g | 0.44 min, method 1 | 199 |
| 3m | 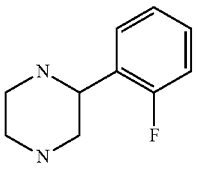 [SMILES: Fc1ccccc1C1CNCCN1] | 3e (4.0 g), 10% Pd/C (400 mg) | Acetic acid, 4 hours | 4.0 g | 0.42 min, method 2 | 181 |
| 3n | 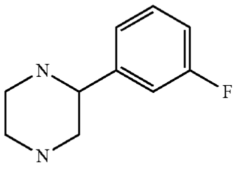 [SMILES: Fc1cccc(C2CNCCN2)c1] | 3f (3.0 g), 10% Pd/C (300 mg) | Ethanol (100 ml), water (20 ml), 72 hours | 2.9 g | 0.53 min, method 1 | 181 |

-continued

| Example | Product | Reactant, Catalyst | Solvent, reaction time | Product amount, | $R_t$ [min], method | MS (ESI + or APCI+, m/z) |
|---|---|---|---|---|---|---|
| 3o | 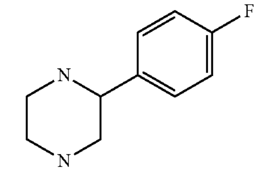 [SMILES: Fc1ccc(C2CNCCN2)cc1] | 3g (3.8 g), 10% Pd/C (300 mg) | Ethanol (100 ml), water (10 ml), 24 hours | 3.8 g | 0.26 min, method 1 | 181 |
| 3p | 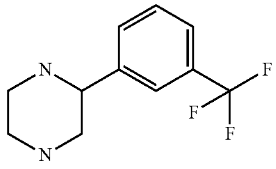 [SMILES: FC(F)(F)c1cccc(C2CNCCN2)c1] | 3h (2.8 g), 10% Pd/C (300 mg) | Ethanol (80 ml), 24 hours | 2.8 g | 0.67 min, method 2 | 231 |

Example 3r

Racemic Mixture

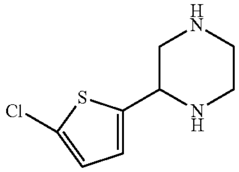 [SMILES: Clc1ccc(C2CNCCN2)s1]

Ethane-1,2-diamine (15.4 ml, 230 mmol) dissolved in 40 ml of anhydrous dioxane is added to a 5° C. cooled solution of 2-Bromo-1-(5-Chloro-Thiophen-2-yl)-ethanone (10 g, 41.7 mmol) dissolved in 120 ml of anhydrous dioxane; the reaction mixture is stirred overnight at room temperature; 30 ml of MeOH and 2 ml of water are added, the reaction mixture is cooled to 0° C. then Sodiumboronhydride (4.4 g, 117 mmol) is added portionwise and the reaction mixture is stirred at room temperature 3 hours. The crude is poured in 160 ml of 10% aqueous HCl solution, washed with EtOAc then the aqueous layer is basified by addition of 36% aqueous NaOH solution and extracted with DCM. The organic layer is separated and concentrated under reduced pressure to obtain the title compound as crude (7.2 g).

UPLC-MS (Method 1): $R_t$=0.53 min

MS (ES+): m/z=203 $[M+H]^+$

Example 3s

Racemic Mixture

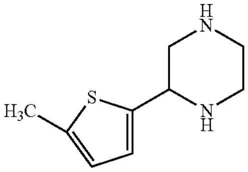

Example 3s is synthesized as described for example 3r starting from example 1b (1.7 g, 6.4 mmol), instead of 2-Bromo-1-(5-Chloro-Thiophen-2-yl)-ethanone, ethane-1,2-diamine (2.4 ml, 35.4 mmol) and sodiumborohydride (731 mg, 38 mmol); after the work-up the crude is purified by silica gel flash chromatography, using DCM/MeOH/$NH_4OH$ (98:2:0.2 to 80:20:2) as eluent, to obtain the title compound (340 mg, 28% yield).

UPLC-MS (Method 1): $R_t$=0.37 min

MS (ES+): m/z=183 $[M+H]^+$

Example 14a

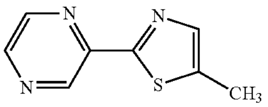

Tetrakis(triphenylphosphine)palladium(0) (751 mg, 0.65 mmol) is added, under nitrogen atmosphere, to a solution of 2-(tributylstannyl)pyrazine (2.4 g, 6.5 mmol) and 2-bromo-5-methylthiazole (2.3 g, 13.0 mmol), in 40 ml of dry toluene previously degassed bubbling nitrogen for 15 minutes and the reaction is refluxed 15 hours. Solvent is removed, the residue is suspended in $Et_2O$ and the precipitate is filtered off. Filtrate is concentrated under reduced pressure and the residue is purified by Silica gel flash cromatography using EtOAc/cyclohexane (from 10:90 to EtOAc 100%) as eluent to obtain the title compound (516 mg, 44% yield).

UPLC-MS (Method 2): $R_t$=0.92 min

MS (ES+): m/z=178 $[M+H]^+$

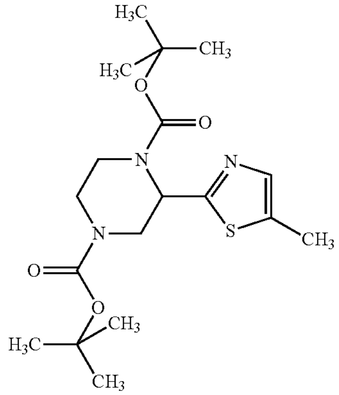

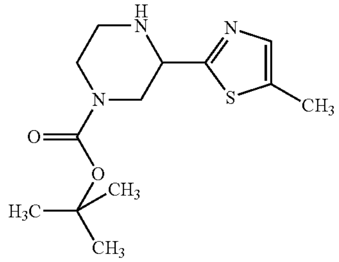

Palladium (70 mg, 10% on carbon) suspended in 5 ml of acetic acid is added to a solution of example 14a (516 mg, 2.85 mmol) in 20 ml of acetic acid, and the reaction is stirred under hydrogen atmosphere (4 bar) overnight. Platinum (IV) oxide hydrate (50 mg) is added and the mixture is further hydrogenated in the same conditions for 24 hours. The catalyst is filtered off over a celite pad, the mixture is concentrated under reduced pressure and the residue is loaded over a SCX cartridge. The obtained product is dissolved in 8 ml of DCM, cooled at 5° C. and a solution of di-tert-butyl-dicarbonate (561 mg, 2.57 mmol) in 2 ml of DCM is then added. After 1 hour stirring, aqueous $NaHCO_3$ is added, the organic layer is separated and concentrated under reduced pressure then the residue is purified by Silica gel flash cromatography using cyclohexane/EtOAc (from 90:10 to EtOAc 100%) as eluent to give example 15a (225 mg, 21% yield) and impure example 15b that is further purified by RP flash chromatography to obtain 50 mg (6% yield) of the desired compound.

| Example | UPLC-MS (Method 2): $R_t$ [min] | MS (ES+): m/z |
|---|---|---|
| 15a | 1.34 | 384 |
| 15b | 0.95 | 284 |

Example 16a

Racemic Mixture

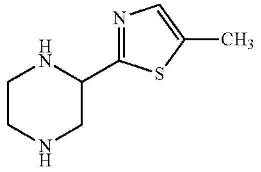

HCl (4N dioxane solution, 2.9 ml, 11.7 mmol) is added to a solution of example 15a (225 mg, 0.59 mmol) dissolved in 6 ml of dioxane and the reaction mixture is stirred at room temperature overnight. Solvent is removed under reduced pressure and the crude is purified over an SCX cartridge to give the title compound (90 mg, 84% yield).

UPLC-MS (Method 2): $R_t$=0.44 min

MS (ES+): m/z=184 $[M+H]^+$

Example 27a

Racemic Mixture

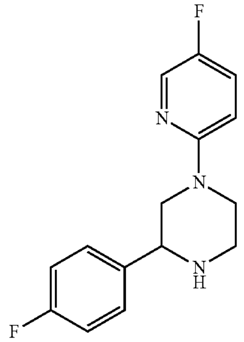 [SMILES: Fc1ccc(C2CN(c3ccc(F)cn3)CCN2)cc1]

Example 3o (100 mg, 0.55 mmol), 2-Chloro-5-Fluoropyridine (67 µl, 0.67 mmol), X-Phos (106 mg, 0.22 mmol), Tris(dibenzylideneacetone)dipalladium(0) (102 mg, 0.11 mmol) and sodium tert-butoxide (107 mg, 1.11 mmol) are suspended under nitrogen atmosphere in 2 ml of previously degassed dioxane then the reaction mixture is heated in a microwave reactor, at 80° C., during 2 hours.

The crude reaction mixture is filtered and then purified by preparative HPLC-MS to obtain the title compound (102 mg, 67% yield)

UPLC-MS (Method 1): $R_t$=0.78 min

MS (ES+): m/z=276 $[M+H]^+$

Example 28a

Racemic Mixture

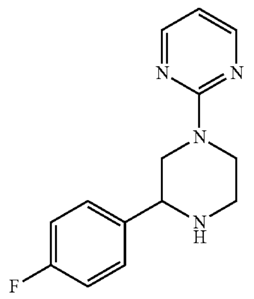 [SMILES: Fc1ccc(C2CN(c3ncccn3)CCN2)cc1]

Example 3o (100 mg, 0.55 mmol), 2-Chloropyrimidine (76.3 mg, 0.67 mmol) and N,N-diisopropylethylamine (192 µl, 1.11 mmol) are dissolved in 1 ml of DMSO and the reaction mixture is heated in a microwave reactor 30 minutes at 120° C. The crude product is partitioned between $Et_2O$ and water; the organic layer is then separated and concentrated under reduced pressure to obtain the title compound (158 mg).

UPLC-MS (Method 2): $R_t$=0.76 min

MS (ES+): m/z=259 [M+H]$^+$

Example 29a

Racemic Mixture

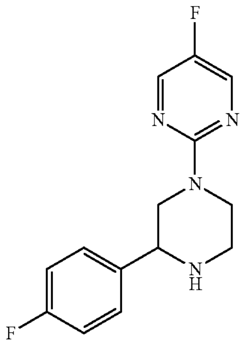 [SMILES: Fc1ccc(C2CN(c3ncc(F)cn3)CCN2)cc1]

Example 29a is synthesized as described for example 28a using example 3o (100 mg, 0.55 mmol), 2-Chloro-5-Fluoropyrimidine (82 μl, 0.67 mmol) instead of 2-Chloropyrimidine, N,N-diisopropylethylamine (192 μl, 1.11 mmol) and 1 ml of DMSO. The crude product is partitioned between $Et_2O$ and water; the organic layer is then separated and concentrated under reduced pressure to obtain of the title compound (160 mg).

UPLC-MS (Method 2): $R_t$=0.98 min

MS (ES+): m/z=277 [M+H]$^+$

Example 30a

Racemic Mixture

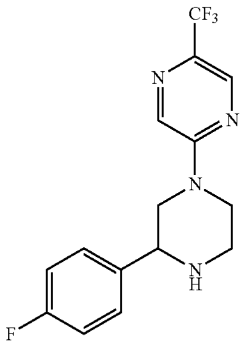 [SMILES: Fc1ccc(C2CN(c3cnc(C(F)(F)F)cn3)CCN2)cc1]

Example 30a is synthesized as described for example 28a using example 3o (600 mg, 3.3 mmol), 2-Bromo-5-(Trifluoromethyl)pyrazine (907 mg, 4.0 mmol) instead of 2-Chloropyrimidine, N,N-diisopropylethylamine (1.1 ml, 6.7 mmol) and 8 ml of DMSO. The mixture is heated in a microwave reactor at 100° C. during 2.5 hours. The crude product is partitioned between EtOAc and water then the organic layer is separated and concentrated under reduced pressure; the residue is purified by Silica gel flash chromatography, using EtOAc/Cyclohexane 1:1 to EtOAc 100% as eluent, to obtain the title compound (800 mg, 72% yield).

HPLC-MS (Method 5): $R_t$=3.21 min

MS (APCI+): m/z=327 [M+H]$^+$

Example 31a

Racemic Mixture

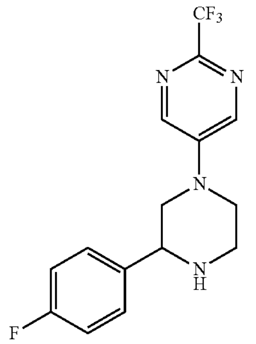 [SMILES: Fc1ccc(C2CN(c3cnc(C(F)(F)F)nc3)CCN2)cc1]

Example 31a is synthesized as described for example 27a using example 3o (300 mg, 1.67 mmol), 5-Bromo-2-(Trifluoromethyl)pyrimidine (453 mg, 2.00 mmol) instead of 2-Chloro-5-Fluoropyridine, X-Phos (317 mg, 0.67 mmol), Tris(dibenzylideneacetone)dipalladium(0) chloroform adduct (345 mg, 0.33 mmol), sodium tert-butoxide (320 mg, 3.33 mmol) and 4 ml of previously degassed dioxane. The mixture is heated in a microwave reactor during 2 hours at 100° C. The crude is partitioned between EtOAc and water, the organic phase is separated, dried and concentrated under reduced pressure; the residue is then purified by Silica gel flash chromatography using Cyclohexane/EtOAc 50:50 to 0:100 as eluent to obtain the title compound (175 mg, 32% yield)

HPLC-MS (Method 5): $R_t$=3.10 min

MS (APCI+): m/z=327 [M+H]$^+$

Example 32a

Racemic Mixture

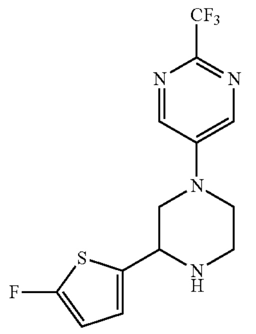 [SMILES: Fc1ccc(C2CN(c3cnc(C(F)(F)F)nc3)CCN2)s1]

Example 32a is synthesized as described for example 27a using example 2a (70 mg, 0.38 mmol) instead of example 3o, 5-Bromo-2-(Trifluoromethyl)pyrimidine (102 mg, 0.45 mmol) instead of 2-Chloro-5-Fluoropyridine, X-Phos (72 mg, 0.15 mmol), Tris(dibenzylideneacetone)dipalladium(0)

chloroform adduct (78 mg, 0.08 mmol), sodium tert-butoxide (72 mg, 0.75 mmol) and 1.5 ml of previously degassed dioxane. The mixture is heated in a microwave reactor 2 hours at 100° C. The crude is partitioned between EtOAc and 1N aqueous HCl, the aqueous phase is separated, basified by addition of 32% aqueous NaOH then it is extracted with EtOAc; the organic layer is dried and concentrated under reduced pressure to obtain the title compound (175 mg) that is used as such without further purification.

UPLC-MS (Method 1): $R_t$=0.83 min

MS (ES+): m/z=333 $[M+H]^+$

Example 33a

Racemic Mixture

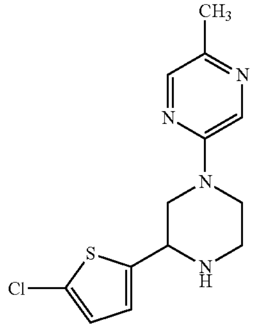 [SMILES: Cc1cnc(N2CCNC(c3ccc(Cl)s3)C2)cn1]

Example 33a is synthesized as described for example 28a using example 3r (150 mg, 0.67 mmol) instead of example 3o, 2-Bromo-5-Methylpyrazine (127 mg, 0.73 mmol) instead of 2-Chloropyrimidine, N,N-diisopropylethylamine (289 μl, 1.66 mmol) and 1 ml of DMSO.

The mixture is heated in a microwave reactor 1 hour at 165° C. The crude product is partitioned between DCM and water then the organic layer is separated and concentrated under reduced pressure; the residue is purified by Silica gel flash chromatography using as eluent DCM/MeOH 100:0 to 90:10 to obtain the title compound (75 mg, 34% yield).

UPLC-MS (Method 1): $R_t$=0.71 min

MS (ES+): m/z=295 $[M+H]^+$

Example 34a

Racemic Mixture

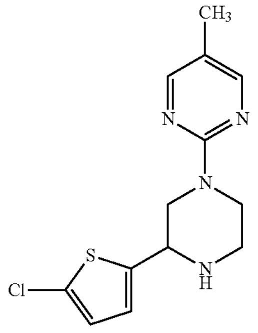 [SMILES: Cc1cnc(N2CCNC(c3ccc(Cl)s3)C2)nc1]

Example 34a is synthesized as described for example 28a using example 3r (100 mg, 0.44 mmol) instead of example 3o, 2-Chloro-5-methylpyrimidine (74 mg, 0.58 mmol) instead of 2-Chloropyrimidine, N,N-diisopropylethylamine (307 μl, 1.78 mmol) and 1 ml of DMSO. The mixture is heated in a microwave reactor during 30 minutes at 120° C. The crude product is purified by preparative HPLC-MS to obtain the title compound as trifluoroacetate salt (55 mg, 30% yield)

UPLC-MS (Method 1): $R_t$=0.81 min

MS (ES+): m/z=295 $[M+H]^+$

Example 35a

Racemic Mixture

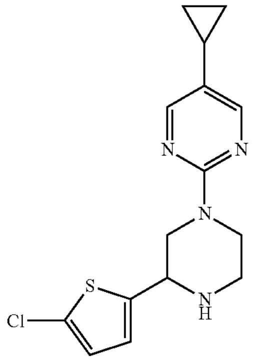 [SMILES: Clc1ccc(C2CN(c3ncc(C4CC4)cn3)CCN2)s1]

Example 35a is synthesized as described for example 28a using example 3r (80 mg, 0.36 mmol) instead of example 3o, 2-Chloro-5-Cyclopropylpyrimidine (73 mg, 0.46 mmol) instead of 2-Chloropyrimidine, N,N-diisopropylethylamine (122 μl, 0.71 mmol) and 1 ml of DMSO. The mixture is heated in a microwave reactor during 30 minutes at 140° C. The crude product is purified by preparative HPLC-MS to obtain the title compound as trifluoroacetate salt (72 mg, 47% yield)

UPLC-MS (Method 1): $R_t$=0.89 min

MS (ES+): m/z=321 $[M+H]^+$

Example 36a

Racemic Mixture

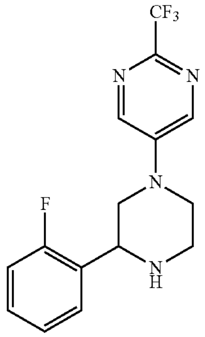 [SMILES: Fc1ccccc1C1CN(c2cnc(C(F)(F)F)nc2)CCN1]

Example 36a is synthesized as described for example 27a using example 3m (290 mg, 1.61 mmol) instead of example 3o, 5-Bromo-2-(Trifluoromethyl)pyrimidine (440 mg, 1.94 mmol) instead of 2-Chloro-5-Fluoropyridine, 2-dicyclohexylphosphino-2'-(N,N-dimethylamino)biphenyl (220 mg, 0.56 mmol) instead of X-Phos, Tris(dibenzylideneacetone)dipalladium(0) (140 mg, 0.15 mmol), potassium tert-butoxide (270 mg, 2.41 mmol) and 2 ml of DMSO. The mixture is heated in a microwave reactor during 40 minutes at 120° C. The crude is partitioned between EtOAc and water, the organic phase is separated, dried and concentrated under reduced pressure then the residue is purified by Silica gel flash chromatography using EtOAc/hexane/MeOH 80:20:1 as eluent to obtain the title compound (140 mg, 27% yield)

HPLC-MS (Method 11): $R_t$=2.53 min

MS (ES+): m/z=327 $[M+H]^+$

Example 37a

Racemic Mixture

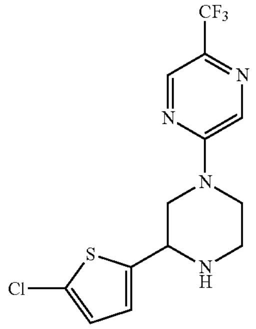 [SMILES: FC(F)(F)c1cnc(N2CCNC(c3ccc(Cl)s3)C2)cn1]

Example 37a is synthesized as described for example 28a using example 3r (70 mg, 0.35 mmol) instead of example 3o, 2-Bromo-5-(Trifluoromethyl)pyrazine (102 mg, 0.45 mmol) instead of 2-Chloropyrimidine, N,N-diisopropylethylamine (239 µl, 1.38 mmol) and 1 ml of DMSO. The mixture is heated in a microwave reactor during 30 minutes at 120° C. The crude product is partitioned between $Et_2O$ and water then the organic layer is separated and concentrated under reduced pressure; the residue is purified by preparative HPLC-MS to obtain the title compound (70 mg, 44% yield) as trifluoroacetate salt.

UPLC-MS (Method 1): $R_t$=0.90 min

MS (ES+): m/z=349 $[M+H]^+$

Example 40b

Racemic Mixture

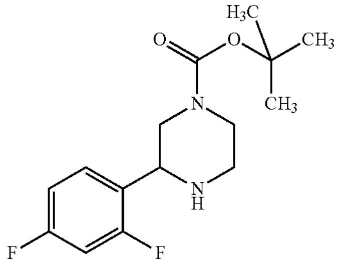 [SMILES: CC(C)(C)OC(=O)N1CCNC(c2ccc(F)cc2F)C1]

N,N-diisopropylethylamine (3.6 ml, 20.8 mmol) is added into a solution of example 31 (2.1 g, 10.4 mmol) dissolved in 50 ml of acetonitrile. Di-tert-butyl-dicarbonate (2.0 g, 9.4 mmol) is added portionwise at 0° C. and the reaction is stirred 2 hours. Water is added, acetonitrile is removed under reduced pressure and the residue is partitioned between DCM and water; the organic layer is separated, dried and concentrated under reduced pressure. The crude product is purified by Silica gel flash chromatography using EtOAc/cylohexane 60:40 to 100:0 to obtain the title compound (2.5 g, 80% yield).

GC-MS (Method 3): $R_t$=11.55 min

MS (EI): m/z=298 $[M]^+$

The following examples are synthesized in analogy to the preparation of example 40b:

| Example | Product | Reactant, amount, solvent | Product amount, yield | $R_t$ [min], method | MS (ESI pos or APCI, or EI m/z) |
|---|---|---|---|---|---|
| 40c (racemic mixture) | 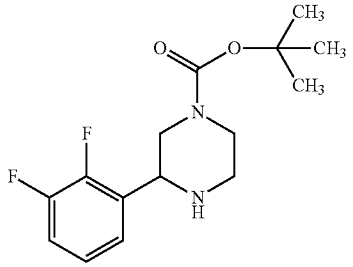 [SMILES: CC(C)(C)OC(=O)N1CCNC(c2cccc(F)c2F)C1] | example 3k (1.8 g, 8.0 mmol) DCM, no base used | 2.3 g | $R_t$ = 0.75 min, Method 1 | 299 $[M + H]^+$ |
| 40d (racemic mixture) | 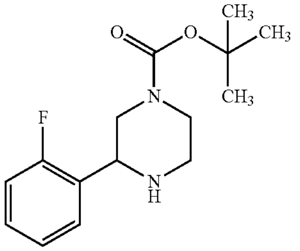 [SMILES: CC(C)(C)OC(=O)N1CCNC(c2ccccc2F)C1] | example 3m (1.9 g, 9.5 mmol, DCM, no base used | 2.8 g | $R_t$ = 1.10 min, Method 2 | 281 $[M + H]^+$ |

-continued

| Example | Product | Reactant, amount, solvent | Product amount, yield | $R_t$ [min], method | MS (ESI pos or APCI, or EI m/z) |
|---|---|---|---|---|---|
| 40e (racemic mixture) | 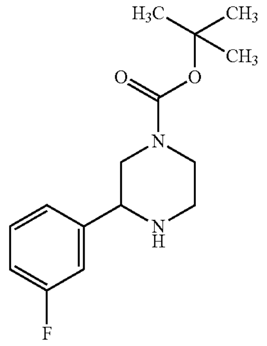 [SMILES: CC(C)(C)OC(=O)N1CCNC(c2cccc(F)c2)C1] | example 3n (2.9 g, 16.2 mmol), DCM, no base used | 4.0 g, 80% (after purification by Silica gel flash chromatography) | $R_t$ = 1.07 min, Method 2 | 281 $[M + H]^+$ |
| 40f (racemic mixture) | 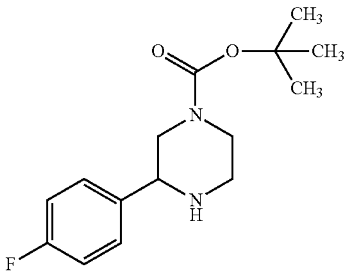 [SMILES: CC(C)(C)OC(=O)N1CCNC(c2ccc(F)cc2)C1] | example 3o (1.8 g, 10.0 mmol), DCM, no base used | 2.7 g, 94% (after purification by Silica gel flash chromatography) | $R_t$ = 2.95 min, Method 5 | 281 $[M + H]^+$ |
| 40g (racemic mixture) | 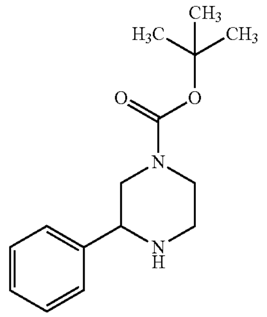 [SMILES: CC(C)(C)OC(=O)N1CCNC(c2ccccc2)C1] | 2-phenyl-piperazine (5.0 g, 30.8 mmol), triethylamine (6.43 ml, 46.2 mmol), DCM | 5.2 g, 64% (after purification by Silica gel flash chromatography) | $R_t$ = 0.9 min, Method 2 | 263 $[M + H]^+$ |
| 40h (racemic mixture) | 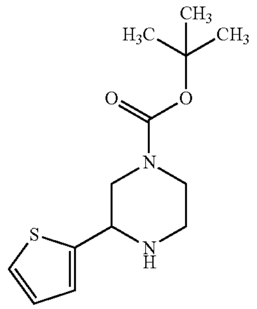 [SMILES: CC(C)(C)OC(=O)N1CCNC(c2cccs2)C1] | 2-Thiophen-2-yl-piperazine (540 mg, 3.2 mmol), DCM, no base used | 805 mg | $R_t$ = 3.06 min, Method 5 | 269 $[M + H]^+$ |

-continued

| Example | Product | Reactant, amount, solvent | Product amount, yield | $R_t$ [min], method | MS (ESI pos or APCI, or EI m/z) |
|---|---|---|---|---|---|
| 40i (racemic mixture) | 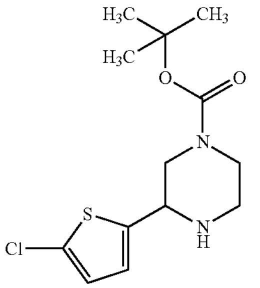 [SMILES: CC(C)(C)OC(=O)N1CCNC(c2ccc(Cl)s2)C1] | example 3r (1.7 g, 7.6 mmol) N,N-diisopropylethylamine (4.0 ml, 22.9 mmol), THF | 2.35 g | $R_t$ = 0.85 min, Method 1 | 303 $[M + H]^+$ |
| 40j (racemic mixture) | 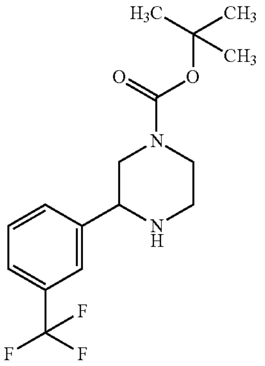 [SMILES: CC(C)(C)OC(=O)N1CCNC(c2cccc(C(F)(F)F)c2)C1] | example 3p (1.1 g, 4.6 mmol), DCM, no base used | 1.2 g, 78% (after purification by Silica gel flash chromatography) | $R_t$ = 3.05 min, Method 7 | 331 $[M + H]^+$ |
| 40k (racemic mixture) | 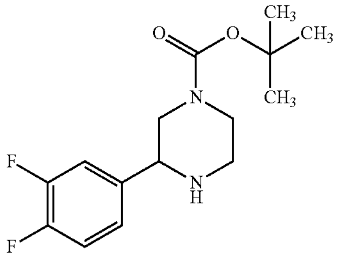 [SMILES: CC(C)(C)OC(=O)N1CCNC(c2ccc(F)c(F)c2)C1] | example 3j (2.6 g, 13.0 mmol), N,N-diisopropylethylamine (4.4 ml, 25.9 mmol), acetonitrile | 2.39 g, 61% (after purification by Silica gel flash chromatography) | $R_t$ = 1.11 min, Method 2 | 299 $[M + H]^+$ |
| 41a (racemic mixture) | 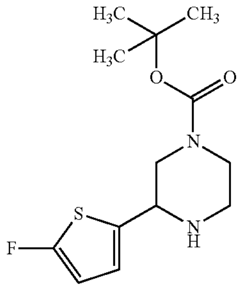 | example 2a (1.3 g, 7.2 mmol), N,N-diisopropylethylamine (2.5 ml, 14.5 mmol), acetonitrile | 1.0 g, 47% (after purification by Silica gel flash chromatography) | $R_t$ = 3.09 min, Method 5 | 287 $[M + H]^+$ |
| 41b (racemic mixture) | 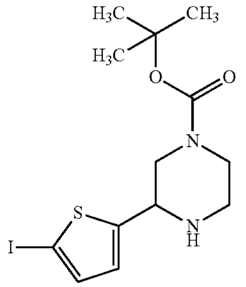 | example 2b (720 mg, 2.5 mmol), N,N-diisopropylethylamine (1.3 ml, 7.3 mmol), acetonitrile | 920 mg | $R_t$ = 1.32 min, Method 2 | 395 $[M + H]^+$ |

-continued

| Example | Product | Reactant, amount, solvent | Product amount, yield | $R_t$ [min], method | MS (ESI pos or APCI, or EI m/z) |
|---|---|---|---|---|---|
| 41c (racemic mixture) | 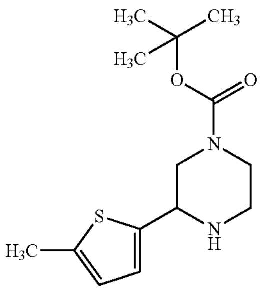 [SMILES: Cc1ccc(C2CN(C(=O)OC(C)(C)C)CCN2)s1] | example 3s (340 mg, 1.8 mmol), N,N-diisopropylethylamine (960 µl, 5.5 mmol), acetonitrile | 410 mg | $R_t$ = 0.82 min, Method 1 | 283 $[M + H]^+$ |

Example 42b

Racemic Mixture

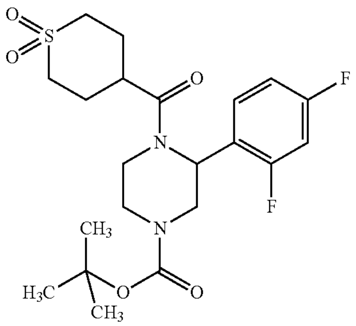 [SMILES: CC(C)(C)OC(=O)N1CCN(C(=O)C2CCS(=O)(=O)CC2)C(c2ccc(F)cc2F)C1]

N-(3-dimethylaminopropyl)-N'-ethylcarbodiimide hydrochloride (3.2 g, 16.6 mmol) is added to a mixture of example 40b (2.5 g, 8.3 mmol), tetrahydro-2H-thiopyran-4-carboxilic acid 1,1-dioxide (3.0 g, 16.6 mmol) and 1-hydroxybenzotriazole (112 mg, 0.8 mmol) in 60 ml of DCM. The reaction mixture is stirred at room temperature overnight then water is added, the organic layer is separated, washed with aqueous $NaHCO_3$ then dried and concentrated under reduced pressure. The residue is purified by Silica gel flash chromatography, using cyclohexane/EtOAc 40:60 to 0:100 as eluent, to obtain the title compound (3.8 g, 97% yield).

HPLC-MS (Method 5): $R_t$=2.80 min

MS (APCI+): m/z=459 $[M+H]^+$

The following examples are synthesized in analogy to the preparation of example 42b:

| Example | Product | Reactant, amount, solvent | Product amount, yield | $R_t$ [min], method | MS (ESI pos or APCI, m/z) |
|---|---|---|---|---|---|
| 42c (racemic mixture) | 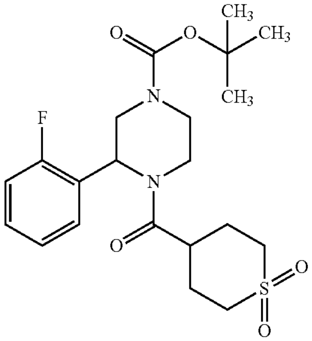 [SMILES: CC(C)(C)OC(=O)N1CCN(C(=O)C2CCS(=O)(=O)CC2)C(c2ccccc2F)C1] | Example 40d (2.7 g, 90% content, 8.7 mmol), DMF/THF 1:1 | 3.5 g, 92% | $R_t$ = 1.02 min, Method 2 | 441 $[M + H]^+$ |

-continued

| Example | Product | Reactant, amount, solvent | Product amount, yield | $R_t$ [min], method | MS (ESI pos or APCI, m/z) |
|---|---|---|---|---|---|
| 42d (racemic mixture) | 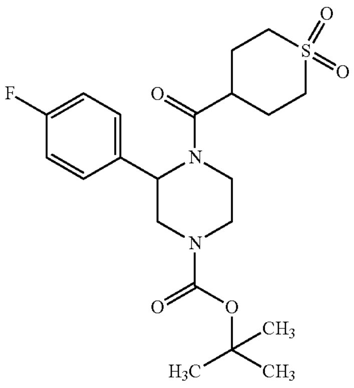 [SMILES: CC(C)(C)OC(=O)N1CCN(C(=O)C2CCS(=O)(=O)CC2)C(c2ccc(F)cc2)C1] | Example 40f (1.7 g, 5.8 mmol), DCM | 2.3 g, 88% | $R_t$ = 1.04 min, Method 2 | 441 $[M + H]^+$ |
| 42e (racemic mixture) | 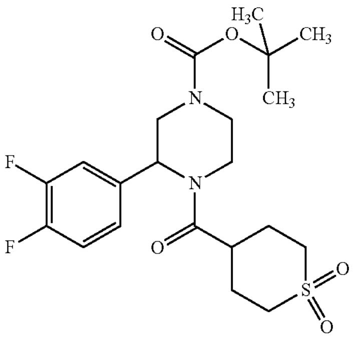 [SMILES: CC(C)(C)OC(=O)N1CCN(C(=O)C2CCS(=O)(=O)CC2)C(c2ccc(F)c(F)c2)C1] | Example 40k (2.4 g, 7.8 mmol), DCM | 3.0 g, 81% | Rt = 2.89 min, Method 5 | 403 [M − 56 + H]+ |
| 42g (racemic mixture) | 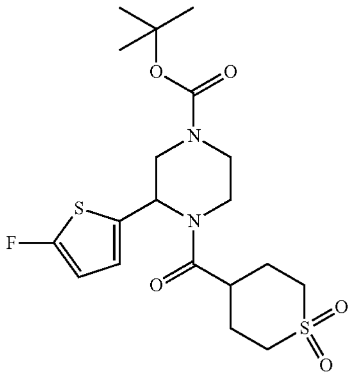 [SMILES: CC(C)(C)OC(=O)N1CCN(C(=O)C2CCS(=O)(=O)CC2)C(c2ccc(F)s2)C1] | Example 41a (1.0 g, 3.6 mmol), DCM | 1.2 g, 75% | $R_t$ = 2.83 min, Method 5 | 447 $[M + H]^+$ |
| 42h (racemic mixture) | 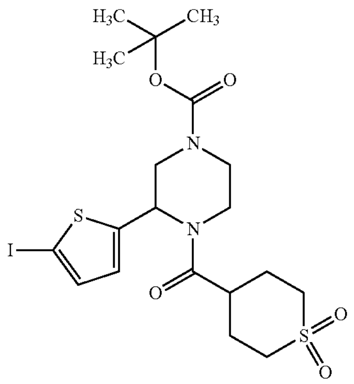 [SMILES: CC(C)(C)OC(=O)N1CCN(C(=O)C2CCS(=O)(=O)CC2)C(c2ccc(I)s2)C1] | Example 41b (920 mg, 2.3 mmol), DCM | 920 mg, 70% | Rt = 3.05 min, Method 5 | 555 [M + H]+ |

Example 43a

Racemic Mixture

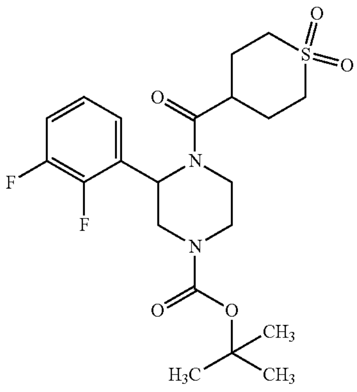 [SMILES: CC(C)(C)OC(=O)N1CCN(C(=O)C2CCS(=O)(=O)CC2)C(c2cccc(F)c2F)C1]

HATU (3.2 g, 8.4 mmol) and N,N-diisopropylethylamine (3.8 ml, 22.0 mmol) are added to a solution of tetrahydro-2H-thiopyran-4-carboxilic acid 1,1-dioxide (1.6 g, 8.8 mmol) in 15 ml of DMF. After 20 minutes stiffing, example 40c (2.3 g, 7.3 mmol) is added, and the reaction is stirred at room temperature overnight. The mixture is concentrated under reduced pressure, then the residue is dissolved in EtOAc and washed with 5% $NaHCO_3$ solution, 5% HCl solution and water. The organic layer is separated, concentrated under reduced pressure and the residue is purified by Silica gel flash cromatography using cyclohexane/EtOAc (from 50:50 to EtOAc 100%) as eluent, to obtain the title compound (2.1 g, 63% yield).

UPLC-MS (Method 1): $R_t$=1.05 min

MS (ES+): m/z=459 $[M+H]^+$

The following examples are synthesized in analogy to the preparation of example 43a:

| Example | Product | Reactant, amount | Product amount, yield | $R_t$ [min], method | MS (ESI pos or APCI, m/z) |
|---|---|---|---|---|---|
| 43b (racemic mixture) | 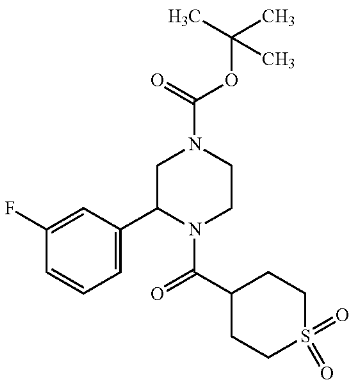 [SMILES: CC(C)(C)OC(=O)N1CCN(C(=O)C2CCS(=O)(=O)CC2)C(c2cccc(F)c2)C1] | Example 40e, (1.2 g, 3.9 mmol), in acetonitrile | 1.2 g, 59% | $R_t$ = 1.21 min, Method 1 | 441 $[M + H]^+$ |
| 43c (racemic mixture) | 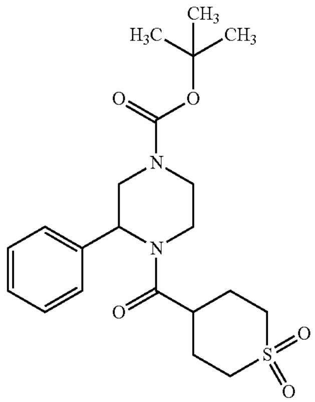 [SMILES: CC(C)(C)OC(=O)N1CCN(C(=O)C2CCS(=O)(=O)CC2)C(c2ccccc2)C1] | Example 40g, (5.20 g, 19.8 mmol) | 7.7 g, 92% | $R_t$ = 3.16 min, Method 8 | 423 $[M + H]^+$ |

-continued
| Example | Product | Reactant, amount | Product amount, yield | $R_t$ [min], method | MS (ESI pos or APCI, m/z) |
|---|---|---|---|---|---|
| 43d (racemic mixture) | 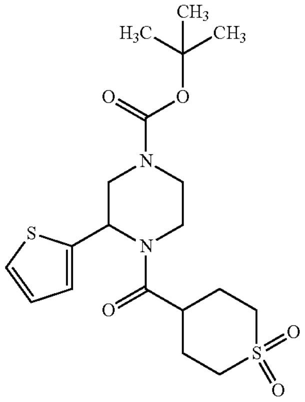 [SMILES: CC(C)(C)OC(=O)N1CCN(C(=O)C2CCS(=O)(=O)CC2)C(c2cccs2)C1] | Example 40h, (1.3 g, 4.7 mmol) | 2.0 g, 98% | $R_t$ = 1.04 min, Method 1 | 429 $[M + H]^+$ |
| 43e (racemic mixture) | 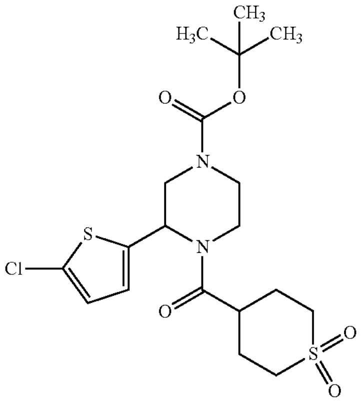 [SMILES: CC(C)(C)OC(=O)N1CCN(C(=O)C2CCS(=O)(=O)CC2)C(c2ccc(Cl)s2)C1] | Example 40i, (1.7 g, 5.3 mmol), in acetonitrile | 2.4 g, 85% | $R_t$ = 1.14 min, Method 1 | 463 $[M + H]^+$ |
| 43f (racemic mixture) | 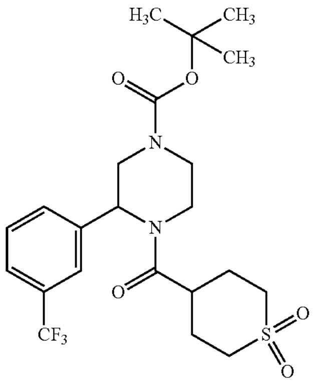 [SMILES: CC(C)(C)OC(=O)N1CCN(C(=O)C2CCS(=O)(=O)CC2)C(c2cccc(C(F)(F)F)c2)C1] | Example 40j, (1.2 g, 3.6 mmol) | 1.2 g, 68% | $R_t$ = 1.18 min, Method 1 | 491 $[M + H]^+$ |

-continued

| Example | Product | Reactant, amount | Product amount, yield | $R_t$ [min], method | MS (ESI pos or APCI, m/z) |
|---|---|---|---|---|---|
| 43g (racemic mixture) | 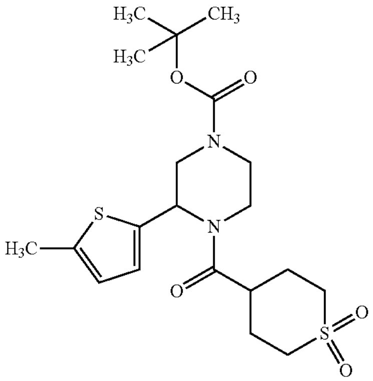 [SMILES: Cc1ccc(C2CN(C(=O)OC(C)(C)C)CCN2C(=O)C2CCS(=O)(=O)CC2)s1] | Example 41c (100 mg, 1.3 mmol), acetonitrile | 690 mg, crude | $R_t$ = 1.10 min, Method 1 | 443 [M + H]+ |

Example 43h

Racemic Mixture

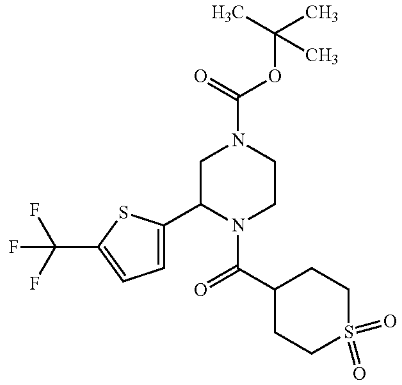 [SMILES: CC(C)(C)OC(=O)N1CCN(C(=O)C2CCS(=O)(=O)CC2)C(c2ccc(C(F)(F)F)s2)C1]

Copper(I) iodide (500 mg, 2.63 mmol) and hexamethylphosphoramide (1.8 ml, 10.1 mmol) are added to a stirred solution of example 42h (1.1 g, 2.02 mmol) dissolved in 6 ml of anhydrous DMF. After 5 minutes stiffing, methyl-2,2-difluoro-2-(fluorosulfonyl)-acetate (1.3 ml, 10.1 mmol) is added and the reaction mixture is heated at 100° C. for 1 hour. The crude is poured into a saturated aqueous $NH_4Cl$ solution and extracted with EtOAc; the organic layer is separated, dried and concentrated under reduced pressure. The residue is purified by silica gel flash chromatography, using cyclohexane/EtOAc 1:1 to 100% EtOAc as eluent, to obtain the title compound (770 mg, 69% yield).

HPLC-MS (Method 5): $R_t$=3.12 min

MS (APCI+): m/z=495 $[M-H]^+$

Example 44b

Racemic Mixture

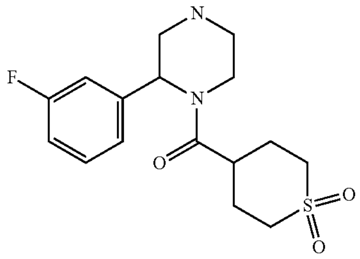 [SMILES: O=C(C1CCS(=O)(=O)CC1)N1CCNCC1c1cccc(F)c1]

Example 43b (1.2 g, 2.3 mmol) is dissolved in 10 ml of dioxane; HCl (4N solution in dioxane, 3.7 ml, 14.8 mmol) is added and the reaction mixture is stirred until complete conversion. The solid is filtered to obtain the desired product as hydrochloride salt (715 mg).

UPLC-MS (Method 1): $R_t$=0.59 min

MS (ES+): m/z=341 $[M+H]^+$

The following examples are synthesized in analogy to the preparation of example 44b, in case using aqueous NaOH solution or $NH_4OH$ to obtain the free base:

| Example | Product | Reactant, amount | Product amount | $R_t$ [min], method | MS (ESI pos or APCI, m/z) |
|---|---|---|---|---|---|
| 44c (racemic mixture) | 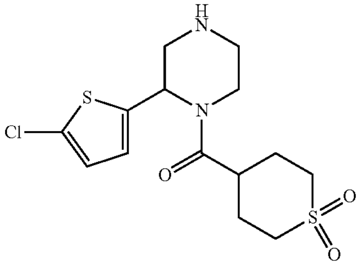 [SMILES: O=C(C1CCS(=O)(=O)CC1)N1CCNCC1c1ccc(Cl)s1] | Example 43e, (5.8 g, 11.0 mmol) | 2.8 g | $R_t$ = 0.63 min, Method 1 | 363 $[M + H]^+$ |
| 44d (racemic mixture) | 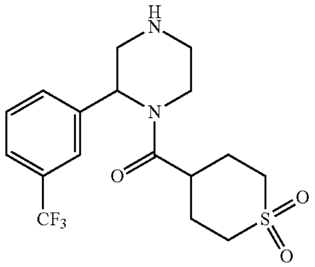 [SMILES: O=C(C1CCS(=O)(=O)CC1)N1CCNCC1c1cccc(C(F)(F)F)c1] | Example 43f, (1.2 g, 2.5 mmol) | 940 mg | $R_t$ = 0.70 min, Method 1 | 391 $[M + H]^+$ |
| 44f (racemic mixture) | 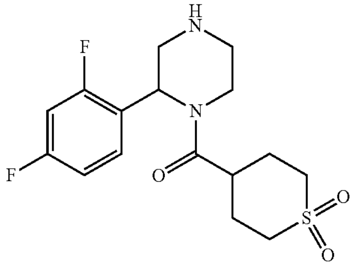 [SMILES: O=C(C1CCS(=O)(=O)CC1)N1CCNCC1c1ccc(F)cc1F] | Example 42b, (3.8 g, 8.2 mmol) | 2.5 g | $R_t$ = 0.57 min, Method 2 | 359 $[M + H]^+$ |
| 44g (racemic mixture) | 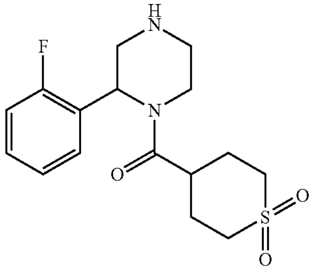 [SMILES: O=C(C1CCS(=O)(=O)CC1)N1CCNCC1c1ccccc1F] | Example 42c, (3.3 g, 7.5 mmol) | 2.5 g | $R_t$ = 0.59 min, Method 2 | 341 $[M + H]^+$ |
| 44h (racemic mixture) | 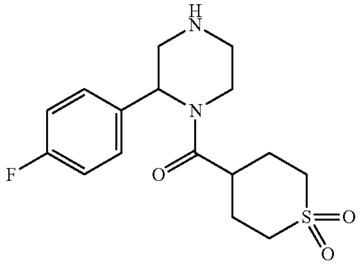 [SMILES: O=C(C1CCS(=O)(=O)CC1)N1CCNCC1c1ccc(F)cc1] | Example 42d, (2.3 g, 5.1 mmol) | 1.7 g | $R_t$ = 0.63 min, Method 2 | 341 $[M + H]^+$ |

-continued

| Example | Product | Reactant, amount | Product amount | $R_t$ [min], method | MS (ESI pos or APCI, m/z) |
|---|---|---|---|---|---|
| 44i (racemic mixture) | 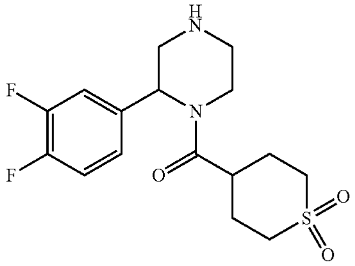 [SMILES: O=C(C1CCS(=O)(=O)CC1)N1CCNCC1c1ccc(F)c(F)c1] | Example 42e, (3.0 g, 6.4 mmol) | 2.1 g | Rt = 1.72 min, Method 5 | 359 [M + H]+ |
| 44k (racemic mixture) | 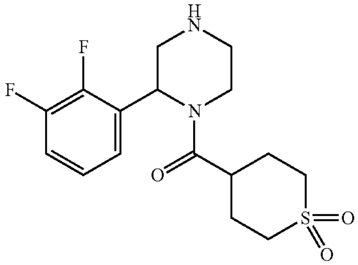 [SMILES: O=C(C1CCS(=O)(=O)CC1)N1CCNCC1c1cccc(F)c1F] | Example 43a, (2.1 g, 4.6 mmol) | 1.6 g | $R_t$ = 0.59 min, Method 1 | 359 $[M + H]^+$ |
| 44l (racemic mixture) | 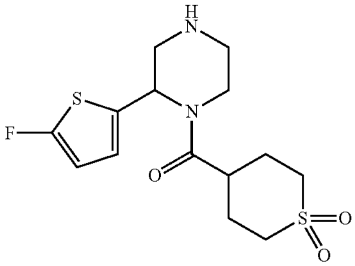 [SMILES: O=C(C1CCS(=O)(=O)CC1)N1CCNCC1c1ccc(F)s1] | Example 42g, (1.2 g, 2.7 mmol) | 750 mg | $R_t$ = 1.73 min, Method 5 | 347 $[M + H]^+$ |
| 44m (racemic mixture) | 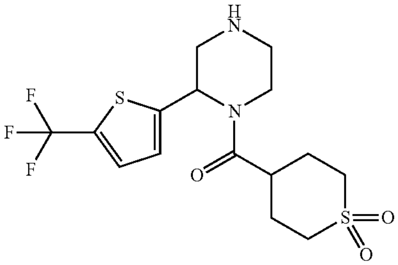 [SMILES: O=C(C1CCS(=O)(=O)CC1)N1CCNCC1c1ccc(C(F)(F)F)s1] | Example 43h, (820 mg, 1.7 mmol) | 575 mg | $R_t$ = 3.11 min, Method 16 | 397 $[M + H]^+$ |
| 44n (racemic mixture) | 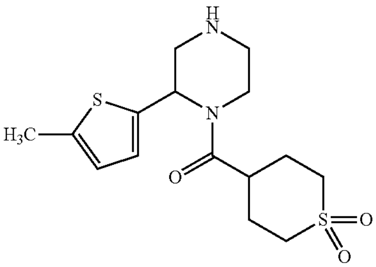 [SMILES: Cc1ccc(C2CNCCN2C(=O)C2CCS(=O)(=O)CC2)s1] | Example 43g, (690 mg, 1.4 mmol) | 470 mg (as hydrochloride salt) | $R_t$ = 0.60 min, Method 1 | 343 $[M + H]^+$ |

Example 45a

Racemic Mixture

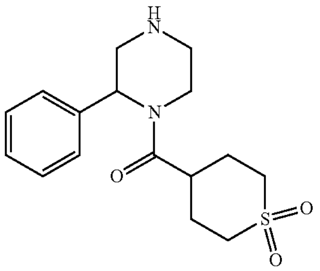 [SMILES: O=C(C1CCS(=O)(=O)CC1)N1CCNCC1c1ccccc1]

Trifluoroacetic acid (14.1 ml, 183.4 mmol) is added to a 0° C. cooled solution of example 43c (7.8 g, 18.3 mmol) in 75 ml of DCM. After 20 hours stiffing at room temperature, solvent is removed under reduced pressure, and the residue is purified over a SCX cartridge, to give the title compound (4.9 g, 83% yield).

UPLC-MS (Method 1): $R_t$=0.55 min

MS (ES+): m/z=323 $[M+H]^+$

Example 46a

Racemic Mixture

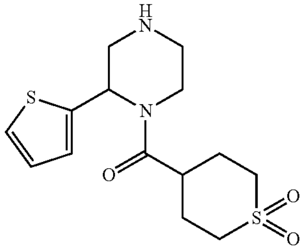 [SMILES: O=C(C1CCS(=O)(=O)CC1)N1CCNCC1c1cccs1]

Example 46a is synthesized as described for example 45a starting from example 43d (2.0 g, 4.7 mmol) using trifluoroacetic acid (3.6 ml, 46.7 mmol) and 20 ml of DCM to obtain 1.5 g of product.

UPLC-MS (Method 4): $R_t$=1.73 min

MS (APCI+): m/z=329 $[M+H]^+$

Example 47a

Racemic Mixture

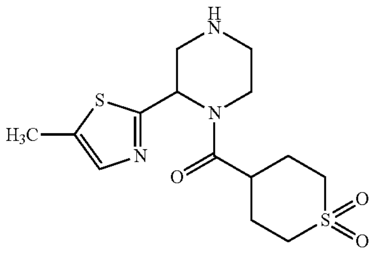 [SMILES: Cc1cnc(C2CNCCN2C(=O)C2CCS(=O)(=O)CC2)s1]

N,N-diisopropylethylamine (45 µl, 0.26 mmol) and 1,1-dioxothiane-4-carbonyl chloride (52 mg, 0.26 mmol previously prepared from the corresponding carboxilic acid and oxalyl chloride in anhydrous DCM) are added to a solution of example 15b (50 mg, 0.18 mmol) in 2 ml of anhydrous DCM under nitrogen atmosphere. The reaction is stirred overnight. The crude product is partitioned between DCM (5 ml) and 5% aqueous $NaHCO_3$ solution; the organic phase is separated, trifluoroacetic acid (400 µl) is added and the reaction is stirred overnight. The solvent is removed under reduced pressure and crude product is purified by SCX cartridge to obtain the title compound (46 mg, 85% content; the content is estimated at 254 nm,).

UPLC-MS (Method 1): $R_t$=0.58 min

MS (ES+): m/z=344 $[M+H]^+$

Example 48a

Racemic Mixture

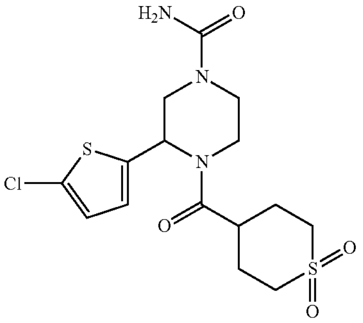 [SMILES: NC(=O)N1CCN(C(=O)C2CCS(=O)(=O)CC2)C(c2ccc(Cl)s2)C1]

A solution of trimethylsilylisocyanate (137 µl, 1.03 mmol) dissolved in 4 ml of anhydrous THF is added dropwise to a suspension of example 44c (340 mg, 0.94 mmol as free base) in 10 ml of anhydrous THF under nitrogen atmosphere and the reaction mixture is stirred 20 hours. The solvent is removed under reduced pressure then a solution of HCl in methanol is added to the residue and the reaction is stirred 30 minutes. The solvent is removed to obtain the title compound (830 mg) used without further purification in the following step.

HPLC-MS (Method 11): $R_t$=2.47 min

MS (ES+): m/z=406 $[M+H]^+$

Example 48b

Racemic Mixture

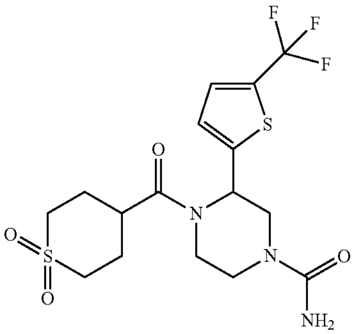 [SMILES: NC(=O)N1CCN(C(=O)C2CCS(=O)(=O)CC2)C(c2ccc(C(F)(F)F)s2)C1]

Example 48b is synthesized as described for example 48a starting from example 44m (300 mg, 0.72 mmol) instead of example 44c, trimethylsilylisocyanate (405 µl, 2.0 mmol) and 10 ml of anhydrous THF to obtain the title compound (307 mg) used without further purification in the following step.

HPLC-MS (Method 10): $R_t$=2.61 min

MS (ES+): m/z=440 $[M+H]^+$

Example 49a

Racemic Mixture

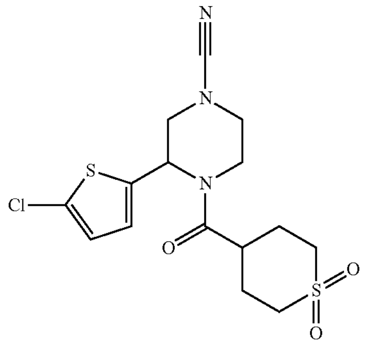 [SMILES: N#CN1CCN(C(=O)C2CCS(=O)(=O)CC2)C(c2ccc(Cl)s2)C1]

Triethylamine (8 μl, 0.06 mmol) and 1.5 ml of 50% NaOH aqueous solution are added to a stirred solution of example 48a (255 mg, 0.57 mmol) dissolved in 20 ml of chloroform and the resulting mixture is vigorously stirred overnight. Two ml of 50% NaOH aqueous solution are added and the reaction mixture is stirred during additional 8 hours. DCM and water are added to the mixture, the phases are separated; the organic layer is dried and concentrated under reduced pressure to obtain 280 mg of title compound used in the following step without further purification.

HPLC-MS (Method 11): $R_t$=3.03 min

MS (ES+): m/z=388 $[M+H]^+$

Example 50a

Racemic Mixture

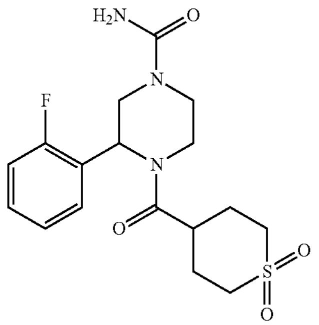 [SMILES: NC(=O)N1CCN(C(=O)C2CCS(=O)(=O)CC2)C(c2ccccc2F)C1]

Example 50a is synthesized as described for example 48a starting from example 44g (600 mg, 1.8 mmol) instead of example 44c and trimethylsilylisocyanate (270 μl, 2.0 mmol) to obtain the title compound (560 mg) used without further purification in the following step.

UPLC-MS (Method 2): $R_t$=0.60 min

MS (ES+): m/z=384 $[M+H]^+$

Example 51a

Racemic Mixture

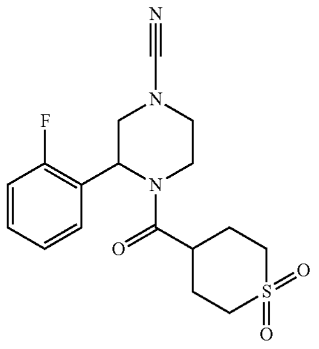 [SMILES: N#CN1CCN(C(=O)C2CCS(=O)(=O)CC2)C(c2ccccc2F)C1]

Triethylamine (20 μl, 0.17 mmol) and 6 ml of 50% aqueous NaOH solution are added to a stirred solution of example 50a (560 mg, 1.46 mmol) dissolved in 10 ml of chloroform and the resulting mixture is vigorously stirred 6 hours. DCM and water are added to the crude and the phases are separated; the organic layer is dried and concentrated under reduced pressure; the residue is purified by Silica gel flash chromatography, using EtOAc/Hexane/MeOH 80:20:1 as eluent, to obtain the title compound (310 mg, 58% yield).

HPLC-MS (Method 17): $R_t$=2.47 min

MS (ES+): m/z=366 $[M+H]^+$

Example 52a

Racemic Mixture

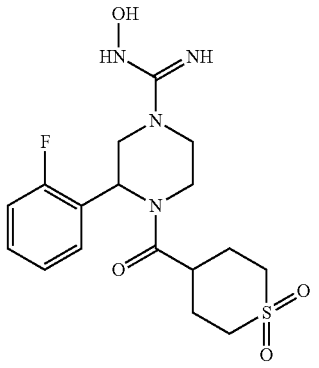 [SMILES: N=C(NO)N1CCN(C(=O)C2CCS(=O)(=O)CC2)C(c2ccccc2F)C1]

Example 51a (300 mg, 0.82 mmol) and hydroxylamine (50% aqueous solution, 120 μl, 1.96 mmol) are dissolved in 3 ml of EtOH and the reaction is heated in a microwave reactor during 30 minutes at 100° C. Solvent is removed under reduced pressure, the residue is partitioned between water and DCM; the organic phase is separated and concentrated under reduced pressure to obtain the title compound (270 mg).

HPLC-MS (Method 17): $R_t$=1.87 min

MS (ES+): m/z=399 $[M+H]^+$

Example 53a

Racemic Mixture

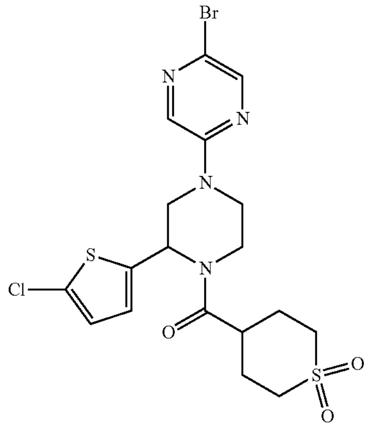 [SMILES: O=C(C1CCS(=O)(=O)CC1)N1CCN(c2cnc(Br)cn2)CC1c1ccc(Cl)s1]

Example 53a is synthesized as described for example 28a using example 44c (150 mg, 0.41 mmol) instead of example 3o, 2,5-dibromopyrazine (108 mg, 0.45 mmol) instead of 2-Chloropyrimidine, N,N-diisopropylethylamine (179 μl, 1.03 mmol) and 1 ml of DMSO. The mixture is heated in a microwave reactor during 2 hours at 130° C. After the work-up the crude is purified by Silica gel flash chromatography using Cyclohexane/EtOAc 60:40 to 20:80 as eluent to obtain the title compound (130 mg, 61% yield).

UPLC-MS (Method 1): $R_t$=1.21 min

MS (ES+): m/z=519-521 $[M+H]^+$

Example 54a

Racemic Mixture

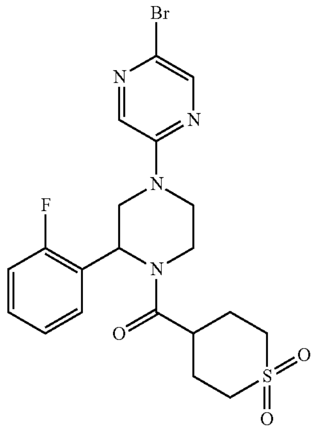 [SMILES: O=C(C1CCS(=O)(=O)CC1)N1CCN(c2cnc(Br)cn2)CC1c1ccccc1F]

Example 54a is synthesized as described for example 53a using example 44g (370 mg, 1.1 mmol) instead of example 44c, 2,5-dibromopyrazine (260 mg, 1.1 mmol), N,N-diisopropylethylamine (210 μl, 1.2 mmol) and 2 ml of DMSO. The mixture is heated in a microwave reactor during 1 hour at 130° C. 460 mg of the title compound are obtained.

UPLC-MS (Method 1): $R_t$=1.09 min

MS (ES+): m/z=497-499 $[M+H]^+$

Example 55a

Racemic Mixture

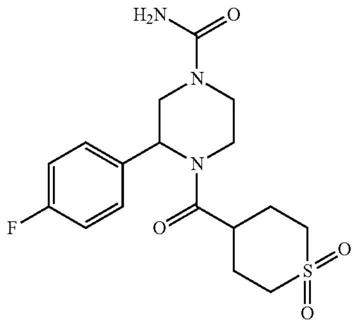 [SMILES: NC(=O)N1CCN(C(=O)C2CCS(=O)(=O)CC2)C(c2ccc(F)cc2)C1]

Example 55a is synthesized as described for example 48a starting from example 44h (350 mg, 1.0 mmol) instead of example 44c and trimethylsilylisocyanate (150 μl, 1.1 mmol) to obtain the title compound (390 mg) used without further purification in the following step.

HPLC-MS (Method 5): $R_t$=1.52 min

MS (APCI+): m/z=384 $[M+H]^+$

Example 56a

Racemic Mixture

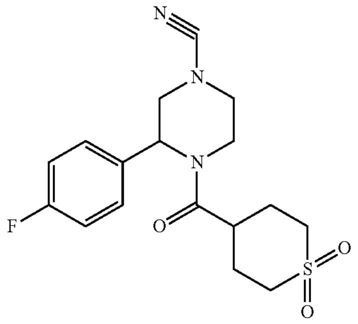 [SMILES: N#CN1CCN(C(=O)C2CCS(=O)(=O)CC2)C(c2ccc(F)cc2)C1]

Example 56a is synthesized as described for example 49a starting from example 55a (310 mg, 0.81 mmol) instead of example 48a, triethylamine (11 μl, 0.08 mmol) and 2.5 ml of 50% NaOH aqueous solution in 8 ml of chloroform; the reaction mixture was stirred overnight. After the work-up and the purification by Silica gel flash chromatography, using DCM/MeOH 95:5 as eluent, the title compound is obtained (149 mg, 45% yield).

HPLC-MS (Method 5): $R_t$=1.96 min

MS (APCI+): m/z=366 $[M+H]^+$

Example 57a

Racemic Mixture

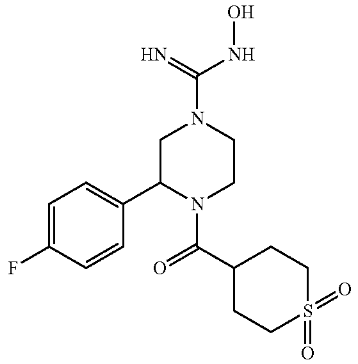 [SMILES: N=C(NO)N1CCN(C(=O)C2CCS(=O)(=O)CC2)C(c2ccc(F)cc2)C1]

Example 57a is synthesized as described for example 52a starting from example 56a (149 mg, 0.41 mmol) instead of example 51a, hydroxylamine hydrochloride (57 mg, 0.82 mmol), N,N-diisopropylethylamine (140 μl, 0.82 mmol) to obtain the title compound (150 mg) used as such without further purification.

HPLC-MS (Method 5): $R_t$=1.46 min

MS (APCI+): m/z=399 $[M+H]^+$

Example 58a

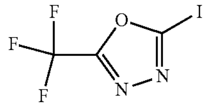

A solution of 5-(Trifluoromethyl)-1,3,4-Oxadiazol-2-amine (300 mg, 2.0 mmol) dissolved in 3 ml of diiodomethane is heated at 100° C. and stirred 2 hours; isoamylnitrite (1.0 ml, 7.8 mmol) is slowly dropped and resulting reaction mixture is further stirred 20 minutes. The crude product is purified by Silica gel flash chromatography using cyclohexane/EtOAc 100:0 to 98:2 to obtain the title compound (95 mg).

GC-MS (Method 3): $R_t$=3.04 min

MS (EI): m/z=263 $[M]^+$

Example 59a

Single Enantiomer; R Configuration

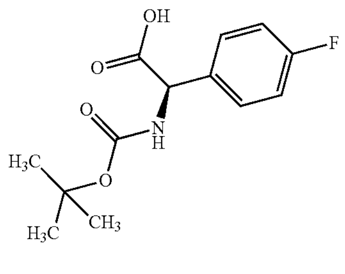 [SMILES: CC(C)(C)OC(=O)N[C@@H](C(=O)O)c1ccc(F)cc1]

$NaHCO_3$ (1.0 g, 11.9 mmol) is added to a stirred suspension of (R)-4-Fluorophenylglicine (1.0 g, 5.9 mmol) in water. After 30 minutes, a solution of di-tert-butyldicarbonate (1.5 g, 7.1 mmol) dissolved in tert-butylalcohol is added dropwise and the resulting reaction mixture is stirred overnight at room temperature. The reaction is diluted with water then with 5% citric acid aqueous solution (until pH 4-5); then the mixture is then extracted with DCM; the organic layer is separated, dried over anhydrous $Na_2SO_4$ and concentrated under reduced pressure to obtain the title compound (1.6 g).

HPLC-MS (Method 17): $R_t$=2.25 min

MS (ES+): m/z=292 $[M+Na]^+$

Example 60a

Single Enantiomer; R Configuration

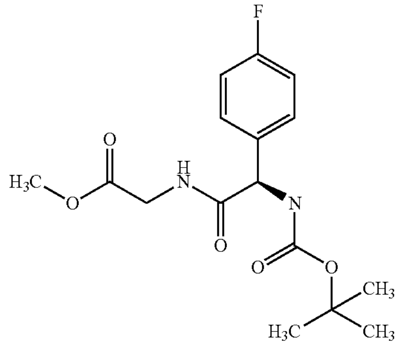 [SMILES: COC(=O)CNC(=O)[C@H](NC(=O)OC(C)(C)C)c1ccc(F)cc1]

$NaHCO_3$ (1.0 g, 11.9 mmol) is added to a stirred mixture of example 59a (1.5 g, 5.6 mmol) and glycine methyl ester hydrochloride (700 mg, 5.6 mmol) dissolved in 40 ml of DCM and 10 ml of anhydrous DMF and the reaction is stirred 30 minutes. 1-Hydroxy-7-azabenzotriazole (830 mg, 6.1 mmol) and N-(3-Dimethylaminopropyl)-N'-Ethylcarbodiimidehydrochloride (1.2 g, 6.1 mmol) are added and the reaction mixture is stirred 16 hours at room temperature. Water and DCM are added, the organic layer is separated, washed with 5% citric acid aqueous solution, dried over anhydrous $Na_2SO_4$ and concentrated under reduced pressure. The residue is purified by Silica gel flash chromatography, using Hexane/EtOAc 6:4 as eluent, to obtain the title compound (1.9 g, 90% yield).

UPLC-MS (Method 2): $R_t$=1.01 min

MS (ES+): m/z=341 $[M+H]^+$

Example 61a

Single Enantiomer; R Configuration

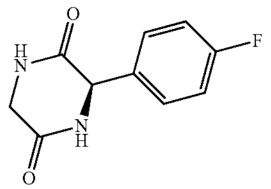 [SMILES: O=C1CNC(=O)[C@@H](c2ccc(F)cc2)N1]

Formic acid (20 ml) is added to example 60a (1.9 g, 5.0 mmol) then, after 1 hour stirring, the acid is removed under reduced pressure, 10 ml of toluene and 25 ml of 2-butanol are added to the residue and the resulting mixture is refluxed 4 hour using a Dean-Stark apparatus. Solvent is removed under reduced pressure then the residue is suspended in EtOAc and filtered to obtain the title compound (550 mg).

UPLC-MS (Method 2): $R_t$=0.53 min

MS (ES+): m/z=209 $[M+H]^+$

Example 62a

Single Enantiomer; R Configuration

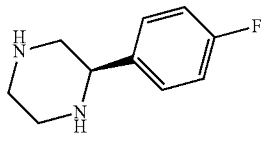 [SMILES: Fc1ccc([C@@H]2CNCCN2)cc1]

Borane-methyl sulfide complex (2.5 ml, 2M THF solution, 5 mmol) is added, at room temperature, to a stirred mixture of example 61a (200 mg, 1.0 mmol) in 5 ml of anhydrous THF under nitrogen atmosphere and the reaction is refluxed 20 hours. After cooling to room temperature, 3 ml of MeOH and 0.5 ml of HCl conc. are added and the mixture is heated 2 hour at 70° C. Solvents are removed under reduced pressure, the residue is partitioned between water and $Et_2O$, the aqueous layer is separated, basified until pH 10 by addition of $NH_4OH$ and extracted with DCM. The organic layer is separated, dried over a phase-separator cartridge and concentrated under reduced pressure to obtain the title compound (120 mg).

UPLC-MS (Method 23): $R_t$=0.47 min

MS (ES+): m/z=181 $[M+H]^+$

Example 63a

Single Enantiomer; R Configuration

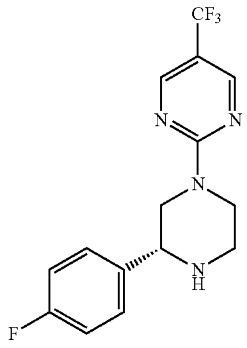 [SMILES: Fc1ccc([C@@H]2CN(c3ncc(C(F)(F)F)cn3)CCN2)cc1]

N,N-Diisopropylethylamine (30 μL, 0.2 mmol) is added to a stirred solution of example 62a (35 mg, 0.2 mmol) and 2-Chloro-5-(Trifluoromethyl)pyrimidine (36 mg, 0.2 mmol) dissolved in 1 ml of anhydrous DMSO; the reaction is heated in a microwave reactor during 2 hours at 100° C. Water and EtOAc are added to the crude, the organic phase is separated, washed with water, dried and concentrated under reduced pressure. The residue is purified by Silica gel flash chromatography, using DCM/MeOH 100:2 as eluent, to obtain the title compound (30 mg, 47% yield).

UPLC-MS (Method 1): $R_t$=0.90 min

MS (ES+): m/z=327 $[M+H]^+$

Chiral HPLC (Method 15): $R_t$=4.38 min

Example 64a

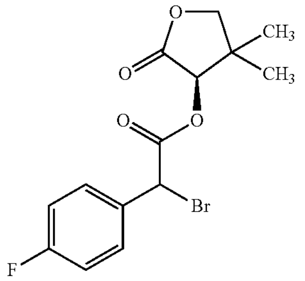 [SMILES: CC1(C)COC(=O)[C@@H]1OC(=O)C(Br)c1ccc(F)cc1]

N,N'-Dicyclohexylcarbodiimide (1.8 g, 8.6 mmol) is added to a stirred solution of alpha-Bromo-4-Fluoropheny-lacetic acid (2.0 g, 8.6 mmol), D-(−)-Pantolactone (1.1 g, 8.6 mmol) and 4-Dimethylaminopyridine (100 mg, 0.8 mmol) in DCM and the reaction mixture is stirred 3 hours. The precipitate is filtered out and the filtrate is concentrated under reduced pressure; the residue is purified by Silica gel flash chromatography, using Hexane/EtOAc 8:2 as eluent, to obtain the title compound (2.6 g, 86% yield).

UPLC-MS (Method 1): $R_t$=1.34 min

MS (ES+): m/z=345-347 $[M+H]^+$

Example 65a

Single Enantiomer; S Configuration

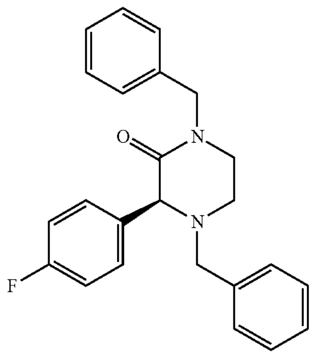 [SMILES: O=C1[C@H](c2ccc(F)cc2)N(Cc2ccccc2)CCN1Cc1ccccc1]

N,N'-dibenzylethylenediamine (2.1 g, 8.6 mmol) is added to a stirred solution of example 64a (2.5 g, 7.2 mmol), tetrabutylammonium iodide (2.7 g, 7.2 mmol) and N,N-Diisopropylethylamine (1.3 ml, 7.4 mmol) in 60 ml of DCM and the reaction mixture is stirred 16 hours. Water is added, the organic phase is separated, dried over anhydrous $Na_2SO_4$ and concentrated under reduced pressure; the residue is purified by Silica gel flash chromatography, using Hexane/EtOAc/MeOH 70:30:1 as eluent, to obtain the title compound (2.2 g, 83% yield).

HPLC-MS (Method 17): $R_t$=5.13 min

MS (ES+): m/z=375 $[M+H]^+$

Chiral HPLC (Method 24): $R_t$=29.7 min

Example 66a

Single Enantiomer; S Configuration

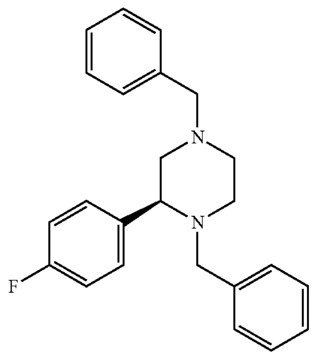 [SMILES: Fc1ccc([C@H]2CN(Cc3ccccc3)CCN2Cc2ccccc2)cc1]

Borane-Methylsulfide complex (2.0 M THF solution, 1.1 ml, 2.3 mmol) is added dropwise to a stirred solution of example 65a (160 mg, 0.4 mmol) in 6 ml of anhydrous THF under nitrogen atmosphere and the reaction mixture is refluxed 8 hours; after cooling to room temperature, 2 ml of MeOH and 0.5 ml of concentrated HCl solution are added and the reaction mixture is refluxed during 1 hour. Solvent is concentrated under reduced pressure, the residue is partitioned between water and $Et_2O$ then the aqueous layer is separated and basified by addition of $NH_4OH$ until pH 10 and extracted with DCM. The organic layer is dried over anhydrous $Na_2SO_4$ and concentrated under reduced pressure to obtain the title compound (110 mg).

UPLC-MS (Method 1): $R_t$=1.13 min

MS (ES+): m/z=361 $[M+H]^+$

Chiral HPLC (Method 24): $R_t$=8.0 min

Example 67a

Single Enantiomer; S Configuration

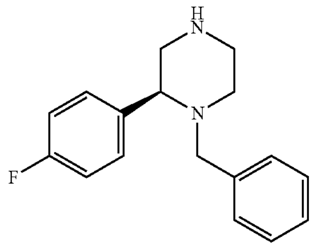 [SMILES: Fc1ccc([C@H]2CNCCN2Cc2ccccc2)cc1]

1-chloroethylchloroformate (0.15 ml, 1.4 mmol) is added to a stirred solution of example 66a (100 mg, 0.3 mmol) dissolved in 2 ml of anhydrous dichloroethane and the reaction mixture is stirred 10 hours. The solvent is concentrated under reduced pressure and 3 ml of MeOH are added to the residue then the reaction mixture is heated at 80° C. 2 hours. Solvent is removed under reduced pressure, the residue is dissolved in water and basified by addition of $NH_4OH$ until pH 10 and the mixture is extracted with DCM; the organic layer is separated, dried over a phase-separator cartridge and concentrated under reduced pressure to obtain the title compound (65 mg).

UPLC-MS (Method 1): $R_t$=0 9 min

MS (ES+): m/z=271 $[M+H]^+$

Example 68a

Single Enantiomer; S Configuration

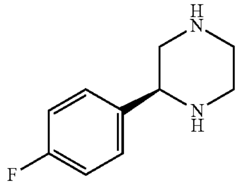 [SMILES: Fc1ccc([C@H]2CNCCN2)cc1]

Palladium hydroxide (40 mg) is added to a stirred solution of example 67a (50 mg, 0.2 mmol) dissolved in glacial acetic acid and the reaction mixture is hydrogenated into a Parr apparatus at 60 PSI for 3 hours. The catalyst is filtered out over a celite pad and the filtrate is concentrated under reduced pressure; the residue is treated with water, basified by addition of $NH_4OH$ (pH 10) and the mixture is extracted with DCM. The organic phase is separated, dried and concentrated under reduced pressure to obtain the title compound (30 mg).

UPLC-MS (Method 1): $R_t$=0.26 min

MS (ES+): m/z=181 $[M+H]^+$

Example 69a

Single Enantiomer; S Configuration

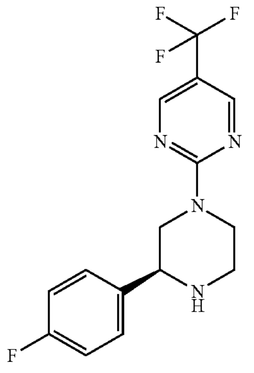 [SMILES: Fc1ccc([C@H]2CN(c3ncc(C(F)(F)F)cn3)CCN2)cc1]

N,N-Diisopropylethylamine (30 μl, 0.2 mmol) is added to a stirred solution of example 68a (30 mg, 0.2 mmol) and 2-Chloro-5-(Trifluoromethyl)pyrimidine (30 mg, 0.2 mmol) and the reaction mixture is heated in a microwave reactor 2 hours at 100° C. The crude is partitioned between water and EtOAc then the organic layer is separated, washed with water, dried over anhydrous $Na_2SO_4$ and concentrated under reduced pressure; the residue is purified by Silica gel flash chromatography, using DCM/MeOH 100:2 as eluent, to obtain the title compound (35 mg, 64% yield).

UPLC-MS (method 1): $R_t$=0.89 min

MS (ES+): m/z=327 $[M+H]^+$

Example 70a

Single Enantiomer

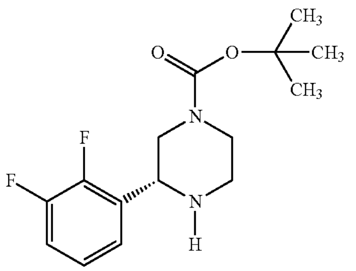 [SMILES: CC(C)(C)OC(=O)N1CCN[C@H](c2cccc(F)c2F)C1]

D-(−)-Mandelic acid (19 g, 124.7 mmol) is added to a solution of racemic 3-(2,3-Difluoro-phenyl)-piperazine-1-carboxylic acid tert-butyl ester (37.2 g, 124.7 mmol, prepared in large scale as described for the example 40c) dissolved in 300 ml of EtOAc; after 30 minutes stirring, the reaction mixture is cooled with an ice/water bath to about 0° C. and stirred 1 hour. The white precipitate is filtered and then cristallized 5 times in refluxing EtOAc; 17.5 g of the mandelate salt are obtained; the chiral HPLC analysis performed on the free base gives enatiomeric excess >98%,. Mother-liquors are collected, the solvent is removed under reduced pressure and the residue is cristallized, as described above, in EtOAc. 3.5 g of salt having enantiomeric excess >98% are obtained. The diastereomeric salts are combined together (21 g) and treted with an aqueous NaOH solution. The aqueous layer is extracted with EtOAc to obtain the title compound as free base (13.3 g).

HPLC-MS (Method 27): $R_t$=4.43 min

MS (ES+): m/z=299 $[M+H]^+$

Chiral HPLC (Method 25): $R_t$=6.88 min

Example 71a

Single Enantiomer

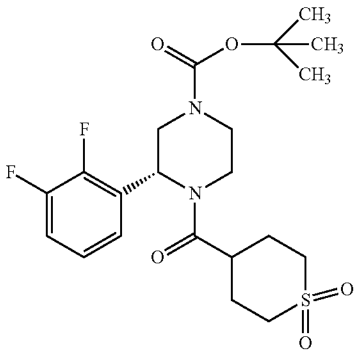 [SMILES: CC(C)(C)OC(=O)N1CCN(C(=O)C2CCS(=O)(=O)CC2)[C@H](c2cccc(F)c2F)C1]

Tetrahydro-2H-thiopyran-4-carboxilic acid 1,1-dioxide (9.53 g, 53.5 mmol), 1-Hydroxy-7-azabenzotriazole (7.3 g, 53.5 mmol) and N-(3-Dimethylaminopropyl)-N'-Ethylcarbodiimidehydrochloride (13.7 g, 71.3 mmol) are added to a solution of example 70a (13.3 g, 44.6 mmol) dissolved in 30 ml of anhydrous DMF and 140 ml of anhydrous THF under nitrogen atmosphere; the reaction mixture is stirred 72 hours then THF is evaporated under reduced pressure and the residue is partitioned between aqueous $NaHCO_3$ solution and EtOAc. The organic layer is separated, dried over anhydrous $Na_2SO_4$ and concentrated under reduced pressure. The crude is suspended in isopropyl ether, stirred, cooled with an ice-water bath and the solid is filtered to obtain the title compound (17.0 g).

HPLC-MS (Method 10): $R_t$=4.43 min

MS (ES+): m/z=403$[M-56+H]^+$ and 359 $[M-100+H]^+$

Chiral HPLC (Method 25): $R_t$=13.27 min

Example 72a

Single Enantiomer

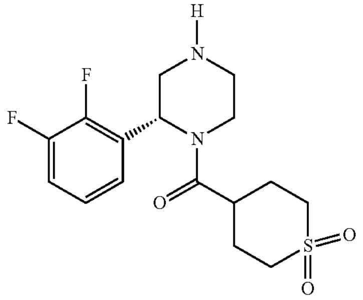 [SMILES: O=C(C1CCS(=O)(=O)CC1)N1CCNC[C@H]1c1cccc(F)c1F]

The example 72a is synthesized as described for example 44b starting from example 71a (17.0 g, 37.1 mmol) using HCl (4N dioxane solution, 140 ml, 560 mmol) and 300 ml of 1,4-dioxane. The obtained hydrochloride salt is dissovled in water, washed with aqueous NaOH solution and extracted with DCM to obtain the title compound (12.2 g).

HPLC-MS (Method 27): $R_t$=2.50 min

MS (APCI+): m/z=359 $[M+H]^+$

Chiral HPLC (Method 9): $R_t$=11.66 min

EXEMPLARY EMBODIMENTS

Example 1

Racemic Mixture

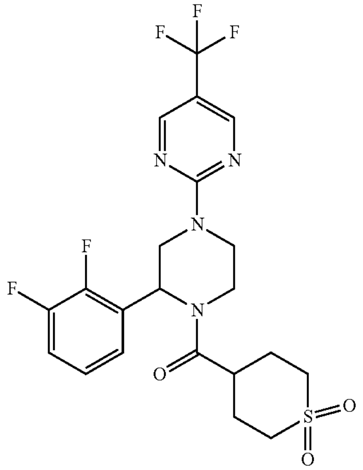 [SMILES: O=C(C1CCS(=O)(=O)CC1)N1CCN(c2ncc(C(F)(F)F)cn2)CC1c1cccc(F)c1F]

Example 44k (300 mg, 0.8 mmol), 2-Chloro-5-(trifluoromethyl)pyrimidine (199 mg, 1.09 mmol) and N,N-diisopropylethylamine (287 μl, 1.67 mmol) are dissolved in 4 ml of anhydrous DMSO and heated in a microwave reactor during 30 minutes at 150° C. The crude is partitioned between EtOAc and water, the organic layer is dried over anhydrous $Na_2SO_4$ then concentrated under reduced pressure to obtain 360 mg of the title product.

HPLC-MS (Method 10): $R_t$=3.54 min

MS (ES+): m/z=505 $[M+H]^+$

The enantiomers are obtained by HPLC using a chiral stationary phase.

Method for Separation:

HPLC apparatus type: Waters 600 Pump; column: Daicel Chiralpack AD-H, 5.0 μm, 250 mm×20 mm; method: eluent hexane/IPA 70:30; flow rate: 15 mL/min, Temperature: 25° C.; UV Detection: 254 nm Example of Separation by Chiral HPLC:

Submitted to separation: 665 mg of Example 1 prepared as described above;

Obtained: 157 mg of enantiomer 1 (Exp. 2) and 40 mg of enantiomer 2 (Exp. 3)

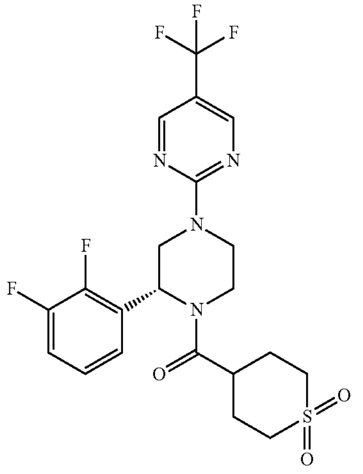

Example 2: enantiomer 1

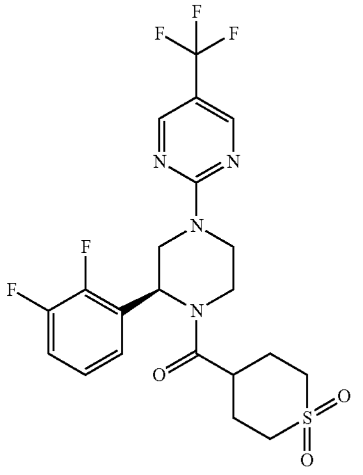 [SMILES: O=C(C1CCS(=O)(=O)CC1)N1CCN(c2ncc(C(F)(F)F)cn2)C[C@@H]1c1cccc(F)c1F]

Example 3: enantiomer 2

| Example | Chiral HPLC $R_t$ [min] | HPLC-MS (Method 10): $R_t$ [min] | MS (ES+): m/z |
|---|---|---|---|
| Exp. 2 | 10.88 (Method 9) | 3.57 | 505 |
| Exp. 3 | 12.19 (Method 9) | 3.57 | 505 |

Alternative Synthesis of Example 2 (Single Enantiomer)

A solution of example 72a (12.2 g, 33.9 mmol), N,N-Diisopropylethylamine (11.6 ml, 67.8 mmol) and 2-Chloro-5-(Trifluoromethyl)pyrimidine (6.8 g, 37.3 mmol) in 100 ml of anhydrous DMSO is heated at 100° C. and stirred 30 minutes. After cooling to room temperature, water is added and the new formed precipitate is filtered and washed with water and with n-hexane. The solid is dissolved in EtOAc and washed with 10% aqueous citric acid solution; the organic layer is separated, dried over anhydrous $Na_2SO_4$ and concentrated under reduced pressure. The residue is suspended in diethylether and filtered; then the resulting solid is purified by silica flash chromatography, using cyclohexane/EtOAc 1:1 to 20:80 as eluent, to obtain the title compound (15.0 g, 88% yield).

HPLC-MS (Method 10): $R_t$=3.52 min

MS (ES+): m/z=505 $[M+H]^+$

Chiral HPLC (Method 9): $R_t$=10.88 min

Example 4

Racemic Mixture

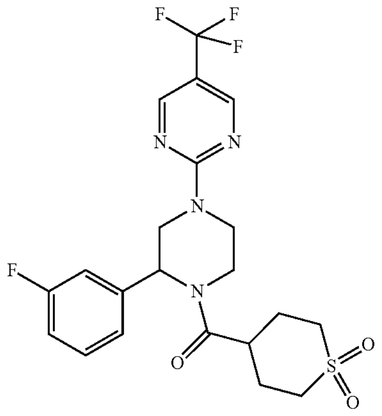 [SMILES: O=C(C1CCS(=O)(=O)CC1)N1CCN(c2ncc(C(F)(F)F)cn2)CC1c1cccc(F)c1]

Example 4 is synthesized as described for example 1 starting from example 44b (free base, 400 mg, 1.18 mmol) instead of example 44k, 2-Chloro-5-(trifluoromethyl)pyrimidine (279 mg, 1.53 mmol), N,N-diisopropylethylamine (402 μl, 2.35 mmol) and 5 ml of anhydrous DMSO. The mixture is heated in a microwave reactor during 30 minutes at 150° C. The crude is purified by Silica gel flash chromatography, using Cyclohexane/EtOAc 70:30 to 20:80 as eluent, to obtain 559 mg (98% yield) of product.

HPLC-MS (Method 10): $R_t$=3.53 min

MS (ES+): m/z=487 $[M+H]^+$

The enantiomers are obtained by HPLC separation using a chiral stationary phase.

Method for Separation:

HPLC apparatus type: Waters 600 Pump; column: Daicel Chiralpack AD-H, 5.0 μm, 250 mm×20 mm; method: eluent hexane/IPA 70:30; flow rate: 15 mL/min, Temperature: 25° C.; UV Detection: 254 nm Example of Separation by Chiral HPLC:

Submitted to separation: 500 mg of Example 4 prepared as described above; Obtained: 103 mg of enantiomer 1 (Exp. 5) and 122 mg of enantiomer 2 (Exp. 6)

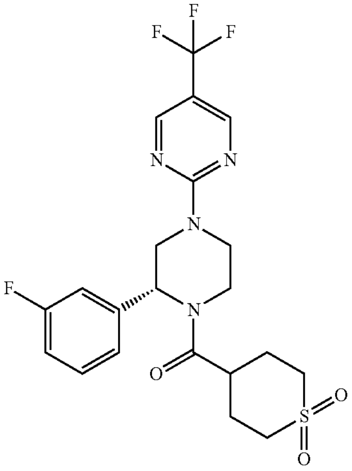

Example 5: enantiomer 1

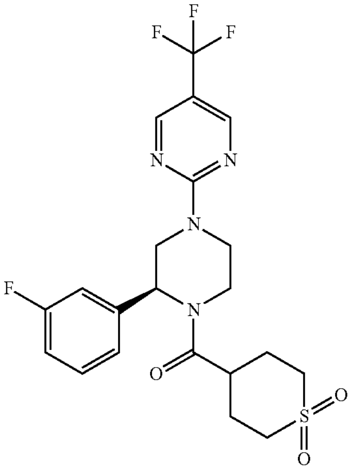

Example 6: enantiomer 2

| Example | Chiral HPLC $R_t$ [min] | HPLC-MS (Method 10): $R_t$ [min] | MS (ES+): m/z |
|---|---|---|---|
| Exp. 5 | 10.62 (Method 9) | 3.58 | 487 |
| Exp. 6 | 11.99 (Method 9) | 3.57 | 487 |

Example 7

Racemic Mixture

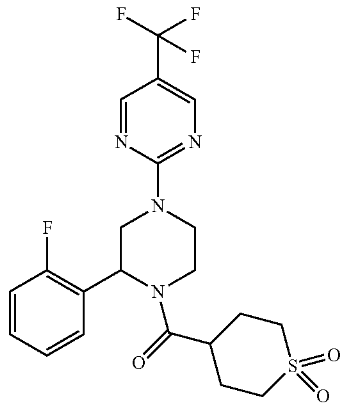 [SMILES: O=C(C1CCS(=O)(=O)CC1)N1CCN(c2ncc(C(F)(F)F)cn2)CC1c1ccccc1F]

Example 7 is synthesized as described for example 1 starting from example 44g (560 mg, 1.65 mmol) instead of example 44k, 2-Chloro-5-(trifluoromethyl)pyrimidine (400 mg, 2.19 mmol), N,N-diisopropylethylamine (570 μl, 3.33 mmol) dissolved in anhydrous DMSO. The mixture is heated in a microwave reactor during 1 hour at 100° C. to obtain, after purification by Silica gel flash chromatography using EtOAc/Hexane/MeOH 70:30:1 as eluent, 680 mg (85% yield) of product.

HPLC-MS (Method 10): $R_t$=3.48 min

MS (ES+): m/z=487 $[M+H]^+$

The enantiomers are obtained by HPLC separation using a chiral stationary phase.

Method for Separation:

HPLC apparatus type: Waters 600 Pump; column: Daicel Chiralpack AD-H, 5.0 μm, 250 mm×20 mm; method: eluent hexane/IPA 70:30; flow rate: 15 mL/min, Temperature: 25° C.; UV Detection: 254 nm Example of Separation by Chiral HPLC:

Submitted to separation: 680 mg of Example 7 prepared as described above; Obtained: 190 mg of enantiomer 1 (Exp. 8) and 90 mg of enantiomer 2 (Exp. 9)

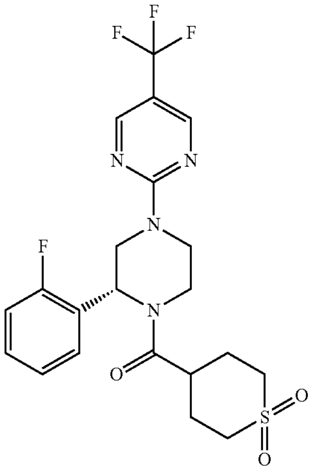 [SMILES: O=C(C1CCS(=O)(=O)CC1)N1CCN(c2ncc(C(F)(F)F)cn2)C[C@H]1c1ccccc1F]

Example 8: enantiomer 1

-continued

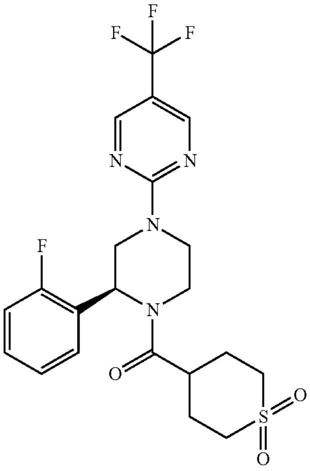 [SMILES: O=C(C1CCS(=O)(=O)CC1)N1CCN(c2ncc(C(F)(F)F)cn2)C[C@@H]1c1ccccc1F]

Example 9: enantiomer 2

| Example | Chiral HPLC $R_t$ [min] | HPLC-MS (Method 10): $R_t$ [min] | MS (ES+): m/z |
|---|---|---|---|
| Exp. 8 | 11.36 (Method 9) | 3.44 | 487 |
| Exp. 9 | 14.82 (Method 9) | 3.43 | 487 |

Example 10

Racemic Mixture

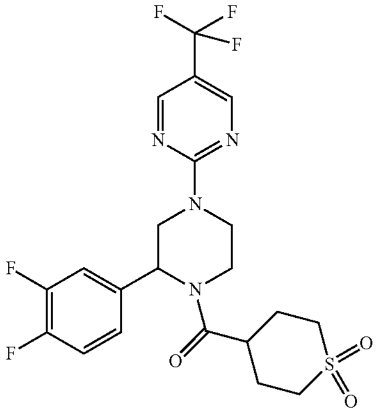 [SMILES: O=C(C1CCS(=O)(=O)CC1)N1CCN(c2ncc(C(F)(F)F)cn2)CC1c1ccc(F)c(F)c1]

Example 10 is synthesized as described for example 1 starting from example 44i (415 mg, 1.16 mmol) instead of example 44k, 2-Chloro-5-(trifluoromethyl)pyrimidine (280 mg, 1.53 mmol), N,N-diisopropylethylamine (396 μl, 2.31 mmol) and 6 ml of anhydrous DMSO; the mixture is heated in a microwave reactor during 30 minutes at 140° C. to obtain 514 mg of the desired product.

HPLC-MS (Method 10): $R_t$=3.60 min

MS (ES+): m/z=505 $[M+H]^+$

The enantiomers are obtained by HPLC separation using a chiral stationary phase.

Method for Separation:

HPLC apparatus type: Waters 600 Pump; column: Daicel Chiralpack IA, 5.0 μm, 250 mm×20 mm; method: eluent hexane/IPA 70:30; flow rate: 15 mL/min, Temperature: 25° C.; UV Detection: 254 nm Example of Separation by Chiral HPLC:

Submitted to separation: 514 mg of Example 10 prepared as described above; Obtained: 190 mg of enantiomer 1 (Exp. 11) and 100 mg of enantiomer 2 (Exp. 12)

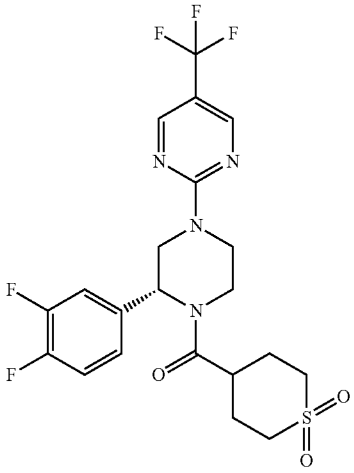 [SMILES: O=C(C1CCS(=O)(=O)CC1)N1CCN(c2ncc(C(F)(F)F)cn2)C[C@H]1c1ccc(F)c(F)c1]

Example 11: enantiomer 1

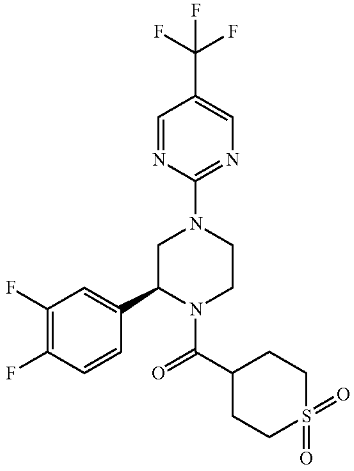 [SMILES: O=C(C1CCS(=O)(=O)CC1)N1CCN(c2ncc(C(F)(F)F)cn2)C[C@@H]1c1ccc(F)c(F)c1]

Example 12: enantiomer 2

| Example | Chiral HPLC $R_t$ [min] | HPLC-MS (Method 10): $R_t$ [min] | MS (ES+): m/z |
|---|---|---|---|
| Exp. 11 | 15.55 (Method 15) | 3.57 | 505 |
| Exp. 12 | 17.57 (Method 15) | 3.58 | 505 |

Example 13

Racemic Mixture

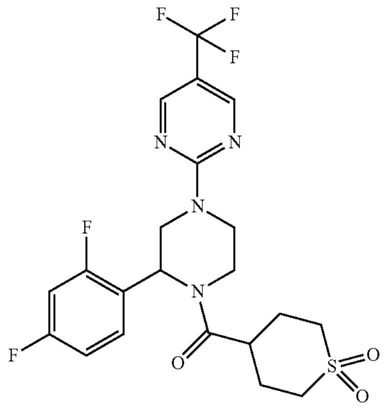 [SMILES: O=C(C1CCS(=O)(=O)CC1)N1CCN(c2ncc(C(F)(F)F)cn2)CC1c1ccc(F)cc1F]

Example 13 is synthesized as described for example 1 starting from example 44f (80 mg, 0.22 mmol) instead of example 44k, 2-Chloro-5-(trifluoromethyl)pyrimidine (60 mg, 0.33 mmol), N,N-diisopropylethylamine (75 μl, 0.44 mmol) and 1 ml of anhydrous DMSO. The mixture is heated in a microwave reactor during 30 minutes 130° C. After purification by preparative HPLC-MS, 84 mg (75% yield) of product are obtained.

HPLC-MS (Method 5): $R_t$=3.08 min

MS (APCI+): m/z=505 $[M+H]^+$

The enantiomers are obtained by HPLC separation using a chiral stationary phase.

Method for Separation:

HPLC apparatus type: Waters 600 Pump; column: Daicel Chiralpack AD-H, 5.0 μm, 250 mm×20 mm; method: eluent hexane/IPA 70:30; flow rate: 15 mL/min, Temperature: 25° C.; UV Detection: 254 nm Example of Separation by Chiral HPLC:

Submitted to separation: 70 mg of Example 13 prepared as described above; Obtained: 26 mg of enantiomer 1 (Exp. 14) and 20 mg of enantiomer 2 (Exp. 15)

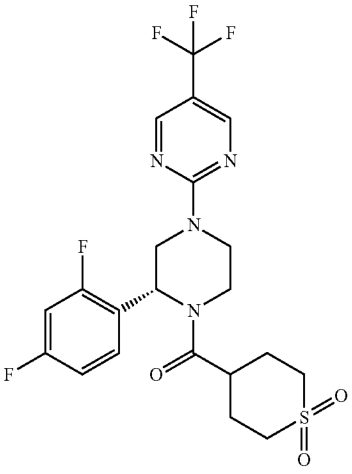 [SMILES: O=C(C1CCS(=O)(=O)CC1)N1CCN(c2ncc(C(F)(F)F)cn2)C[C@H]1c1ccc(F)cc1F]

Example 14: enantiomer 1

-continued

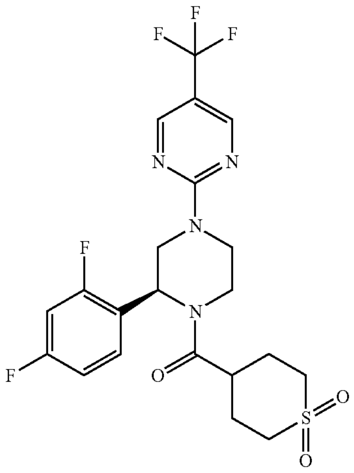 [SMILES: O=C(C1CCS(=O)(=O)CC1)N1CCN(c2ncc(C(F)(F)F)cn2)C[C@@H]1c1ccc(F)cc1F]

Example 15: enantiomer 2

| Example | Chiral HPLC $R_t$ [min] | HPLC-MS (Method 10): $R_t$ [min] | MS (ES+): m/z |
|---|---|---|---|
| Exp. 14 | 11.76 (Method 9) | 3.58 | 505 |
| Exp. 15 | 16.59 (Method 9) | 3.56 | 505 |

Example 16

Racemic Mixture

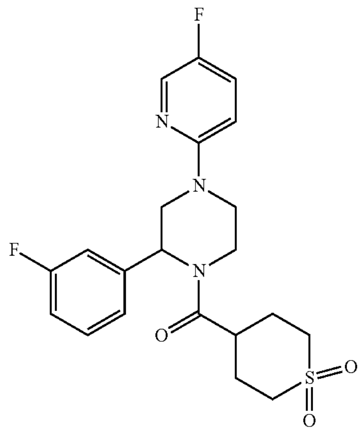 [SMILES: O=C(C1CCS(=O)(=O)CC1)N1CCN(c2ccc(F)cn2)CC1c1cccc(F)c1]

Example 44b (70 mg of free base, 0.21 mmol), 2-Chloro-5-Fluoropyridine (25 μl, 0.25 mmol), X-Phos (39 mg, 0.08 mmol), Tris(dibenzylideneacetone)dipalladium(0) (38 mg, 0.04 mmol) and sodium tert-butoxide (39 mg, 0.41 mmol) are suspended under nitrogen atmosphere in 2 ml of previously degassed dioxane; the reaction mixture is heated in a microwave reactor, at 90° C., 2 hours.

The crude product is partitioned between water and EtOAc, the organic layer is separated, dried and concentrated under reduced pressure; the residue is purified by preparative HPLC-MS to obtain the title compound (30 mg, 34% yield)

HPLC-MS (Method 10): $R_t$=3.25 min

MS (ES+): m/z=436 $[M+H]^+$

Example 17

Racemic Mixture

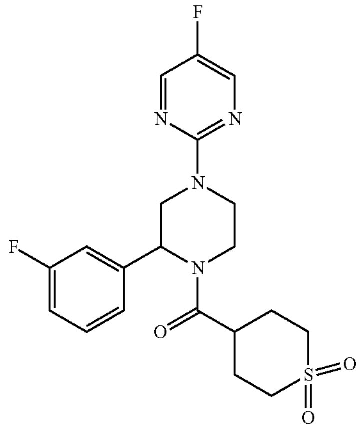 [SMILES: O=C(C1CCS(=O)(=O)CC1)N1CCN(c2ncc(F)cn2)CC1c1cccc(F)c1]

Example 17 is synthesized as described for example 1 starting from example 44b (70 mg of free base, 0.21 mmol) instead of example 44k, 2-Chloro-5-Fluoropyrimidine (41 μl, 0.33 mmol) instead of 2-Chloro-5-(trifluoromethyl)pyrimidine, N,N-diisopropylethylamine (71 μl, 0.41 mmol) and 2 ml of anhydrous DMSO The reaction mixture is heated in a microwave reactor during 2 hours at 120° C. The crude product is purified by preparative HPLC-MS to obtain the title compound (62 mg, 69% yield).

HPLC-MS (Method 10): $R_t$=3.12 min

MS (ES+): m/z=437 $[M+H]^+$

Example 18

Racemic Mixture

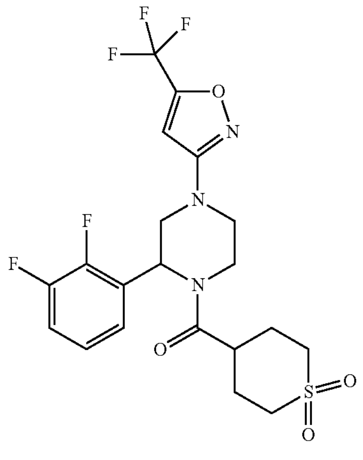 [SMILES: O=C(C1CCS(=O)(=O)CC1)N1CCN(c2cc(C(F)(F)F)on2)CC1c1cccc(F)c1F]

N,N-diisopropylethylamine (72 μl, 0.42 mmol) followed, portionwise, by 1,1-dibromoformaldoxime (85 mg, 0.42 mmol) are added into a cooled solution (−20° C.) of example 44k (150 mg, 0.42 mmol) dissolved in 5 ml of anhydrous THF, under nitrogen atmosphere; the reaction mixture is stirred 1.5 hours and the temperature increased to 0° C. 2-Bromo-3,3,3-trifluoropropene (215 μl, 2.09 mmol) is added dropwise followed by triethylamine (76 μl, 0.54 mmol) and the reaction is stirred 1 hour at 0° C. and then 24 hours at room temperature. The crude is diluted with EtOAc and washed with water; the organic phase is concentrated under reduced pressure and the residue is purified by preparative HPLC-MS to obtain the title compound (41 mg, 20% yield).

HPLC-MS (Method 10): $R_t$=3.44 min

MS (ES+): m/z=494 $[M+H]^+$

Example 19

Racemic Mixture

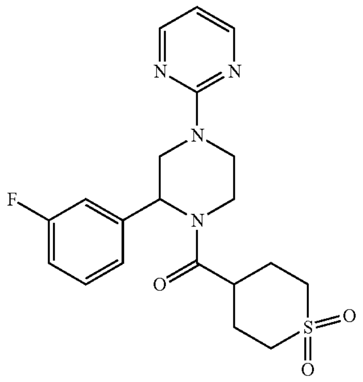 [SMILES: O=C(C1CCS(=O)(=O)CC1)N1CCN(c2ncccn2)CC1c1cccc(F)c1]

Example 19 is synthesized as described for example 1 starting from example 44b (80 mg of free base, 0.23 mmol) instead of example 44k, 2-Chloro-Pyrimidine (40 mg, 0.35 mmol) instead of 2-Chloro-5-(trifluoromethyl)pyrimidine, N,N-diisopropylethylamine (80 μl, 0.46 mmol) and 1 ml of anhydrous DMSO. The reaction mixture is heated in a microwave reactor during 30 minutes at 130° C. After the work-up, the crude product is purified by preparative HPLC-MS to obtain the title compound (43 mg, 45% yield).

HPLC-MS (Method 5): $R_t$=2.52 min

MS (APCI+): m/z=419 $[M+H]^+$

Example 20

Racemic Mixture

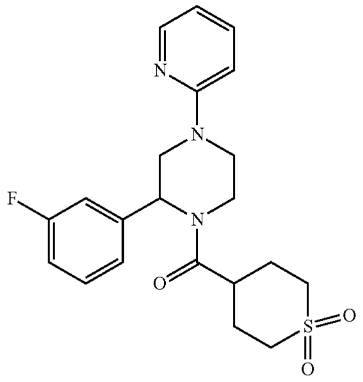 [SMILES: O=C(C1CCS(=O)(=O)CC1)N1CCN(c2ccccn2)CC1c1cccc(F)c1]

Example 20 is synthesized as described for example 16 starting from example 44b (80 mg of free base, 0.24 mmol), 2-Bromopyridine (27 μl, 0.28 mmol) instead of 2-Chloro-5-Fluoropyridine, X-Phos (45 mg, 0.09 mmol), Tris(dibenzylideneacetone)dipalladium(0) (43 mg, 0.05 mmol), sodium tert-butoxide (45 mg, 0.47 mmol) in degassed Dioxane. The reaction mixture is heated in a microwave reactor at 100° C. during 2 hours. After the work-up, the crude product is purified by preparative HPLC-MS to obtain, the title compound (32 mg, 33% yield).

HPLC-MS (Method 5): $R_t$=2.70 min

MS (APCI+): m/z=418 [M+H]$^+$

Example 21

Racemic Mixture

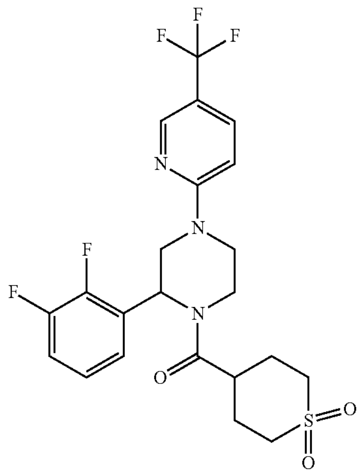 [SMILES: O=C(C1CCS(=O)(=O)CC1)N1CCN(c2ccc(C(F)(F)F)cn2)CC1c1cccc(F)c1F]

Example 21 is synthesized as described for example 1 starting from example 44k (100 mg, 0.28 mmol), 2-Fluoro-5-(trifluoromethyl)Pyridine (51 μl, 0.42 mmol) instead of 2-Chloro-5-(trifluoromethyl)pyrimidine, N,N-diisopropylethylamine (96 μl, 0.56 mmol) in DMSO. The reaction mixture is heated in a microwave reactor during 30 minutes at 130° C.; the crude product is purified by preparative HPLC-MS to obtain the title compound (92 mg, 66% yield).

HPLC-MS (Method 10): $R_t$=3.67 min

MS (ES+): m/z=504 [M+H]$^+$

Example 22

Racemic Mixture

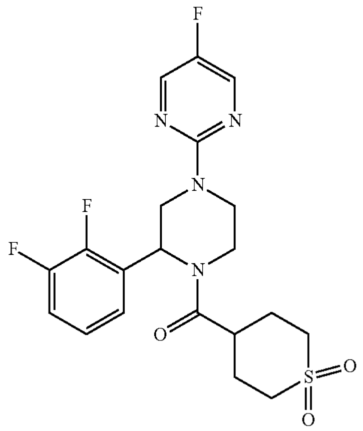 [SMILES: O=C(C1CCS(=O)(=O)CC1)N1CCN(c2ncc(F)cn2)CC1c1cccc(F)c1F]

Example 22 is synthesized as described for example 1 starting from example 44k (70 mg, 0.21 mmol), 2-Chloro-5-Fluoropyrimidine (41 μl, 0.33 mmol) instead of 2-Chloro-5-(trifluoromethyl)pyrimidine, N,N-diisopropylethylamine (76 μl, 0.45 mmol) and 1 ml of anhydrous DMSO. The reaction mixture is heated in a microwave reactor during 30 minutes at 130° C. After the work-up, the crude product is purified by preparative HPLC-MS to obtain the title compound (67 mg, 66% yield).

HPLC-MS (Method 10): $R_t$=3.25 min

MS (ES+): m/z=455 [M+H]$^+$

Example 23

Racemic Mixture

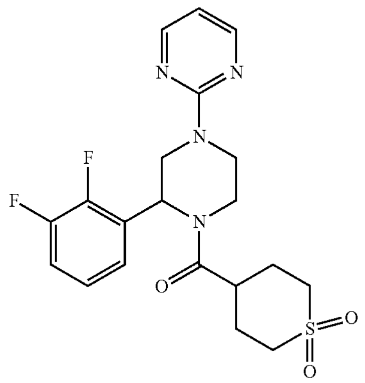 [SMILES: O=C(C1CCS(=O)(=O)CC1)N1CCN(c2ncccn2)CC1c1cccc(F)c1F]

Example 23 is synthesized as described for example 1 starting from example 44k (80 mg, 0.23 mmol), 2-Chloro-Pyrimidine (38 mg, 0.33 mmol) instead of 2-Chloro-5-(trifluoromethyl)pyrimidine, N,N-diisopropylethylamine (77 μl, 0.45 mmol) and 1 ml of anhydrous DMSO. The reaction mixture is heated in a microwave reactor during 30 minutes at 130° C. After the work-up, the crude product is purified by preparative HPLC-MS to obtain the title compound (82 mg, 84% yield).

HPLC-MS (Method 10): $R_t$=2.90 min

MS (ES+): m/z=437 [M+H]$^+$

Example 24

Racemic Mixture

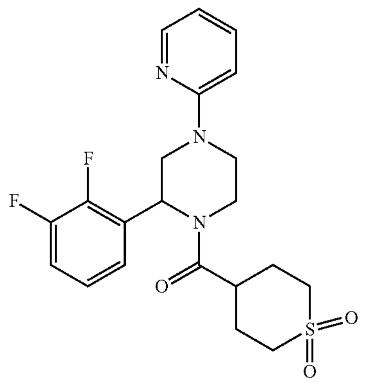 [SMILES: O=C(C1CCS(=O)(=O)CC1)N1CCN(c2ccccn2)CC1c1cccc(F)c1F]

Example 24 is synthesized as described for example 16 starting from example 44k (100 mg, 0.28 mmol) instead of example 44b, 2-Bromopyridine (32 μl, 0.33 mmol) instead of 2-Chloro-5-Fluoropyridine, X-Phos (53 mg, 0.11 mmol), Tris (dibenzylideneacetone)dipalladium(0) (51 mg, 0.06 mmol), sodium tert-butoxide (54 mg, 0.56 mmol) and degassed Dioxane. The reaction mixture is heated in a microwave reactor at 100° C. during 2 hours. After the work-up, the crude product is purified by preparative HPLC-MS to obtain the title compound (55 mg, 45% yield).

HPLC-MS (Method 5): $R_t$=2.72 min

MS (APCI+): m/z=436 [M+H]$^+$

Example 25

Racemic Mixture

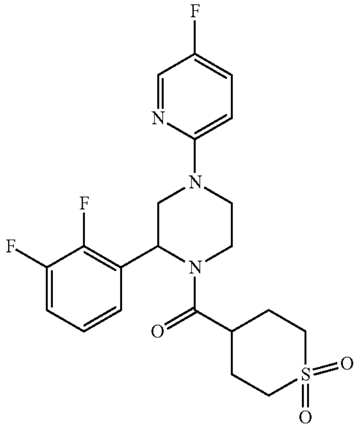 [SMILES: O=C(C1CCS(=O)(=O)CC1)N1CCN(c2ccc(F)cn2)CC1c1cccc(F)c1F]

Example 25 is synthesized as described for example 16 starting from example 44k (120 mg, 0.33 mmol) instead of example 44b, 2-Chloro-5-Fluoropyridine (40 µl, 0.39 mmol), X-Phos (63 mg, 0.13 mmol), Tris(dibenzylideneacetone)dipalladium(0) (60 mg, 0.07 mmol), sodium tert-butoxide (63 mg, 0.66 mmol) and degassed Dioxane. The reaction mixture is heated in a microwave reactor at 100° C. during 2 hours. After the work-up, the crude product is purified by preparative HPLC-MS to obtain the title compound (64 mg, 43% yield).

HPLC-MS (Method 5): $R_t$=2.91 min

MS (APCI+): m/z=454 $[M+H]^+$

Example 26

Racemic Mixture

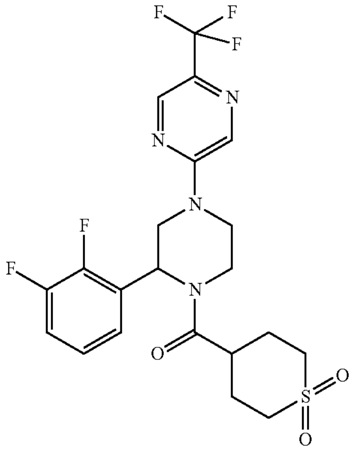 [SMILES: O=C(C1CCS(=O)(=O)CC1)N1CCN(c2cnc(C(F)(F)F)cn2)CC1c1cccc(F)c1F]

Example 26 is synthesized as described for example 1 starting from example 44k (70 mg, 0.18 mmol), 2-Bromo-5-(trifluoromethyl)pyrazine (60 mg, 0.26 mmol) instead of 2-Chloro-5-(trifluoromethyl)pyrimidine, N,N-diisopropylethylamine (60 µl, 0.35 mmol) and 1 ml of anhydrous DMSO. The reaction mixture is heated in a microwave reactor during 30 minutes at 150° C. After the work-up, the crude product is purified by preparative HPLC-MS to obtain the title compound (43 mg, 48% yield).

HPLC-MS (Method 10): $R_t$=3.52 min

MS (ES+): m/z=505 $[M+H]^+$

Example 27

Racemic Mixture

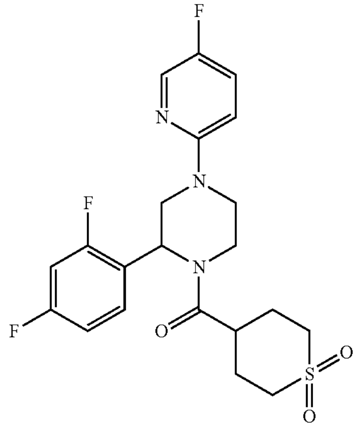 [SMILES: O=C(C1CCS(=O)(=O)CC1)N1CCN(c2ccc(F)cn2)CC1c1ccc(F)cc1F]

Example 27 is synthesized as described for example 16 starting from example 44f (80 mg, 0.22 mmol) instead of example 44b, 2-Chloro-5-Fluoropyridine (35 mg, 0.26 mmol), X-Phos (42 mg, 0.09 mmol), Tris(dibenzylideneacetone)dipalladium(0) (40 mg, 0.04 mmol), sodium tert-butoxide (42 mg, 0.44 mmol) and degassed Dioxane. The reaction mixture is heated in a microwave reactor at 100° C. during 2 hours. After the work-up, the crude product is purified by Silica gel flash chromatography using cyclohexane/EtOAc 30:70 to 0:100 as eluent to obtain the title compound (35 mg, 35% yield).

HPLC-MS (Method 10): $R_t$=3.29 min

MS (ES+): m/z=454 $[M+H]^+$

Example 28

Racemic Mixture

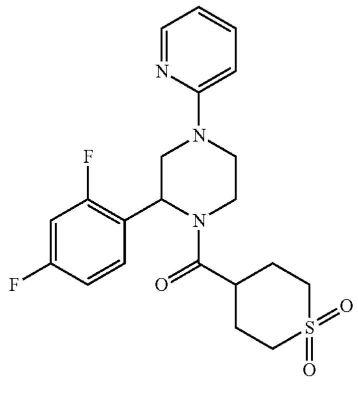 [SMILES: O=C(C1CCS(=O)(=O)CC1)N1CCN(c2ccccn2)CC1c1ccc(F)cc1F]

Example 28 is synthesized as described for example 16 starting from example 44f (80 mg, 0.22 mmol) instead of example 44b, 2-Bromopyridine (25 µl, 0.26 mmol) instead of 2-Chloro-5-Fluoropyridine, X-Phos (42 mg, 0.09 mmol), Tris(dibenzylideneacetone)dipalladium(0) (40 mg, 0.04 mmol), sodium tert-butoxide (42 mg, 0.44 mmol) and degassed Dioxane. The reaction mixture is heated in a microwave reactor at 100° C. during 2 hours. After the work-up, the crude product is purified by Silica gel flash chromatography using cyclohexane/EtOAc 20:80 to 0:100 as eluent to obtain the title compound (57 mg, 59% yield).

HPLC-MS (Method 5): $R_t$=2.72 min

MS (APCI+): m/z=436 $[M+H]^+$

Example 29

Racemic Mixture

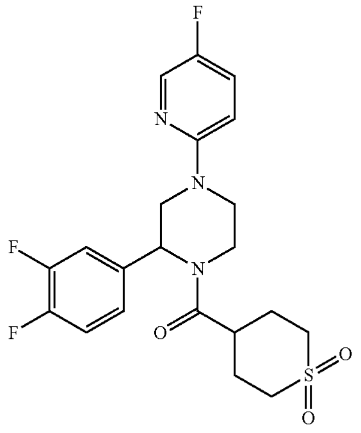 [SMILES: O=C(C1CCS(=O)(=O)CC1)N1CCN(c2ccc(F)cn2)CC1c1ccc(F)c(F)c1]

Example 29 is synthesized as described for example 16 starting from example 44i (80 mg, 0.22 mmol) instead of example 44b, 2-Chloro-5-Fluoropyridine (35 mg, 0.26 mmol), X-Phos (42 mg, 0.09 mmol), Tris(dibenzylideneacetone)dipalladium(0) (40 mg, 0.04 mmol), sodium tert-butoxide (42 mg, 0.44 mmol) and degassed Dioxane. The reaction mixture is heated in a microwave reactor at 100° C. during 2 hours. After the work-up, the crude product is purified by Silica gel flash chromatography using cyclohexane/EtOAc 30:70 to 0:100 as eluent to obtain the title compound (59 mg, 58% yield).

HPLC-MS (Method 10): $R_t$=3.38 min

MS (ES+): m/z=454 $[M+H]^+$

Example 30

Racemic Mixture

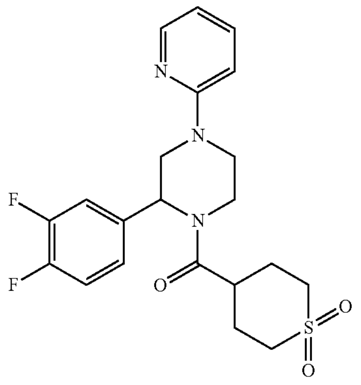 [SMILES: O=C(C1CCS(=O)(=O)CC1)N1CCN(c2ccccn2)CC1c1ccc(F)c(F)c1]

Example 30 is synthesized as described for example 16 starting from example 44i (80 mg, 0.22 mmol) instead of example 44b, 2-Bromopyridine (32 μl, 0.26 mmol) instead of 2-Chloro-5-Fluoropyridine, X-Phos (42 mg, 0.09 mmol), Tris(dibenzylideneacetone)dipalladium(0) (40 mg, 0.04 mmol), sodium tert-butoxide (42 mg, 0.44 mmol) and degassed Dioxane. The reaction mixture is heated in a microwave reactor at 100° C. during 2 hours. After the work-up, the crude product is purified by Silica gel flash chromatography using cyclohexane/EtOAc 20:80 to 0:100 as eluent to obtain the title compound (54 mg, 56% yield).

HPLC-MS (Method 5): $R_t$=2.76 min

MS (APCI+): m/z=436 $[M+H]^+$

Example 31

Racemic Mixture

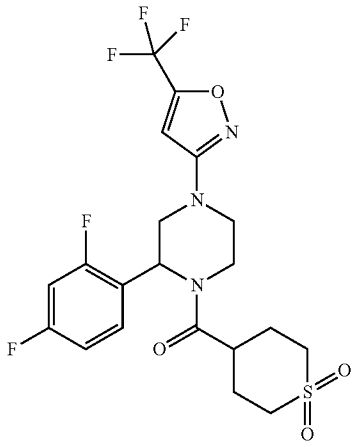 [SMILES: O=C(C1CCS(=O)(=O)CC1)N1CCN(c2cc(C(F)(F)F)on2)CC1c1ccc(F)cc1F]

Example 31 is synthesized as described for example 18 starting from example 44f (100 mg, 0.27 mmol) instead of example 44k, N,N-diisopropylethylamine (47 μl, 0.27 mmol), 1,1-dibromoformaldoxime (56 mg, 0.27 mmol), 2-Bromo-3,3,3-trifluoropropene (140 μl, 1.37 mmol), triethylamine (76 μl, 0.55 mmol) and 2 ml of anhydrous THF. After the work-up, the crude product is purified by Silica gel flash chromatography using cyclohexane/EtOAc 40:60 to 20:80 as eluent to obtain the title compound (47 mg, 34% yield).

HPLC-MS (Method 10): $R_t$=3.54 min

MS (ES+): m/z=494 $[M+H]^+$

Example 32

Racemic Mixture

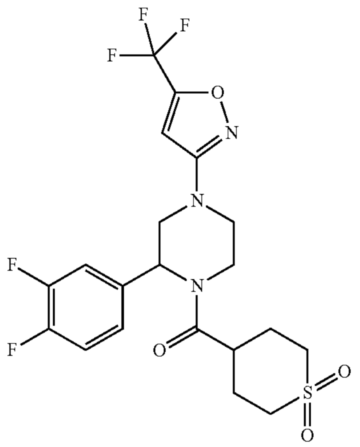 [SMILES: O=C(C1CCS(=O)(=O)CC1)N1CCN(c2cc(C(F)(F)F)on2)CC1c1ccc(F)c(F)c1]

Example 32 is synthesized as described for example 18 starting from example 44i (100 mg, 0.27 mmol) instead of example 44k, N,N-diisopropylethylamine (47 μl, 0.27 mmol), 1,1-dibromoformaldoxime (56 mg, 0.27 mmol), 2-Bromo-3,3,3-trifluoropropene (140 μl, 1.37 mmol), triethylamine (76 μl, 0.55 mmol) and 2 ml of anhydrous THF. After the work-up, the crude product is purified by Silica gel flash chromatography using cyclohexane/EtOAc 30:70 to 20:80 as eluent to obtain the title compound (45 mg, 33% yield).

HPLC-MS (Method 10): $R_t$=3.59 min

MS (ES+): m/z=494 $[M+H]^+$

Example 33

Racemic Mixture

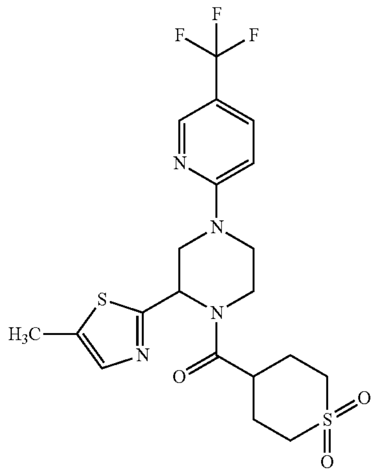 [SMILES: Cc1cnc(C2CN(c3ccc(C(F)(F)F)cn3)CCN2C(=O)C2CCS(=O)(=O)CC2)s1]

Example 33 is synthesized as described for example 1 starting from example 47a (46 mg, 85% content estimated at 254 nm, 0.11 mmol) instead of example 44k, 2-Fluoro-5-(trifluoromethyl)pyridine (17 μl, 0.14 mmol) instead of 2-Chloro-5-(trifluoromethyl)pyrimidine, N,N-diisopropylethylamine (39 μl, 0.23 mmol) and anhydrous DMSO. The reaction mixture is heated in a microwave reactor at 100° C. during 1 hour. The crude product is purified by preparative HPLC-MS to obtain the title compound (11 mg, 19% yield).

HPLC-MS (Method 5): $R_t$=2.85 min

MS (APCI+): m/z=489 $[M+H]^+$

Example 34

Racemic Mixture

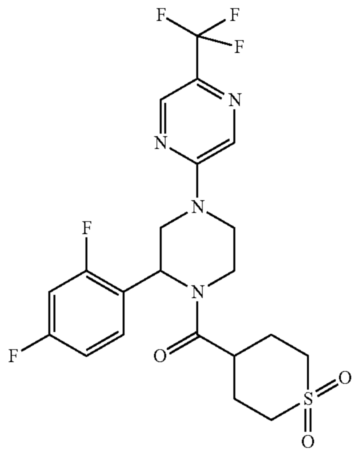 [SMILES: O=C(C1CCS(=O)(=O)CC1)N1CCN(c2cnc(C(F)(F)F)cn2)CC1c1ccc(F)cc1F]

Example 34 is synthesized as described for example 1 starting from example 44f (80 mg, 0.22 mmol) instead of example 44k, 2-Bromo-5-(trifluoromethyl)pyrazine (75 mg, 0.33 mmol) instead of 2-Chloro-5-(trifluoromethyl)pyrimidine, N,N-diisopropylethylamine (75 μl, 0.44 mmol) and 1 ml of anhydrous DMSO. The reaction mixture is heated in a microwave reactor at 130° C. during 30 minutes. After the work-up, the crude product is purified by Silica gel flash chromatography using cyclohexane/EtOAc 20:80 to 0:100 as eluent to obtain the title compound (83 mg, 74% yield).

HPLC-MS (Method 5): $R_t$=2.96 min

MS (APCI+): m/z=505 $[M+H]^+$

Example 35

Racemic Mixture

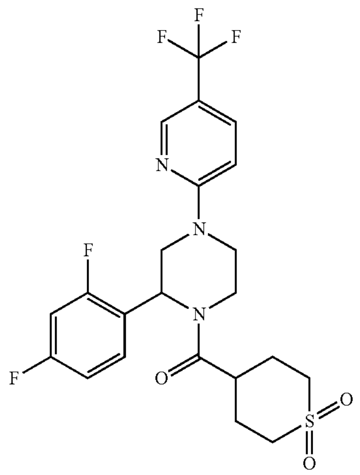 [SMILES: O=C(C1CCS(=O)(=O)CC1)N1CCN(c2ccc(C(F)(F)F)cn2)CC1c1ccc(F)cc1F]

Example 35 is synthesized as described for example 1 starting from example 44f (80 mg, 0.22 mmol) instead of example 44k, 2-Fluoro-5-(trifluoromethyl)Pyridine (54 mg, 0.33 mmol) instead of 2-Chloro-5-(trifluoromethyl)pyrimidine, N,N-diisopropylethylamine (75 μl, 0.44 mmol and 1 ml of anhydrous DMSO. The reaction mixture is heated in a microwave reactor at 130° C. during 30 minutes. After the work-up, the crude product is purified by Silica gel flash chromatography using cyclohexane/EtOAc 20:80 to 0:100 as eluent to obtain the title compound (37 mg, 33% yield).

HPLC-MS (Method 5): $R_t$=3.17 min

MS (APCI+): m/z=504 $[M+H]^+$

Example 36

Racemic Mixture

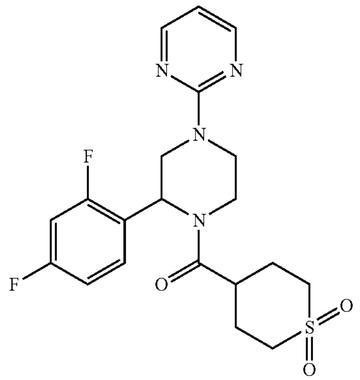 [SMILES: O=C(C1CCS(=O)(=O)CC1)N1CCN(c2ncccn2)CC1c1ccc(F)cc1F]

Example 36 is synthesized as described for example 1 starting from example 44f (80 mg, 0.23 mmol) instead of example 44k, 2-Chloro-Pyrimidine (38 mg, 0.33 mmol) instead of 2-Chloro-5-(trifluoromethyl)pyrimidine, N,N-diisopropylethylamine (75 μl, 0.44 mmol) and 1 ml of anhydrous DMSO. The reaction mixture is heated in a microwave reactor at 130° C. during 30 minutes. The crude product is purified by preparative HPLC-MS to obtain the title compound (77 mg, 79% yield).

HPLC-MS (Method 5): $R_t$=2.37 min

MS (APCI+): m/z=437 $[M+H]^+$

Example 37

Racemic Mixture

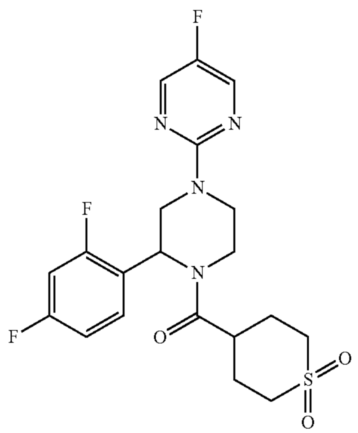 [SMILES: O=C(C1CCS(=O)(=O)CC1)N1CCN(c2ncc(F)cn2)CC1c1ccc(F)cc1F]

Example 37 is synthesized as described for example 1 starting from example 44f (80 mg, 0.23 mmol) instead of example 44k, 2-Chloro-5-Fluoro-Pyrimidine (44 mg, 0.33 mmol) instead of 2-Chloro-5-(trifluoromethyl)pyrimidine, N,N-diisopropylethylamine (75 μl, 0.44 mmol) and 1 ml of anhydrous DMSO. The reaction mixture is heated in a microwave reactor at 130° C. during 30 minutes. The crude product is purified by preparative HPLC-MS to obtain the title compound (52 mg, 51% yield).

HPLC-MS (Method 5): $R_t$=2.67 min

MS (APCI+): m/z=455 $[M+H]^+$

Example 38

Racemic Mixture

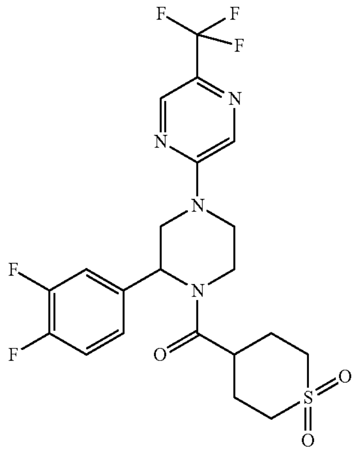 [SMILES: O=C(C1CCS(=O)(=O)CC1)N1CCN(c2cnc(C(F)(F)F)cn2)CC1c1ccc(F)c(F)c1]

Example 38 is synthesized as described for example 1 starting from example 44i (80 mg, 0.22 mmol) instead of example 44k, 2-Bromo-5-(trifluoromethyl)pyrazine (75 mg, 0.23 mmol) instead of 2-Chloro-5-(trifluoromethyl)pyrimidine, N,N-diisopropylethylamine (75 μl, 0.44 mmol) and 1 ml of anhydrous DMSO. The reaction mixture is heated in a microwave reactor at 130° C. during 30 minutes. After the work-up, the crude product is purified by Silica gel flash chromatography using cyclohexane/EtOAc 20:80 to 0:100 as eluent to obtain the title compound (71 mg, 63% yield).

HPLC-MS (Method 5): $R_t$=3.00 min

MS (APCI+): m/z=505 $[M+H]^+$

Example 39

Racemic Mixture

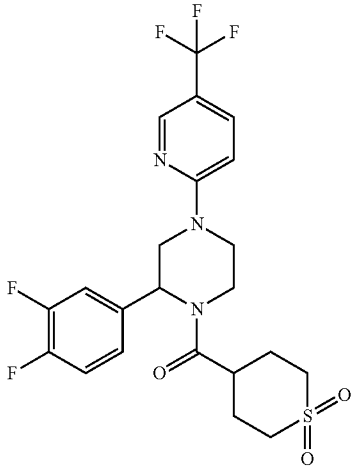 [SMILES: O=C(C1CCS(=O)(=O)CC1)N1CCN(c2ccc(C(F)(F)F)cn2)CC1c1ccc(F)c(F)c1]

Example 39 is synthesized as described for example 1 starting from example 44i (80 mg, 0.22 mmol) instead of example 44k, 2-Fluoro-5-(trifluoromethyl)Pyridine (54 mg, 0.33 mmol) instead of 2-Chloro-5-(trifluoromethyl)pyrimidine, N,N-diisopropylethylamine (75 μl, 0.44 mmol) and 1 ml of anhydrous DMSO. The reaction mixture is heated in a microwave reactor at 130° C. during 30 minutes. After EtOAc/$H_2O$ work-up, the crude product is purified by Silica gel flash chromatography using cyclohexane/EtOAc 20:80 to 0:100 as eluent to obtain the title compound (77 mg, 68% yield).

HPLC-MS (Method 5): $R_t$=3.19 min

MS (APCI+): m/z=504 $[M+H]^+$

Example 40

Racemic Mixture

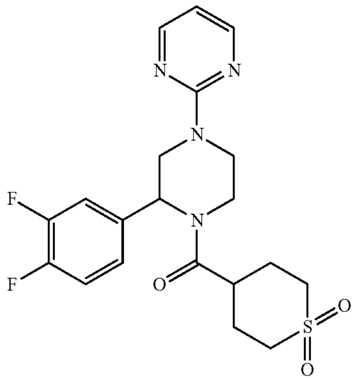 [SMILES: O=C(C1CCS(=O)(=O)CC1)N1CCN(c2ncccn2)CC1c1ccc(F)c(F)c1]

Example 40 is synthesized as described for example 1 starting from example 44i (80 mg, 0.23 mmol) instead of example 44k, 2-Chloro-Pyrimidine (38 mg, 0.33 mmol) instead of 2-Chloro-5-(trifluoromethyl)pyrimidine, N,N-diisopropylethylamine (75 μl, 0.44 mmol) and 1 ml of anhydrous DMSO. The reaction mixture is heated in a microwave reactor at 130° C. during 30 minutes. After the work-up, the crude product is purified by Silica gel flash chromatography using cyclohexane/EtOAc 20:80 to 0:100 as eluent to obtain the title compound (74 mg, 76% yield).

HPLC-MS (Method 5): $R_t$=2.50 min

MS (APCI+): m/z=437 $[M+H]^+$

Example 41

Racemic Mixture

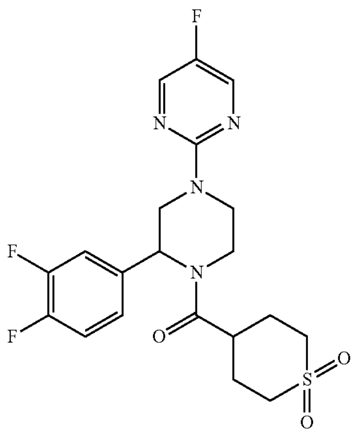 [SMILES: O=C(C1CCS(=O)(=O)CC1)N1CCN(c2ncc(F)cn2)CC1c1ccc(F)c(F)c1]

Example 41 is synthesized as described for example 1 starting from example 44i (80 mg, 0.23 mmol) instead of example 44k, 2-Chloro-5-Fluoro-Pyrimidine (44 mg, 0.33 mmol) instead of 2-Chloro-5-(trifluoromethyl)pyrimidine, N,N-diisopropylethylamine (75 μl, 0.44 mmol) and 1 ml of anhydrous DMSO. The reaction mixture is heated in a microwave reactor at 130° C. during 30 minutes. After the work-up, the crude product is purified by Silica gel flash chromatography using cyclohexane/EtOAc 20:80 to 0:100 as eluent to obtain the title compound (44 mg, 43% yield).

HPLC-MS (Method 5): $R_t$=2.78 min

MS (APCI+): m/z=455 $[M+H]^+$

Example 42 (Enantiomer 1) and Example 43 (Enantiomer 2)

The racemic mixture of the title compounds is synthesized as described for example 1 starting from example 44h (205 mg, 0.60 mmol) instead of example 44k, 2-Fluoro-5-(trifluoromethyl)Pyridine (106 μl, 0.88 mmol) instead of 2-Chloro-5-(trifluoromethyl)pyrimidine, N,N-diisopropylethylamine (210 μl, 1.21 mmol) and anhydrous DMSO. The reaction mixture is heated in a microwave reactor at 100° C. during 1 hour. $H_2O$ was added and the resulting solid was filtered to obtain the racemic compound (277 mg).

UPLC-MS (Method 1): $R_t$=1.16 min

MS (ES+): m/z=486 $[M+H]^+$

The enantiomers are obtained by HPLC separation using a chiral stationary phase.

Method for Separation:

HPLC apparatus type: Waters 600 Pump; column: Daicel Chiralpack IA, 5.0 μm, 250 mm×20 mm; method: eluent hexane/IPA 60:40; flow rate: 15 mL/min, Temperature: 25° C.; UV Detection: 254 nm Example of Separation by Chiral HPLC:

Submitted to separation: 266 mg of racemic mixture prepared as described above; Obtained: 94 mg of enantiomer 1 (Exp. 42) and 99 mg of enantiomer 2 (Exp. 43)

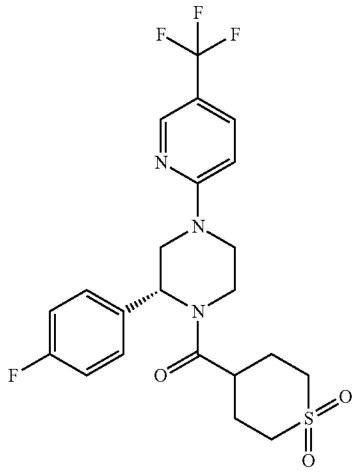 [SMILES: O=C(C1CCS(=O)(=O)CC1)N1CCN(c2ccc(C(F)(F)F)cn2)C[C@H]1c1ccc(F)cc1]

Example 42: enantiomer 1

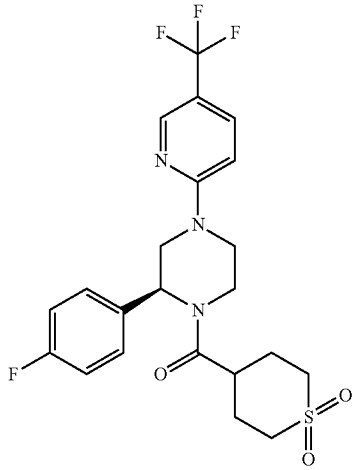 [SMILES: O=C(C1CCS(=O)(=O)CC1)N1CCN(c2ccc(C(F)(F)F)cn2)C[C@@H]1c1ccc(F)cc1]

Example 43: enantiomer 2

| Example | Chiral HPLC $R_t$ [min] | HPLC-MS (Method 5): $R_t$ [min] | MS (APCI+): m/z |
|---|---|---|---|
| Exp. 42 | 11.74 (Method 12) | 3.12 | 486 |
| Exp. 43 | 13.89 (Method 12) | 3.15 | 486 |

Example 44

Racemic Mixture

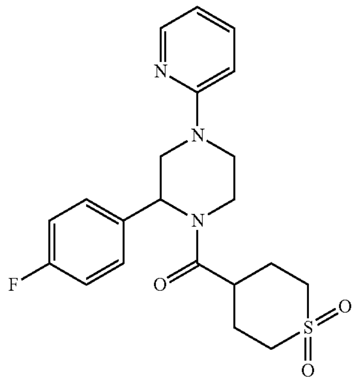 [SMILES: O=C(C1CCS(=O)(=O)CC1)N1CCN(c2ccccn2)CC1c1ccc(F)cc1]

Example 44 is synthesized as described for example 16 starting from example 44h (60 mg, 0.18 mmol) instead of example 44b, 2-Bromopyridine (20 μl, 0.21 mmol) instead of 2-Chloro-5-Fluoropyridine, X-Phos (17 mg, 0.04 mmol), Tris (dibenzylideneacetone)dipalladium(0) (16 mg, 0.02 mmol), sodium tert-butoxide (34 mg, 0.35 mmol) and degassed Dioxane. The reaction mixture is heated in a microwave reactor at 80° C. during 2 hour. The crude reaction mixture is filtered and the filtrate is concentrated under reduced pressure; the residue is purified by SCX cartridge and then by preparative HPLC-MS to obtain the title compound (43 mg, 59% yield).

HPLC-MS (Method 5): $R_t$=2.57 min

MS (APCI+): m/z=418 $[M+H]^+$

Example 45

Racemic Mixture

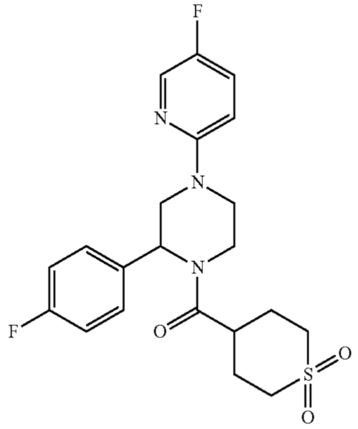 [SMILES: O=C(C1CCS(=O)(=O)CC1)N1CCN(c2ccc(F)cn2)CC1c1ccc(F)cc1]

Example 45 is synthesized as described for example 43a starting from example 27a (102 mg, 0.37 mmol) instead of example 40c, HATU (183 mg, 0.48 mmol), N,N-diisopropylethylamine (159 μl, 0.93 mmol), tetrahydro-2H-thiopyran-4-carboxilic acid 1,1-dioxide (86 mg, 0.48 mmol) and 2 ml of DMF. The crude reaction mixture is purified by preparative HPLC-MS to obtain the title compound (132 mg, 82% yield).

HPLC-MS (Method 5): $R_t$=2.77 min

MS (APCI+): m/z=436 $[M+H]^+$

Example 46

Racemic Mixture

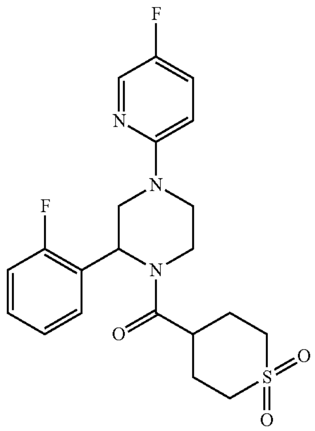 [SMILES: O=C(C1CCS(=O)(=O)CC1)N1CCN(c2ccc(F)cn2)CC1c1ccccc1F]

Example 46 is synthesized as described for example 16 starting from example 44g (100 mg, 0.29 mmol) instead of example 44b, 2-Chloro-5-Fluoropyridine (50 mg, 0.38 mmol), X-Phos (56 mg, 0.12 mmol), Tris(dibenzylideneacetone)dipalladium(0)-chloroform adduct (61 mg, 0.06 mmol), sodium tert-butoxide (56 mg, 0.59 mmol) and degassed Dioxane. The reaction mixture is heated in a microwave reactor at 100° C. during 2 hours to obtain 80 mg (63% yield) of title compound after purification by preparative HPLC-MS.

HPLC-MS (Method 5): $R_t$=2.71 min

MS (APCI+): m/z=436 $[M+H]^+$

Example 47

Racemic Mixture

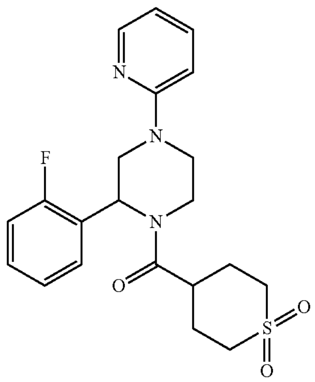 [SMILES: O=C(C1CCS(=O)(=O)CC1)N1CCN(c2ccccn2)CC1c1ccccc1F]

Example 47 is synthesized as described for example 16 starting from example 44g (100 mg, 0.29 mmol) instead of example 44b, 2-Bromopyridine, (32 μl, 0.35 mmol), X-Phos (15 mg, 0.03 mmol), Tris(dibenzylideneacetone)dipalladium (0)-chloroform adduct (14 mg, 0.01 mmol) sodium tert-butoxide (56 mg, 0.59 mmol) and degassed Doxane. The reaction mixture is heated in a microwave reactor at 100° C.

during 2 hours to obtain 90 mg (73% yield) of title compound after purification by preparative HPLC-MS.

HPLC-MS (Method 5): $R_t$=2.50 min

MS (APCI+): m/z=418 [M+H]$^+$

Example 48

Racemic Mixture

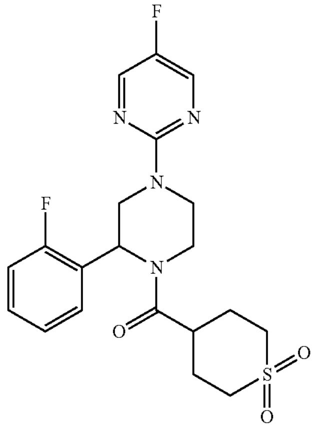 [SMILES: O=C(C1CCS(=O)(=O)CC1)N1CCN(c2ncc(F)cn2)CC1c1ccccc1F]

Example 48 is synthesized as described for example 1 starting from example 44g (100 mg, 0.29 mmol) instead of example 44k, 2-Chloro-5-Fluoropyrimidine (46 mg, 0.35 mmol) instead of 2-Chloro-5-(trifluoromethyl)pyrimidine, N,N-diisopropylethylamine (60 μl, 0.35 mmol) and 2 ml of anhydrous DMSO. The reaction mixture is heated in a microwave reactor at 100° C. during 2 hours. After the work-up, crude product is purified by preparative HPLC-MS to obtain the title compound (85 mg, 66% yield).

HPLC-MS (Method 5): $R_t$=2.62 min

MS (APCI+): m/z=437 [M+H]$^+$

Example 49

Racemic Mixture

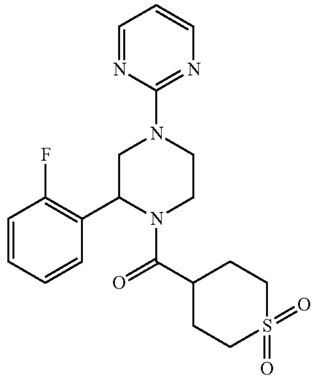 [SMILES: O=C(C1CCS(=O)(=O)CC1)N1CCN(c2ncccn2)CC1c1ccccc1F]

Example 49 is synthesized as described for example 1 starting from example 44g (100 mg, 0.29 mmol) instead of example 44k, 2-Chloro-Pyrimidine (40 mg, 0.35 mmol) instead of 2-Chloro-5-(trifluoromethyl)pyrimidine, N,N-diisopropylethylamine (60 μl, 0.35 mmol) and 2 ml of anhydrous DMSO. The reaction mixture is heated in a microwave reactor at 100° C. during 2 hours. After the work-up, the crude product is purified by Silica gel flash chromatography using DCM/MeOH 100:2 as eluent to obtain the title compound (85 mg, 69% yield).

HPLC-MS (Method 5): $R_t$=2.25 min

MS (APCI+): m/z=419 [M+H]$^+$

Example 50

Racemic Mixture

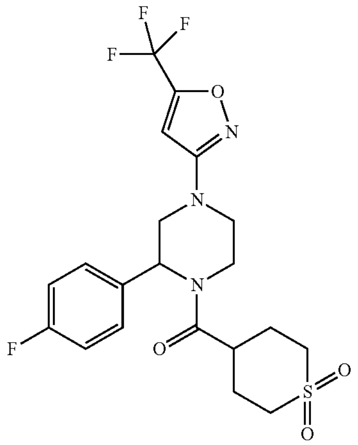 [SMILES: O=C(C1CCS(=O)(=O)CC1)N1CCN(c2cc(C(F)(F)F)on2)CC1c1ccc(F)cc1]

N,N-diisopropylethylamine (0.97 ml, 5.68 mmol) is slowly added under nitrogen atmosphere to a cooled (−20° C.) suspension of 1,1-dibromoformaldoxime (1.1 g, 5.68 mmol) and example 44h (1.9 g, 5.68 mmol) in 20 ml of anhydrous THF. The temperature is increased at 0° C. and the reaction is stirred 20 minutes. 2-Bromo-3,3,3-trifluoropropene (3.0 ml, 28.5 mmol) is added dropwise followed by triethylamine (1.2 ml, 8.53 mmol), the reaction is stirred 30 minutes at 0° C. and then at room temperature overnight. The crude is diluted with EtOAc and washed with water, aqueous HCl solution and brine; the organic phase is dried and concentrated under reduced pressure; the residue is purified by Silica gel flash chromatography using EtOAc/cyclohexane 30:70 to 100:0 to obtain the title compound (1.2 g, 45% yield).

HPLC-MS (Method 5): $R_t$=2.97 min

MS (APCI+): m/z=476 [M+H]$^+$

The enantiomers are obtained by HPLC separation using a chiral stationary phase.

Method for Separation:

HPLC apparatus type: Waters 600 Pump; column: Daicel Chiralpack IA, 5.0 μm, 250 mm×20 mm; method: eluent hexane/IPA 60:40; flow rate: 15 mL/min, Temperature: 25° C.; UV Detection: 230 nm Example of Separation by Chiral HPLC:

Submitted to separation: 1.2 g of Example 50 prepared as described above; Obtained: 418 mg of enantiomer 1 (Exp. 51) and 484 mg of enantiomer 2 (Exp. 52)

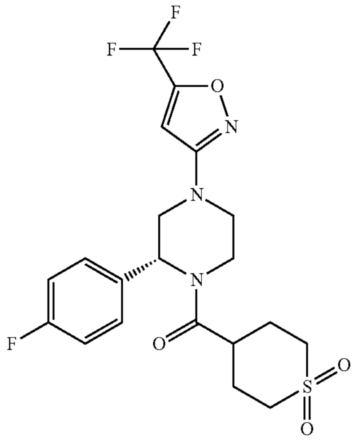 [SMILES: O=C(C1CCS(=O)(=O)CC1)N1CCN(c2cc(C(F)(F)F)on2)C[C@H]1c1ccc(F)cc1]

Example 51: enantiomer 1

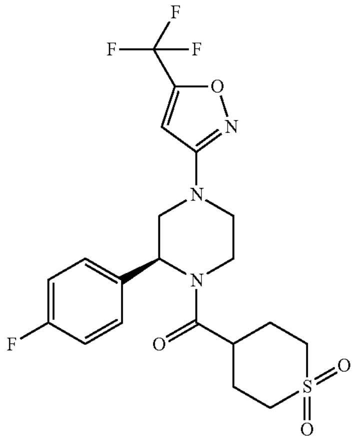 [SMILES: O=C(C1CCS(=O)(=O)CC1)N1CCN(c2cc(C(F)(F)F)on2)C[C@@H]1c1ccc(F)cc1]

Example 52: enantiomer 2

| Example | Chiral HPLC $R_t$ [min] | HPLC-MS (Method 5): $R_t$ [min] | MS (APCI+): m/z |
|---|---|---|---|
| Exp. 51 | 8.39 (Method 13) | 2.96 | 476 |
| Exp. 52 | 10.61 (Method 13) | 2.95 | 476 |

Example 53

Racemic Mixture

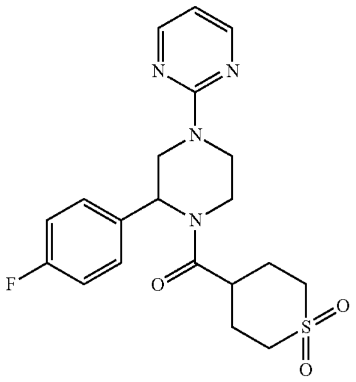 [SMILES: O=C(C1CCS(=O)(=O)CC1)N1CCN(c2ncccn2)CC1c1ccc(F)cc1]

Example 53 is synthesized as described for example 43a starting from example 28a (158 mg, 0.55 mmol) instead of example 40c, HATU (251 mg, 0.66 mmol), N,N-diisopropylethylamine (236 μl, 1.38 mmol), tetrahydro-2H-thiopyran-4-carboxilic acid 1,1-dioxide (118 mg, 0.66 mmol) and 2 ml of DMF. The crude product is purified by preparative HPLC-MS to obtain the title compound (170 mg, 74% yield).

HPLC-MS (Method 5): $R_t$=2.35 min

MS (APCI+): m/z=419 $[M+H]^+$

Example 54

Racemic Mixture

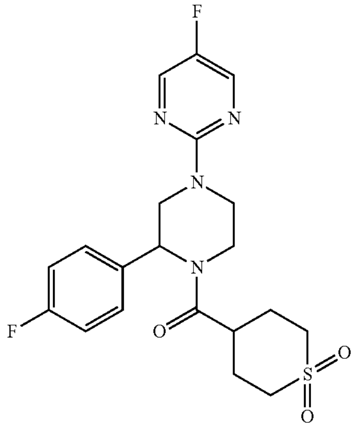 [SMILES: O=C(C1CCS(=O)(=O)CC1)N1CCN(c2ncc(F)cn2)CC1c1ccc(F)cc1]

Example 54 is synthesized as described for example 43a starting from example 29a (152 mg, 0.55 mmol) instead of example 40c, HATU (251 mg, 0.66 mmol), N,N-diisopropylethylamine (236 μl, 1.38 mmol), tetrahydro-2H-thiopyran-4-carboxilic acid 1,1-dioxide (118 mg, 0.66 mmol) and 2 ml of DMF. The crude product is purified by preparative HPLC-MS to obtain the title compound (91 mg, 38% yield).

HPLC-MS (Method 14): $R_t$=5.56 min

MS (APCI+): m/z=437 $[M+H]^+$

Example 55

Racemic Mixture

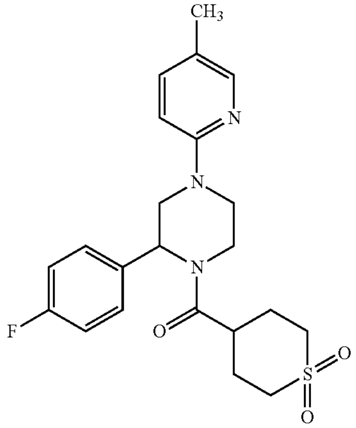 [SMILES: Cc1ccc(N2CCN(C(=O)C3CCS(=O)(=O)CC3)C(c3ccc(F)cc3)C2)nc1]

Example 55 is synthesized as described for example 16 starting from example 44h (80 mg, 0.23 mmol) instead of example 44b, 2-Bromo-5-Methylpyridine (48 mg, 0.28 mmol) instead of 2-Chloro-5-Fluoropyridine, X-Phos (44 mg, 0.09 mmol), Tris(dibenzylideneacetone)dipalladium(0) (42 mg, 0.05 mmol), sodium tert-butoxide (44 mg, 0.46 mmol) and degassed Dioxane. The reaction mixture is heated in a microwave reactor at 100° C. during 2 hours. After the work-up the residue is purified by Silica gel flash chromatography using DCM/MeOH 97:3 as eluent to obtain 68 mg (67% yield) of title compound HPLC-MS (Method 5): $R_t$=2.76 min MS (APCI+): m/z=432 $[M+H]^+$ Example 56

Racemic Mixture

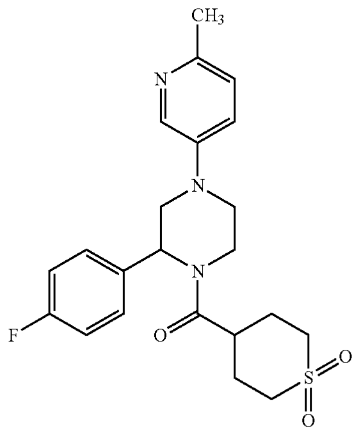 [SMILES: Cc1ccc(N2CCN(C(=O)C3CCS(=O)(=O)CC3)C(c3ccc(F)cc3)C2)cn1]

Example 56 is synthesized as described for example 16 starting from example 44h (80 mg, 0.23 mmol) instead of example 44b, 2-Methyl-5-Bromopyridine (48 mg, 0.28 mmol) instead of 2-Chloro-5-Fluoropyridine, X-Phos (44 mg, 0.09 mmol), Tris(dibenzylideneacetone)dipalladium(0) (42 mg, 0.05 mmol), sodium tert-butoxide (44 mg, 0.46 mmol) and degassed Dioxane. The reaction mixture is heated in a microwave reactor at 100° C. during 2 hours. After the work-up the residue is purified by Silica gel flash chromatography using DCM/MeOH 97:3 as eluent to obtain the title compound (65 mg, 64% yield)

HPLC-MS (Method 5): $R_t$=2.43 min

MS (APCI+): m/z=432 $[M+H]^+$

Example 57

Racemic Mixture

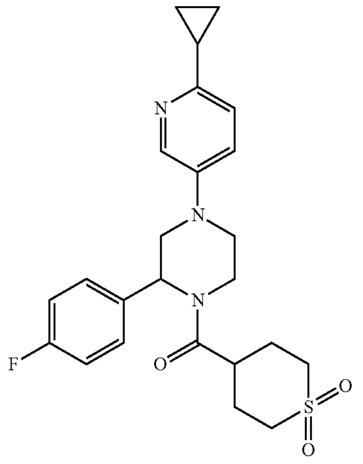 [SMILES: O=C(C1CCS(=O)(=O)CC1)N1CCN(c2ccc(C3CC3)nc2)CC1c1ccc(F)cc1]

Example 57 is synthesized as described for example 16 starting from example 44h (80 mg, 0.23 mmol) instead of example 44b, 3-Bromo-6-(Cyclopropyl)pyridine (55 mg, 0.28 mmol) instead of 2-Chloro-5-Fluoropyridine, X-Phos (44 mg, 0.09 mmol), Tris(dibenzylideneacetone)dipalladium (0) (42 mg, 0.05 mmol), sodium tert-butoxide (44 mg, 0.46 mmol) and degassed Dioxane. The reaction mixture is heated in a microwave reactor at 100° C. during 2 hours. After the work-up the residue is purified by Silica gel flash chromatography using DCM/MeOH 97:3 as eluent to obtain the title compound (22 mg, 21% yield)

HPLC-MS (Method 5): $R_t$=2.72 min

MS (APCI+): m/z=458 $[M+H]^+$

Example 58

Racemic Mixture

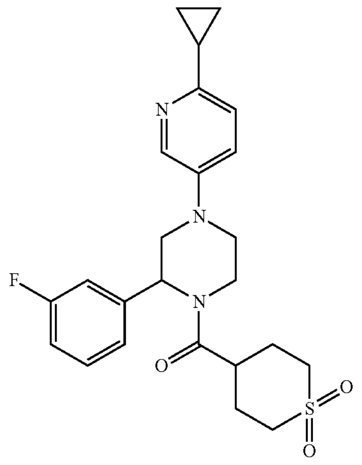 [SMILES: O=C(C1CCS(=O)(=O)CC1)N1CCN(c2ccc(C3CC3)nc2)CC1c1cccc(F)c1]

Example 58 is synthesized as described for example 16 starting from example 44b (100 mg of free base, 0.29 mmol), 3-Bromo-6-(Cyclopropyl)pyridine (75 mg, 0.29 mmol) instead of 2-Chloro-5-Fluoropyridine, 9,9-Dimethyl-4,5-Bis (Di-tert-Butylphosphino)Xantene (15 mg, 0.03 mmol) instead of X-phos, Tris(dibenzylideneacetone)dipalladium (0)-chloroform adduct (30 mg, 0.03 mmol), sodium tert-butoxide (57 mg, 0.59 mmol) and degassed Dioxane. The reaction mixture is heated in a microwave reactor at 100° C. during 2 hours. After the work-up the residue is purified by preparative HPLC-MS to obtain the title compound (41 mg, 31% yield)

HPLC-MS (Method 16): $R_t$=3.27 min

MS (APCI+): m/z=458 $[M+H]^+$

Example 59

Racemic Mixture

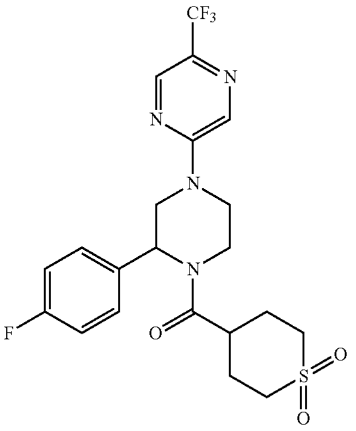 [SMILES: O=C(C1CCS(=O)(=O)CC1)N1CCN(c2cnc(C(F)(F)F)cn2)CC1c1ccc(F)cc1]

Example 59 is synthesized as described for example 42b starting from example 30a (800 mg, 2.40 mmol) instead of example 40b, N-(3-dimethylaminopropyl)-N'-ethylcarbodiimide hydrochloride (691 mg, 3.60 mmol), tetrahydro-2H-thiopyran-4-carboxilic acid 1,1-dioxide (642 mg, 3.60 mmol), 1-hydroxybenzotriazole (32 mg, 0.24 mmol) and 2 ml of DCM. The crude product is partitioned between DCM and water, the organic layer is separated and concentrated under reduced pressure. The residue is purified by Silica gel flash chromatography using cyclohexane/EtOAc 50:50 to 0:100 as eluent to obtain the title compound (820 mg, 63% yield).

HPLC-MS (Method 10): $R_t$=3.47 min

MS (ES+): m/z=487 $[M+H]^+$

The enantiomers are obtained by HPLC separation using a chiral stationary phase.

Method for Separation:

HPLC apparatus type: Waters 600 Pump; column: Daicel Chiralpack IA, 5.0 μm, 250 mm×20 mm; method: eluent hexane/IPA 62:38; flow rate: 15 mL/min, Temperature: 25° C.; UV Detection: 254 nm Example of Separation by Chiral HPLC:

Submitted to separation: 800 mg of Example 59 prepared as described above; Obtained: 330 mg of enantiomer 1 (Exp. 60) and 339 mg of enantiomer 2 (Exp. 61)

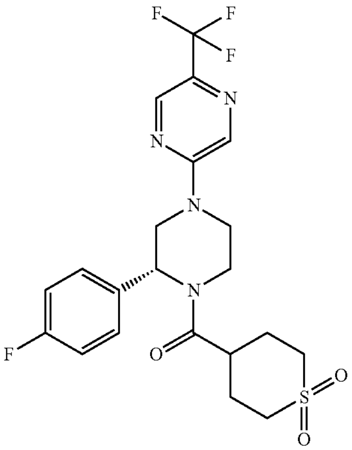 [SMILES: O=C(C1CCS(=O)(=O)CC1)N1CCN(c2cnc(C(F)(F)F)cn2)C[C@H]1c1ccc(F)cc1]

Example 60: enantiomer 1

-continued

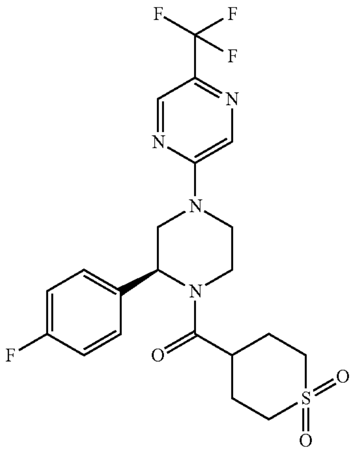 [SMILES: O=C(C1CCS(=O)(=O)CC1)N1CCN(c2cnc(C(F)(F)F)cn2)C[C@@H]1c1ccc(F)cc1]

Example 61: enantiomer 2

| Example | Chiral HPLC $R_t$ [min] | HPLC-MS (Method 5): $R_t$ [min] | MS (APCI+): m/z |
|---|---|---|---|
| Exp. 60 | 14.35 (Method 12) | 2.90 | 487 |
| Exp. 61 | 15.91 (Method 12) | 2.90 | 487 |

Example 62

Racemic Mixture

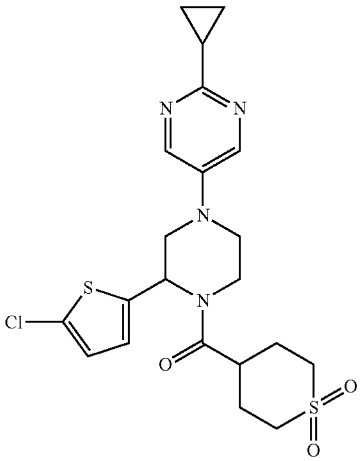 [SMILES: O=C(C1CCS(=O)(=O)CC1)N1CCN(c2cnc(C3CC3)nc2)CC1c1ccc(Cl)s1]

Example 62 is synthesized as described for example 16 starting from example 44c (100 mg, 0.28 mmol) instead of example 44b, 5-Bromo-2-Cyclopropylpyrimidine (66 mg, 0.33 mmol) instead of 2-Chloro-5-Fluoropyridine, X-Phos (53 mg, 0.11 mmol), Tris(dibenzylideneacetone)dipalladium (0) (51 mg, 0.06 mmol), sodium tert-butoxide (53 mg, 0.55 mmol) and degassed Dioxane. The reaction mixture is heated in a microwave reactor at 100° C. during 1.5 hours. After addition of EtOAc the formed solid is filtered out and the filtrate is concentrated under reduced pressure; the residue is first purified by preparative HPLC-MS then by SCX cartridge to obtain the title compound (25 mg, 19% yield)

HPLC-MS (Method 5): $R_t$=2.69 min

MS (APCI+): m/z=481 $[M+H]^+$

Example 63

Racemic Mixture

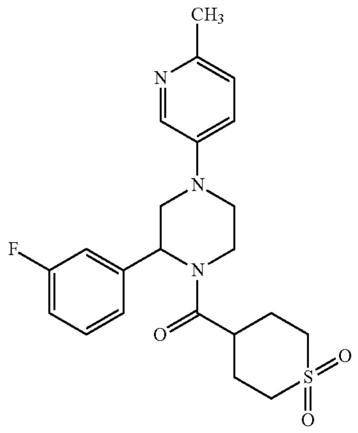 [SMILES: Cc1ccc(N2CCN(C(=O)C3CCS(=O)(=O)CC3)C(c3cccc(F)c3)C2)cn1]

Example 63 is synthesized as described for example 16 starting from example 44b (100 mg of free base, 0.29 mmol), 2-Methyl-5-Bromopyridine (51 mg, 0.29 mmol) instead of 2-Chloro-5-Fluoropyridine, 9,9-Dimethyl-4,5-Bis(Di-tert-Butylphosphino)Xantene (15 mg, 0.03 mmol) instead of X-phos, Tris(dibenzylideneacetone)dipalladium(0)-chloroform adduct (30 mg, 0.03 mmol), sodium tert-butoxide (57 mg, 0.59 mmol) and degassed Dioxane. The reaction mixture is heated in a microwave reactor at 100° C. during 2 hours. After the work-up the residue is purified by preparative HPLC-MS to obtain the title compound (64 mg, 51% yield)

HPLC-MS (Method 5): $R_t$=2.38 min

MS (APCI+): m/z=432 $[M+H]^+$

Example 64

Racemic Mixture

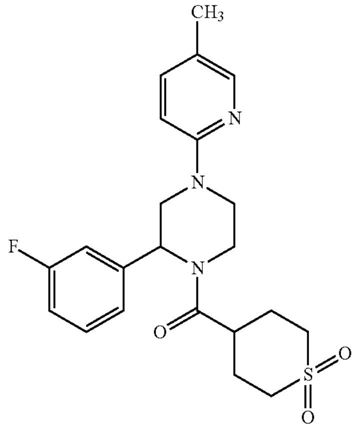 [SMILES: Cc1ccc(N2CCN(C(=O)C3CCS(=O)(=O)CC3)C(c3cccc(F)c3)C2)nc1]

Example 64 is synthesized as described for example 16 starting from example 44b (100 mg of free base, 0.29 mmol), 2-Bromo-5-Methylpyridine (51 mg, 0.29 mmol) instead of 2-Chloro-5-Fluoropyridine, 9,9-Dimethyl-4,5-Bis(Di-tert-Butylphosphino)Xantene (15 mg, 0.03 mmol) instead of X-phos, Tris(dibenzylideneacetone)dipalladium(0)-chloroform adduct (30 mg, 0.03 mmol), sodium tert-butoxide (57 mg, 0.59 mmol) and degassed Dioxane. The reaction mixture is heated in a microwave reactor at 100° C. during 2 hours. After EtOAc/water work-up the residue is purified by preparative HPLC-MS to obtain the title compound (59 mg, 46% yield)

HPLC-MS (Method 5): $R_t$=2.76 min

MS (APCI+): m/z=432 $[M+H]^+$

Example 65

Racemic Mixture

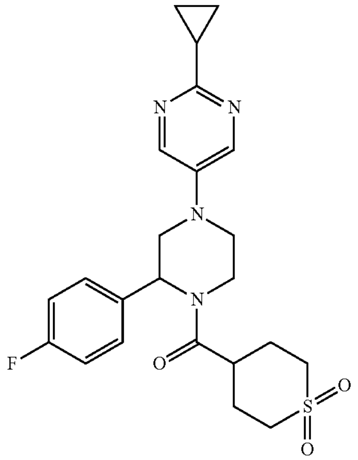 [SMILES: O=C(C1CCS(=O)(=O)CC1)N1CCN(c2cnc(C3CC3)nc2)CC1c1ccc(F)cc1]

Example 65 is synthesized as described for example 16 starting from example 44h (70 mg, 0.20 mmol) instead of example 44b, 5-Bromo-2-Cyclopropylpyrimidine (48 mg, 0.24 mmol) instead of 2-Chloro-5-Fluoropyridine, X-Phos (38 mg, 0.08 mmol), Tris(dibenzylideneacetone)dipalladium (0) (37 mg, 0.04 mmol), sodium tert-butoxide (39 mg, 0.40 mmol) and degassed Dioxane. The reaction mixture is heated in a microwave reactor at 100° C. during 2 hours. After addition of EtOAc the formed solid is filtered out over a celite pad and the filtrate is concentrated under reduced pressure; the residue is first purified by preparative HPLC-MS then by a work-up with DCM/citric acid to obtain the title compound (37 mg, 39% yield)

HPLC-MS (Method 5): $R_t$=2.45 min

MS (APCI+): m/z=459 $[M+H]^+$

Example 66

Racemic Mixture

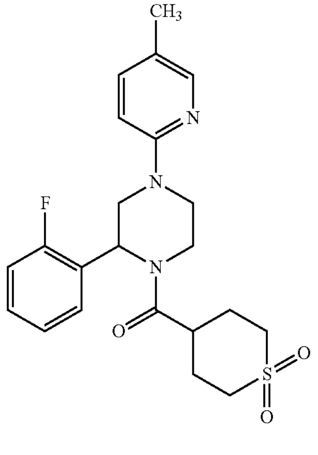 [SMILES: Cc1ccc(N2CCN(C(=O)C3CCS(=O)(=O)CC3)C(c3ccccc3F)C2)nc1]

Example 66 is synthesized as described for example 16 starting from example 44g (76 mg, 0.22 mmol) instead of example 44b, 2-Bromo-5-Methylpyridine (46 mg, 0.27 mmol) instead of 2-Chloro-5-Fluoropyridine, X-phos (43 mg, 0.09 mmol), Tris(dibenzylideneacetone)dipalladium(0)-chloroform adduct (46 mg, 0.04 mmol), sodium tert-butoxide (43 mg, 0.45 mmol) and degassed Dioxane. The reaction mixture is heated in a microwave reactor at 100° C. during 2 hours. After the work-up the residue is purified by Silica gel flash chromatography using DCM/MeOH 100:2 as eluent to obtain the title compound (65 mg, 67% yield)

HPLC-MS (Method 5): $R_t$=2.68 min

MS (APCI+): m/z=432 $[M+H]^+$

Example 67

Racemic Mixture

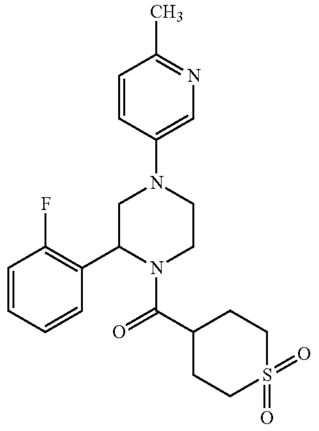 [SMILES: Cc1ccc(N2CCN(C(=O)C3CCS(=O)(=O)CC3)C(c3ccccc3F)C2)cn1]

Example 67 is synthesized as described for example 16 starting from example 44g (76 mg, 0.22 mmol) instead of example 44b, 2-Methyl-5-Bromopyridine (42 mg, 0.24 mmol) instead of 2-Chloro-5-Fluoropyridine, X-phos (43 mg, 0.09 mmol), Tris(dibenzylideneacetone)dipalladium(0)-chloroform adduct (46 mg, 0.04 mmol), sodium tert-butoxide (43 mg, 0.45 mmol) and 2 ml of degassed Dioxane. The reaction mixture is heated in a microwave reactor at 100° C. during 2 hours. After the work-up the residue is purified by Silica gel flash chromatography using DCM/MeOH 100:4 as eluent to obtain the title compound (60 mg, 62% yield)

HPLC-MS (Method 5): $R_t$=2.33 min

MS (APCI+): m/z=432 $[M+H]^+$

Example 68

Racemic Mixture

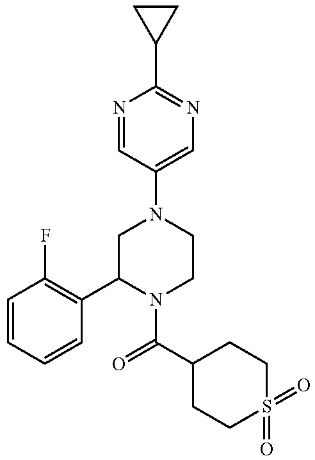 [SMILES: O=C(C1CCS(=O)(=O)CC1)N1CCN(c2cnc(C3CC3)nc2)CC1c1ccccc1F]

Example 68 is synthesized as described for example 16 starting from example 44g (100 mg, 0.29 mmol) instead of example 44b, 5-Bromo-2-Cyclopropylpyrimidine (70 mg, 0.35 mmol) instead of 2-Chloro-5-Fluoropyridine, 2-dicyclohexylphosphino-2'-(N,N-dimethylamino)biphenyl (35 mg, 0.09 mmol) instead X-Phos, Tris(dibenzylideneacetone)dipalladium(0) (27 mg, 0.03 mmol), potassium tert-butoxide (50 mg, 0.45 mmol) and degassed Dioxane. The reaction mixture is heated in a microwave reactor at 130° C. during 1 hour. After the work-up the residue is purified by Silica gel flash chromatography using DCM/MeOH 100:4 as eluent to obtain the title compound (20 mg, 15% yield)

HPLC-MS (Method 5): $R_t$=3.32 min

MS (APCI+): m/z=459 $[M+H]^+$

Example 69

Racemic Mixture

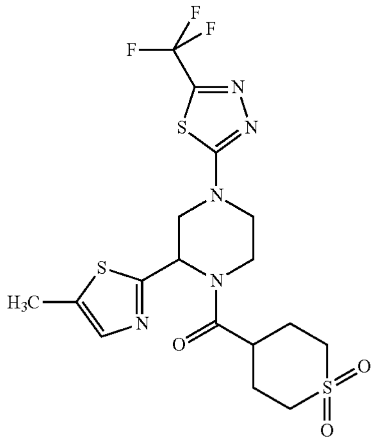 [SMILES: Cc1cnc(C2CN(c3nnc(C(F)(F)F)s3)CCN2C(=O)C2CCS(=O)(=O)CC2)s1]

N,N-diisopropylethylamine (47 μl, 0.27 mmol) is added into a stirred solution of example 16a (25 mg, 0.14 mmol) and 2-Chloro-5-Trifluoromethyl-(1,3,4)-Thiadiazole (19.7 μl, 0.18 mmol) dissolved in 1 ml of anhydrous DMSO. The reaction mixture is heated in a microwave reactor at 100° C. for 30 minutes. The crude is partitioned between $Et_2O$ and 5% aqueous $NaHCO_3$, the aqueous layer is extracted with 1:1 $Et_2O$/EtOAc mixture and then the collected organic phases are dried and concentrated under reduced pressure; the obtained crude intermediate is dissolved in 2 ml of anhydrous DCM, N,N-diisopropylethylamine (35 μl, 0.20 mmol) and 1,1-dioxothiane-4-carbonyl chloride (40 mg, 0.20 mmol previously prepared from the corresponding carboxilic acid and oxalyl chloride in anhydrous DCM) are added and the reaction is stirred overnight. DCM is added and the reaction mixture is washed with 1N aqueous HCl; the organic layer is separated, dried and concentrated under reduced pressure; the residue is purified by preparative HPLC-MS and then by Silica gel flash chromatography using Cyclohexane/EtOAc 40:60 to 0:100 as eluent to obtain the title product (12 mg, 18% yield).

HPLC-MS (Method 5): $R_t$=2.56 min

MS (APCI+): m/z=496 $[M+H]^+$

Example 70

Racemic Mixture

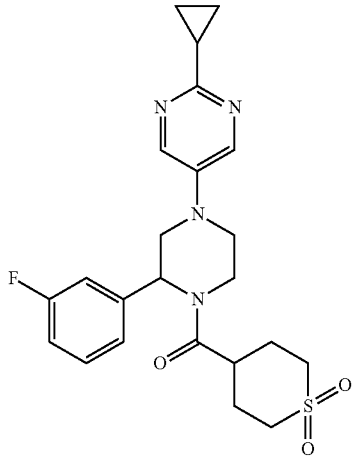 [SMILES: O=C(C1CCS(=O)(=O)CC1)N1CCN(c2cnc(C3CC3)nc2)CC1c1cccc(F)c1]

Example 70 is synthesized as described for example 16 starting from example 44b (100 mg of free base, 0.29 mmol), 5-Bromo-2-Cyclopropylpyrimidine (70 mg, 0.35 mmol) instead of 2-Chloro-5-Fluoropyridine, X-Phos (56 mg, 0.12 mmol), Tris(dibenzylideneacetone)dipalladium(0) (54 mg, 0.06 mmol), sodium tert-butoxide (56 mg, 0.59 mmol) and 2 ml of degassed Dioxane. The reaction mixture is heated in a microwave reactor at 100° C. during 2 hours. The crude reaction mixture is filtered and washed with EtOAc, the filtrate is concentrated under reduced pressure and the residue is purified by preparative HPLC-MS; collected fractions are concentrated under reduced pressure and the product is partitioned between EtOAc and aqueous HCl solution. The organic layer is separated, washed with 5% aqueous $NaHCO_3$ solution; it is dried and concentrated under reduced pressure to obtain the title compound (61 mg).

HPLC-MS (Method 10): $R_t$=2.93 min

MS (ES+): m/z=459 $[M+H]^+$

Example 71

Racemic Mixture

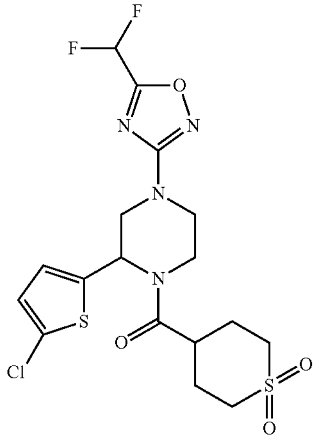 [SMILES: O=C(C1CCS(=O)(=O)CC1)N1CCN(c2noc(C(F)F)n2)CC1c1ccc(Cl)s1]

Example 49a (280 mg) and hydroxylamine (50% aqueous solution, 78 μl, 1.27 mmol) are dissolved in 2 ml of EtOH and the reaction is heated in a microwave reactor during 30 minutes at 100° C. The solvent is removed under reduced pressure to obtain 200 mg of crude 3-(5-Chloro-thiophen-2-yl)-4-(1,1-dioxo-hexahydro-1lambda*6*-thiopyran-4-carbonyl)-N-hydroxy-piperazine-1-carboxamidine intermediate (HPLC-MS (Method 11):$R_t$=1.99 min, MS (ES+): m/z=421 $[M+H]^+$) that is dissolved in 2 ml of acetonitrile; difluoroacetic anhydride (109 mg, 0.63 mmol) and N,N-diisopropylethylamine (160 μl, 0.94 mmol) are added and the reaction is heated in a microwave reactor during 30 minutes at 100° C. The solvent is removed and the crude is partitioned between EtOAc and water, the organic layer is separated and concentrated under reduced pressure; the residue is purified by Silica gel flash chromatography using DCM/MeOH 99:1 to 90:10 as eluent to obtain the title compound (35 mg, 10% yield over two steps).

HPLC-MS (Method 5): $R_t$=3.00 min

MS (APCI+): m/z=481 $[M+H]^+$

Example 72

Racemic Mixture

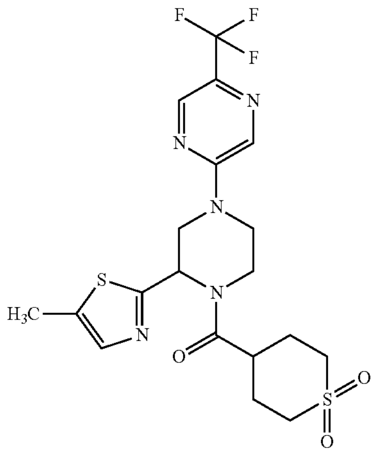 [SMILES: Cc1cnc(C2CN(c3cnc(C(F)(F)F)cn3)CCN2C(=O)C2CCS(=O)(=O)CC2)s1]

Example 72 is synthesized as described for example 69 starting from example 16a (25 mg, 0.14 mmol), N,N-diisopropylethylamine (47 μl, 0.27 mmol for the first step, 35 μl, 0.20 for the second), 2-Bromo-5-Trifluoromethylpyrazine (40 mg, 0.18 mmol) instead 2-Chloro-5-Trifluoromethyl-(1,3,4)-Thiadiazole, 1,1-dioxothiane-4-carbonyl chloride (40 mg, 0.20 mmol previously prepared from the corresponding carboxilic acid and oxalyl chloride in anhydrous DCM), to obtain, after the purification, the title compound (17 mg, 26% yield).

HPLC-MS (Method 5): $R_t$=2.83 min

MS (APCI+): m/z=490 $[M+H]^+$

Example 73

Racemic Mixture

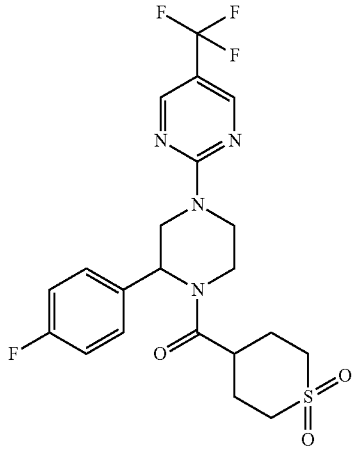 [SMILES: O=C(C1CCS(=O)(=O)CC1)N1CCN(c2ncc(C(F)(F)F)cn2)CC1c1ccc(F)cc1]

Example 73 is synthesized as described for example 1 starting from example 44h (60 mg, 0.18 mmol) instead of example 44k, 2-Chloro-5-(trifluoromethyl)pyrimidine (48 mg, 0.26 mmol), N,N-diisopropylethylamine (91 μl, 0.53 mmol) and 1 ml of anhydrous DMSO. The reaction mixture is heated in a microwave reactor at 100° C. during 2 hours. The crude is purified by preparative HPLC-MS to obtain the title compound (69 mg, 79% yield).

HPLC-MS (Method 10): $R_t$=3.63 min

MS (ES+): m/z=487 $[M+H]^+$

The enantiomers are obtained by HPLC separation using a chiral stationary phase.

Method for Separation:

HPLC apparatus type: Waters 600 Pump; column: Daicel Chiralpack IA, 5.0 μm, 250 mm×20 mm; method: eluent hexane/IPA 70:30; flow rate: 15 mL/min, Temperature: 26° C.; UV Detection: 254 nm Example of Separation by Chiral HPLC:

Submitted to separation: 620 mg of Example 73; Obtained: 217 mg of enantiomer 1 (Exp. 74) and 223 mg of enantiomer 2 (Exp. 75)

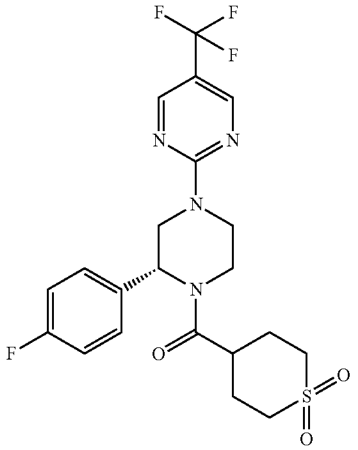

Example 74: enantiomer 1

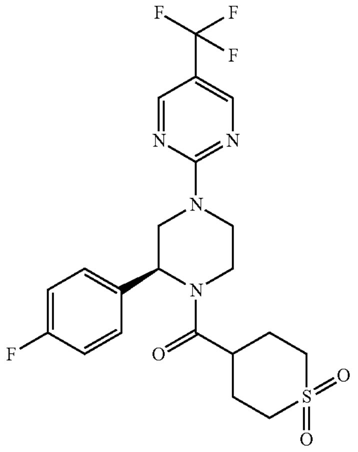 [SMILES: O=C(C1CCS(=O)(=O)CC1)N1CCN(c2ncc(C(F)(F)F)cn2)C[C@@H]1c1ccc(F)cc1]

Example 75: enantiomer 2

| Example | Chiral HPLC $R_t$ [min] | HPLC-MS (Method 10): $R_t$ [min] | MS (ES+): m/z |
|---|---|---|---|
| Exp. 74 | 14.85 (Method 15) | 3.61 | 487 |
| Exp. 75 | 19.42 (Method 15) | 3.60 | 487 |

Alternative Synthesis of Example 74 (Single Enantiomer; R-Configuration)

N-(3-Dimethylaminopropyl)-N-Ethylcarbodiimidehydrochloride (15 mg, 0.1 mmol) is added to a stirred solution of example 63a (20 mg, 0.1 mmol), tetrahydro-2H-thiopyran-4-carboxilic acid 1,1-dioxide (15 mg, 0.1 mmol) and 1-Hydroxy-7-azabenzotriazole (10 mg, 0.1 mmol) dissolved in 0.5 ml of DMF and 1.5 ml of anhydrous THF under nitrogen atmosphere; the reaction is then stirred 16 hours. THF is removed under reduced pressure and the residue is partitioned between water and EtOAc. The organic layer is separated, dried over anhydrous $Na_2SO_4$ and concentrated under reduced pressure. Crude product is purified by Silica gel flash chromatography, using EtOAc/Hexane/MeOH 70:30:1 as eluent, to obtain the title compound (26 mg, 97% yield; enantiomeric excess 97.4%).

HPLC-MS (Method 10): $R_t$=3.60 min

MS (ES+): m/z=487 $[M+H]^+$

Chiral HPLC (Method 15): $R_t$=14.9 min, 98.7% at 230 nm (R-Enantiomer)

20.0 min, 1.3% at 230 nm (S-enantiomer)

Alternative Synthesis of Example 75 (Single Enantiomer; S-Configuration)

N-(3-Dimethylaminopropyl)-N-Ethylcarbodiimidehydrochloride (25 mg, 0.1 mmol) is added to a stirred solution of example 69a (30 mg, 0.1 mmol), tetrahydro-2H-thiopyran-4-carboxilic acid 1,1-dioxide (20 mg, 0.1 mmol) and 1-Hydroxy-7-azabenzotriazole (12 mg, 0.1 mmol) dissolved in 0.5 ml of DMF and 1.5 ml of anhydrous THF under nitrogen atmosphere then the reaction is stirred 16 hours. THF is removed under reduced pressure and the residue is partitioned between water and EtOAc. The organic layer is separated, washed with 5% $NaHCO_3$ aqueous solution, dried over anhydrous $Na_2SO_4$ and concentrated under reduced pressure. The crude product is purified by Silica gel flash chromatography, using DCM/MeOH 100:2 as eluent, to obtain the title compound (30 mg, 74% yield; enantiomeric excess 89%).

UPLC-MS (Method 1): $R_t$=1.18 min

MS (ES+): m/z=487 $[M+H]^+$

Chiral HPLC (Method 15): $R_t$=15.1 min, 5.5% (R-Enantiomer)

$R_t$=19.0 min, 94.5% (S-Enantiomer)

Example 76

Racemic Mixture

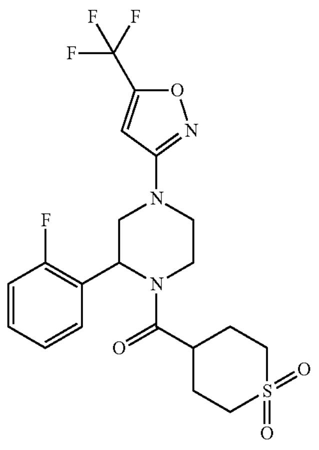 [SMILES: O=C(C1CCS(=O)(=O)CC1)N1CCN(c2cc(C(F)(F)F)on2)CC1c1ccccc1F]

Example 76 is synthesized as described for example 50 using N,N-diisopropylethylamine (100 µl, 0.58 mmol), 1,1-dibromoformaldoxime (120 mg, 0.59 mmol), example 44g (200 mg, 0.59 mmol) instead of example 44h, 2-Bromo-3,3,3-trifluoropropene (0.31 ml, 2.94 mmol), triethylamine (100 µl, 1.22 mmol). After the work-up the residue is purified by Silica gel flash chromatography using DCM/MeOH 100:3 as eluent to obtain the title compound (70 mg, 25% yield).

HPLC-MS (Method 5): $R_t$=3.03 min

MS (APCI+): m/z=476 $[M+H]^+$

Example 77

Racemic Mixture

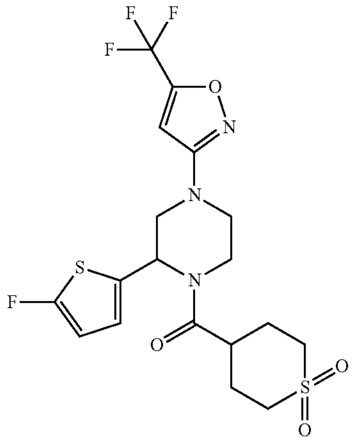 [SMILES: O=C(C1CCS(=O)(=O)CC1)N1CCN(c2cc(C(F)(F)F)on2)CC1c1ccc(F)s1]

Example 77 is synthesized as described for example 50 using N,N-diisopropylethylamine (48 µl, 0.28 mmol), 1,1-dibromoformaldoxime (57 mg, 0.28 mmol), example 441 (100 mg, 0.28 mmol) instead of example 44h, 2-Bromo-3,3,3-trifluoropropene (247 mg, 1.41 mmol), triethylamine (79 µl, 0.57 mmol). After the work-up the residue is purified by Silica gel flash chromatography using EtOAc/cyclohexane 50:50 to 100:0 as eluent then by preparative HPLC-MS to obtain the title compound (42 mg, 30% yield).

HPLC-MS (Method 5): $R_t$=3.17 min

MS (APCI+): m/z=482 $[M+H]^+$

Example 78

Racemic Mixture

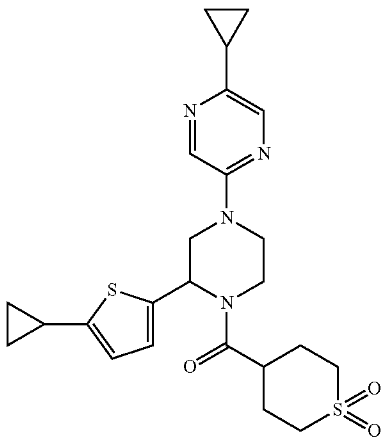 [SMILES: O=C(C1CCS(=O)(=O)CC1)N1CCN(c2cnc(C3CC3)cn2)CC1c1ccc(C2CC2)s1]

Example 53a (54 mg, 0.11 mmol), potassium cyclopropyltrifluoroborate (31 mg, 0.21 mmol), butyl-1-adamanthylphosphine (1.5 mg), palladium(II) acetate (0.5 mg) and cesium carbonate (102 mg, 0.31 mmol) are suspended in 0.9 ml of toluene and 0.1 ml of water and the reaction mixture is heated in a microwave reactor during 2 hours at 100° C. Potassium cyclopropyltrifluoroborate (31 mg, 0.21 mmol) is added a second time and the reaction is heated in a microwave reactor during 2 hours at 100° C.

The mixture is diluted with EtOAc and water, the organic layer is separated and concentrated under reduce pressure then the residue is suspended in 0.9 ml of toluene and 0.1 ml of water, potassium cyclopropyltrifluoroborate (61 mg, 0.42 mmol), butyl-1-adamanthylphosphine (2 mg), palladium(II) acetate (1 mg) and cesium carbonate (102 mg, 0.31 mmol) are added and the reaction mixture is heated in a microwave reactor during 1 hour at 115° C.

EtOAc and water are added, the aqueous layer is further extracted with DCM then the organic phases are collected, dried and concentrated under reduced pressure. The residue is purified by preparative HPLC-MS to obtain the title compound (11 mg, 22% yield).

HPLC-MS (Method 5): $R_t$=3.21 min

MS (APCI+): m/z=487 $[M+H]^+$

Example 79

Racemic Mixture

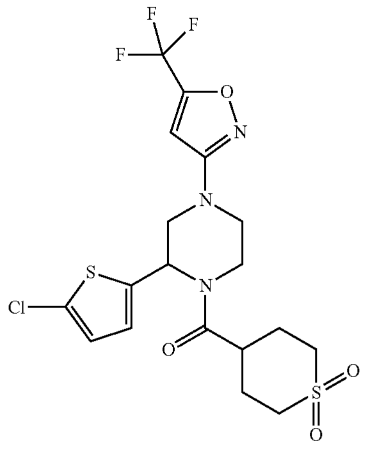 [SMILES: O=C(C1CCS(=O)(=O)CC1)N1CCN(c2cc(C(F)(F)F)on2)CC1c1ccc(Cl)s1]

Example 79 is synthesized as described for example 50 using N,N-diisopropylethylamine (71 μl, 0.41 mmol), 1,1-dibromoformaldoxime (84 mg, 0.41 mmol), example 44c (150 mg, 0.41 mmol) instead of example 44h, 2-Bromo-3,3,3-trifluoropropene (213 μl, 2.07 mmol), triethylamine (75 μl, 0.54 mmol). After the work-up the residue is purified by Silica gel flash chromatography using DCM/MeOH 100:0 to 90:10 as eluent then by preparative HPLC-MS to obtain the title compound (33 mg, 16% yield).

HPLC-MS (Method 5): $R_t$=3.40 min

MS (APCI+): m/z=498 $[M+H]^+$

Example 80

Racemic Mixture

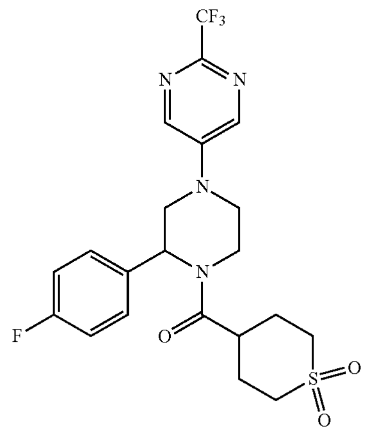 [SMILES: O=C(C1CCS(=O)(=O)CC1)N1CCN(c2cnc(C(F)(F)F)nc2)CC1c1ccc(F)cc1]

Example 80 is synthesized as described for example 42b starting from example 31a (175 mg, 0.54 mmol) instead of example 40b, N-(3-dimethylaminopropyl)-N'-ethylcarbodiimide hydrochloride (154 mg, 0.80 mmol), tetrahydro-2H-thiopyran-4-carboxilic acid 1,1-dioxide (143 mg, 0.80 mmol) and 1-hydroxybenzotriazole (7 mg, 0.05 mmol), 5 ml of DCM. The crude is partitioned between DCM and water, the organic layer is washed with aqueous $NaHCO_3$, dried and concentrated under reduced pressure and the residue is purified by Silica gel flash cromatography using EtOAc/cyclohexane 60:40 to 100:0 as eluent, to obtain the title compound (111 mg, 42% yield).

HPLC-MS (Method 5): $R_t$=2.80 min

MS (APCI+): m/z=487 $[M+H]^+$

Example 81

Racemic Mixture

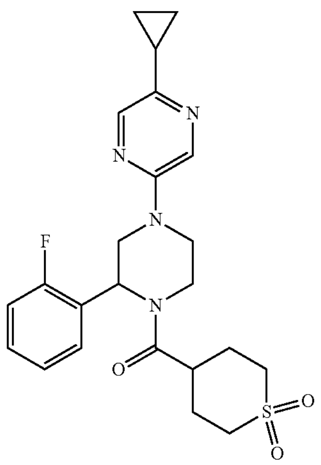 [SMILES: O=C(C1CCS(=O)(=O)CC1)N1CCN(c2cnc(C3CC3)cn2)CC1c1ccccc1F]

Example 54a (280 mg, 0.51 mmol), potassium cyclopropyltrifluoroborate (210 mg, 1.42 mmol), butyl-1-adamanthylphosphine (60 mg, 0.17 mmol), palladium(II) acetate (13 mg, 0.06 mmol) and $K_3PO_4$ (420 mg, 1.98 mmol) are suspended in 5 ml of degassed toluene and 0.25 ml of water and the reaction mixture is heated in a microwave reactor during 1 hour at 130° C. The crude is partitioned between EtOAc and water, the organic layer is separated, dried over $Na_2SO_4$ and concentrated under reduced pressure. The residue is purified by Silica gel flash chromatography using DCM/MeOH 100:2 as eluent to obtain 45 mg (19% yield) of the title compound.

HPLC-MS (Method 16): $R_t$=3.94 min

MS (ES+): m/z=459 [M+H]$^+$

Example 82

Racemic Mixture

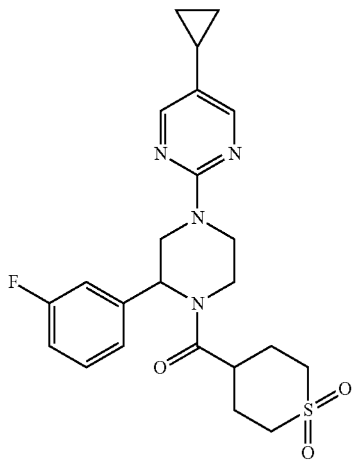 [SMILES: O=C(C1CCS(=O)(=O)CC1)N1CCN(c2ncc(C3CC3)cn2)CC1c1cccc(F)c1]

Example 82 is synthesized as described for example 1 starting from example 44b (100 mg of free base, 0.29 mmol) instead of example 44k, 2-Chloro-5-cyclopropylpyrimidine (68 mg, 0.43 mmol) instead of 2-Chloro-5-(trifluoromethyl) pyrimidine, N,N-diisopropylethylamine (98 μl, 0.58 mmol) and 2 ml of anhydrous DMSO. The reaction mixture is heated 2 hours at 115° C. in a microwave reactor; the crude is purified by preparativer HPLC-MS to obtain the title compound (41 mg, 31% yield)

HPLC-MS (Method 5): $R_t$=2.93 min

MS (APCI+): m/z=459 [M+H]$^+$

Example 83

Racemic Mixture

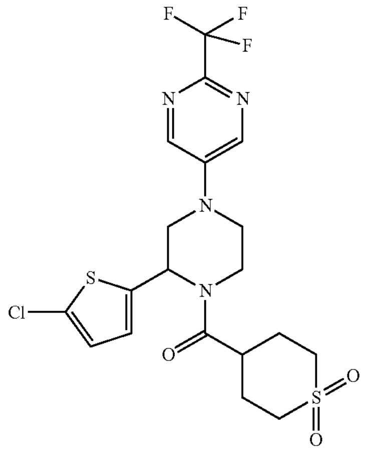 [SMILES: O=C(C1CCS(=O)(=O)CC1)N1CCN(c2cnc(C(F)(F)F)nc2)CC1c1ccc(Cl)s1]

Example 83 is synthesized as described for example 16 starting from example 44c (100 mg of the corresponding hydrochloride, 0.24 mmol) instead of example 44b, 5-Bromo-2-(trifluoromethyl)pyrimidine (64 mg, 0.28 mmol) instead of 2-Chloro-5-Fluoropyridine, X-Phos (45 mg, 0.09 mmol), Tris(dibenzylideneacetone)dipalladium(0)-chloroform adduct (49 mg, 0.05 mmol) and sodium tert-butoxide (57 mg, 0.59 mmol) in 2 ml of dioxane. The reaction mixture is heated 1.5 hours at 100° C. in a microwave reactor. The reaction mixture is diluted with EtOAc, filtered over a celite pad and then it is concentrated under reduced pressure. The residue is purified by Silica gel flash chromatography using cyclohexane/EtOAc 98:2 to 70:30 as eluent to obtain 24 mg (20% yield) of the title product.

HPLC-MS (Method 14): $R_t$=6.12 min

MS (APCI+): m/z=509 [M+H]$^+$

Example 84

Racemic Mixture

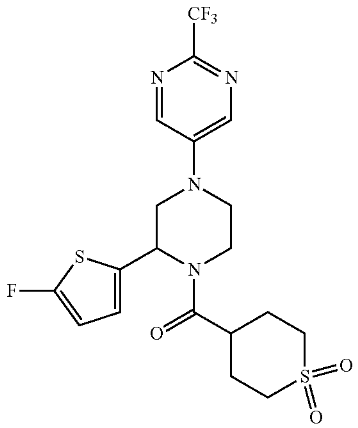 [SMILES: O=C(C1CCS(=O)(=O)CC1)N1CCN(c2cnc(C(F)(F)F)nc2)CC1c1ccc(F)s1]

Example 84 is synthesized as described for example 42b starting from example 32a (30 mg, 0.08 mmol) instead of example 40b, N-(3-dimethylaminopropyl)-N'-ethylcarbodiimide hydrochloride (23 mg, 0.12 mmol), tetrahydro-2H-thiopyran-4-carboxilic acid 1,1-dioxide (22 mg, 0.12 mmol) and 1-hydroxybenzotriazole (1 mg, 0.01 mmol), 3 ml of DCM. The crude is partitioned between DCM and water, the organic layer is washed with aqueous $NaHCO_3$, dried and concentrated under reduced pressure. The residue is purified by Silica gel flash cromatography using EtOAc/cyclohexane 50:50 to 100:0 as eluent, to obtain the title compound (11 mg, 26% yield).

HPLC-MS (Method 16): $R_t$=4.05 min

MS (ES+): m/z=493 [M+H]$^+$

Example 85

Racemic Mixture

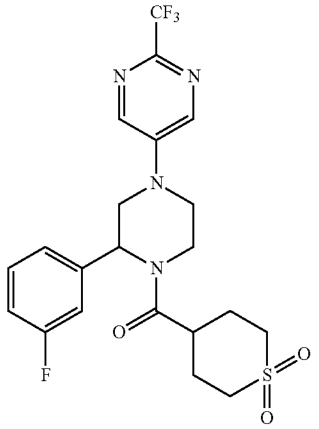 [SMILES: O=C(C1CCS(=O)(=O)CC1)N1CCN(c2cnc(C(F)(F)F)nc2)CC1c1cccc(F)c1]

Example 85 is synthesized as described for example 16 starting from example 44b (100 mg of free base, 0.29 mmol), 5-Bromo-2-(trifluoromethyl)pyrimidine (80 mg, 0.35 mmol) instead 2-Chloro-5-Fluoropyridine, X-Phos (56 mg, 0.12 mmol), Tris(dibenzylideneacetone)dipalladium(0) chloroform adduct (61 mg, 0.06 mmol), sodium tert-butoxide (56 mg, 0.59 mmol) and degassed Dioxane; the reaction mixture is heated in a microwave reactor during 2 hours at 100° C. The crude reaction mixture is filtered and purified by preparative HPLC-MS to obtain the title compound (86 mg, 60% yield).

HPLC-MS (Method 5): $R_t$=2.70 min

MS (APCI+): m/z=487 $[M+H]^+$

Example 86

Racemic Mixture

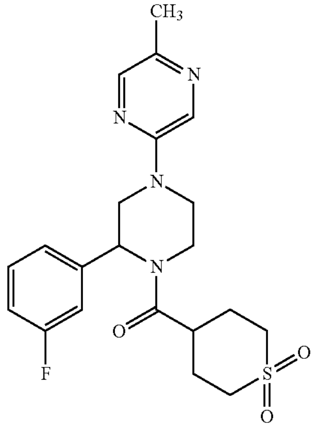 [SMILES: Cc1cnc(N2CCN(C(=O)C3CCS(=O)(=O)CC3)C(c3cccc(F)c3)C2)cn1]

Example 86 is synthesized as described for example 16 starting from example 44b (100 mg of free base, 0.29 mmol), 2-Bromo-5-methylpyrazine (61 mg, 0.35 mmol) instead of 2-Chloro-5-Fluoropyridine, X-Phos (56 mg, 0.12 mmol), Tris (dibenzylideneacetone)dipalladium(0) chloroform adduct (61 mg, 0.06 mmol), sodium tert-butoxide (56 mg, 0.59 mmol) and degassed Dioxane; the reaction mixture is heated in a microwave reactor at 100° C. during 2 hours. The crude reaction mixture is filtered and purified by preparative HPLC-MS to obtain the title compound (86 mg, 67% yield).

HPLC-MS (Method 5): $R_t$=2.37 min

MS (APCI+): m/z=433 $[M+H]^+$

Example 87

Racemic Mixture

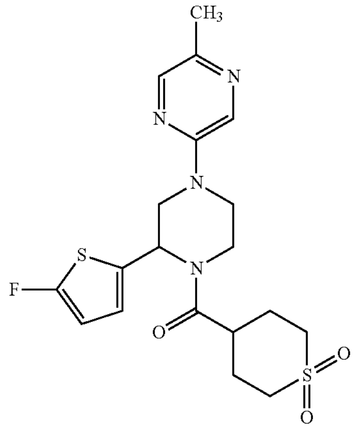

Example 87 is synthesized as described for example 16 starting from example 441 (60 mg, 0.17 mmol), 2-Bromo-5-methylpyrazine (35 mg, 0.20 mmol) instead of 2-Chloro-5-Fluoropyridine, 2-Dicyclohexylphosphino-2',6'-Dimethoxy-biphenyl (21 mg, 0.05 mmol) instead X-Phos, Tris (dibenzylideneacetone)dipalladium(0) (16 mg, 0.02 mmol), potassium tert-butoxide (29 mg, 0.25 mmol) and Dioxane; the reaction mixture is heated in a microwave reactor at 130° C. during 1 hour. After the work-up crude product was purified by preparative HPLC-MS to obtain the title compound (37 mg, 49% yield).

HPLC-MS (Method 5): $R_t$=2.48 min

MS (APCI+): m/z=439 $[M+H]^+$

Example 88

Racemic Mixture

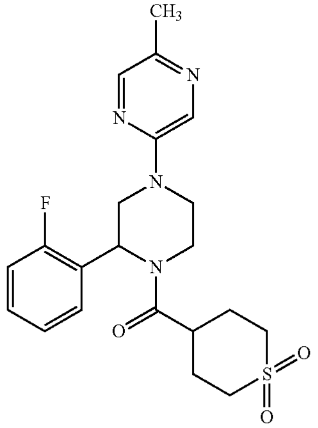 [SMILES: Cc1cnc(N2CCN(C(=O)C3CCS(=O)(=O)CC3)C(c3ccccc3F)C2)cn1]

Example 88 is synthesized as described for example 16 starting from example 44g (100 mg, 0.29 mmol), 2-Bromo-5-methylpyrazine (60 mg, 0.35 mmol) instead of 2-Chloro-5-Fluoropyridine, 2-dicyclohexylphosphino-2'-(N,N-dimethylamino)biphenyl (40 mg, 0.10 mmol) instead X-Phos, Tris(dibenzylideneacetone)dipalladium(0) (27 mg, 0.03 mmol), potassium tert-butoxide (50 mg, 0.45 mmol) and Dioxane; the reaction mixture is heated at 130° C. in a microwave reactor during 1 hour. After the work-up crude product was purified by preparative HPLC-MS to obtain the title compound (20 mg, 16% yield).

HPLC-MS (Method 5): $R_t$=2.33 min

MS (APCI+): m/z=433 [M+H]$^+$

Example 89

Racemic Mixture

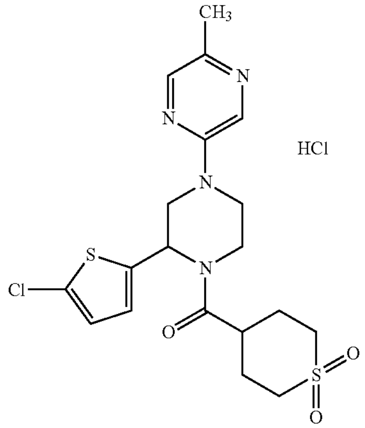 [SMILES: Cc1cnc(N2CCN(C(=O)C3CCS(=O)(=O)CC3)C(c3ccc(Cl)s3)C2)cn1 ; Cl]

HCl

Example 89 is synthesized as described for example 43a starting from example 33a (75 mg, 0.23 mmol) instead of example 40c, HATU (105 mg, 0.27 mmol) and N,N-diisopropylethylamine (120 μl, 0.69 mmol), tetrahydro-2H-thiopyran-4-carboxilic acid 1,1-dioxide (45 mg, 0.25 mmol), 4 ml of acetonitrile instead of DMF. After the work-up the residue is purified by preparative HPLC-MS to obtain the title compound (23 mg, 20% yield) as hydrochloride by addition of 37% HCl during the evaporation.

HPLC-MS (Method 5): $R_t$=2.63 min

MS (APCI+): m/z=455 [M+H]$^+$

Example 90

Racemic Mixture

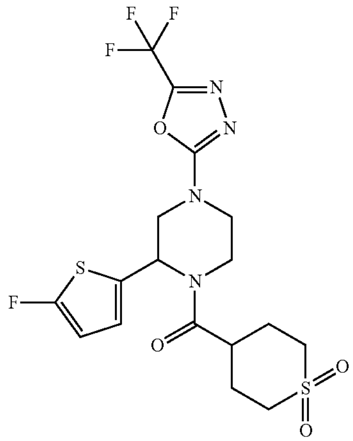 [SMILES: O=C(C1CCS(=O)(=O)CC1)N1CCN(c2nnc(C(F)(F)F)o2)CC1c1ccc(F)s1]

Example 58a (56 mg, 0.21 mmol) is added into a solution of example 441 (50 mg, 0.14 mmol) and N,N-diisopropylethylamine (36 μl, 0.21 mmol) dissolved in 1 ml of DMSO. After 6 hours stirring the reaction mixture is purified by preparative HPLC-MS to obtain the title compound (41 mg, 59% yield).

HPLC-MS (Method 5): $R_t$=2.71 min

MS (APCI+): m/z=483 [M+H]$^+$

Example 91

Racemic Mixture

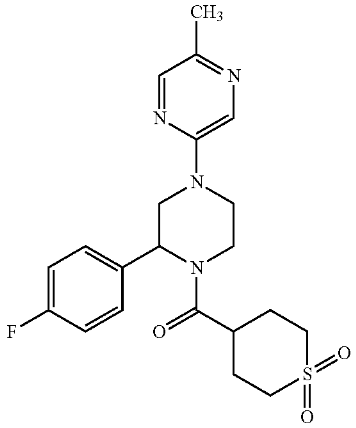

Example 91 is synthesized as described for example 16 starting from example 44h (60 mg, 0.17 mmol) instead of example 44b, 2-Bromo-5-methylpyrazine (36 mg, 0.21 mmol) instead of 2-Chloro-5-Fluoropyridine, 2-Dicyclohexylphosphino-2',6'-Dimethoxybiphenyl (21 mg, 0.05 mmol) instead of X-Phos, Tris(dibenzylideneacetone)dipalladium(0) (16 mg, 0.02 mmol), potassium tert-butoxide (29 mg, 0.25 mmol) and Dioxane; the reaction mixture is heated at 130° C. in a microwave reactor during 1 hour. After the work-up, the crude product is purified by preparative HPLC-MS to obtain the title compound (39 mg, 51% yield).

HPLC-MS (Method 10): $R_t$=2.84 min

MS (ES+): m/z=433 [M+H]$^+$

Example 92

Racemic Mixture

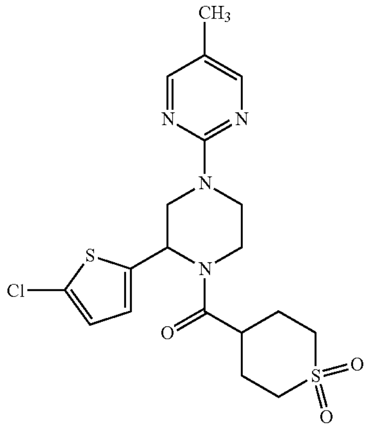 [SMILES: Cc1cnc(N2CCN(C(=O)C3CCS(=O)(=O)CC3)C(c3ccc(Cl)s3)C2)nc1]

Example 92 is synthesized as described for example 89 starting from example 34a (55 mg, 0.13 mmol) instead of example 33a, HATU (61 mg, 0.16 mmol) and N,N-diisopropylethylamine (70 μl, 0.40 mmol), tetrahydro-2H-thiopyran-4-carboxilic acid 1,1-dioxide (26 mg, 0.15 mmol), 2 ml of acetonitrile. After the work-up the residue is purified by preparative HPLC-MS to obtain the title compound (29 mg, 47% yield).

HPLC-MS (Method 5): $R_t$=2.88 min

MS (APCI+): m/z=455 [M+H]$^+$

Example 93

Racemic Mixture

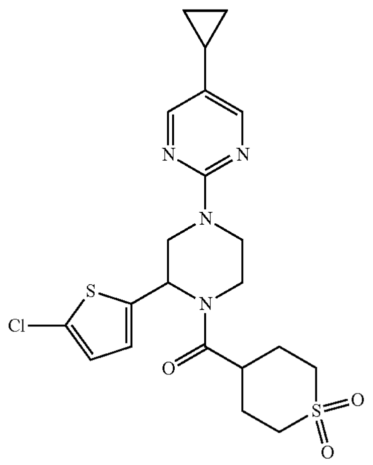 [SMILES: O=C(C1CCS(=O)(=O)CC1)N1CCN(c2ncc(C3CC3)cn2)CC1c1ccc(Cl)s1]

Example 93 is synthesized as described for example 89 starting from example 35a (70 mg, 0.16 mmol) instead of example 33a, HATU (73 mg, 0.19 mmol) and N,N-diisopropylethylamine (84 μl, 0.48 mmol), tetrahydro-2H-thiopyran-4-carboxilic acid 1,1-dioxide (32 mg, 0.18 mmol), 4 ml of acetonitrile. After the work-up the residue is purified by preparative HPLC-MS to obtain the title compound (48 mg, 62% yield).

HPLC-MS (Method 5): $R_t$=3.17 min

MS (APCI+): m/z=481 $[M+H]^+$

Example 94

Racemic Mixture

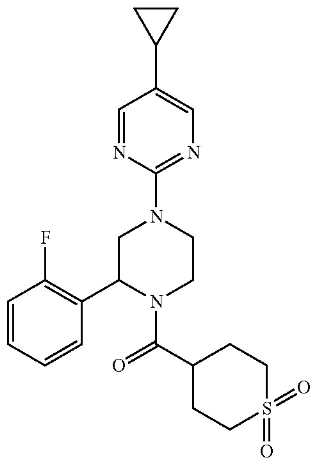 [SMILES: O=C(C1CCS(=O)(=O)CC1)N1CCN(c2ncc(C3CC3)cn2)CC1c1ccccc1F]

Example 94 is synthesized as described for example 1 starting from example 44g (200 mg, 0.59 mmol) instead of example 44k, 2-Chloro-5-cyclopropylpyrimidine (130 mg, 0.84 mmol) instead of 2-Chloro-5-(trifluoromethyl)pyrimidine, N,N-diisopropylethylamine (190 μl, 1.11 mmol) and 2 ml of anhydrous DMSO; the reaction mixture is heated at 100° C. during 30 minutes in a microwave reactor; after work-up the crude is purified by Silica gel flash chromatography using EtOAc/hexane/MeOH 80:20:1 to obtain the title compound (110 mg, 41% yield)

HPLC-MS (Method 10): $R_t$=3.28 min

MS (ES+): m/z=459 $[M+H]^+$

Example 95

Racemic Mixture

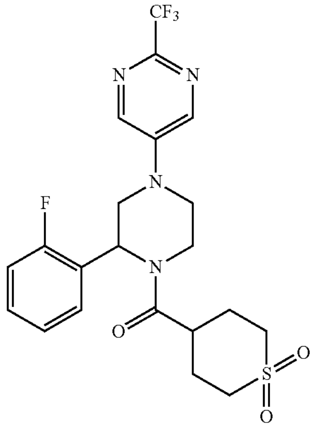 [SMILES: O=C(C1CCS(=O)(=O)CC1)N1CCN(c2cnc(C(F)(F)F)nc2)CC1c1ccccc1F]

Example 95 is synthesized as described for example 42b starting from example 36a (130 mg, 0.36 mmol) instead of example 40b, N-(3-dimethylaminopropyl)-N'-ethylcarbodiimide hydrochloride (140 mg, 0.73 mmol), tetrahydro-2H-thiopyran-4-carboxilic acid 1,1-dioxide (85 mg, 0.48 mmol) and 1-hydroxybenzotriazole (6 mg, 0.04 mmol) in DMF/THF 1:1 mixture instead of DCM. After the aqueous work-up the residue is purified by Silica gel flash chromatography, using hexane/EtOAc/MeOH 20:80:1 as eluent, to obtain the title compound (110 mg, 63% yield)

HPLC-MS (Method 10): $R_t$=3.25 min

MS (ES+): m/z=487 $[M+H]^+$

Example 96

Racemic Mixture

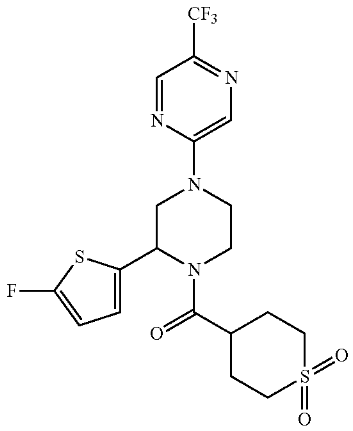 [SMILES: O=C(C1CCS(=O)(=O)CC1)N1CCN(c2cnc(C(F)(F)F)cn2)CC1c1ccc(F)s1]

Example 96 is synthesized as described for example 1 starting from example 441 (50 mg, 0.14 mmol) instead example 44k, 2-Bromo-5-(trifluoromethyl)pyrazine (49 mg, 0.22 mmol) instead 2-Chloro-5-(trifluoromethyl)pyrimidine, N,N-diisopropylethylamine (49 μl, 0.29 mmol) and 1 ml of anhydrous DMSO; the reaction mixture is heated at 130° C. during 30 minutes in a microwave reactor; after the water/EtOAc work-up the crude is purified by Silica gel flash chromatography using EtOAc/cyclohexane 60:40 to 100:0 as eluent to obtain the title compound (37 mg, 51% yield)

HPLC-MS (Method 5): $R_t$=2.98 min

MS (APCI+): m/z=493 $[M+H]^+$

Example 97

Racemic Mixture

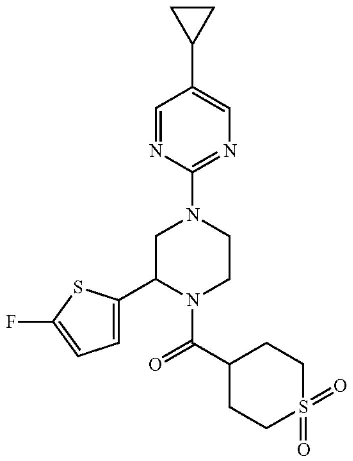 [SMILES: O=C(C1CCS(=O)(=O)CC1)N1CCN(c2ncc(C3CC3)cn2)CC1c1ccc(F)s1]

Example 97 is synthesized as described for example 1 starting from example 441 (50 mg, 0.14 mmol) instead of example 44k, 2-Chloro-5-cyclopropylpyrimidine (34 mg, 0.22 mmol) instead of 2-Chloro-5-(trifluoromethyl)pyrimidine, N,N-diisopropylethylamine (49 μl, 0.29 mmol) and 1 ml of anhydrous DMSO; the reaction mixture is heated during 30 minutes at 130° C. in a microwave reactor; the crude is purified by preparative HPLC-MS to obtain the title compound (13 mg, 19% yield)

HPLC-MS (Method 5): $R_t$=2.96 min

MS (APCI+): m/z=465 $[M+H]^+$

Example 98

Racemic Mixture

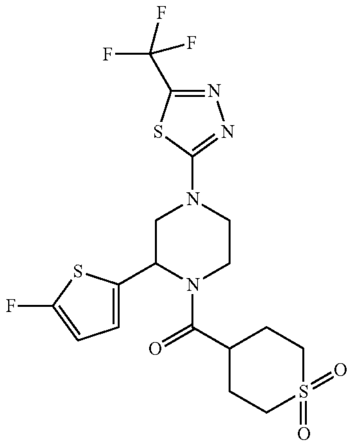 [SMILES: O=C(C1CCS(=O)(=O)CC1)N1CCN(c2nnc(C(F)(F)F)s2)CC1c1ccc(F)s1]

Example 98 is synthesized as described for example 1 starting from example 441 (50 mg, 0.14 mmol) instead example 44k, 2-Chloro-5-trifluoromethyl-(1,3,4)-thiadiazole (40 mg, 0.21 mmol) instead 2-Chloro-5-(trifluoromethyl)pyrimidine, N,N-diisopropylethylamine (50 μl, 0.29 mmol) and 1 ml of anhydrous DMSO; the reaction mixture is heated during 30 minutes at 130° C. in a microwave reactor; after the work-up the crude is purified by Silica gel flash chromatography using EtOAc/cyclohexane 60:40 to 100:0 as eluent to obtain the title compound (51 mg, 72% yield)

HPLC-MS (Method 5): $R_t$=3.44 min

MS (APCI+): m/z=499 $[M+H]^+$

Example 99

Racemic Mixture

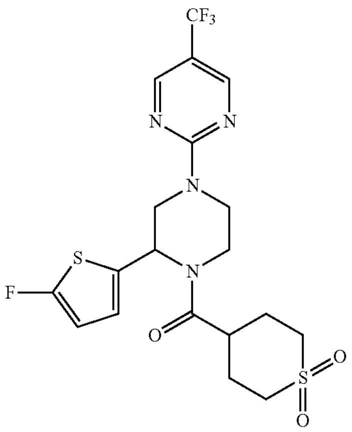 [SMILES: O=C(C1CCS(=O)(=O)CC1)N1CCN(c2ncc(C(F)(F)F)cn2)CC1c1ccc(F)s1]

Example 99 is synthesized as described for example 1 starting from example 441 (50 mg, 0.14 mmol) instead example 44k, 2-Chloro-5-(trifluoromethyl)pyrimidine (39 mg, 0.21 mmol), N,N-diisopropylethylamine (49 μl, 0.28 mmol) and 1 ml of anhydrous DMSO; the reaction mixture is heated during 30 minutes at 130° C. in a microwave reactor; the crude is purified by preparative HPLC-MS to obtain the title compound (47 mg, 67% yield)

HPLC-MS (Method 10): $R_t$=3.15 min

MS (ES+): m/z=493 $[M+H]^+$

Example 100

Racemic Mixture

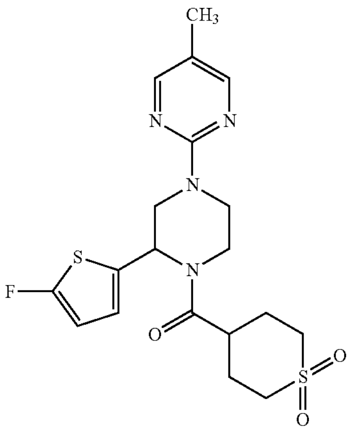

Example 100 is synthesized as described for example 1 starting from example 441 (70 mg, 0.20 mmol) instead example 44k, 2-Chloro-5-Methylpyrimidine (39 mg, 0.30 mmol), N,N-diisopropylethylamine (69 μl, 0.40 mmol) and 1 ml of anhydrous DMSO; the reaction mixture is heated during 30 minutes at 130° C. in a microwave reactor; the crude is purified by preparative HPLC-MS to obtain the title compound (16 mg, 18% yield)

HPLC-MS (Method 5): $R_t$=2.67 min

MS (APCI+): m/z=439 [M+H]$^+$

Example 101

Racemic Mixture

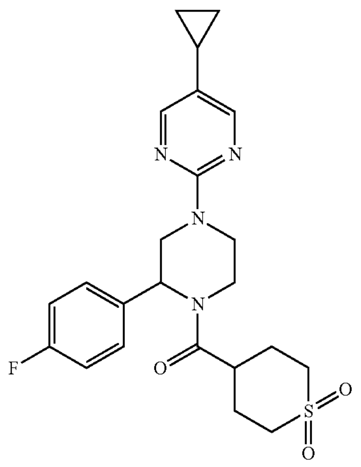 [SMILES: O=C(C1CCS(=O)(=O)CC1)N1CCN(c2ncc(C3CC3)cn2)CC1c1ccc(F)cc1]

Example 101 is synthesized as described for example 1 starting from example 44h (50 mg, 0.15 mmol) instead example 44k, 2-Chloro-5-cyclopropylpyrimidine (34 mg, 0.22 mmol) instead 2-Chloro-5-(trifluoromethyl)pyrimidine, N,N-diisopropylethylamine (50 μl, 0.29 mmol) and 1 ml of anhydrous DMSO; the reaction mixture is heated during 30 minutes at 130° C. in a microwave reactor; the crude is purified by preparative HPLC-MS to obtain the title compound (19 mg, 28% yield)

HPLC-MS (Method 5): $R_t$=2.87 min

MS (APCI+): m/z=459 [M+H]$^+$

Example 102 (Enantiomer 1) and Example 103 (Enantiomer 2)

The racemic mixture of the title compounds is synthesized as described for example 1 starting from example 44c (90 mg of the corresponding hydrochloride, 0.2 mmol) instead of example 44k, 2-Chloro-5-(trifluoromethyl)pyrimidine (52 mg, 0.3 mmol), N,N-diisopropylethylamine (133 μl, 0.8 mmol) and 1 ml of anhydrous DMSO; the reaction mixture is heated during 1 hour at 150° C. in a microwave reactor; the crude is purified by preparative HPLC-MS to obtain 73 mg (75% yield) of racemic product.

HPLC-MS (Method 4): $R_t$=7.07 min

MS (APCI+): m/z=509 [M+H]$^+$

The enantiomers are obtained by HPLC separation using a chiral stationary phase.

Method for Separation:

HPLC apparatus type: Waters 600 Pump; column: Daicel Chiralpack IA, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 504 mg of racemic mixture;

Obtained: 181 mg of enantiomer 1 (Exp. 102) and 183 mg of enantiomer 2 (Exp. 103)

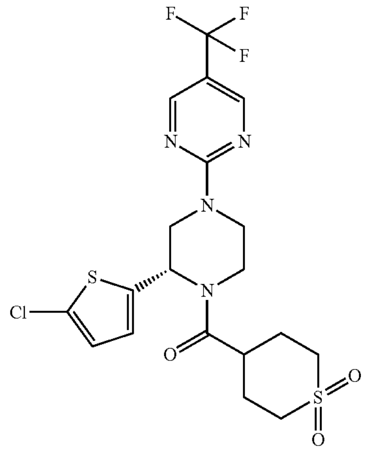 [SMILES: O=C(C1CCS(=O)(=O)CC1)N1CCN(c2ncc(C(F)(F)F)cn2)C[C@H]1c1ccc(Cl)s1]

Example 102: enantiomer 1

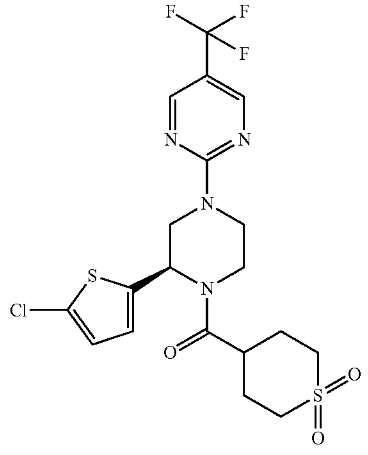 [SMILES: O=C(C1CCS(=O)(=O)CC1)N1CCN(c2ncc(C(F)(F)F)cn2)C[C@@H]1c1ccc(Cl)s1]

Example 103: enantiomer 2

| Example | Chiral HPLC $R_t$ [min] | HPLC-MS (Method 5): $R_t$ [min] | MS (APCI+): m/z |
|---|---|---|---|
| Exp. 102 | 14.09 (Method 15) | 3.32 | 509 |
| Exp. 103 | 17.90 (Method 15) | 3.34 | 509 |

Example 104

Racemic Mixture

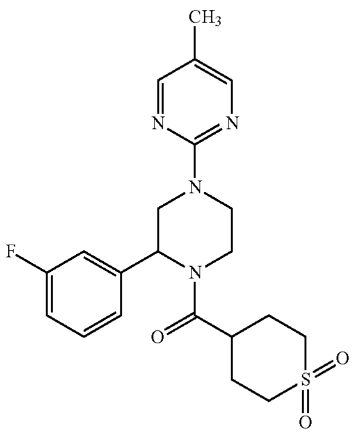 [SMILES: Cc1cnc(N2CCN(C(=O)C3CCS(=O)(=O)CC3)C(c3cccc(F)c3)C2)nc1]

Example 104 is synthesized as described for example 1 starting from example 44b (60 mg of the corresponding hydrochloride, 0.19 mmol) instead of example 44k, 2-Chloro-5-Methylpyrimidine (24 mg, 0.19 mmol) instead of 2-Chloro-5-(trifluoromethyl)pyrimidine, N,N-diisopropylethylamine (107 μl, 0.62 mmol) and 1 ml of anhydrous DMSO; the reaction mixture is heated during 30 minutes at 120° C. in a microwave reactor; the crude is purified by preparative HPLC-MS to obtain the title compound (23 mg, 34% yield)

HPLC-MS (Method 10): $R_t$=3.08 min

MS (ES+): m/z=433 $[M+H]^+$

Example 105

Racemic Mixture

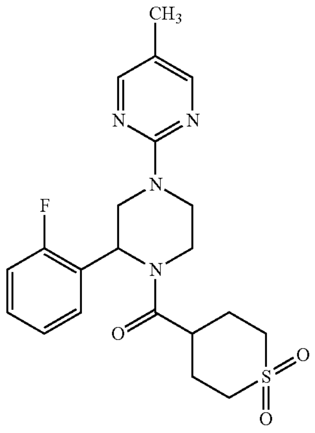 [SMILES: Cc1cnc(N2CCN(C(=O)C3CCS(=O)(=O)CC3)C(c3ccccc3F)C2)nc1]

Example 105 is synthesized as described for example 1 starting from example 44g (130 mg, 0.38 mmol) instead of example 44k, 2-Chloro-5-Methylpyrimidine (65 mg, 0.51 mmol) instead of 2-Chloro-5-(trifluoromethyl)pyrimidine, N,N-diisopropylethylamine (120 μl, 0.70 mmol) and 1 ml of anhydrous DMSO; the reaction mixture is heated during 30 minutes at 100° C. in a microwave reactor; after the work-up the crude is purified by Silica gel flash chromatography using EtOAc/hexane/MeOH 80:20:1 as eluent to obtain the title compound (60 mg, 36% yield)

HPLC-MS (Method 10): $R_t$=2.94 min

MS (ES+): m/z=433 $[M+H]^+$

Example 106

Racemic Mixture

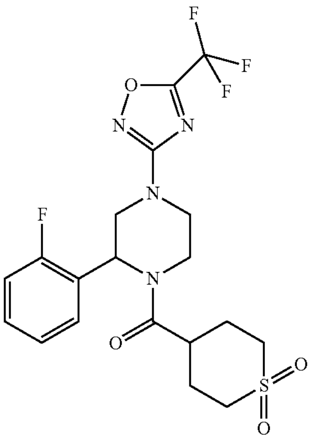 [SMILES: O=C(C1CCS(=O)(=O)CC1)N1CCN(c2noc(C(F)(F)F)n2)CC1c1ccccc1F]

Trifluoroacetic anhydride (180 μl, 1.29 mmol) is added into a stirred solution of example 52a (170 mg, 0.43 mmol) and triethylamine (230 μl, 1.65 mmol) dissolved in anhydrous acetonitrile; the reaction mixture is heated in a microwave reactor 35 minutes at 110° C. The solvent is removed under reduced pressure, the residue is partitioned between EtOAc and water then the organic layer is separated, dried over $Na_2SO_4$ and concentrated under reduced pressure; the crude is purified by Silica gel flash chromatography using EtOAc/hexane/MeOH 60:40:1 as eluent to obtain the title compound (90 mg, 44% yield).

HPLC-MS (Method 10): $R_t$=3.50 min

MS (ES+): m/z=477 $[M+H]^+$

Example 107

Racemic Mixture

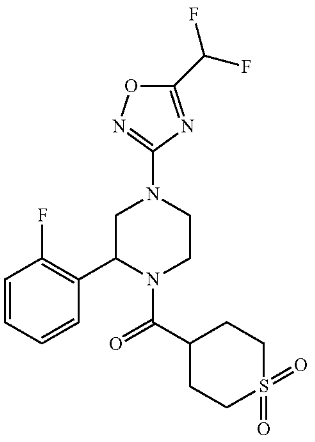 [SMILES: O=C(C1CCS(=O)(=O)CC1)N1CCN(c2noc(C(F)F)n2)CC1c1ccccc1F]

Example 107 is synthesized as described for example 106 starting from difluoroacetic anhydride (100 μl, 0.80 mmol) instead of trifluoroacetic anhydride, example 52a (100 mg, 0.25 mmol) and triethylamine (140 μl, 1.01 mmol) to obtain the title product (60 mg, 52% yield).

HPLC-MS (Method 10): $R_t$=3.18 min

MS (ES+): m/z=459 $[M+H]^+$

Example 108

Racemic Mixture

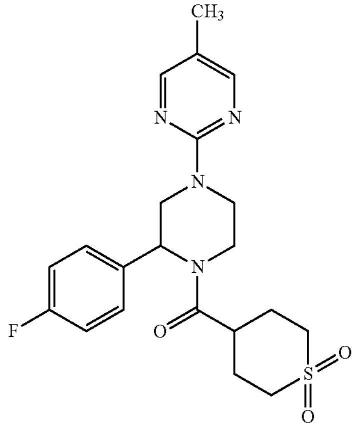 [SMILES: Cc1cnc(N2CCN(C(=O)C3CCS(=O)(=O)CC3)C(c3ccc(F)cc3)C2)nc1]

Example 108 is synthesized as described for example 1 starting from example 44h (50 mg, 0.15 mmol) instead of example 44k, 2-Chloro-5-Methylpyrimidine (28 mg, 0.22 mmol) instead of 2-Chloro-5-(trifluoromethyl)pyrimidine, N,N-diisopropylethylamine (50 μl, 0.29 mmol) and 1 ml of anhydrous DMSO; the reaction mixture is heated during 30 minutes at 120° C. in a microwave reactor; the crude is purified by preparative HPLC-MS to obtain the title compound (19 mg, 29% yield).

HPLC-MS (Method 5): $R_t$=2.59 min

MS (APCI+): m/z=433 $[M+H]^+$

Example 109

Racemic Mixture

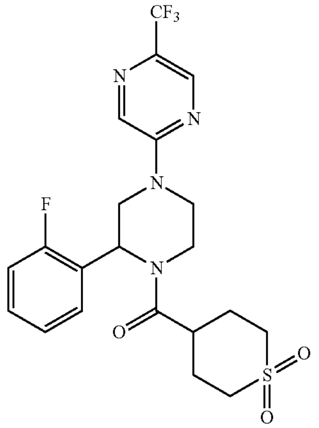 [SMILES: O=C(C1CCS(=O)(=O)CC1)N1CCN(c2cnc(C(F)(F)F)cn2)CC1c1ccccc1F]

Example 109 is synthesized as described for example 1 starting from example 44g (80 mg, 0.24 mmol) instead of example 44k, 2-Bromo-5-(trifluoromethyl)pyrazine (70 mg, 0.31 mmol) instead of 2-Chloro-5-(trifluoromethyl)pyrimidine, N,N-diisopropylethylamine (80 μl, 0.48 mmol) and 1 ml of anhydrous DMSO; the reaction mixture is heated during 30 minutes at 100° C. in a microwave reactor. After the work-up the crude is purified by Silica gel flash chromatography using EtOAc/hexane/MeOH 80:20:1 as eluent to obtain the title compound (80 mg, 70% yield).

HPLC-MS (Method 5): $R_t$=2.95 min

MS (APCI+): m/z=487 $[M+H]^+$

Example 110

Racemic Mixture

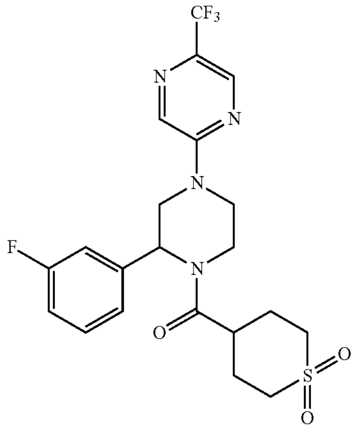 [SMILES: O=C(C1CCS(=O)(=O)CC1)N1CCN(c2cnc(C(F)(F)F)cn2)CC1c1cccc(F)c1]

Example 110 is synthesized as described for example 1 starting from example 44b (60 mg of the corresponding hydrochloride, 0.15 mmol) instead of example 44k, 2-Bromo-5-(trifluoromethyl)pyrazine (42 mg, 0.19 mmol) instead 2-Chloro-5-(trifluoromethyl)pyrimidine, N,N-diisopropylethylamine (107 μl, 0.62 mmol) and 1 ml of anhydrous DMSO; the reaction mixture is heated during 30 minutes at 120° C. in a microwave reactor. The crude is purified by preparative HPLC-MS to obtain the title compound (24 mg, 32% yield)

HPLC-MS (Method 10): $R_t$=3.48 min

MS (ES+): m/z=487 $[M+H]^+$

Example 111

Racemic Mixture

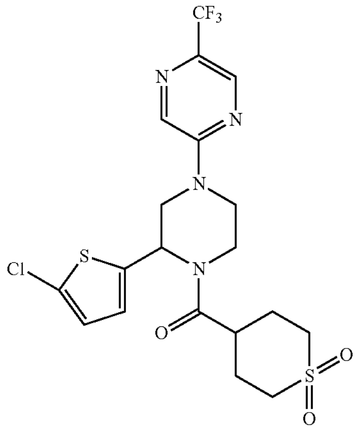 [SMILES: O=C(C1CCS(=O)(=O)CC1)N1CCN(c2cnc(C(F)(F)F)cn2)CC1c1ccc(Cl)s1]

Example 111 is synthesized as described for example 89 starting from example 37a (70 mg of the corresponding trifluoroacetate, 0.15 mmol) instead example 33a, HATU (69 mg, 0.18 mmol) and N,N-diisopropylethylamine (79 μl, 0.45 mmol), tetrahydro-2H-thiopyran-4-carboxilic acid 1,1-dioxide (30 mg, 0.17 mmol), 4 ml of acetonitrile. After the work-up the residue is purified by preparative HPLC-MS to obtain the title compound (34 mg, 44% yield).

HPLC-MS (Method 5): $R_t$=3.37 min

MS (APCI+): m/z=509 $[M+H]^+$

Example 112

Racemic Mixture

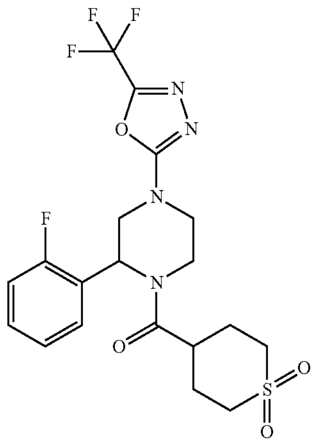 [SMILES: O=C(C1CCS(=O)(=O)CC1)N1CCN(c2nnc(C(F)(F)F)o2)CC1c1ccccc1F]

A solution of 5-(Trifluoromethyl)-1,3,4-Oxadiazol-2-amine (300 mg, 1.96 mmol) dissolved in 1.5 ml of diiodomethane is heated at 100° C.; isoamylnitrite (1.04 ml, 7.81 mmol) is then slowly added dropwise and resulting reaction mixture is stirred 1 hour. The crude reaction is purified by Silica gel flash chromatography using hexane/$Et_2O$ 9:1 as eluent then the resulting 2-Iodo-5-trifluoromethyl-[1,3,4]oxadiazole intermediate is added into a solution of example 44g (280 mg, 0.82 mmol) and N,N-diisopropylethylamine (430 μl, 2.51 mmol) dissolved in 3 ml of DMSO. After 2 hours stiffing, water and EtOAc are added, the organic phase is separated and concentrated under reduced pressure. The residue is purified by Silica gel flash chromatography using EtOAc/hexane/MeOH 80:20:1 as eluent to obtain the title compound (200 mg, 51% yield).

HPLC-MS (Method 10): $R_t$=3.10 min

MS (ES+): m/z=477 $[M+H]^+$

Example 113

Racemic Mixture

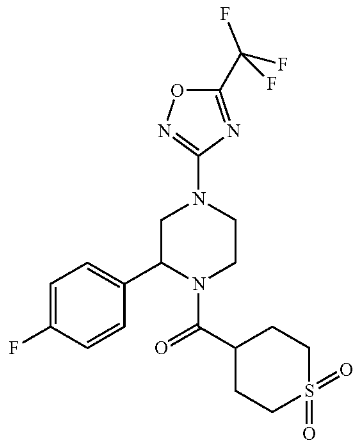 [SMILES: O=C(C1CCS(=O)(=O)CC1)N1CCN(c2noc(C(F)(F)F)n2)CC1c1ccc(F)cc1]

Example 113 is synthesized as described for example 106 starting from example 57a (75 mg,) instead of example 52a, trifluoroacetic anhydride (52 μl, 0.38 mmol), triethylamine (97 μl, 0.56 mmol) in 3 ml of anhydrous acetonitrile; the reaction mixture is heated at 100° C. during 20 minutes. The crude is partitioned between water and DCM, solvent is removed under reduced pressure and the residue is purified by Silica gel flash chromatography, using EtOAc/Cyclohexane 30:70 to EtOAc 100% as eluent, to obtain the title compound (23 mg, 25% yield).

HPLC-MS (Method 10): $R_t$=3.56 min

MS (ES+): m/z=477 $[M+H]^+$

Example 114

Racemic Mixture

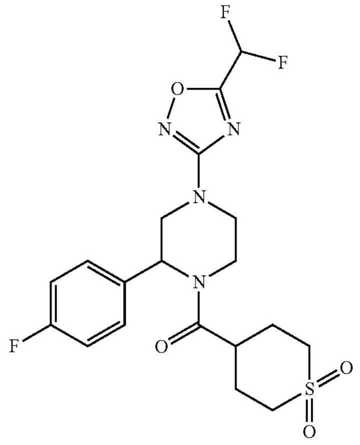 [SMILES: O=C(C1CCS(=O)(=O)CC1)N1CCN(c2noc(C(F)F)n2)CC1c1ccc(F)cc1]

Example 114 is synthesized as described for example 113 starting from example 57a (75 mg), difluoroacetic anhydride (47 μl, 0.38 mmol), triethylamine (97 μl, 0.56 mmol) in 3 ml of anhydrous acetonitrile; the reaction mixture is heated at 100° C. during 20 minutes. The crude is partitioned between water and DCM, solvent is removed under reduced pressure and the residue is purified by Silica gel flash chromatography, using EtOAc/Cyclohexane 50:50 to EtOAc 100% as eluent, to obtain the title compound (36 mg, 42% yield).

HPLC-MS (Method 10): $R_t$=3.27 min

MS (ES+): m/z=459 [M+H]$^+$

Example 115

Racemic Mixture

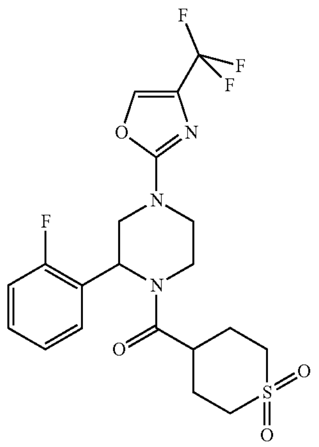 [SMILES: O=C(C1CCS(=O)(=O)CC1)N1CCN(c2nc(C(F)(F)F)co2)CC1c1ccccc1F]

Example 115 is synthesized as described for example 1 starting from example 44g (80 mg, 0.24 mmol) instead of example 44k, 2-Bromo-4-Trifluoromethyl-oxazole (76 mg, 0.35 mmol) instead 2-Chloro-5-(trifluoromethyl)pyrimidine, N,N-diisopropylethylamine (80 μl, 0.47 mmol) dissolved in DMSO. The crude product is purified by Silica gel flash chromatography, using EtOAc/Hexane/MeOH 70:30:1 as eluent, to obtain the title compound (50 mg, 45% yield).

HPLC-MS (Method 10): $R_t$=3.31 min

MS (ES+): m/z=476 [M+H]$^+$

Example 116

Racemic Mixture

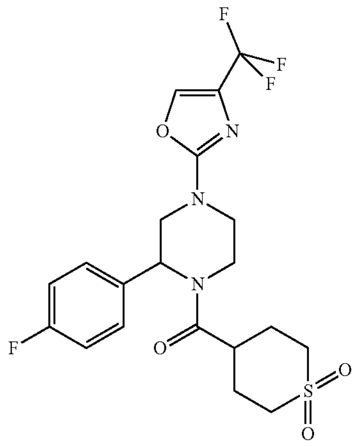 [SMILES: O=C(C1CCS(=O)(=O)CC1)N1CCN(c2nc(C(F)(F)F)co2)CC1c1ccc(F)cc1]

Example 55a (80 mg, 0.20 mmol) and 3-Bromo-1,1,1-trifluoroacetone (115 μl, 1.02 mmol are dissolved in 1 ml of tert-butylalcohol and heated during 8 hours at 90° C. The solvent is removed under reduced pressure and the residue is purified by preparative HPLC-MS to obtain the title compound (62 mg, 63% yield).

HPLC-MS (Method 10): $R_t$=3.38 min

MS (ES+): m/z=476 [M+H]$^+$

Example 117

Racemic Mixture

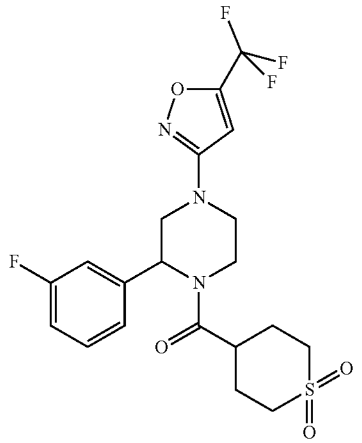 [SMILES: O=C(C1CCS(=O)(=O)CC1)N1CCN(c2cc(C(F)(F)F)on2)CC1c1cccc(F)c1]

2,2,6,6-Tetramethylpiperidine (68 μl, 0.39 mmol) followed by 1,1-dibromoformaldoxime (78 mg, 0.39 mmol) are added, under nitrogen atmosphere, into a cooled solution (−20° C.) of example 44b (128 mg of free base, 0.37 mmol) dissolved in 2 ml of anhydrous THF. After 2 hours stirring (meanwhile the temperature increase to 0° C.). 2-Bromo-3,3,3-trifluoropropene (199 μl, 1.93 mmol) is added followed by triethylamine (67 μl, 0.46 mmol, dissolved in 1 ml of anhydrous THF); after 3 hours, the temperature is increased to room temperature and the reaction mixture is further stirred overnight; the crude is purified by preparative HPLC-MS to obtain the title compound (13 mg, 8% yield).

HPLC-MS (Method 5): $R_t$=2.98 min

MS (APCI+): m/z=476 [M+H]$^+$

Example 118

Racemic Mixture

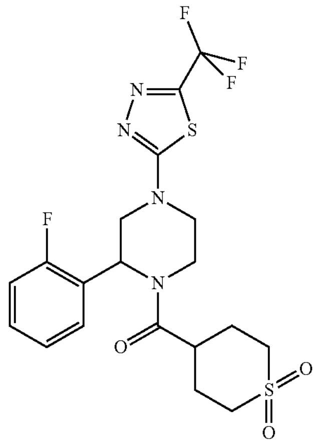 [SMILES: O=C(C1CCS(=O)(=O)CC1)N1CCN(c2nnc(C(F)(F)F)s2)CC1c1ccccc1F]

Example 118 is synthesized as described for example 1 starting from example 44g (80 mg, 0.24 mmol) instead of example 44k, 2-Chloro-5-trifluoromethyl-(1,3,4)-thiadiazole (70 mg, 0.37 mmol) instead of 2-Chloro-5-(trifluoromethyl) pyrimidine, N,N-diisopropylethylamine (80 μl, 0.48 mmol) and dry DMSO; the reaction mixture is heated during 30 minutes at 150° C. in a microwave reactor. The reaction mixture is poured into EtOAc/water mixture, the organic layer is separated, washed with water and dried over anhydrous $Na_2SO_4$ and concentrated under reduced pressure. The residue is purified by Silica gel flash chromatography using EtOAc/Hexane/MeOH 70:30:1 as eluent to obtain the title compound (85 mg, 73% yield).

HPLC-MS (Method 10): $R_t$=3.26 min

MS (ES+): m/z=493 $[M+H]^+$

Example 119

Racemic Mixture

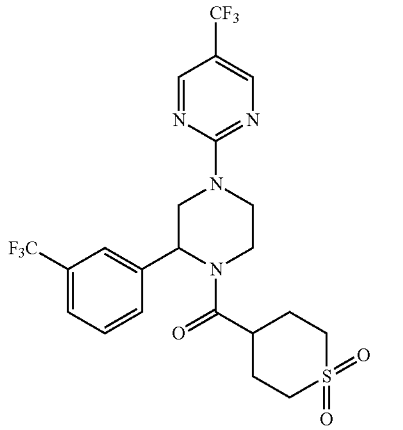 [SMILES: O=C(C1CCS(=O)(=O)CC1)N1CCN(c2ncc(C(F)(F)F)cn2)CC1c1cccc(C(F)(F)F)c1]

Example 119 is synthesized as described for example 1 starting from example 44d (78 mg, 0.20 mmol) instead of example 44k, 2-Chloro-5-(trifluoromethyl)pyrimidine (48 mg, 0.26 mmol), N,N-diisopropylethylamine (68 μl, 0.40 mmol) and dry DMSO; the reaction mixture is heated during 30 minutes at 150° C. in a microwave reactor. The reaction mixture is poured into $Et_2O$/water mixture, the organic layer is separated, washed with 1N aqueous HCl then dried and concentrated under reduced pressure to obtain the title compound (98 mg, 92% yield).

HPLC-MS (Method 10): $R_t$=3.78 min

MS (ES+): m/z=537 $[M+H]^+$

Example 120

Racemic Mixture

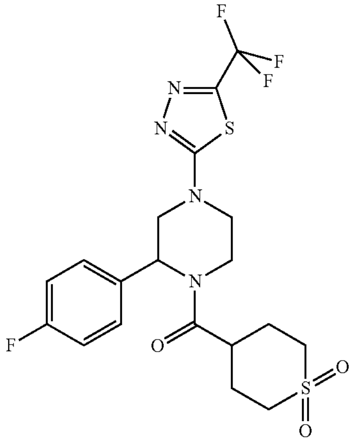 [SMILES: O=C(C1CCS(=O)(=O)CC1)N1CCN(c2nnc(C(F)(F)F)s2)CC1c1ccc(F)cc1]

Example 120 is synthesized as described for experiment 118 starting from example 44h (80 mg, 0.24 mmol) instead of example 44g, 2-Chloro-5-trifluoromethyl-(1,3,4)-thiadiazole (42 μl, 0.38 mmol), N,N-diisopropylethylamine (80 μl, 0.48 mmol) and dry DMSO; the reaction mixture is heated during 30 minutes at 150° C. in a microwave reactor;. The reaction mixture is purified by preparative HPLC-MS to obtain the title compound (87 mg, 74% yield).

HPLC-MS (Method 10): $R_t$=3.35 min

MS (ES+): m/z=493 $[M+H]^+$

Example 125

Racemic Mixture

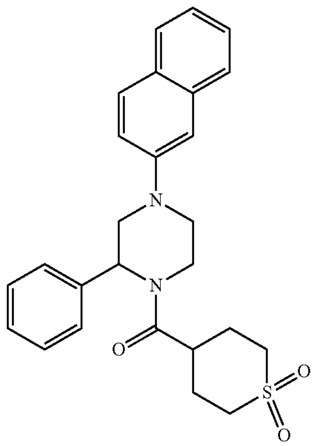 [SMILES: O=C(C1CCS(=O)(=O)CC1)N1CCN(c2ccc3ccccc3c2)CC1c1ccccc1]

2-Naphtaleneboronic acid (52 mg, 0.30 mmol) is added, followed by copper(II) acetate (50 mg, 0.28 mmol), to a solution of example 45a (22 mg of the corresponding trifluoroacetate salt, 0.05 mmol) and N,N-diisopropylethylamine (50 μl, 0.29 mmol) dissolved in 2 ml of dichloromethane; the reaction mixture is stirred 72 hours at room temperature. Water is added, the organic phase is separated and concentrated under reduced pressure then the residue is purified by preparative HPLC-MS to obtain the title compound (8.7 mg, 39% yield).

HPLC-MS (Method 21): $R_t$=0.96 min

MS: m/z=449 $[M+H]^+$

The following examples are synthesized in analogy to the preparation of example 125:

| Example | Product | Reactant | Boronic acid or ester | Product amount, yield | $R_t$ [min], method | MS m/z) |
|---|---|---|---|---|---|---|
| 121 (racemic mixture) | 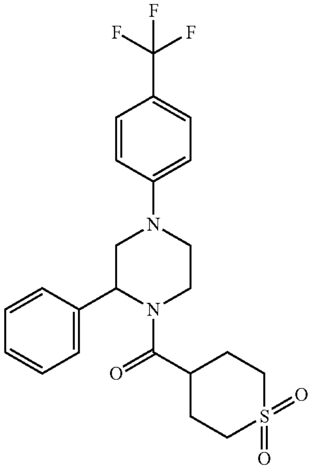 [SMILES: O=C(C1CCS(=O)(=O)CC1)N1CCN(c2ccc(C(F)(F)F)cc2)CC1c1ccccc1] | Example 45a (trifluoroacetate salt) | 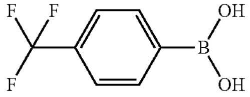 [SMILES: OB(O)c1ccc(C(F)(F)F)cc1] | 2.6 mg, 11% | $R_t$ = 0.95 min, Method 21 | 467 $[M + H]^+$ |
| 122 (racemic mixture) | 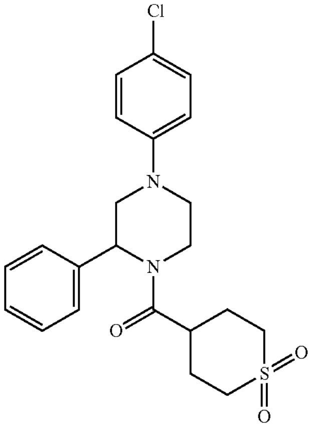 [SMILES: O=C(C1CCS(=O)(=O)CC1)N1CCN(c2ccc(Cl)cc2)CC1c1ccccc1] | Example 45a (trifluoroacetate salt) | 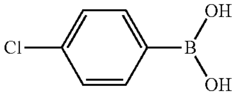 | 8.3 mg, 38% | $R_t$ = 0.93 min, Method 21 | 433 $[M + H]^+$ |
| 123 (racemic mixture) | 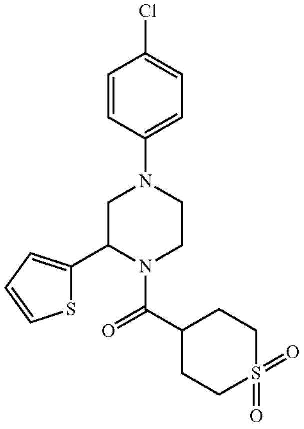 [SMILES: O=C(C1CCS(=O)(=O)CC1)N1CCN(c2ccc(Cl)cc2)CC1c1cccs1] | Example 46a (trifluoroacetate salt) | 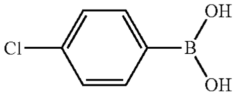 | 5.7 mg, 26% | $R_t$ = 0.93 min, Method 21 | 439 $[M + H]^+$ |

-continued
| Example | Product | Reactant | Boronic acid or ester | Product amount, yield | $R_t$ [min], method | MS m/z) |
|---|---|---|---|---|---|---|
| 124 (racemic mixture) | 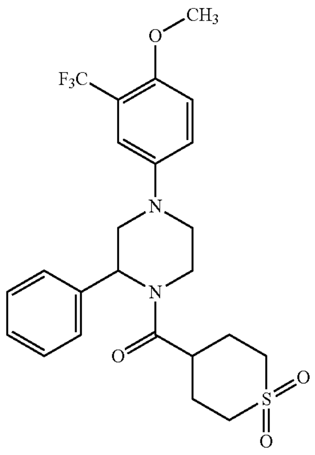 [SMILES: COc1ccc(N2CCN(C(=O)C3CCS(=O)(=O)CC3)C(c3ccccc3)C2)cc1C(F)(F)F] | Example 45a (trifluoroacetate salt) | 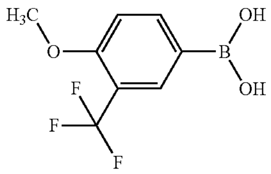 | 2.1 mg, 8.5% | $R_t$ = 0.93 min, Method 21 | 497 $[M + H]^+$ |
| 126 (racemic mixture) | 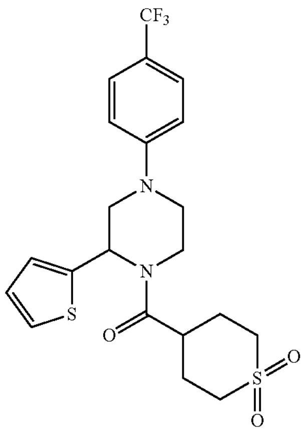 | Example 46a (trifluoroacetate salt) | 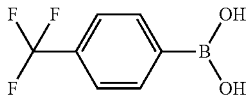 | 1.7 mg, 7% | $R_t$ = 0.95 min, Method 21 | 473 $[M + H]^+$ |
| 128 (racemic mixture) | 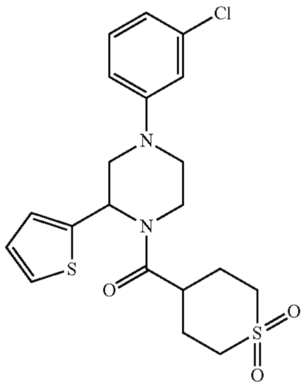 [SMILES: O=C(C1CCS(=O)(=O)CC1)N1CCN(c2cccc(Cl)c2)CC1c1cccs1] | Example 46a (trifluoroacetate salt) | 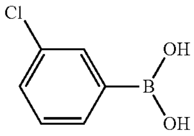 | 6.3 mg, 29% | $R_t$ = 0.92 min, Method 21 | 439 $[M + H]^+$ |

-continued
| Example | Product | Reactant | Boronic acid or ester | Product amount, yield | $R_t$ [min], method | MS m/z) |
|---|---|---|---|---|---|---|
| 130 (racemic mixture) | 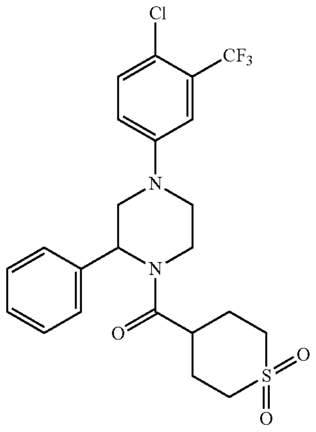 [SMILES: O=C(C1CCS(=O)(=O)CC1)N1CCN(c2ccc(Cl)c(C(F)(F)F)c2)CC1c1ccccc1] | Example 45a (trifluoroacetate salt) | 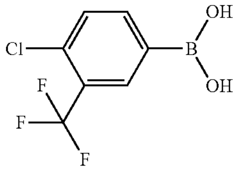 [SMILES: OB(O)c1ccc(Cl)c(C(F)(F)F)c1] | 1.0 mg, 4% | $R_t$ = 1.01 min, Method 21 | 501 $[M + H]^+$ |
| 131 (racemic mixture) | 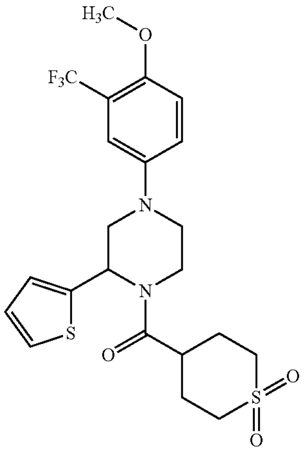 [SMILES: COc1ccc(N2CCN(C(=O)C3CCS(=O)(=O)CC3)C(c3cccs3)C2)cc1C(F)(F)F] | Example 46a (trifluoroacetate salt) | 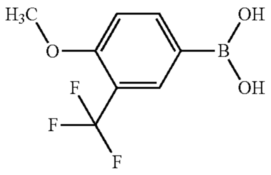 | 2.5 mg, 10% | $R_t$ = 0.93 min, Method 21 | 503 $[M + H]^+$ |
| 132 (racemic mixture) | 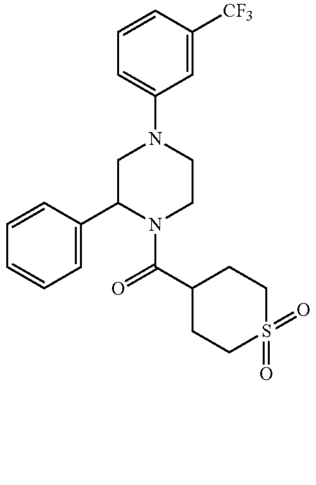 [SMILES: O=C(C1CCS(=O)(=O)CC1)N1CCN(c2cccc(C(F)(F)F)c2)CC1c1ccccc1] | Example 45a (trifluoroacetate salt) | 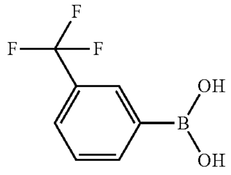 [SMILES: OB(O)c1cccc(C(F)(F)F)c1] | 3.7 mg, 16% | $R_t$ = 0.95 min, Method 21 | 467 $[M + H]^+$ |

-continued
| Example | Product | Reactant | Boronic acid or ester | Product amount, yield | $R_t$ [min], method | MS m/z) |
|---|---|---|---|---|---|---|
| 134 (racemic mixture) | 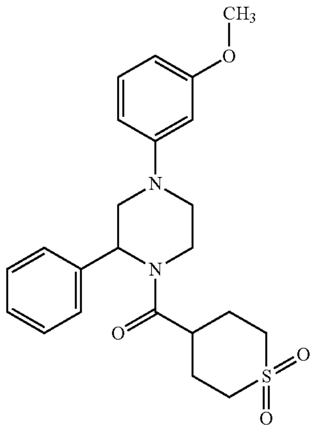 [SMILES: COc1cccc(N2CCN(C(=O)C3CCS(=O)(=O)CC3)C(c3ccccc3)C2)c1] | Example 45a (trifluoroacetate salt) | 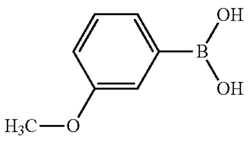 | 8.2 mg, 38% | $R_t$ = 0.84 min, Method 21 | 429 $[M + H]^+$ |
| 136 (racemic mixture) | 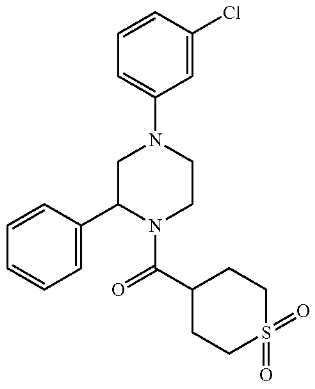 [SMILES: O=C(C1CCS(=O)(=O)CC1)N1CCN(c2cccc(Cl)c2)CC1c1ccccc1] | Example 45a (trifluoroacetate salt) | 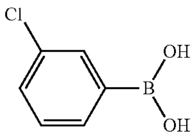 | 7.4 mg, 34% | $R_t$ = 0.93 min, Method 21 | 433 $[M + H]^+$ |
| 137 (racemic mixture) | 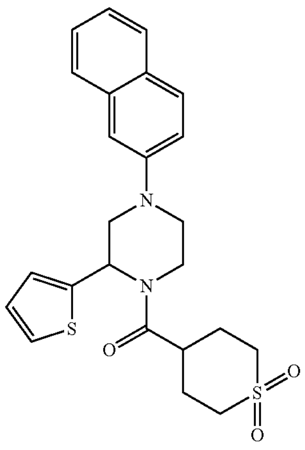 [SMILES: O=C(C1CCS(=O)(=O)CC1)N1CCN(c2ccc3ccccc3c2)CC1c1cccs1] | Example 46a (trifluoroacetate salt) | 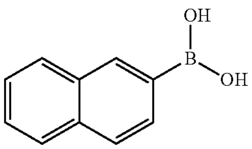 [SMILES: OB(O)c1ccc2ccccc2c1] | 7.7 mg, 34% | $R_t$ = 0.95 min, Method 21 | 455 $[M + H]^+$ |

-continued
| Example | Product | Reactant | Boronic acid or ester | Product amount, yield | $R_t$ [min], method | MS m/z) |
|---|---|---|---|---|---|---|
| 138 (racemic mixture) | 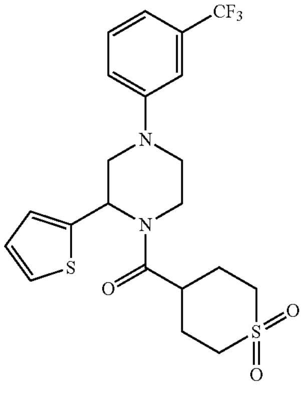 | Example 46a (trifluoroacetate salt) | 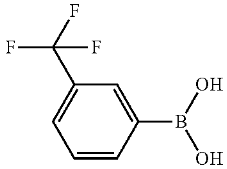 [SMILES: OB(O)c1cccc(C(F)(F)F)c1] | 3.7 mg, 16% | $R_t$ = 0.95 min, Method 21 | 473 $[M + H]^+$ |
| 139 (racemic mixture) | 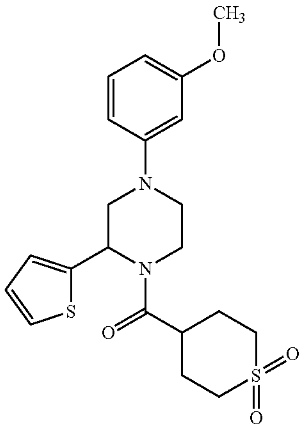 [SMILES: COc1cccc(N2CCN(C(=O)C3CCS(=O)(=O)CC3)C(c3cccs3)C2)c1] | Example 46a (trifluoroacetate salt) | 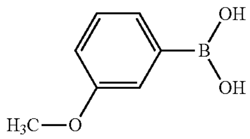 | 9.0 mg, 41% | $R_t$ = 0.83 min, Method 21 | 435 $[M + H]^+$ |
| 142 (racemic mixture) | 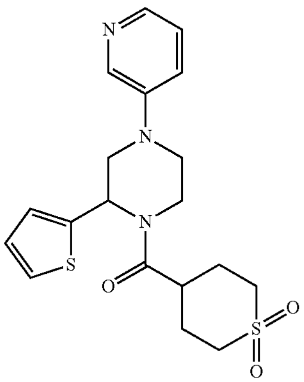 [SMILES: O=C(C1CCS(=O)(=O)CC1)N1CCN(c2cccnc2)CC1c1cccs1] | Example 46a (trifluoroacetate salt) | 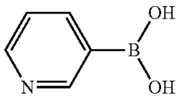 | 3.7 mg, 18% | $R_t$ = 0.78 min, Method 22 | 406 $[M + H]^+$ |

-continued

| Example | Product | Reactant | Boronic acid or ester | Product amount, yield | $R_t$ [min], method | MS m/z) |
|---|---|---|---|---|---|---|
| 143 (racemic mixture) | 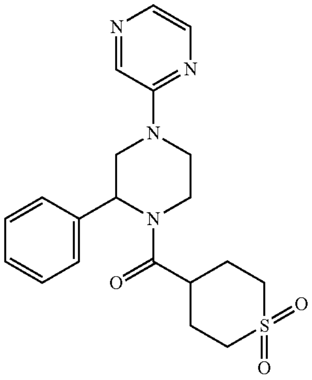 [SMILES: O=C(C1CCS(=O)(=O)CC1)N1CCN(c2cnccn2)CC1c1ccccc1] | Example 45a (trifluoroacetate salt) | 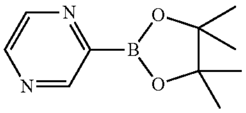 | 1.6 mg, 8% | $R_t$ = 0.59 min, Method 21 | 401 $[M + H]^+$ |
| 129 (racemic mixture) | 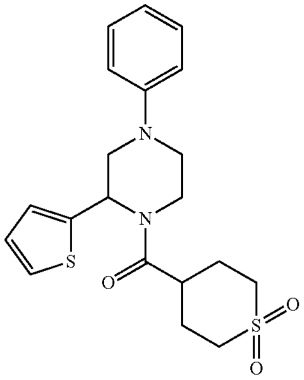 [SMILES: O=C(C1CCS(=O)(=O)CC1)N1CCN(c2ccccc2)CC1c1cccs1] | Example 46a (33 mg, 0.1 mmol, no N,N-diisopropyl-ethylamine used) | 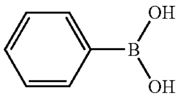 | 11.0 mg, 27% | $R_t$ = 1.81 min, Method 18 | 405 $[M + H]^+$ |
| 144 (racemic mixture) | 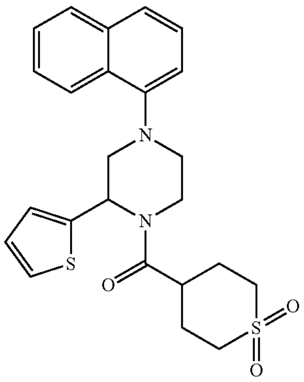 [SMILES: O=C(C1CCS(=O)(=O)CC1)N1CCN(c2cccc3ccccc23)CC1c1cccs1] | Example 46a (33 mg, 0.1 mmol, no N,N-diisopropyl-ethylamine used) | 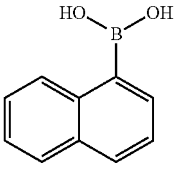 [SMILES: OB(O)c1cccc2ccccc12] | 5.1 mg, 11% | $R_t$ = 1.98 min, Method 18 | 455 $[M + H]^+$ |

Example 127

Racemic Mixture

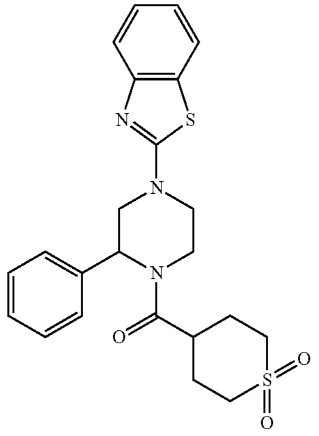 [SMILES: O=C(C1CCS(=O)(=O)CC1)N1CCN(c2nc3ccccc3s2)CC1c1ccccc1]

2-Chlorobenzothiazole (8.5 mg, 0.05 mmol), example 45a (22 mg of the corresponding trifluoroacetate salt, 0.05 mmol) and N,N-diisopropylethylamine (50 µl, 0.29 mmol) are dissolved in 2 ml of N-Methyl-2-Pyrrolidinone and heated overnight at 180° C. The reaction mixture is purified by preparative HPLC-MS to obtain the title compound (8 mg, 35% yield).

HPLC-MS (Method 20): $R_t$=0.84 min

MS: m/z=456 $[M+H]^+$

The following examples are synthesized in analogy to the preparation of example 127:

| Example | Product | Reactants | Product amount, yield | $R_t$ [min], method | MS (m/z) |
|---|---|---|---|---|---|
| 135 (racemic mixture) | 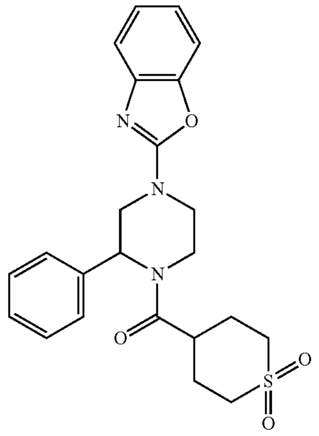 [SMILES: O=C(C1CCS(=O)(=O)CC1)N1CCN(c2nc3ccccc3o2)CC1c1ccccc1] | 45a (22 mg, 0.05 mmol of TFA salt), 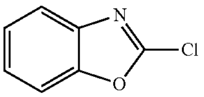 | 14.0 mg, 64% | $R_t$ = 0.80 min, Method 20 | 440 $[M + H]^+$ |
| 145 (racemic mixture) | 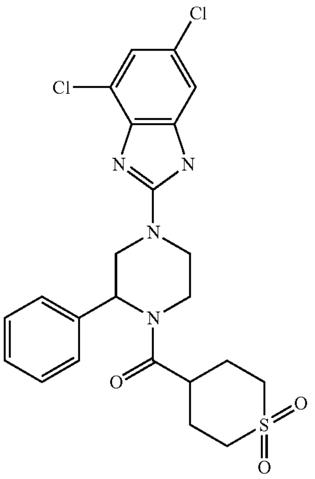 [SMILES: O=C(C1CCS(=O)(=O)CC1)N1CCN(c2nc3c(Cl)cc(Cl)cc3[nH]2)CC1c1ccccc1] | 45a (22 mg, 0.05 mmol of TFA salt), 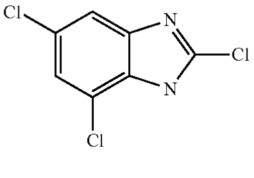 [SMILES: Clc1cc(Cl)c2[nH]c(Cl)nc2c1] | 3.3 mg, 13% | $R_t$ = 0.81 min, Method 20 | 507 $[M + H]^+$ |

-continued
| Example | Product | Reactants | Product amount, yield | $R_t$ [min], method | MS (m/z) |
|---|---|---|---|---|---|
| 147 (racemic mixture) | 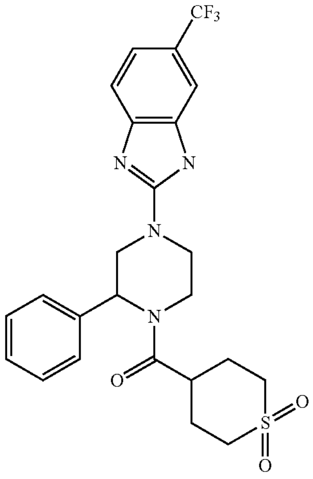 [SMILES: O=C(C1CCS(=O)(=O)CC1)N1CCN(c2nc3ccc(C(F)(F)F)cc3[nH]2)CC1c1ccccc1] | 45a (22 mg, 0.05 mmol of TFA salt), 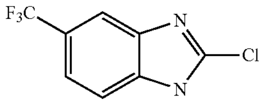 [SMILES: FC(F)(F)c1ccc2[nH]c(Cl)nc2c1] | 8.2 mg, 32% | $R_t$ = 0.80 min, Method 20 | 507 $[M + H]^+$ |
| 140 (racemic mixture) | 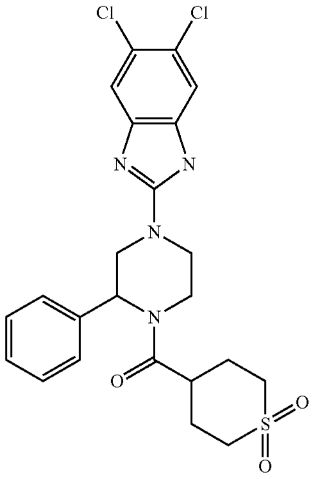 [SMILES: O=C(C1CCS(=O)(=O)CC1)N1CCN(c2nc3cc(Cl)c(Cl)cc3[nH]2)CC1c1ccccc1] | 45a (22 mg, 0.05 mmol of TFA salt), 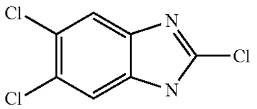 [SMILES: Clc1nc2cc(Cl)c(Cl)cc2[nH]1] | 8.1 mg, 32% | $R_t$ = 0.81 min, Method 20 | 507 $[M + H]^+$ |
| 133 (racemic mixture) | 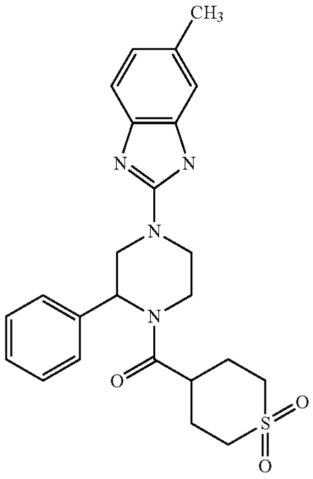 [SMILES: Cc1ccc2nc(N3CCN(C(=O)C4CCS(=O)(=O)CC4)C(c4ccccc4)C3)[nH]c2c1] | 45a (22 mg, 0.05 mmol of TFA salt), 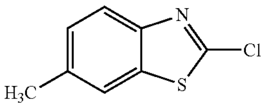 | 10.0 mg, 43% | $R_t$ = 0.89 min, Method 20 | 470 $[M + H]^+$ |

-continued

| Example | Product | Reactants | Product amount, yield | $R_t$ [min], method | MS (m/z) |
|---|---|---|---|---|---|
| 146 (racemic mixture) | 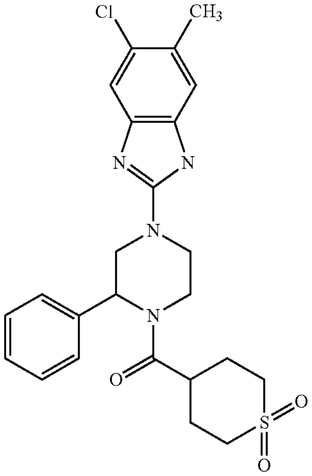 [SMILES: Cc1cc2[nH]c(N3CCN(C(=O)C4CCS(=O)(=O)CC4)C(c4ccccc4)C3)nc2cc1Cl] | 45a (22 mg, 0.05 mmol of TFA salt), 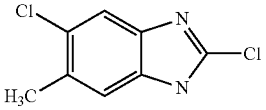 | 1.9 mg, 8% | $R_t$ = 0.80 min, Method 20 | 487 $[M + H]^+$ |

Example 141

Racemic Mixture

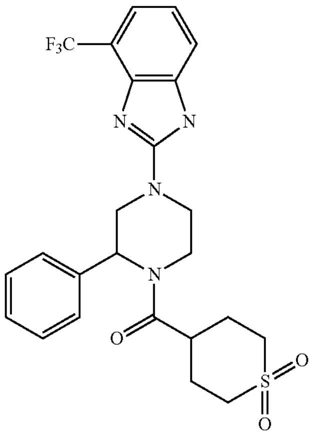 [SMILES: O=C(C1CCS(=O)(=O)CC1)N1CCN(c2nc3c(C(F)(F)F)cccc3[nH]2)CC1c1ccccc1]

2-Chloro-7-(Trifluoromethyl)-1H-Benzimidazole (220 mg, 1.0 mmol), 2-Phenyl-piperazine-1-carboxylic acid tert-butyl ester (400 mg, 1.5 mmol), N,N-diisopropylethylamine (500 µl, 2.9 mmol) are dissolved in 3 ml of acetonitrile and heated in a microwave reactor 1.5 hours at 160° C. and then 30 minutes at 170° C. The reaction mixture is stirred into an open flask at 90° C. to evaporate the solvent then the residue is dissolved in 4 ml of DCM; trifluoroacetic acid (2.0 ml, 26.0 mmol) is added and the reaction mixture is stirred until complete deprotection occurs; it is then concentrated at 50° C. The residue is dissolved in MeOH, basified by addition of Triethylamine and purified by preparative HPLC-MS to obtain 255 mg (74% yield) of the intermediate 2-(3-Phenyl-piperazin-1-yl)-4-trifluoromethyl-1H-benzoimidazole.

N,N-diisopropylethylamine (50 µl, 0.29 mmol) and HATU (40 mg, 0.11 mmol) are added into a solution of tetrahydro-2H-thiopyran-4-carboxylic acid 1,1-dioxide (18 mg, 0.10 mmol) dissolved in 2 ml of DMF. After 10 minutes stirring, 2-(3-Phenyl-piperazin-1-yl)-4-trifluoromethyl-1H-benzoimidazole (35 mg, 0.10 mmol, prepared as described above) is added and the reaction mixture is stirred overnight, diluted with Methanol, water and trifluoroacetic acid and finally purified by preparative HPLC-MS to obtain the title compound (41 mg, 81% yield on the last step).

HPLC-MS (Method 19): $R_t$=1.19 min

MS: m/z=507 $[M+H]^+$

Example 148 (Enantiomer 1) and Example 149 (Enantiomer 2)

The racemic mixture of the title compounds is synthesized as described for example 1 starting from example 44c (300 mg, 0.71 mmol of the corresponding hydrochloride) instead of example 44k, 2-Chloro-5-(Trifluoromethyl)-(1,3,4)-thiadiazole (200 mg, 1.06 mmol) instead of 2-Chloro-5-(trifluoromethyl)pyrimidine and N,N-diisopropylethylamine (489 µl, 2.82 mmol) in 4 ml of anhydrous DMSO. The reaction mixture is heated in a microwave reactor at 150° C. during 30 minutes. The crude is partitioned between DCM and water;

the organic layer is dried over anhydrous $Na_2SO_4$ and concentrated under reduced pressure to obtain 240 mg of the racemic mixture.

UPLC-MS (Method 1): $R_t$=1.39 min

MS (ES+): m/z=515 [M+H]$^+$

The enantiomers are obtained by HPLC separation using a chiral stationary phase.

Method for Separation:

HPLC apparatus type: Waters 600 Pump; column: Daicel Chiralpack IA, 5.0 μm, 250 mm×20 mm; method: eluent hexane/IPA 70:30; flow rate: 15 mL/min, Temperature: 25° C.; UV Detection: 254 nm Example of Separation by Chiral HPLC:

Submitted to separation: 240 mg of racemic mixture prepared as described above; Obtained: 80 mg of enantiomer 1 (Exp. 148) and 90 mg of enantiomer 2 (Exp. 149)

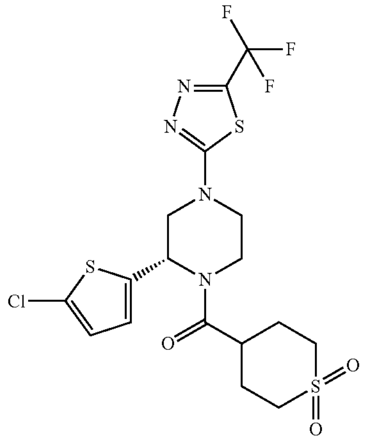 [SMILES: O=C(C1CCS(=O)(=O)CC1)N1CCN(c2nnc(C(F)(F)F)s2)C[C@H]1c1ccc(Cl)s1]

Example 148: enantiomer 1

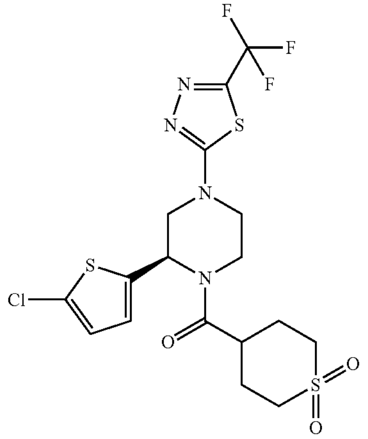 [SMILES: O=C(C1CCS(=O)(=O)CC1)N1CCN(c2nnc(C(F)(F)F)s2)C[C@@H]1c1ccc(Cl)s1]

Example 149: enantiomer 2

| Example | Chiral HPLC $R_t$ [min] | HPLC-MS (Method 5): $R_t$ [min] | MS (APCI+): m/z |
|---|---|---|---|
| Exp. 148 | 20.36 (Method 15) | 3.03 | 515 |
| Exp. 149 | 24.80 (Method 15) | 3.00 | 515 |

Example 150

Racemic Mixture

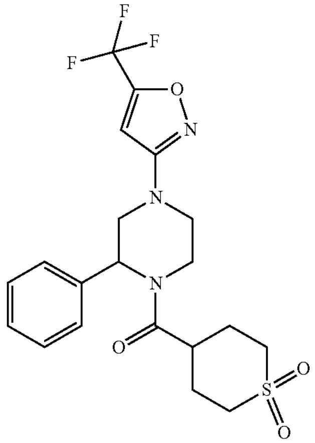 [SMILES: O=C(C1CCS(=O)(=O)CC1)N1CCN(c2cc(C(F)(F)F)on2)CC1c1ccccc1]

Example 150 is synthesized as described for example 117 starting from example 45a (150 mg, 0.47 mmol) instead of example 44b, using 2,2,6,6-Tetramethylpiperidine (82 μl, 0.47 mmol), 1,1-dibromoformaldoxime (94 mg, 0.47 mmol), 2-Bromo-3,3,3-trifluoropropene (240 μl, 2.33 mmol) and triethylamine (97 μl, 0.70 mmol). The crude is partitioned between water and EtOAc; the organic layer is separated, concentrated under reduced pressure and the residue is purified by preparative HPLC-MS to obtain the title compound (33 mg, 15% yield).

HPLC-MS (Method 5): $R_t$=2.91 min

MS (APCI+): m/z=458 [M+H]$^+$

Example 151

Racemic Mixture

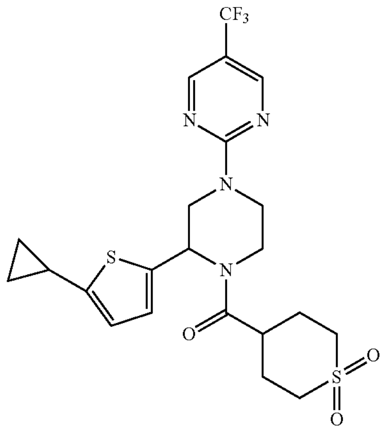 [SMILES: O=C(C1CCS(=O)(=O)CC1)N1CCN(c2ncc(C(F)(F)F)cn2)CC1c1ccc(C2CC2)s1]

A solution of example 44c (100 mg of the corresponding hydrochloride, 0.25 mmol), 2-chloro-5-(trifluoromethyl)-pyrimidine (55 mg, 0.30 mmol) and N,N-diisopropylethylamine (129 μl, 0.75 mmol) dissolved in 1 ml of anhydrous DMSO is heated in a microwave reactor during 30 minutes at 150° C. The crude is purified by preparative HPLC-MS and the obtained impure intermediate is suspended in 0.9 ml of anhydrous toluene; potassium cyclopropyltrifluoroborate (37 mg, 0.25 mmol), butyldi-1-adamantylphosphine (3 mg, 0.01 mmol), palladium acetate (1 mg, 0.01 mmol), cesium carbonate (245 mg, 0.75 mmol) and 0.1 ml of water are added and the reaction mixture is heated in a microwave reactor during 2 hours at 100° C. The solvent is removed under reduced pressure, the residue is suspended in DMF, filtered and purified by preparative HPLC-MS to obtain the title compound (18.7 mg, 14% yield).

HPLC-MS (Method 16): Rt=4.63 min

MS (ES+): m/z=515 [M+H]+

Example 152

Racemic Mixture

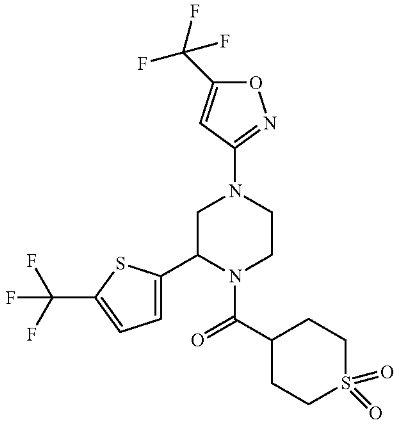 [SMILES: O=C(C1CCS(=O)(=O)CC1)N1CCN(c2cc(C(F)(F)F)on2)CC1c1ccc(C(F)(F)F)s1]

Example 152 is synthesized as described for example 117 starting from example 44m (90 mg, 0.23 mmol) instead of example 44b, using 2,2,6,6-Tetramethylpiperidine (40 μl, 0.23 mmol), 1,1-dibromoformaldoxime (46 mg, 0.23 mmol), 2-Bromo-3,3,3-trifluoropropene (117 μl, 1.14 mmol) and triethylamine (39 μl, 0.27 mmol). The crude is partitioned between water and EtOAc, the organic layer is separated and concentrated under reduced pressure. The residue is purified by silica gel flash chromatography, using cyclohexane/EtOAc 1:1 to 100% EtOAc as eluent, to obtain the impure title compound that is further purified by preparative HPLC-MS to obtain 5 mg (4% yield) of pure product.

HPLC-MS (Method 14): $R_t$=6.82 min

MS (APCI+): m/z=532 $[M+H]^+$

Example 153

Racemic Mixture

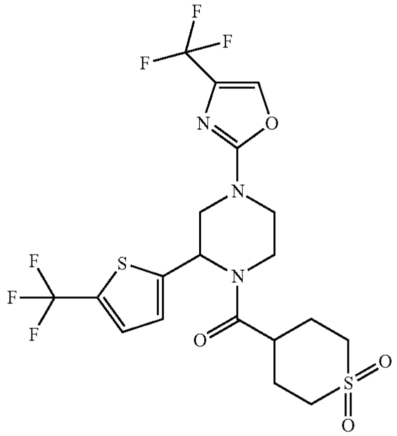 [SMILES: O=C(C1CCS(=O)(=O)CC1)N1CCN(c2nc(C(F)(F)F)co2)CC1c1ccc(C(F)(F)F)s1]

Example 153 is synthesized as described for example 116 starting from example 48b (80 mg, 0.72 mmol) instead of example 55a, 3-Bromo-1,1,1-trifluoroacetone (58 μl, 0.55 mmol), 3 ml of tert-butylacohol, heating for 16 hours at 80° C. The solvent is removed under reduced pressure and the residue is purified by silica gel flash chromatography, using cyclohexane/EtOAc 1:1 to 100% EtOAc as eluent, to obtain the title compound (36 mg, 35% yield).

HPLC-MS (Method 14): $R_t$=6.58 min

MS (APCI+): m/z=532 $[M+H]^+$

Example 154

Racemic Mixture

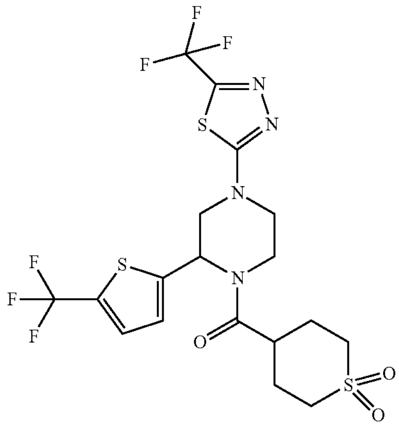 [SMILES: O=C(C1CCS(=O)(=O)CC1)N1CCN(c2nnc(C(F)(F)F)s2)CC1c1ccc(C(F)(F)F)s1]

Example 154 is synthesized as described for example 1 starting from example 44m (as hydrochloride salt, 100 mg, 0.19 mmol) instead of example 44k, 2-Chloro-5-trifluoromethyl-(1,3,4)-thiadiazole (54 mg, 0.29 mmol) instead 2-Chloro-5-(trifluoromethyl)pyrimidine, N,N-diisopropylethylamine (133 μl, 0.77 mmol) and 1 ml of anhydrous DMSO; the reaction mixture is heated during 30 minutes at 150° C. in a microwave reactor; the crude is purified preparative HPLC-MS to obtain the title compound (98 mg, 93% yield)

HPLC-MS (Method 10): $R_t$=3.72 min

MS (ES+): m/z=549 $[M+H]^+$

The enantiomers are obtained by HPLC using a chiral stationary phase.

Method for Separation:

HPLC apparatus type: Waters 600 Pump; column: Daicel Chiralpack IA, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 75 mg of Example 154 prepared as described above; Obtained: 30 mg of enantiomer 1 (Exp. 155) and 30 mg of enantiomer 2 (Exp. 156)

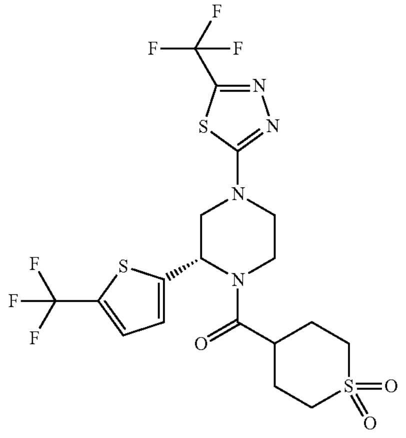 [SMILES: O=C(C1CCS(=O)(=O)CC1)N1CCN(c2nnc(C(F)(F)F)s2)C[C@H]1c1ccc(C(F)(F)F)s1]

Example 155: enantiomer 1

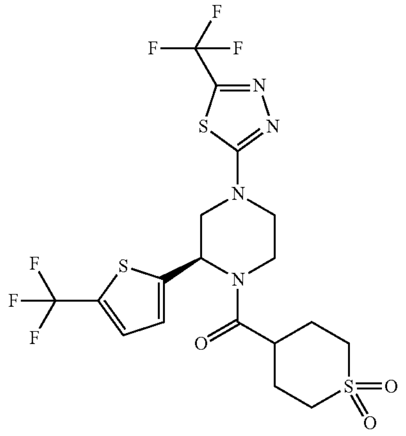 [SMILES: O=C(C1CCS(=O)(=O)CC1)N1CCN(c2nnc(C(F)(F)F)s2)C[C@@H]1c1ccc(C(F)(F)F)s1]

Example 156: enantiomer 2

| Example | Chiral HPLC $R_t$ [min] | HPLC-MS (Method 10): $R_t$ [min] | MS (ES+): m/z |
|---|---|---|---|
| Exp. 155 | 15.05 (Method 15) | 3.72 | 549 |
| Exp. 156 | 17.59 (Method 15) | 3.72 | 549 |

Example 157

Racemic Mixture

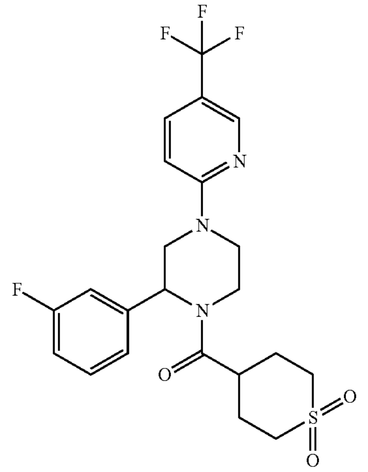 [SMILES: O=C(C1CCS(=O)(=O)CC1)N1CCN(c2ccc(C(F)(F)F)cn2)CC1c1cccc(F)c1]

Example 157 is synthesized as described for example 1 starting from example 44b (40 mg, 0.11 mmol) instead of example 44k, 2-Chloro-5-(Trifluoromethyl)pyridine (20 μl, 0.16 mmol) instead of 2-Chloro-5-(trifluoromethyl)pyrimidine and N,N-diisopropylethylamine (73 μl, 0.42 mmol) in 1 ml of anhydrous DMSO. The crude product is purified by preparative HPLC-MS to obtain 27 mg (52% yield) of the title compound.

HPLC-MS (Method 5): $R_t$=3.11 min

MS (APCI+): m/z=486 $[M+H]^+$

Example 158

Racemic Mixture

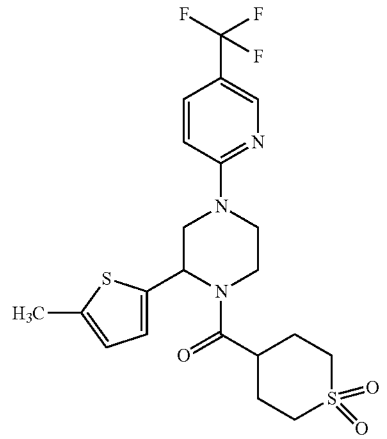 [SMILES: Cc1ccc(C2CN(c3ncc(C(F)(F)F)cn3)CCN2C(=O)C2CCS(=O)(=O)CC2)s1]

Example 158 is synthesized as described for example 1 starting from example 44n (30 mg, 0.08 mmol) instead of example 44k, 2-Chloro-5-(Trifluoromethyl)pyridine (20 μl, 0.12 mmol) instead of 2-Chloro-5-(trifluoromethyl)pyrimidine and N,N-diisopropylethylamine (55 μl, 0.32 mmol) in 1 ml of anhydrous DMSO. The reaction mixture is heated in a microwave reactor during 1.5 hours at 150° C. and the crude product is purified by preparative HPLC-MS to obtain 26 mg (60% yield) of the title compound.

HPLC-MS (Method 4): $R_t$=6.97 min

MS (APCI+): m/z=488 $[M+H]^+$

Example 159

Racemic Mixture

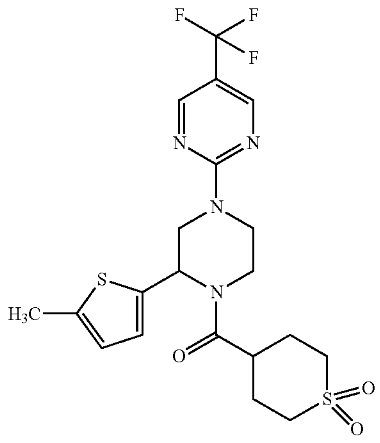

Example 159 is synthesized as described for example 1 starting from example 44n (30 mg, 0.08 mmol) instead of example 44k, 2-Chloro-5-(trifluoromethyl)pyrimidine (22 mg, 0.12 mmol) and N,N-diisopropylethylamine (55 μl, 0.32 mmol) in 1 ml of anhydrous DMSO. The crude product is purified by preparative HPLC-MS to obtain 23 mg (55% yield) of the title compound.

HPLC-MS (Method 4): $R_t$=6.94 min

MS (APCI+): m/z=489 $[M+H]^+$

Example 160

Racemic Mixture

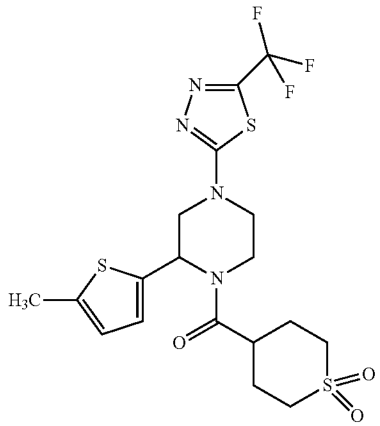 [SMILES: Cc1ccc(C2CN(c3nnc(C(F)(F)F)s3)CCN2C(=O)C2CCS(=O)(=O)CC2)s1]

Example 160 is synthesized as described for example 1 starting from example 44n (40 mg, 0.11 mmol) instead of example 44k, 2-Chloro-5-trifluoromethyl-(1,3,4)-thiadiazole (30 mg, 0.16 mmol) instead of 2-Chloro-5-(trifluoromethyl) pyrimidine and N,N-diisopropylethylamine (73 μl, 0.42 mmol) in 1 ml of anhydrous DMSO. The crude product is purified by preparative HPLC-MS to obtain 28 mg (50% yield) of the title compound.

HPLC-MS (Method 4): $R_t$=6.43 min

MS (APCI+): m/z=495 $[M+H]^+$

Example 161

Racemic Mixture

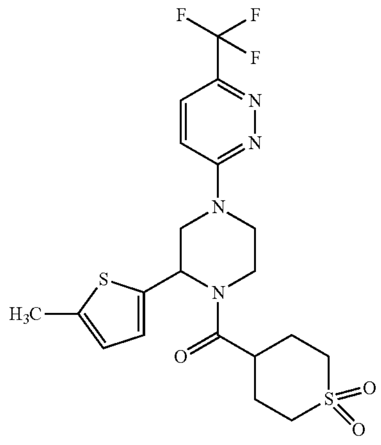

Example 161 is synthesized as described for example 1 starting from example 44n (35 mg, 0.09 mmol) instead of example 44k, 3-Chloro-6-trifluoromethyl-pyridazine (25 mg, 0.14 mmol) instead of 2-Chloro-5-(trifluoromethyl)-pyrimidine and N,N-diisopropylethylamine (64 μl, 0.37 mmol) in 1 ml of anhydrous DMSO. The crude product is purified by preparative HPLC-MS to obtain 30 mg (62% yield) of the corresponding hydrochloride salt adding a solution of HCl in dioxane during the evaporation step.

HPLC-MS (Method 4): $R_t$=6.20 min

MS (APCI+): m/z=489 $[M+H]^+$

The invention claimed is:

1. A compound of the formula (I) or a salt thereof (I)

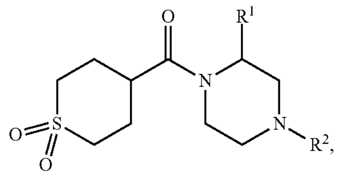

wherein $R^1$ represents phenyl or a 5 or 6 membered monocyclic heteroaryl having 1, 2, or 3 heteroatoms independently selected from O, N or S, wherein the phenyl or the heteroaryl is optionally substituted with one or more $R^3$;

$R^2$ represents aryl, a 5 or 6 membered monocyclic heteroaryl or a 8 to 10 membered bicyclic heteroaryl, the mono- or bicyclic heteroaryl having 1, 2, or 3 heteroatoms independently selected from O, N or S, wherein the aryl or the heteroaryl is optionally substituted with one or more $R^4$;

$R^3$ is a halogen, a $C_{1-4}$-alkyl or a $C_{3-6}$-cycloalkyl, wherein the $C_{1-4}$-alkyl or the $C_{3-6}$-cycloalkyl is optionally substituted with one or more halogens;

$R^4$ is a halogen, —CN, $C_{1-4}$-alkyl, $C_{3-6}$-cycloalkyl, —$C_{1-3}$-alkyl —$C_{3-6}$-cycloalkyl or —O—$C_{1-6}$ alkyl, wherein the $C_{1-4}$-alkyl, $C_{3-6}$-cycloalkyl, $—C_{1-3}$-alkyl $—C_{3-6}$-cycloalkyl or the $—O—C_{1-6}$-alkyl is optionally substituted with one or more halogens.

2. The compound of claim 1 or a salt thereof, wherein $R^1$ is selected from the group consisting of

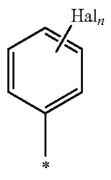

and

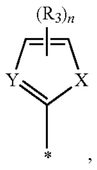

, wherein

Hal is a halogen, n is 0, 1 or 2, $R^3$ is a halogen, a $C_{1-4}$-alkyl or a $C_{3-6}$-cycloalkyl, wherein the $C_{1-4}$-alkyl or the $C_{3-6}$-cycloalkyl is optionally substituted with one or more halogens, X is S or O, Y is N or CH.

3. The compound of claim 1 or a salt thereof, wherein $R^1$ is selected from the group consisting of

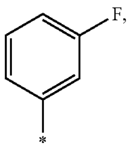

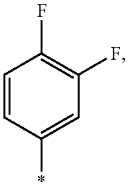

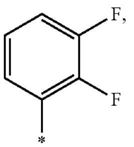

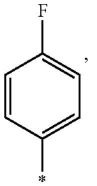

,

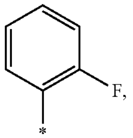

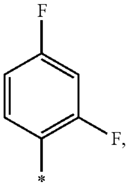

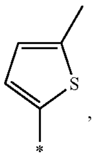

,

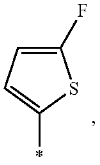

,

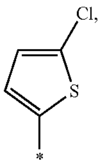

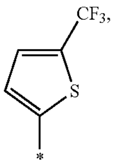

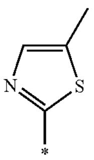

and

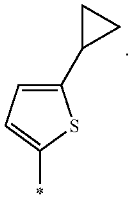

.

4. The compound of claim 1 or salt thereof, wherein $R^1$ represents

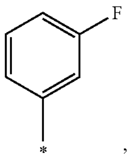

,

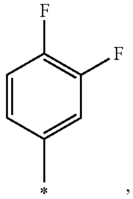

,

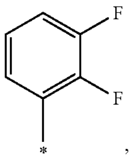

,

-continued

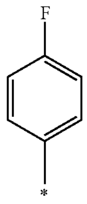

or

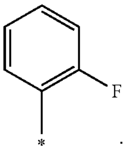

.

5. The compound claim 1 or salt thereof, wherein $R^2$ is selected from the group consisting of naphthyl,

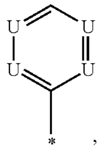

,

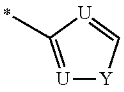

,

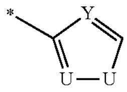

and

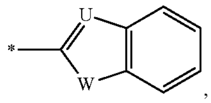

, wherein

U is independently from each other N or CH with the proviso that the ring systems bear a maximum of three N-atoms, Y is O or S, W is O, S or NH and wherein the above mentioned ring systems are optionally substituted with one or more $R^4$ being selected from the group consisting of a halogen, —CN, $C_{1-4}$ alkyl, $C_{3-6}$ cycloalkyl, $—C_{1-3}$-alkyl $—C_{3-6}$-cycloalkyl or $—O—C_{1-6}$ alkyl, wherein the $C_{1-4}$ alkyl, $C_{3-6}$ cycloalkyl, $—C_{1-3}$-alkyl $—C_{3-6}$-cycloalkyl or the $—O—C_{1-6}$ alkyl is optionally substituted with one or more halogen(s).

6. The compound of claim 1 or salt thereof, wherein $R^2$ represents

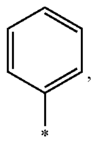

,

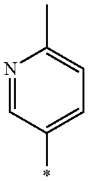

,

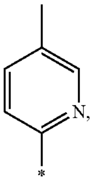

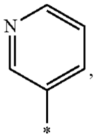

,

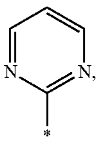

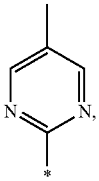

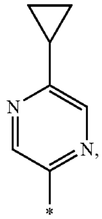

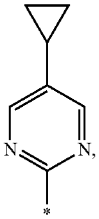

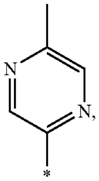

-continued
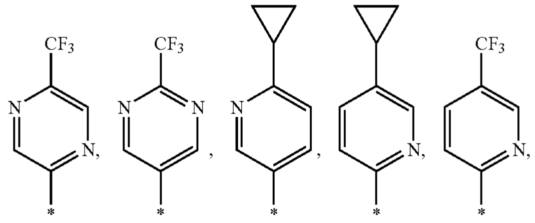
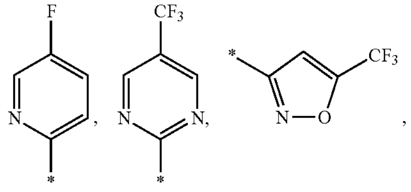
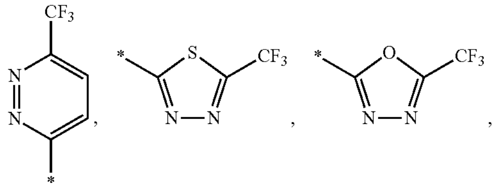
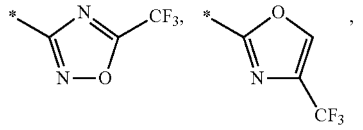
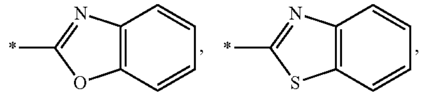
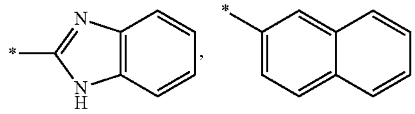
or
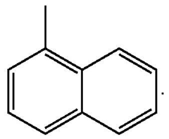
7. The compound of claim 1 or salt thereof, wherein $R^2$ represents
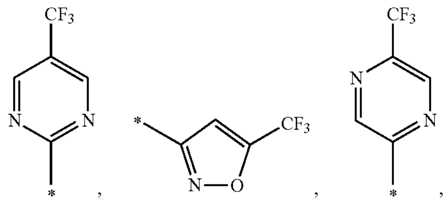
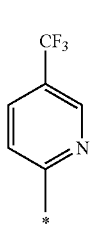
or
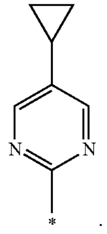
8. The compound of claim 1 or salt thereof, wherein $R^2$ represents
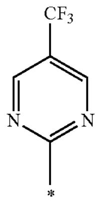
or
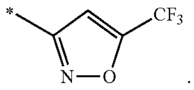
9. The compound of claim 1 or a salt thereof selected form the group consisting of
1
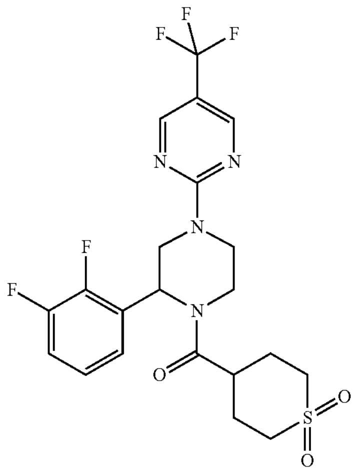
2
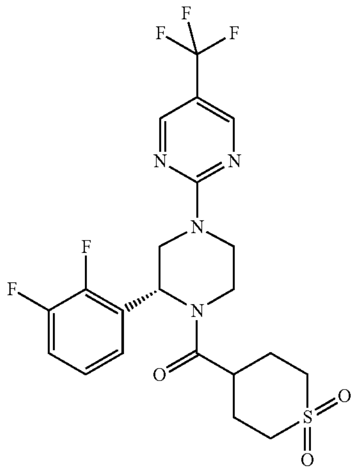

-continued
3
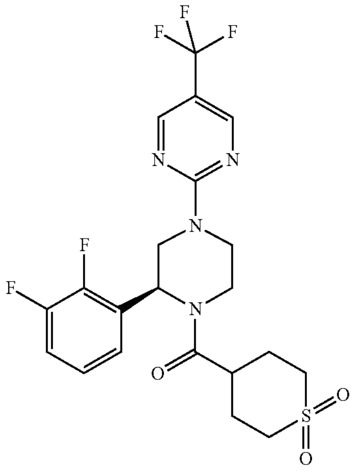
4
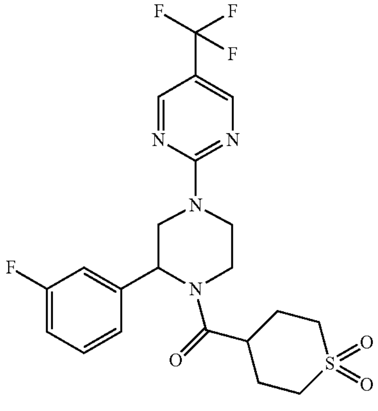
5
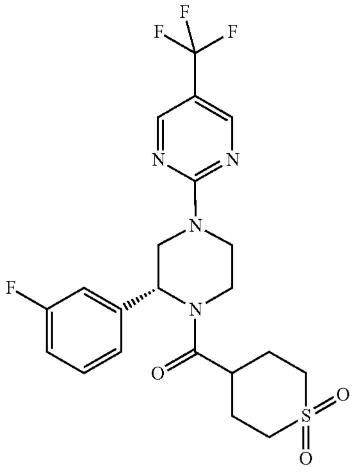
-continued
6
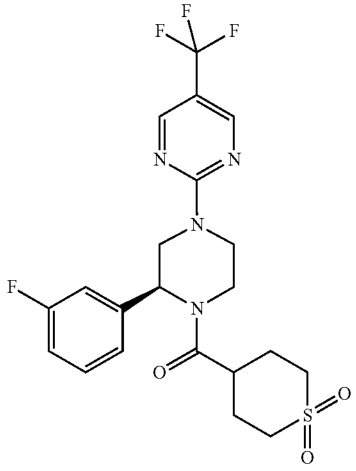
7
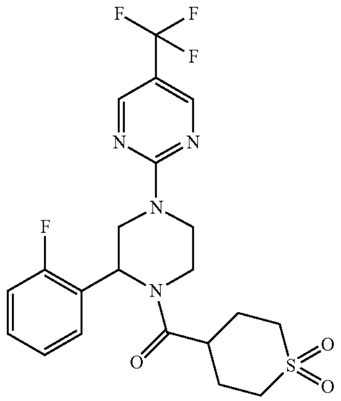
8
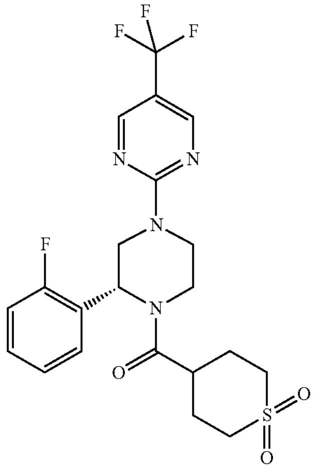

-continued
9
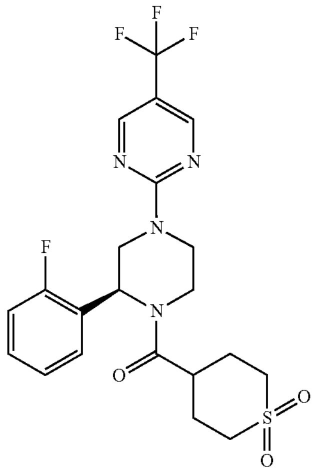
10
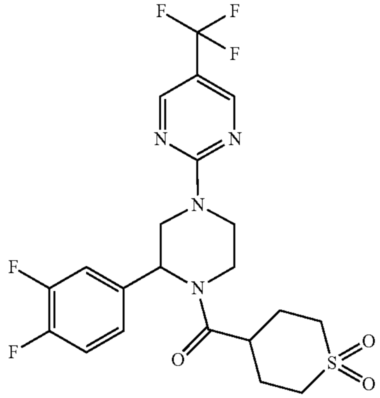
11
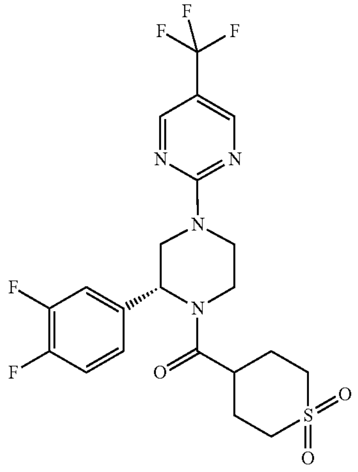
-continued
12
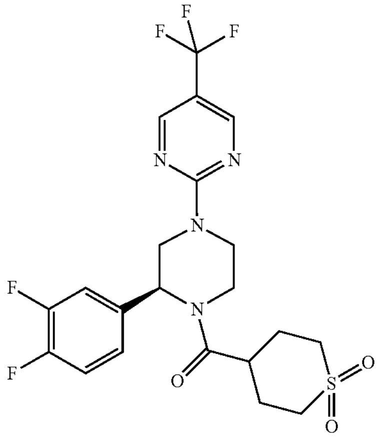
13
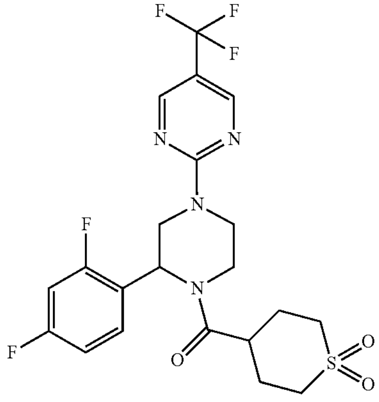
14
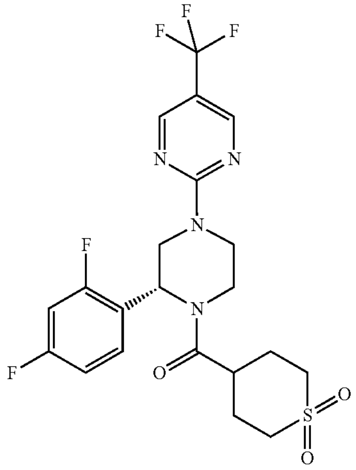

-continued
15
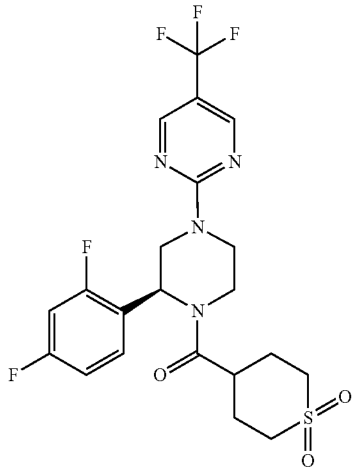
16
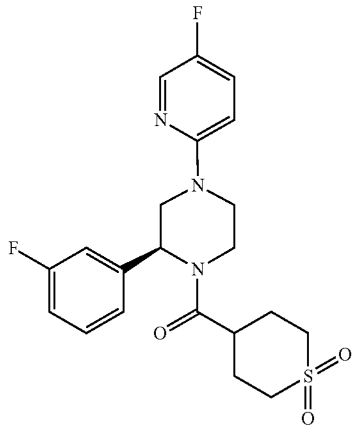
17
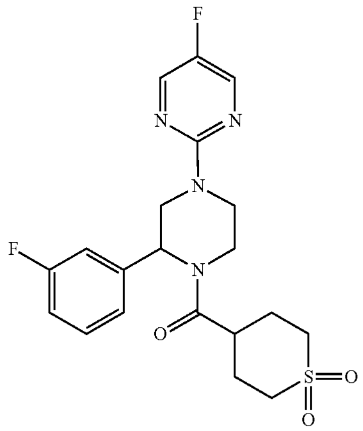
-continued
18
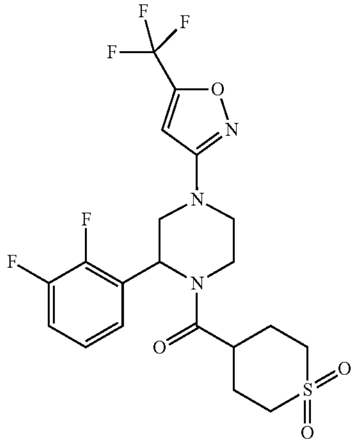
19
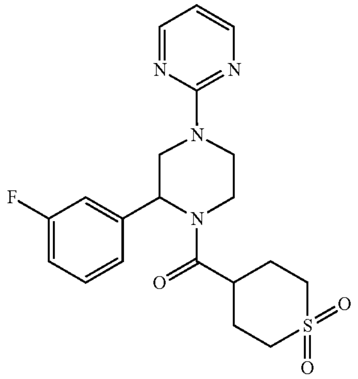
20
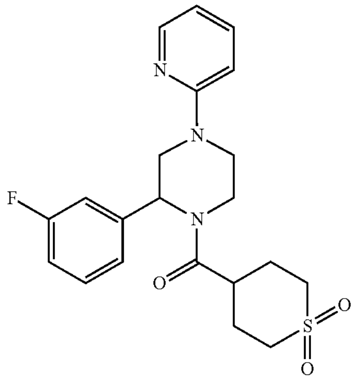

-continued
21
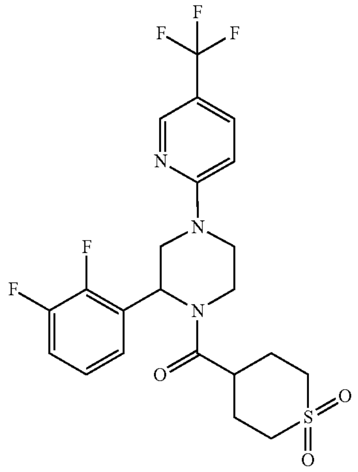
22
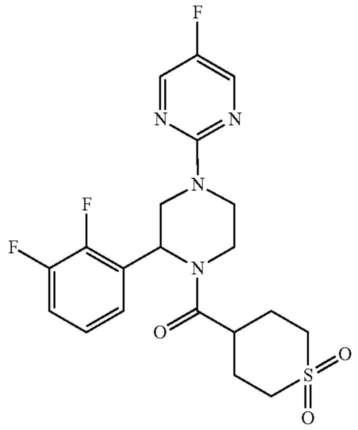
23
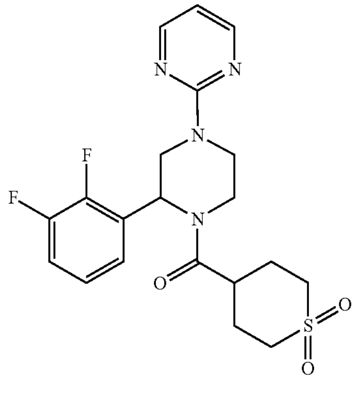
-continued
24
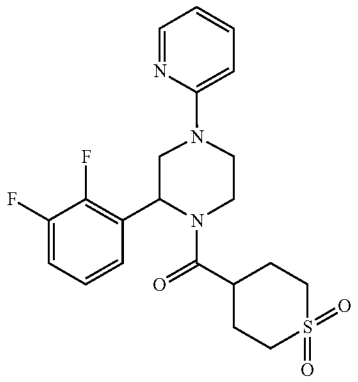
25
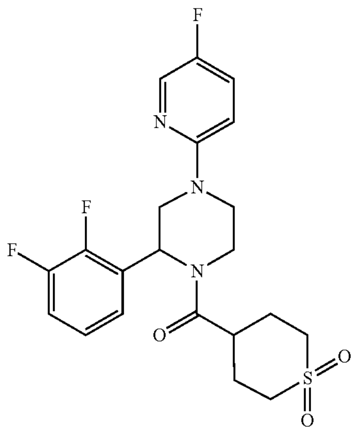
26
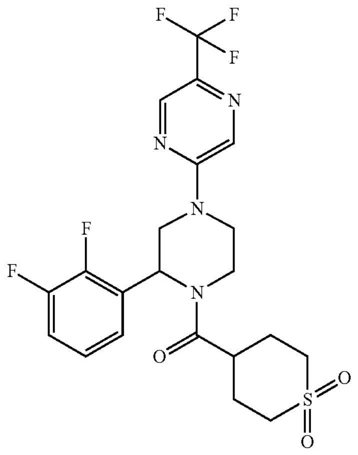

27
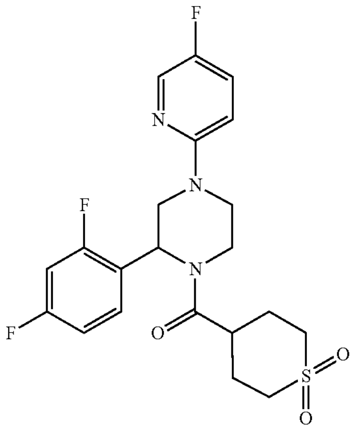
28
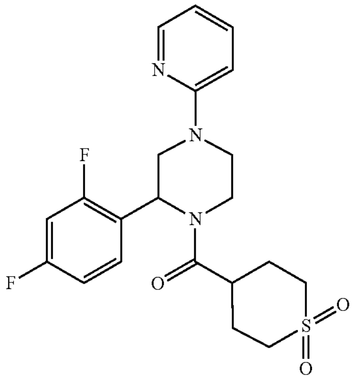
29
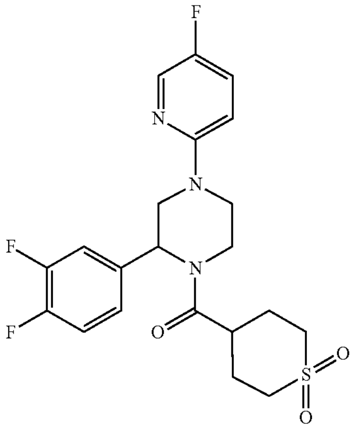
30
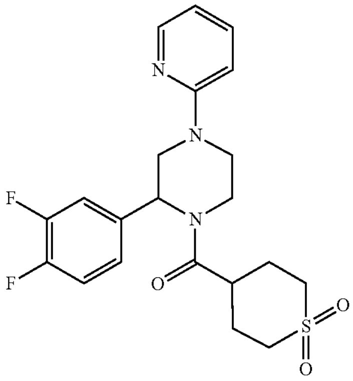
31
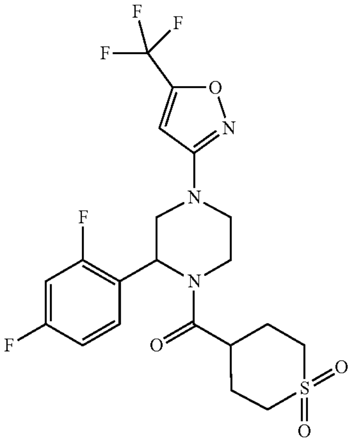
32
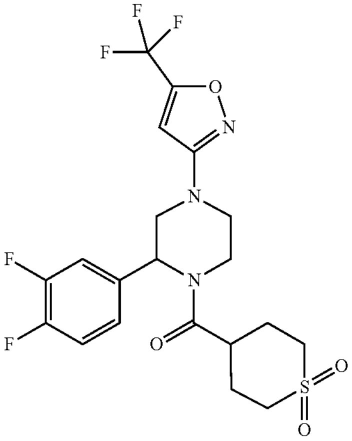
33
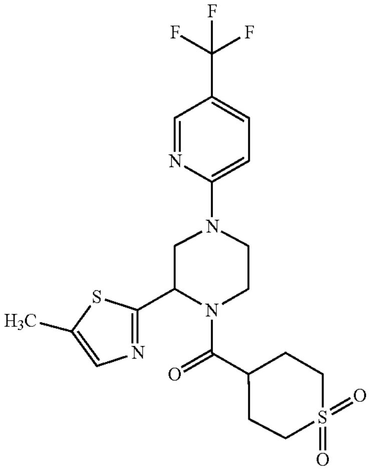

34
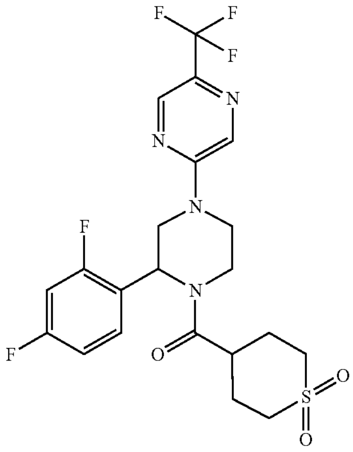
35
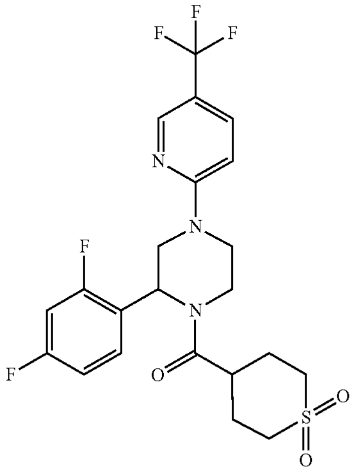
36
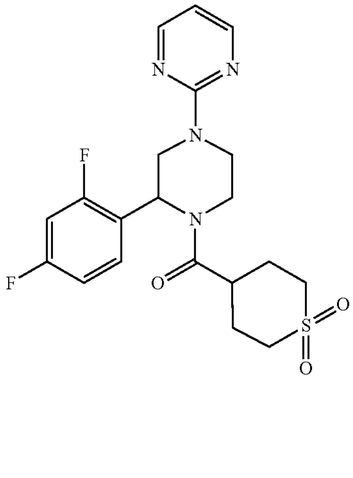
37
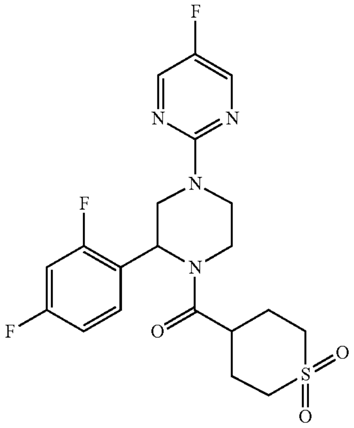
38
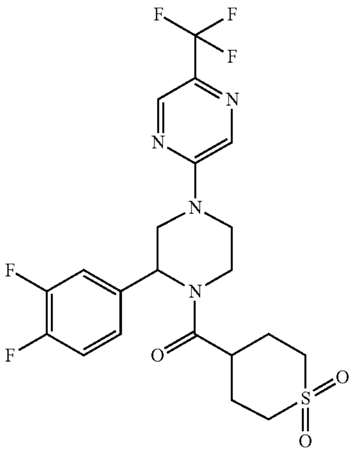
39
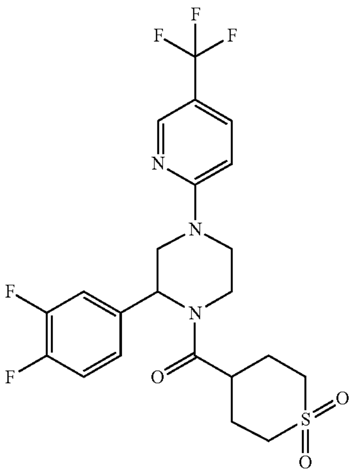

-continued
40
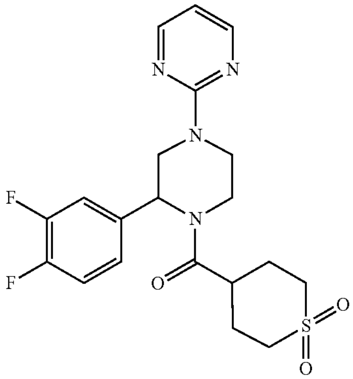
41
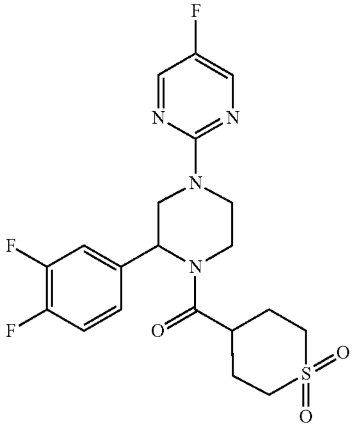
42
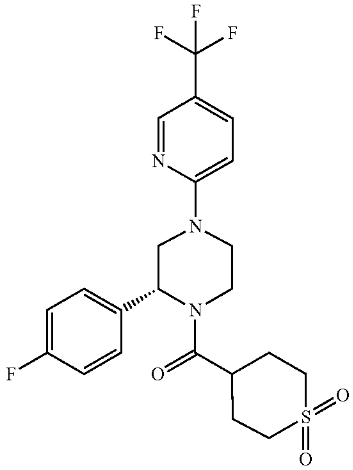
-continued
43
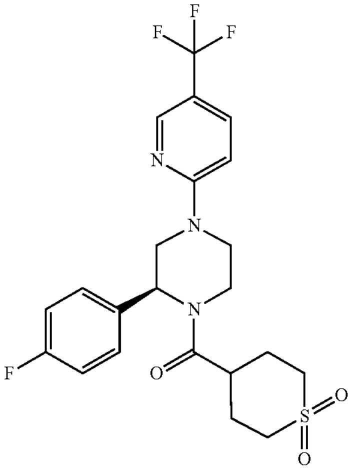
44
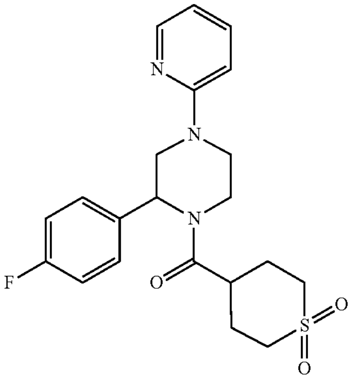
45
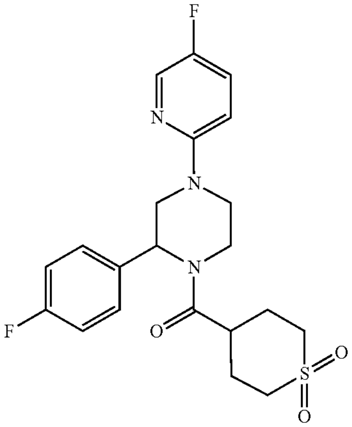

-continued
46
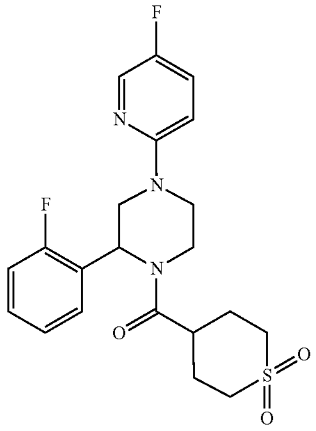
47
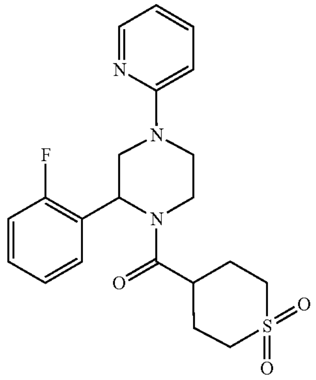
48
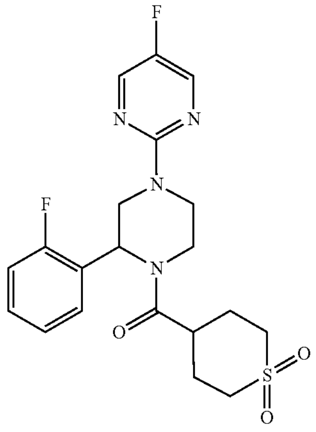
49
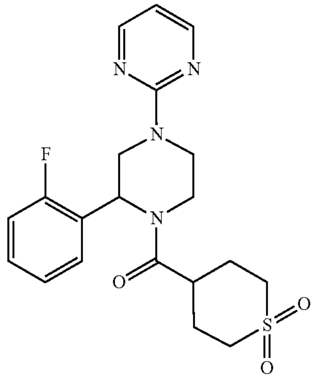
-continued
50
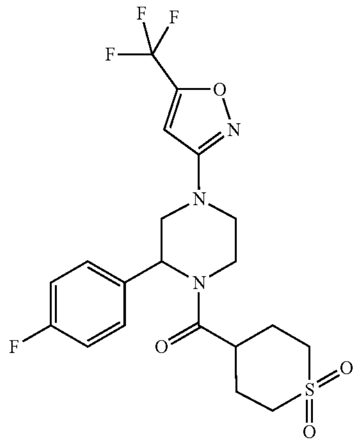
51
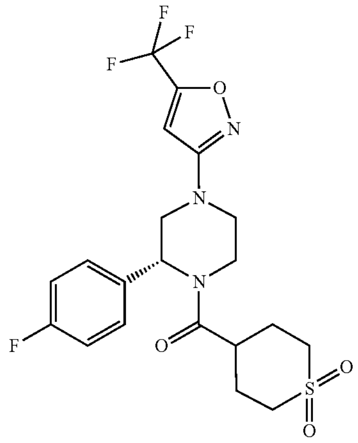
52
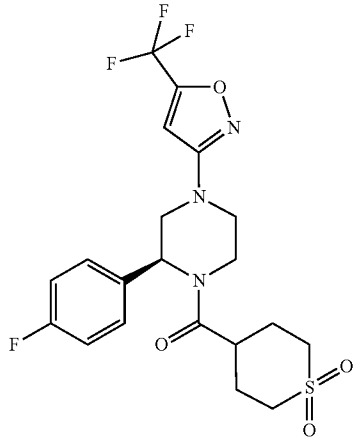

-continued
53
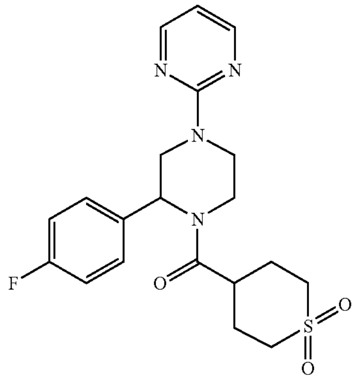
54
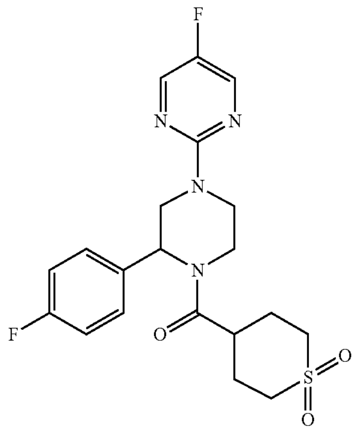
55
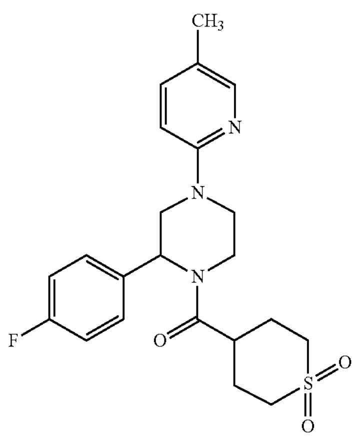
-continued
56
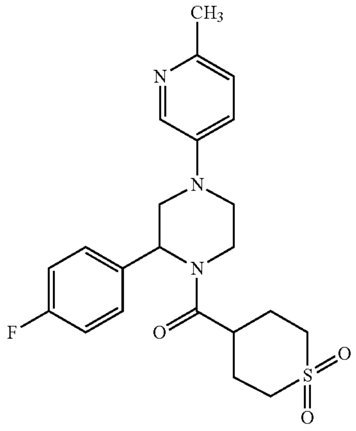
57
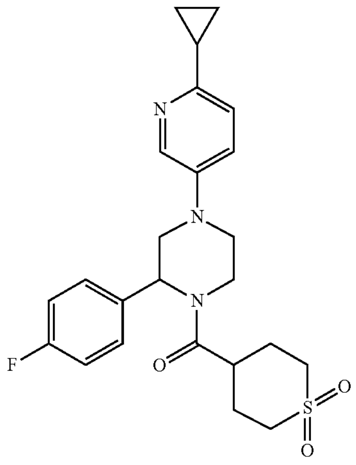
58
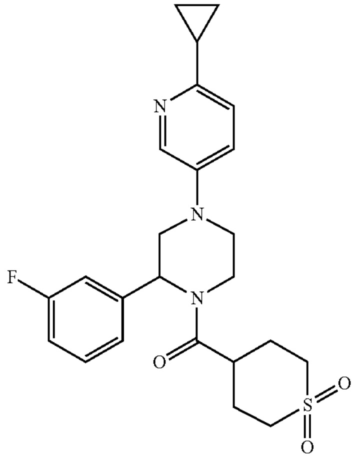

-continued
59
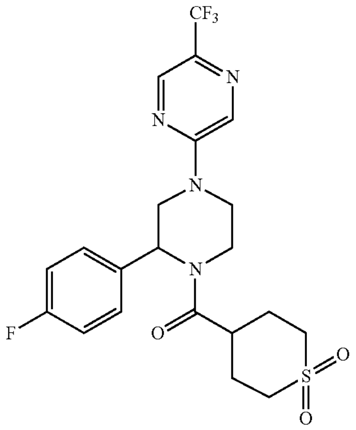
60
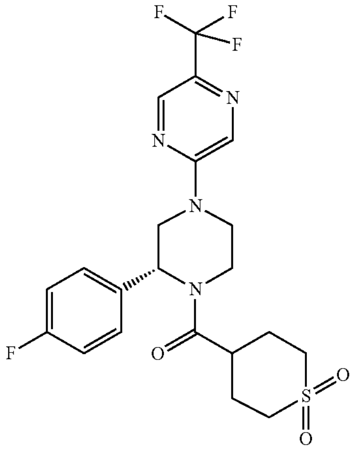
61
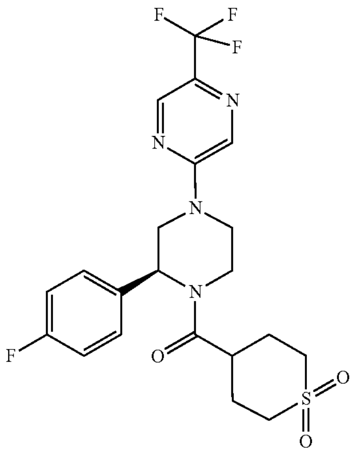
-continued
62
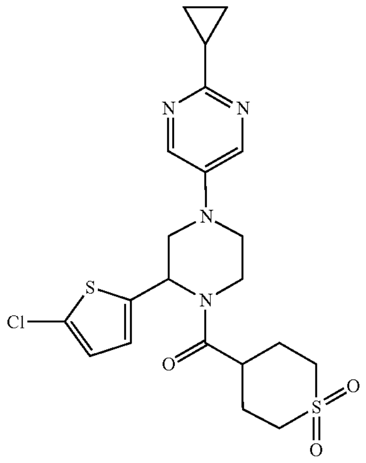
63
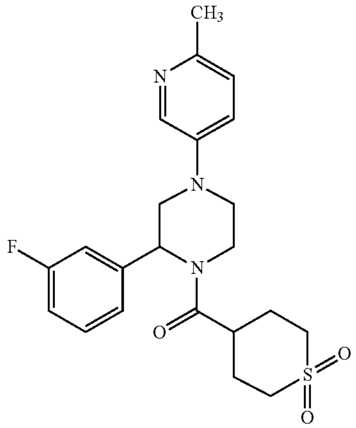
64
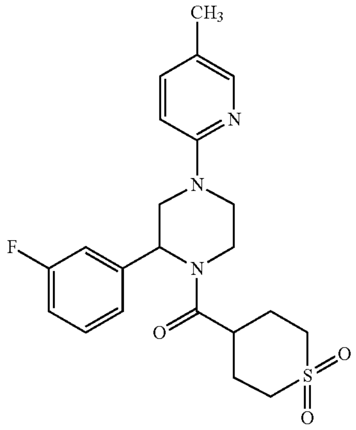

65
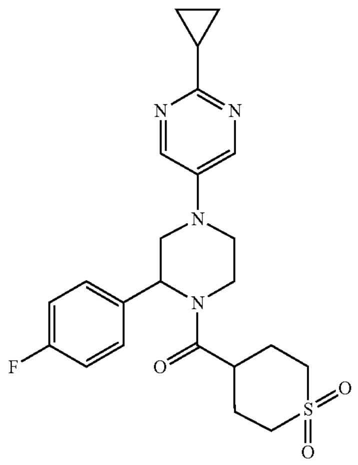
66
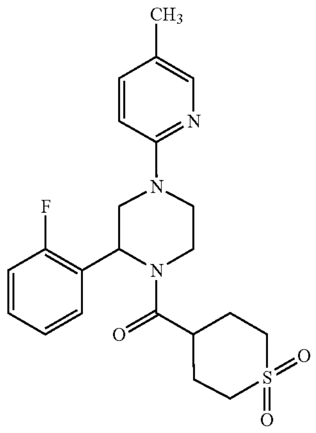
67
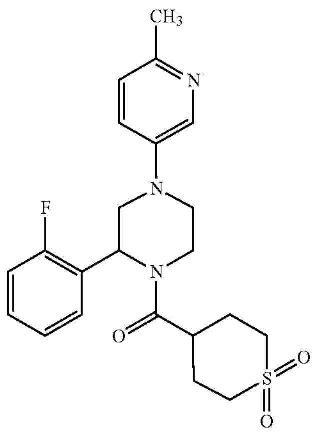
68
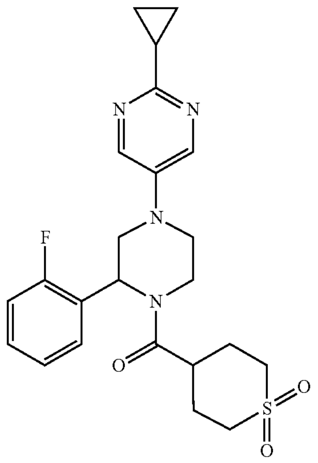
69
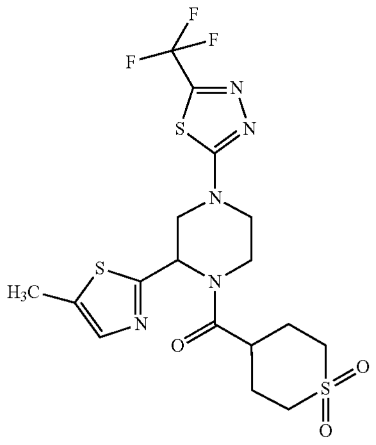
70
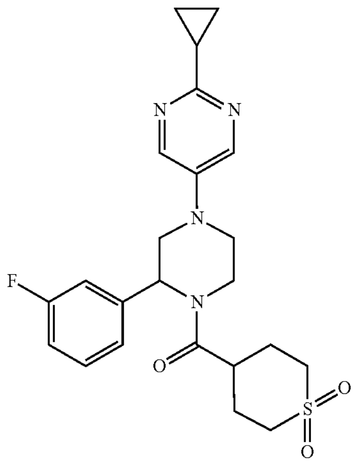

-continued
71
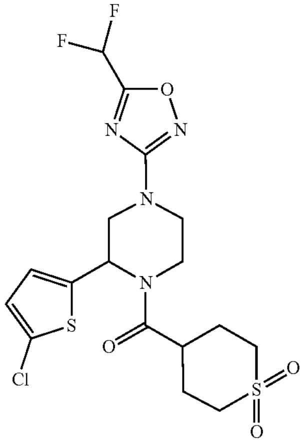
72
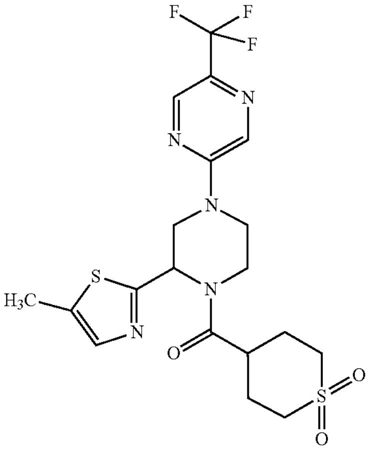
73
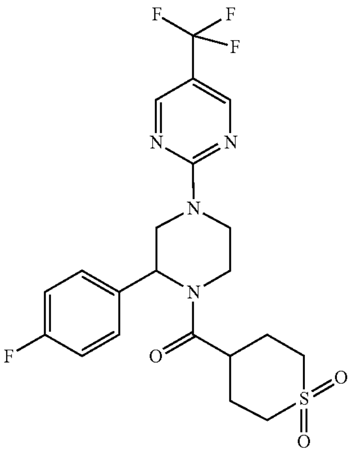
-continued
74
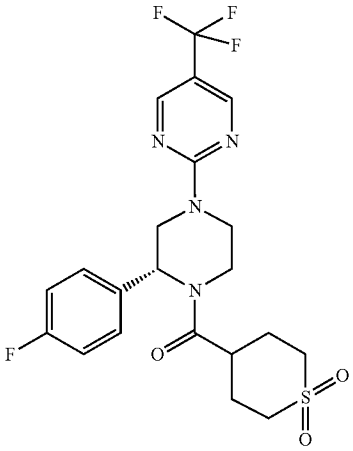
75
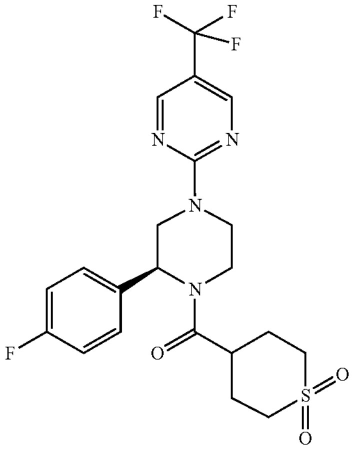
76
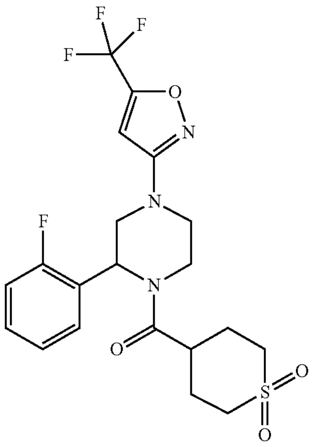

-continued
77
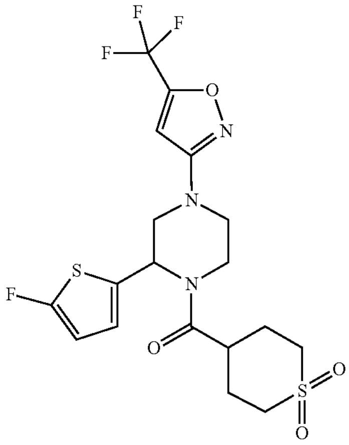
78
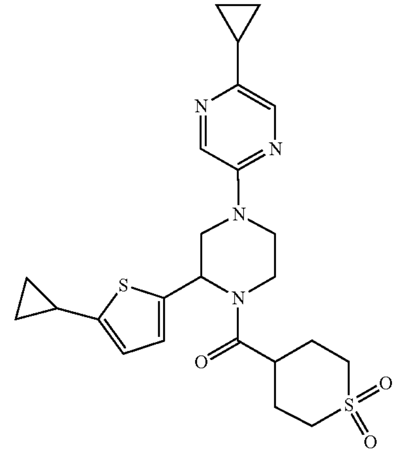
79
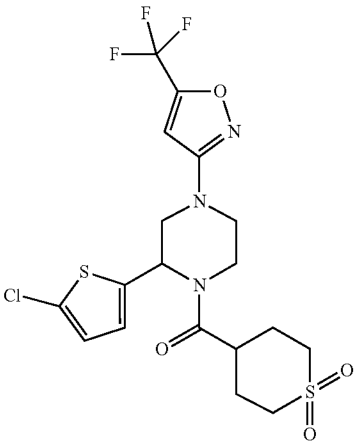
-continued
80
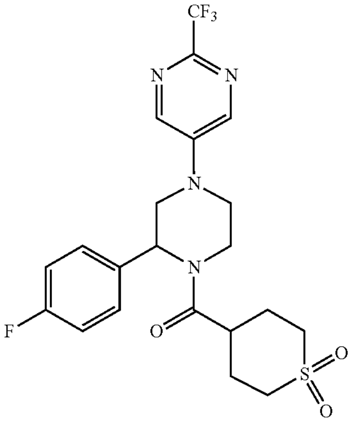
81
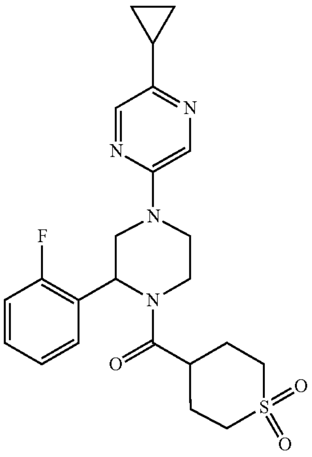
82
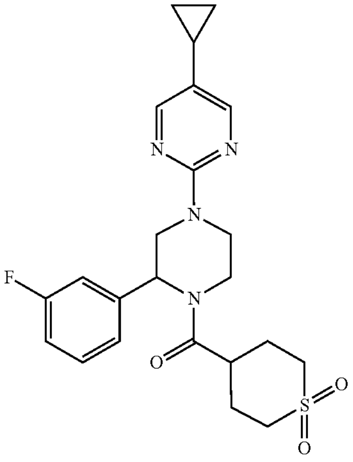

-continued
83
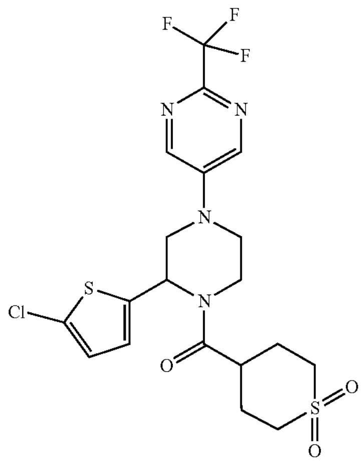
84
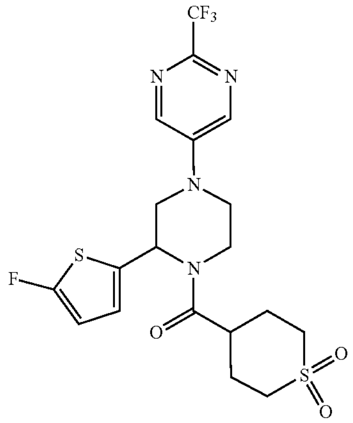
85
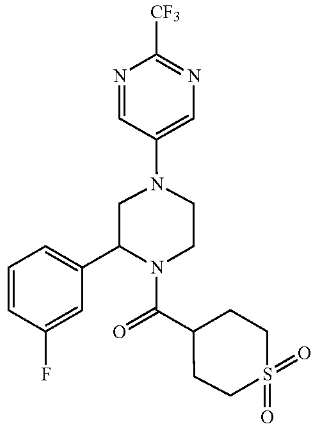
-continued
86
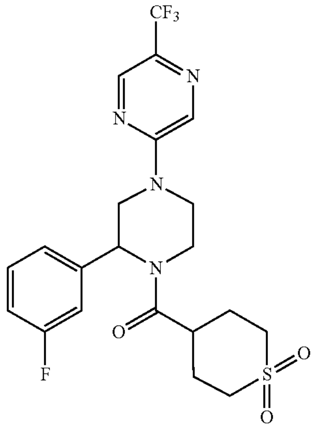
87
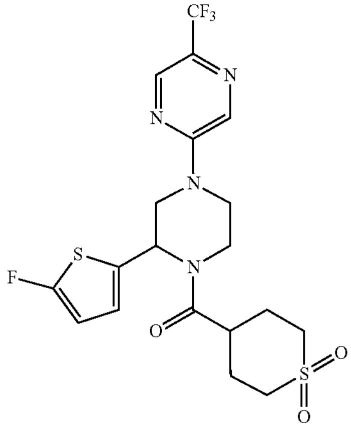
88
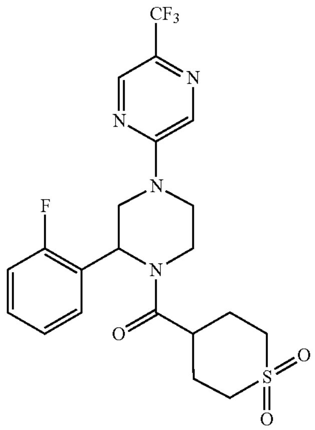

-continued
89
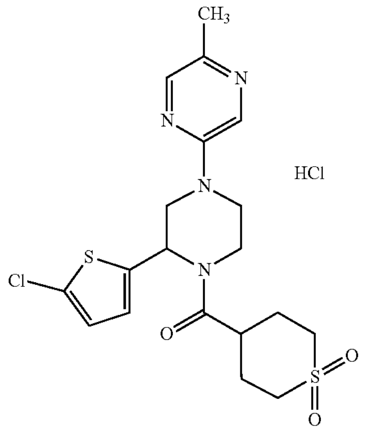
90
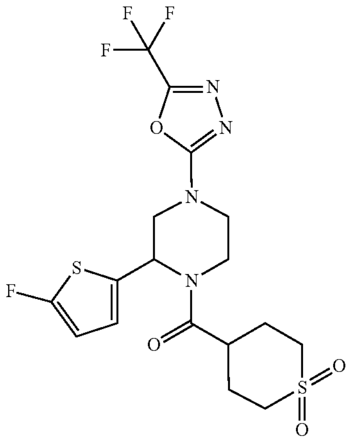
91
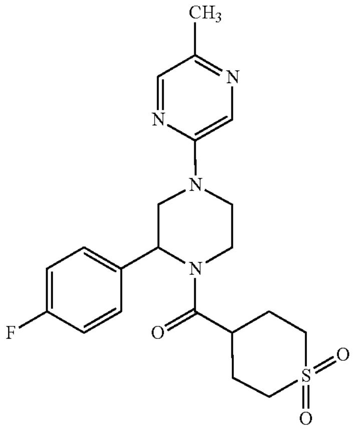
-continued
92
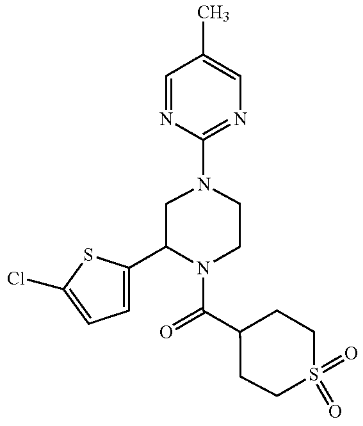
93
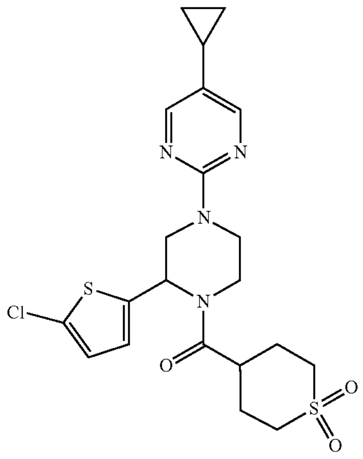
94
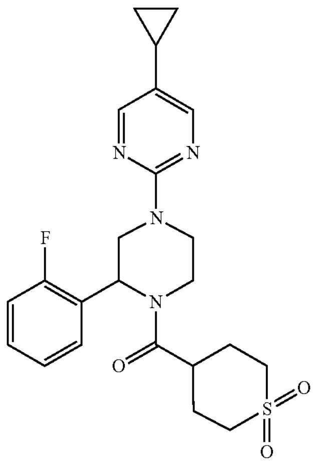

-continued
95
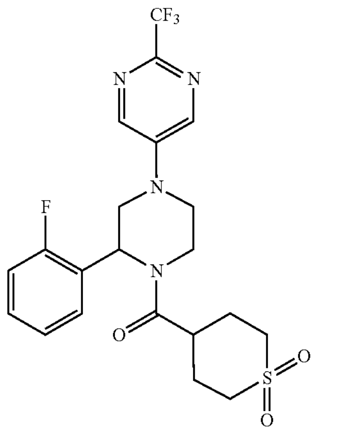
96
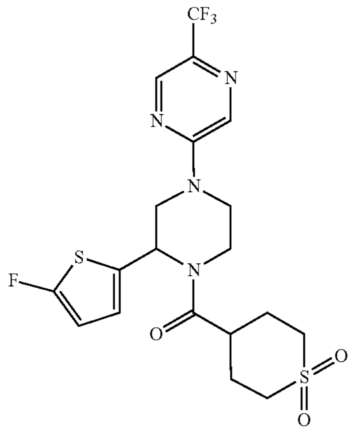
97
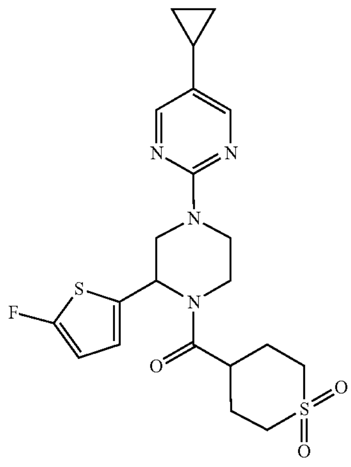
-continued
98
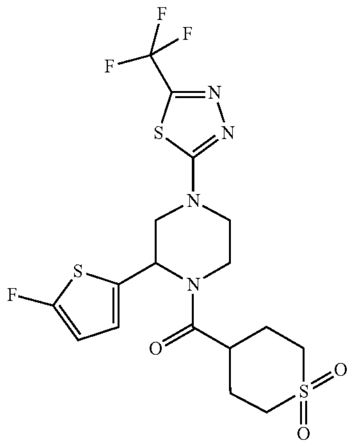
99
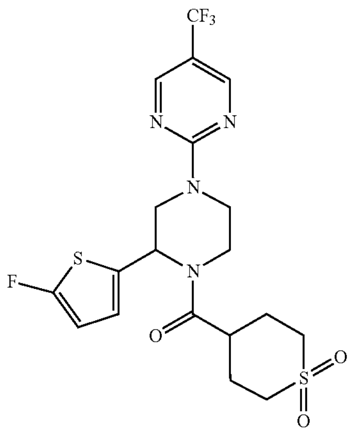
100
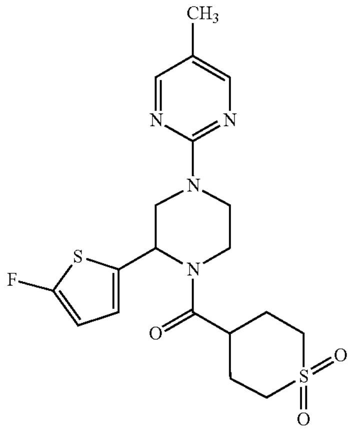

-continued
101
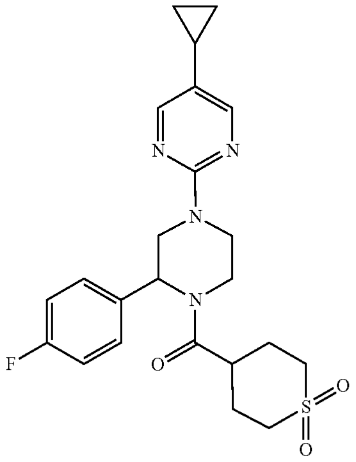
102
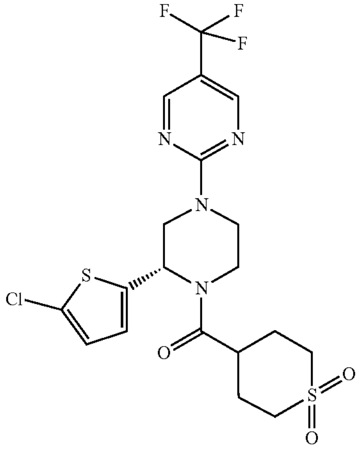
103
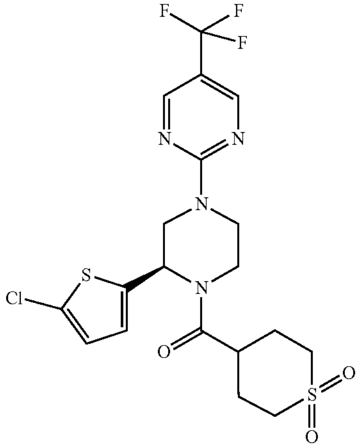
-continued
104
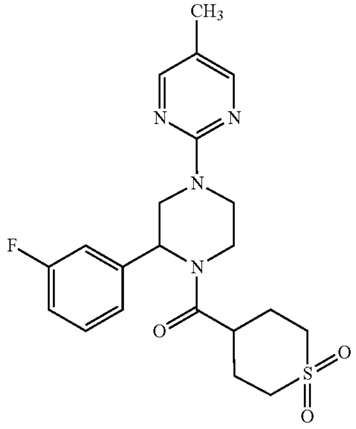
105
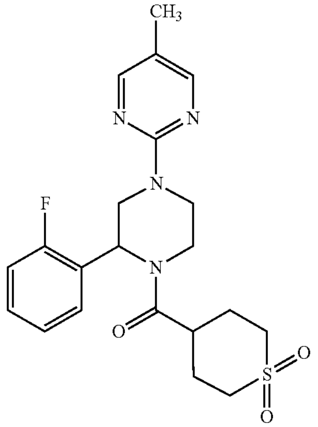
106
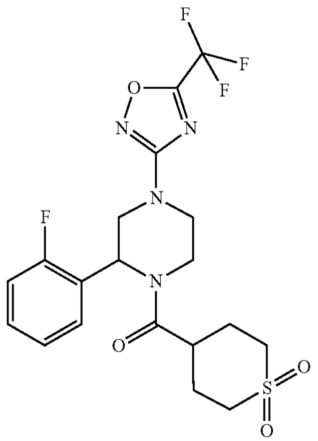

-continued
107
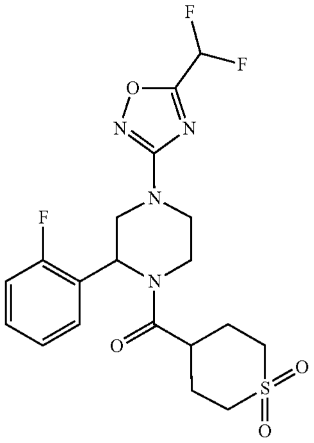
108
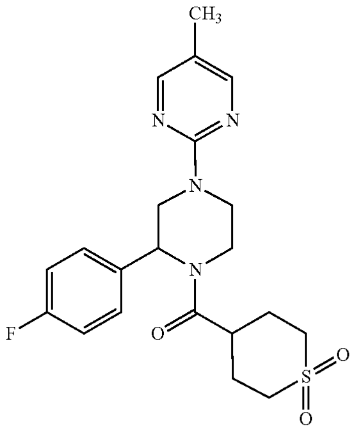
109
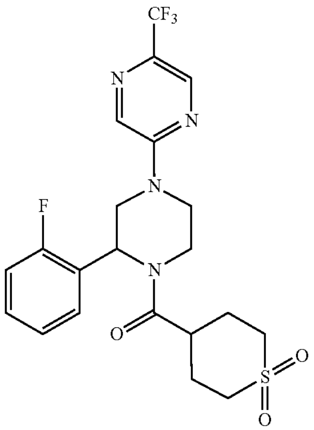
-continued
110
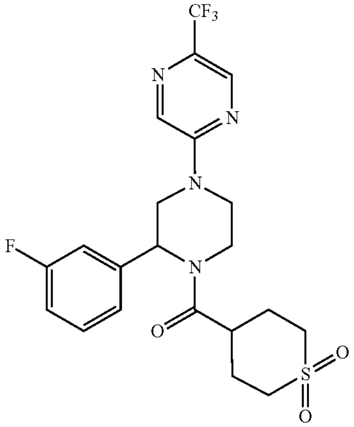
111
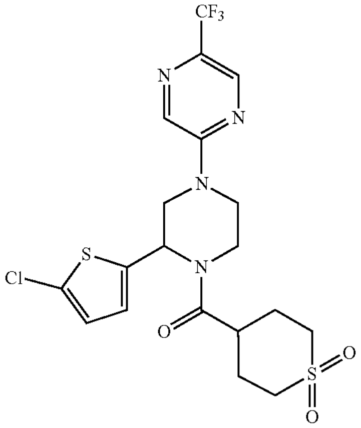
112
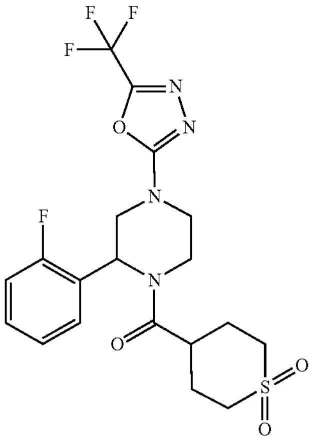

-continued
113
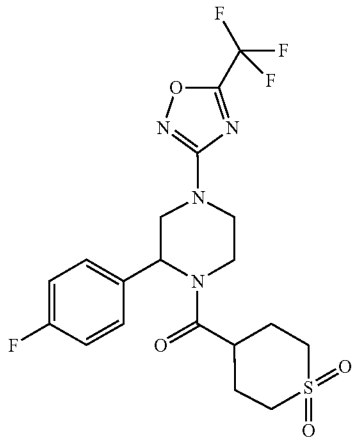
114
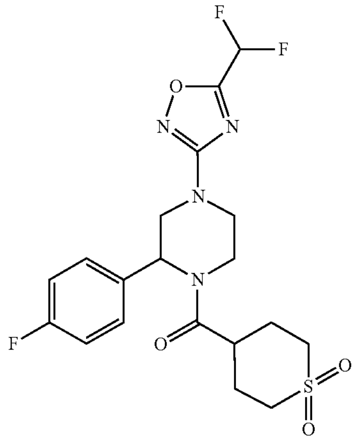
115
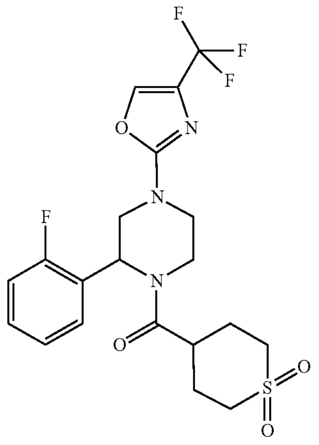
-continued
116
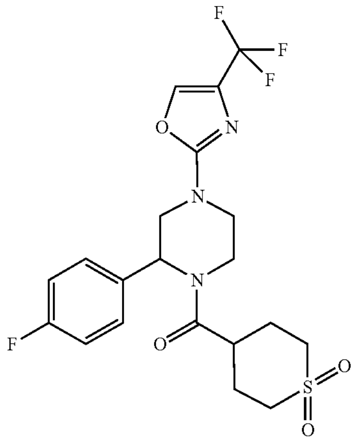
117
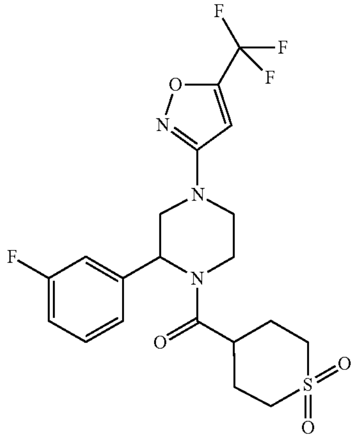
118
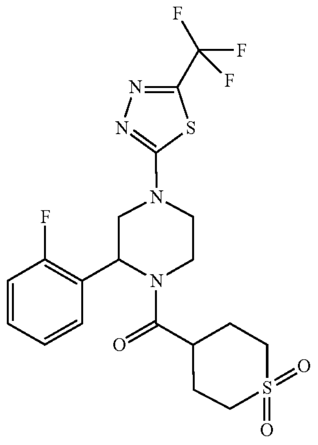

-continued
119
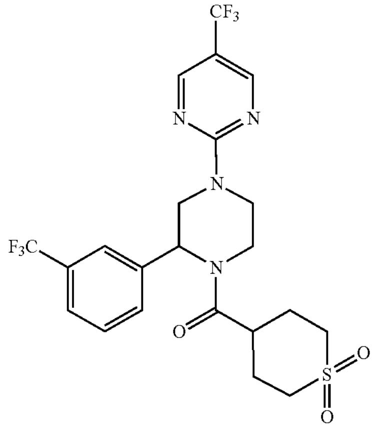
120
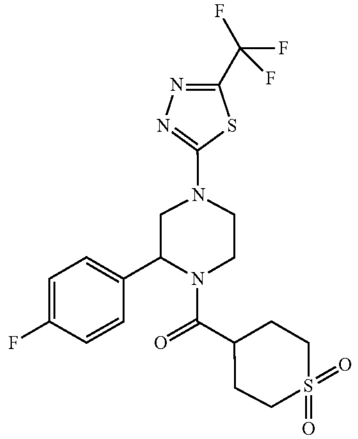
121
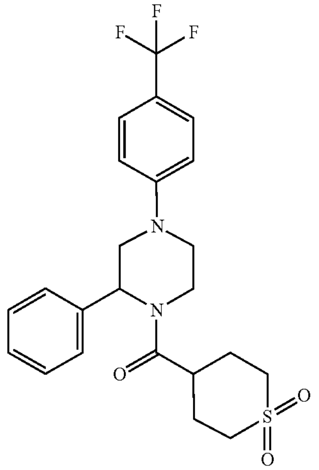
-continued
122
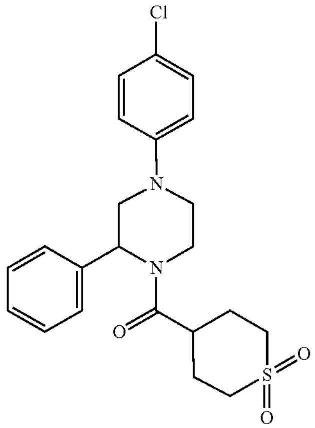
123
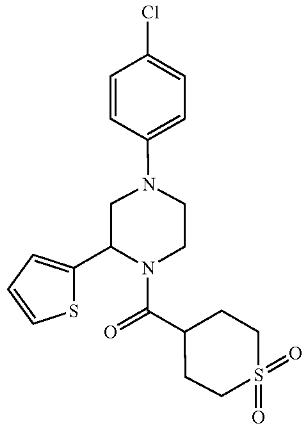
124
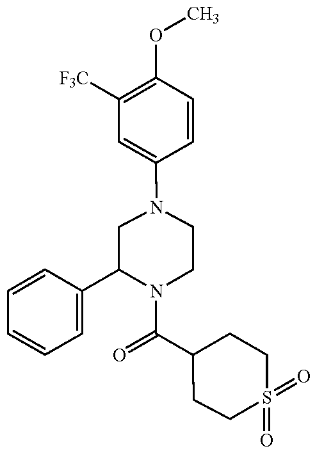

-continued
125
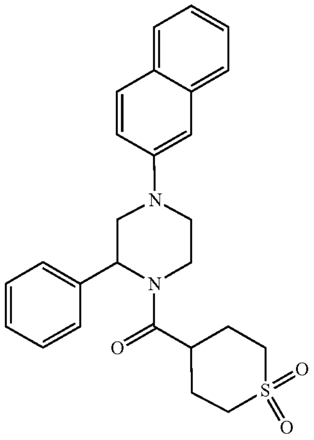
126
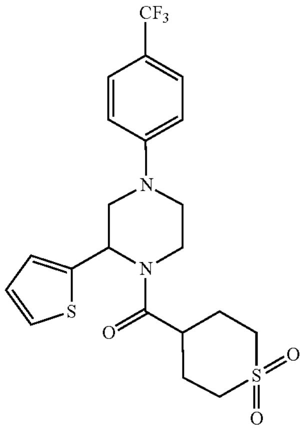
127
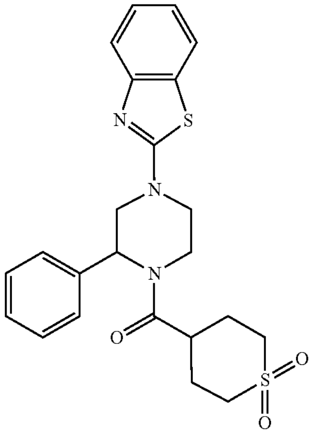
-continued
128
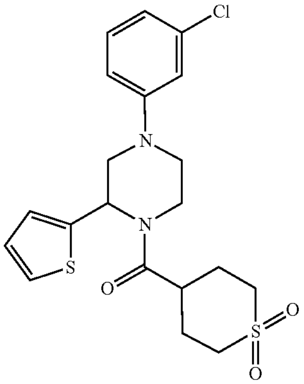
129
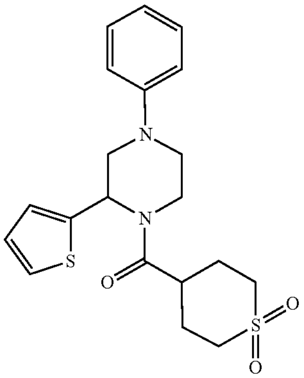
130
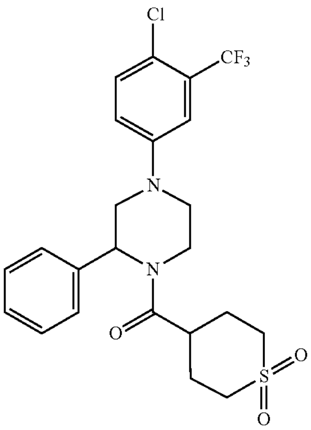
131
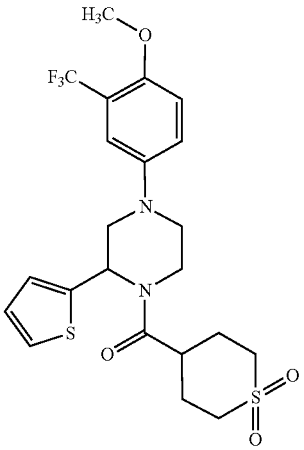

-continued
132
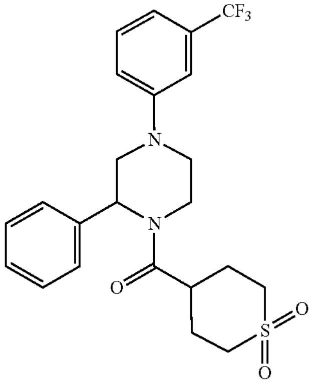
133
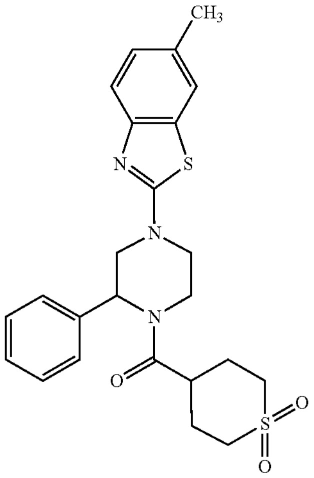
134
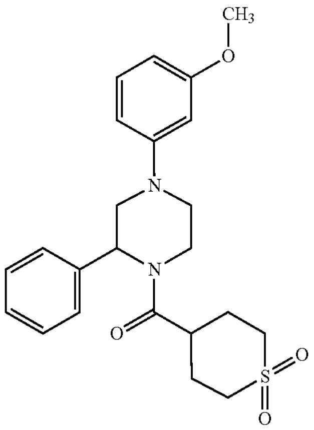
-continued
135
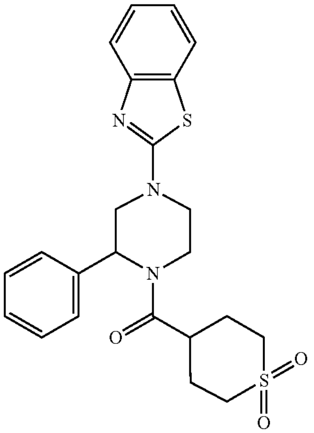
136
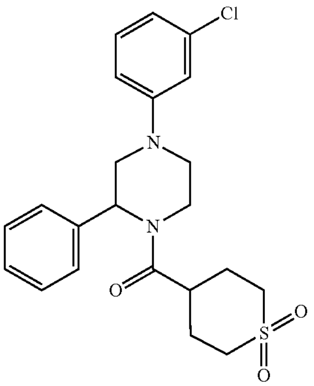
137
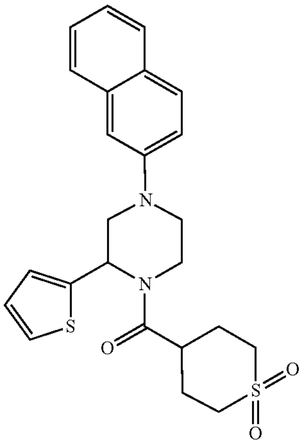
138
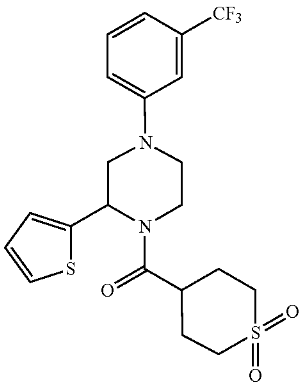

-continued
139
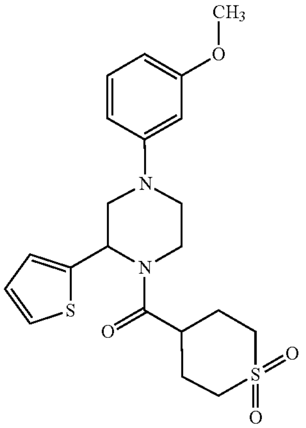
140
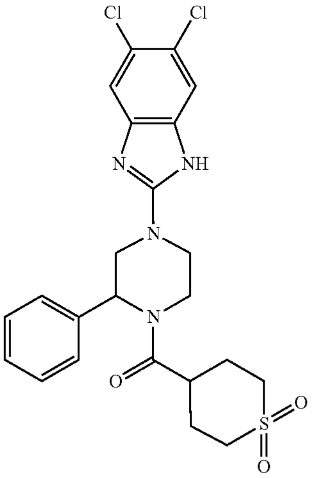
141
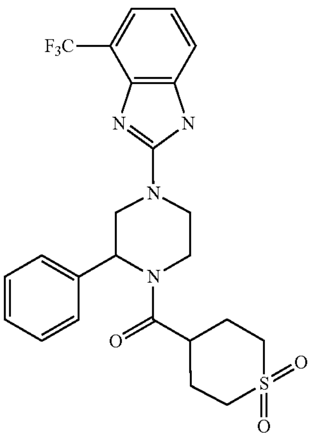
-continued
142
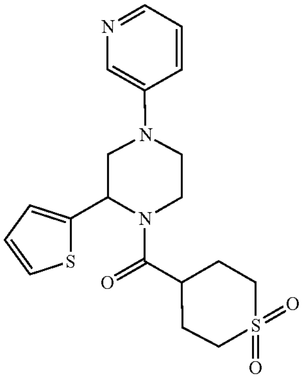
143
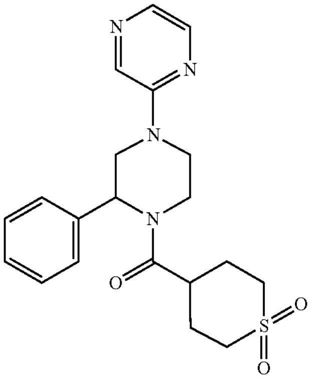
144
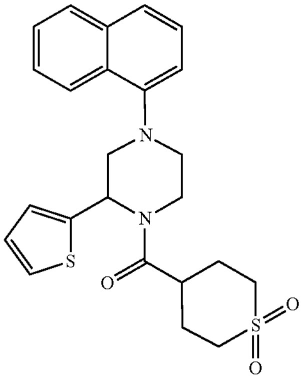
145
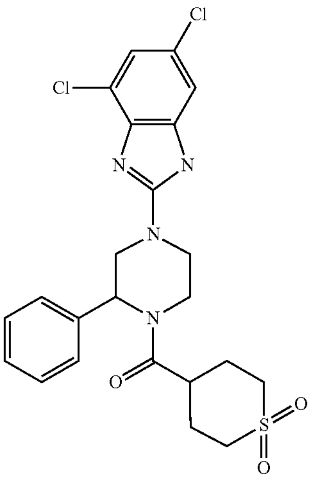

-continued
146
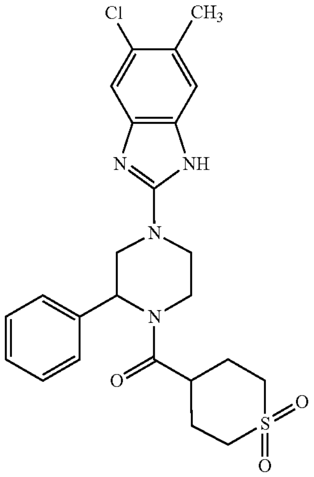
147
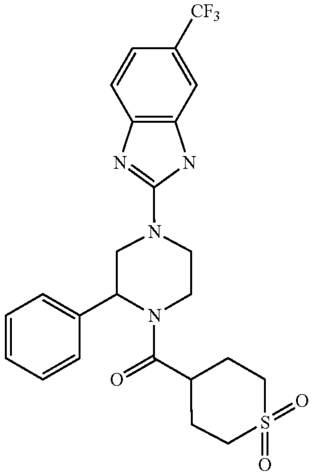
148
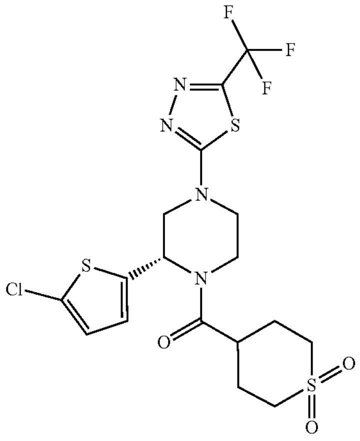
-continued
149
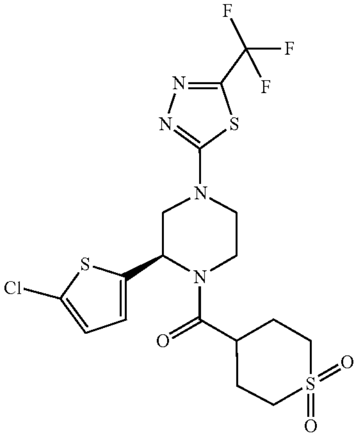
150
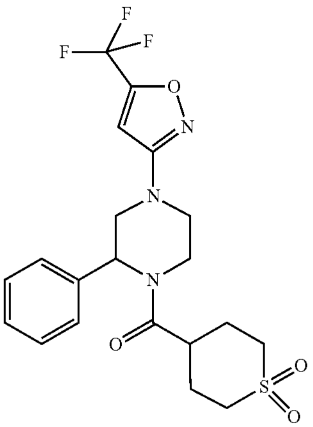
151
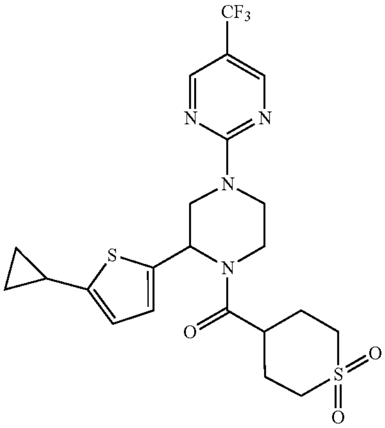

152
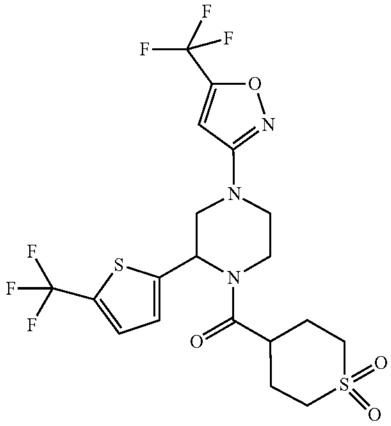
153
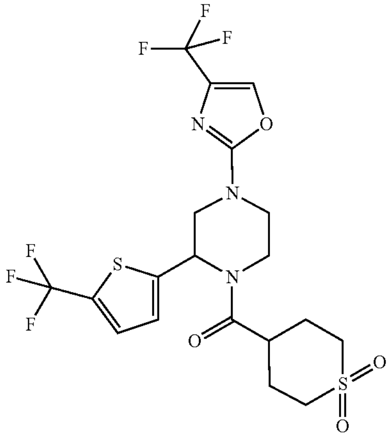
154
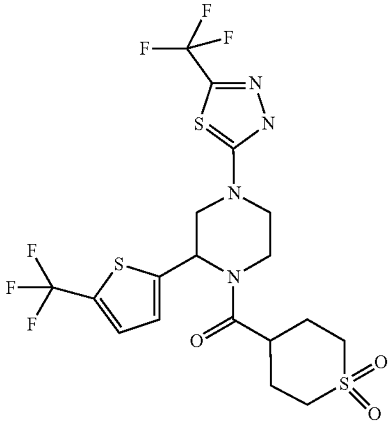
155
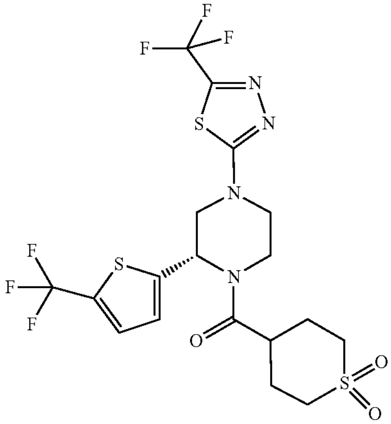
156
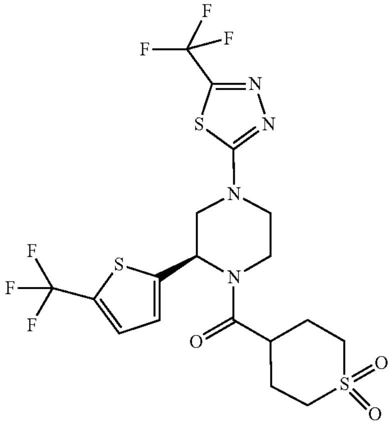
157
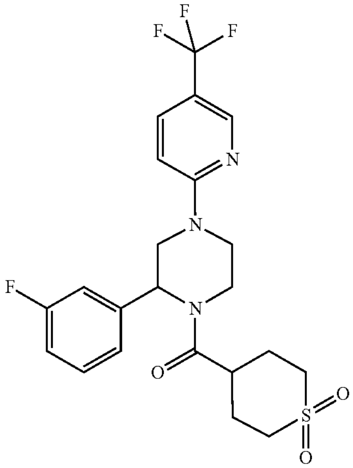

-continued

158

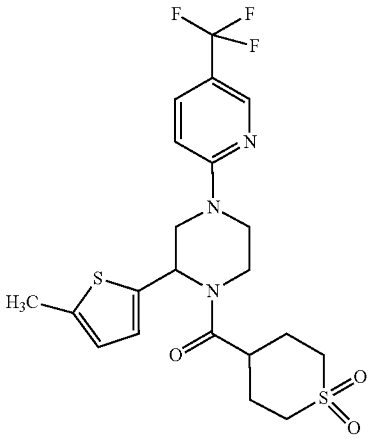

159

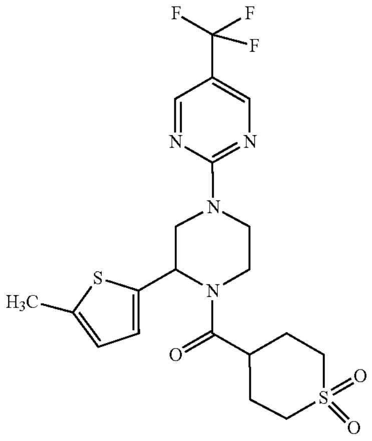

160

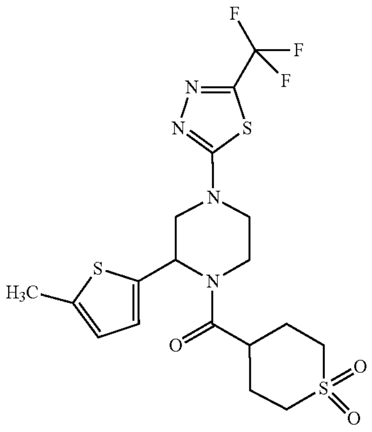

and

-continued

161

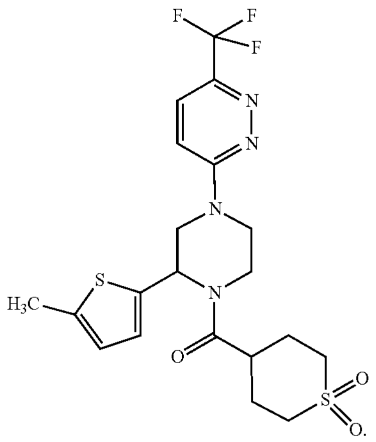

10. A method for treatment of cognitive impairment associated with schizophrenia, which comprises administering to a human suffering from schizophrenia a therapeutically effective amount of a compound according to claim 1.

11. A pharmaceutical composition or medicament comprising the compound according to claim 1 and a pharmaceutically acceptable carrier or diluent.

12. The compound of claim 1, wherein the compound is

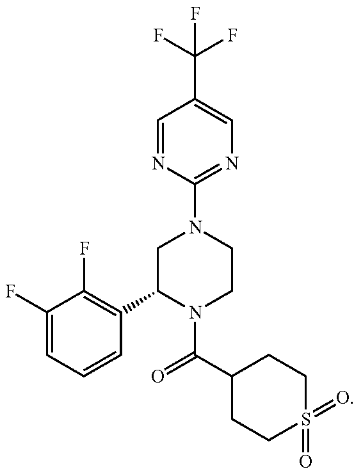 [SMILES: O=C(C1CCS(=O)(=O)CC1)N1CCN(c2ncc(C(F)(F)F)cn2)C[C@H]1c1cccc(F)c1F]

13. The compound of claim 1, wherein the compound is
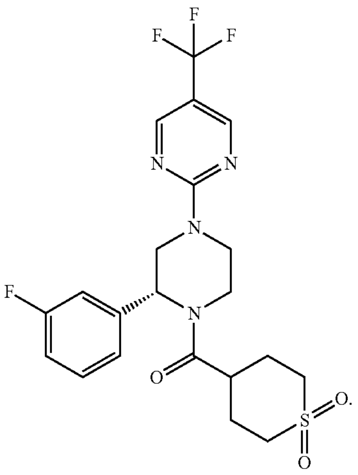 [SMILES: O=C(C1CCS(=O)(=O)CC1)N1CCN(c2ncc(C(F)(F)F)cn2)C[C@H]1c1cccc(F)c1]
14. The compound of claim 1, wherein the compound is
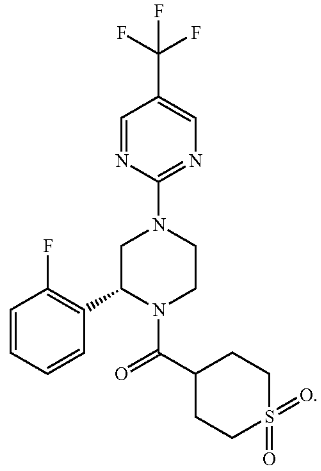 [SMILES: O=C(C1CCS(=O)(=O)CC1)N1CCN(c2ncc(C(F)(F)F)cn2)C[C@H]1c1ccccc1F]
15. The compound of claim 1, wherein the compound is
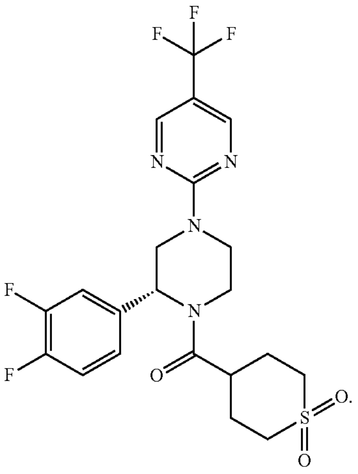 [SMILES: O=C(C1CCS(=O)(=O)CC1)N1CCN(c2ncc(C(F)(F)F)cn2)C[C@H]1c1ccc(F)c(F)c1]
16. The compound of claim 1, wherein the compound is
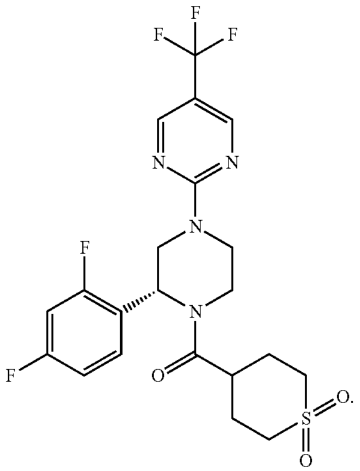 [SMILES: O=C(C1CCS(=O)(=O)CC1)N1CCN(c2ncc(C(F)(F)F)cn2)C[C@H]1c1ccc(F)cc1F]
17. The compound of claim 1, wherein the compound is
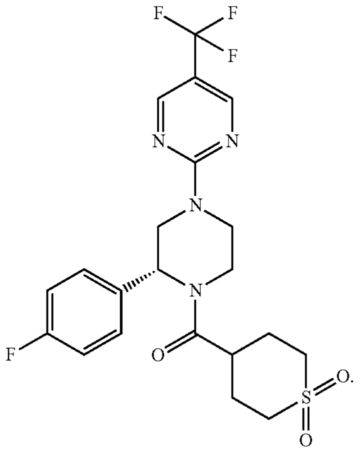 [SMILES: O=C(C1CCS(=O)(=O)CC1)N1CCN(c2ncc(C(F)(F)F)cn2)C[C@H]1c1ccc(F)cc1]
18. The compound of claim 1, wherein the compound is
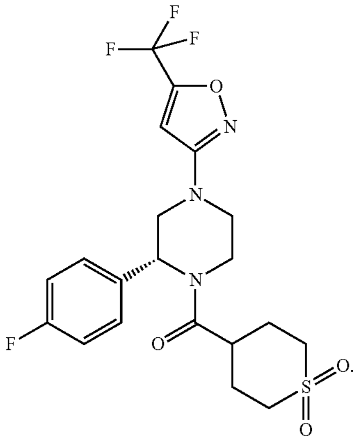 [SMILES: O=C(C1CCS(=O)(=O)CC1)N1CCN(c2cc(C(F)(F)F)on2)C[C@H]1c1ccc(F)cc1]
* * * * *